US012780819B2

(12) United States Patent
Bannen et al.

(10) Patent No.: US 12,780,819 B2
(45) Date of Patent: Nov. 3, 2026

(54) COMPOUNDS AND METHODS OF USE

(71) Applicant: Exelixis, Inc., Alameda, CA (US)

(72) Inventors: Lynne Bannen, Alameda, CA (US); Wei Xu, Alameda, CA (US); Yong Wang, Alameda, CA (US); Andrew Raub, Alameda, CA (US); Benjamin Spangler, Alameda, CA (US); Justin Salvant, Alameda, CA (US); Kin Tso, Alameda, CA (US); Faming Jiang, Alameda, CA (US)

(73) Assignee: Exelixis, Inc., Alameda, CA (US)

( * ) Notice: Subject to any disclaimer, the term of this patent is extended or adjusted under 35 U.S.C. 154(b) by 1006 days.

(21) Appl. No.: 17/800,084

(22) PCT Filed: Feb. 23, 2021

(86) PCT No.: PCT/US2021/019294

§ 371 (c)(1),
(2) Date: Aug. 16, 2022

(87) PCT Pub. No.: WO2021/173591

PCT Pub. Date: Sep. 2, 2021

(65) Prior Publication Data

US 2023/0151003 A1 May 18, 2023

Related U.S. Application Data

(60) Provisional application No. 63/121,418, filed on Dec. 4, 2020, provisional application No. 62/980,954, filed on Feb. 24, 2020.

(51) Int. Cl.
*C07D 471/04* (2006.01)
*C07D 401/12* (2006.01)
*C07D 519/00* (2006.01)

(52) U.S. Cl.
CPC ......... *C07D 471/04* (2013.01); *C07D 401/12* (2013.01); *C07D 519/00* (2013.01)

(58) Field of Classification Search
CPC .................................................... C07D 471/04
See application file for complete search history.

(56) References Cited

U.S. PATENT DOCUMENTS

| | | | |
|---|---|---|---|
| 7,732,613 | B2 | 6/2010 | Kim |
| 8,685,983 | B2 | 4/2014 | Kim et al. |
| 9,522,902 | B2 | 12/2016 | Dandu et al. |

FOREIGN PATENT DOCUMENTS

| | | | | |
|---|---|---|---|---|
| CN | 101248059 | A1 | 8/2008 | |
| CN | 104072480 | A | 10/2014 | |
| CN | 105461687 | B | 4/2016 | |
| CN | 108530426 | A | 9/2018 | |
| CN | 109896997 | A | 6/2019 | |
| CN | 110330479 | A | 10/2019 | |
| EP | 3026045 | A1 | 6/2016 | |
| EP | 3239147 | A1 | 11/2017 | |
| WO | 2007/033196 | A1 | 3/2007 | |
| WO | 2008/048375 | A1 | 4/2008 | |
| WO | 2013/074633 | A1 | 5/2013 | |
| WO | 2013/180949 | A1 | 12/2013 | |
| WO | WO-2015012298 | A1 * | 1/2015 | ................ A61P 9/00 |
| WO | 2020/038460 | | 2/2020 | |
| WO | 2020/042618 | | 3/2020 | |
| WO | 2020/047184 | A1 | 3/2020 | |
| WO | 2021012717 | A1 | 1/2021 | |
| WO | 2021/062245 | A1 | 4/2021 | |
| WO | 2021/173591 | A1 | 9/2021 | |

OTHER PUBLICATIONS

Clark et al., "A flexible high content imaging assay for profiling macrophage efferocytosis", Journal of Immunological Methods, Elsevier Science Publishers B.V.,Amsterdam, NL, vol. 473, Jul. 29, 2019, XP085783040.
International Search Report & Written Opinion dated Apr. 23, 2021 for PCT/US2021/019294, 10 pages.
International Search Report & Written Opinion dated Apr. 8, 2022 for PCT/US2022/016915, 21 pages.
International Search Report & Written Opinion dated Nov. 20, 2020 for PCT/US2020/052850, 18 pages.
Li et al., "Design, synthesis and antitumour activity of bisquinoline derivatives connected by 4-oxy-3-fluoroaniline moiety", European Journal of Medicinal Chemistry, Elsevier, Amsterdam, NL, vol. 64, Apr. 15, 2013, pp. 62-73, XP028566334.
Liu et al., "Design, synthesis and biological evaluation of novel 4-phenoxyquinoline derivatives containing 3-oxo-3,4-dihydroquinoxaline moiety as c-Met kinase inhibitors", Bioorganic & Medicinal Chemistry, Elsevier, NL, vol. 25, No. 16, Jun. 27, 2017, pp. 4475-4486, XP085133591.
Tang et al., "Design, synthesis, and structure-activity relationships of novel 6,7-disubstituted-4-phenoxyquinoline derivatives as potential antitumor agents", European Journal of Medicinal Chemistry, Elsevier, Amsterdam, NL, vol. 69, Aug. 19, 2013, pp. 77-89, XP028762794.
Tang, et al, "Synthesis and antiproliferative activity of 6,7-disubstituted-4-phenoxyquinoline derivatives bearing the 1,8-naphthyridin-2-one moiety", European Journal of Medicinal Chemistry, vol. 158, Oct. 2018, pp. 201-213, XP055748184.
Zhang et al., "Discovery of Novel c-Met Inhibitors Bearing a 3-Carboxyl Piperidin-2-one Scaffold", Molecules, vol. 19, No. 2, Feb. 24, 2014, pp. 2655-2673, XP055460997.
Zhang et al., "Discovery of novel type II c-Met inhibitors based on BMS-777607", European Journal of Medicinal Chemistry, vol. 80, Apr. 21, 2014, pp. 254-266, XP055394473.

* cited by examiner

*Primary Examiner* — John S Kenyon
*Assistant Examiner* — Sara Elizabeth Bell
(74) *Attorney, Agent, or Firm* — Sheppard Mullin Richter & Hampton LLP

(57) ABSTRACT

The present disclosure relates generally to nitrogen-containing fused heteroaryl compounds and pharmaceutical compositions comprising the same, suitable as modulators of protein kinases, and methods for their use in treating disorders mediated, at least in part by, protein kinases, such as a disease, disorder, or condition that is mediated, at least in part, by c-Met, Axl, Mer and/or KDR activity.

15 Claims, No Drawings

COMPOUNDS AND METHODS OF USE

CROSS REFERENCE TO RELATED APPLICATIONS

This application is a U.S. National Stage Application under 35 U.S.C. § 371 of International Application No. PCT/US2021/019294, filed Feb. 23, 2021, which claims the benefit under 35 U.S.C. § 119(e) of U.S. Provisional Application No. 62/980,954, filed Feb. 24, 2020, and U.S. Provisional Application No. 63/121,418, filed Dec. 4, 2020, each of which is hereby incorporated by reference in its entirety.

FIELD

Provided herein are compounds and pharmaceutical compositions suitable as modulators of protein kinases, and methods for their use in treating disorders mediated, at least in part by, protein kinases.

BACKGROUND

Human Axl belongs to the TAM subfamily of receptor tyrosine kinases that includes Mer. TAM kinases are characterized by an extracellular ligand binding domain consisting of two immunoglobulin-like domains and two fibronectin type III domains. Axl is overexpressed in a number of tumor cell types and was initially cloned from patients with chronic myelogenous leukemia. When overexpressed, Axl exhibits transforming potential. Axl signaling is believed to cause tumor growth through activation of proliferative and anti-apoptotic signaling pathways. Axl has been associated with cancers including, but not limiting to lung cancer, myeloid leukemia, uterine cancer, ovarian cancer, gliomas, melanoma, thyroid cancer, renal cell carcinoma, osteosarcoma, gastric cancer, prostate cancer, and breast cancer. The over-expression of Axl results in a poor prognosis for patients with the indicated cancers.

Activation of Mer, like Axl, conveys downstream signaling pathways that cause tumor growth and activation. Mer binds ligands such as the soluble protein Gas-6. Gas-6 binding to Mer induces autophosphorylation of Mer on its intracellular domain, resulting in downstream signal activation. Over-expression of Mer in cancer cells leads to increased metastasis, most likely by generation of soluble Mer extracellular domain protein as a decoy receptor. Tumor cells secrete a soluble form of the extracellular Mer receptor which reduces the ability of soluble Gas-6 ligand to activate Mer on endothelial cells, leading to cancer progression.

c-Met, is the prototypic member of a subfamily of heterodimeric receptor tyrosine kinases (RTKs) which include Met, Ron and Sea. Expression of c-Met occurs in a wide variety of cell types including epithelial, endothelial and mesenchymal cells where activation of the receptor induces cell migration, invasion, proliferation and other biological activities associated with invasive cell growth. Signal transduction through c-Met receptor activation is responsible for many of the characteristics of tumor cells.

Therefore, a need exists for new compounds that modulate Axl, Mer and c-Met kinases for the treatment of cancers.

SUMMARY

Provided herein are compounds that inhibit c-Met, Axl, Mer and/or KDR. In certain embodiments, the compounds are of Formula (I) or a pharmaceutically acceptable salt, stereoisomer, or mixture of stereoisomers thereof, as described herein.

Also provided herein are pharmaceutical compositions comprising a compound as described herein, or a pharmaceutically acceptable salt, stereoisomer, or mixture of stereoisomers thereof, and a pharmaceutically acceptable carrier or excipient.

Some embodiments provide for methods of modulating in vivo activity of a protein kinase in a subject, the method comprising administering to the subject a therapeutically effective amount of a compound as described herein, or a pharmaceutically acceptable salt, stereoisomer, or mixture of stereoisomers thereof, or a pharmaceutical composition as described herein.

Some embodiments provide for methods of treating a disease, disorder, or syndrome in a subject, the method comprising administering to the subject in need thereof a therapeutically effective amount of a compound as described herein, or a pharmaceutically acceptable salt, stereoisomer, or mixture of stereoisomers thereof, or a pharmaceutical composition as described herein, wherein the disease, disorder, or syndrome is mediated at least in part by modulating in vivo activity of a protein kinase.

The disclosure also provides compositions, including pharmaceutical compositions, kits that include the compounds, and method of using (or administering) and making the compounds. The disclosure further provides compounds and/or compositions for use in a method of treating a disease, disorder, or condition that is mediated, at least in part, by c-Met, Axl, Mer and/or KDR activity. Moreover, the disclosure provides uses of the compounds or compositions thereof in the manufacture of a medicament for the treatment of a disease, disorder, or condition that is mediated, at least in part, by c-Met, Axl, Mer and/or KDR.

DETAILED DESCRIPTION

Definitions

As used in the present specification, the following words, phrases and symbols are generally intended to have the meanings as set forth below, except to the extent that the context in which they are used indicates otherwise.

A dash ("–") that is not between two letters or symbols is used to indicate a point of attachment for a substituent. For example, $—C(O)NH_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $—(CH_2)_3CH_3$), sec-butyl (i.e., $—CH(CH_3)CH_2CH_3$), isobutyl (i.e., $—CH_2CH(CH_3)_2$) and tert-butyl (i.e., $—C(CH_3)_3$); and "propyl" includes n-propyl (i.e., $—(CH_2)_2CH_3$) and isopropyl (i.e., $—CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylthio" refers to the group "alkyl-S—". "Alkylsulfinyl" refers to the group "alkyl-S(O)—"•"Alkylsulfonyl" refers to the group "alkyl-$S(O)_2$—". "Alkylsulfonylalkyl" refers to -alkyl-$S(O)_2$-alkyl.

"Acyl" refers to a group $—C(O)R^y$, wherein $R^y$ is hydrogen, alkyl, alkenyl, alkynyl, cycloalkyl, heterocycloalkyl, aryl, heteroalkyl or heteroaryl; each of which may be optionally substituted, as defined herein. Examples of acyl include, e.g., formyl, acetyl, cyclohexylcarbonyl, cyclohexylmethyl-carbonyl and benzoyl.

"Amido" refers to both a "C-amido" group which refers to the group $—C(O)NR^yR^z$ and an "N-amido" group which refers to the group $—NR^yC(O)R^z$, wherein $R^y$ and $R^z$ are independently hydrogen, alkyl, alkenyl, alkynyl, cycloalkyl, heterocycloalkyl, aryl, heteroalkyl or heteroaryl; each of which may be optionally substituted, as defined herein, or $R^y$ and $R^z$ are taken together to form a cycloalkyl or heterocycloalkyl; each of which may be optionally substituted, as defined herein.

"Amino" refers to the group $—NR^yR^z$ wherein $R^y$ and $R^z$ are independently hydrogen, alkyl, alkenyl, alkynyl, cycloalkyl, heterocycloalkyl, aryl, heteroalkyl or heteroaryl; each of which may be optionally substituted, as defined herein.

"Amidino" refers to $—C(NR^y)(NR^z_2)$, wherein $R^y$ and $R^z$ are independently hydrogen, alkyl, alkenyl, alkynyl, cycloalkyl, heterocycloalkyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocycloalkyl, the resulting ring system is heterocycloalkyl.

"Arylalkyl" or "Aralkyl" refers to the group "aryl-alkyl-".

"Carbamoyl" refers to $—C(O)NR^yR^z$. "O-carbamoyl" refers to $—O—C(O)NR^yR^z$ and "N-carbamoyl" refers to $—NR^yC(O)OR^z$, wherein $R^y$ and $R^z$ are independently hydrogen, alkyl, alkenyl, alkynyl, cycloalkyl, heterocycloalkyl, aryl, heteroalkyl or heteroaryl; each of which may be optionally substituted, as defined herein.

"Carboxyl ester" or "ester" refer to both $—OC(O)R^x$ and $—C(O)OR^x$, wherein $R^x$ is alkyl, alkenyl, alkynyl, cycloalkyl, heterocycloalkyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{320}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. In some embodiments, one or more ring carbons of "cycloalkyl" can be optionally replaced by a carbonyl group. Examples of such cycloalkyl include cyclohexanone-4-yl, and the like. Further, the term cycloalkyl is intended to encompass moieties that have one or more aromatic ring fused (i.e., having a bond in common with) to the cycloalkyl ring, e.g., benzo or thienyl derivatives of cyclopentane, cyclohexane, and the like. A cycloalkyl group containing a fused aromatic ring can be attached through any ring-forming atom including a ring-forming atom of the fused aromatic ring. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-".

"Guanidino" refers to $—NR^yC(=NR^z)(NR^yR^z)$, wherein each $R^y$ and $R^z$ are independently hydrogen, alkyl, alkenyl, alkynyl, cycloalkyl, heterocycloalkyl, aryl, heteroalkyl or heteroaryl; each of which may be optionally substituted, as defined herein.

"Hydrazino" refers to $—NHNH_2$.

"Imino" refers to a group $—C(NR^y)R^z$, wherein $R^y$ and $R^z$ are each independently hydrogen, alkyl, alkenyl, alkynyl, cycloalkyl, heterocycloalkyl, aryl, heteroalkyl or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocycloalkyl, aryl, heteroalkyl or heteroaryl; each of which may be optionally substituted, as defined herein.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., 1 to 6 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6 or 1 to 3) hydrogen atoms are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocycloalkyl, aryl, heteroalkyl or heteroaryl; each of which may be optionally substituted, as defined herein. Examples of heteroalkyl groups include, e.g., ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.) and amines (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where R$^y$ is hydrogen, alkyl, alkenyl, alkynyl, cycloalkyl, heterocycloalkyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, boron, phosphorus and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-14, or 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. In some embodiments, any ring-forming N in a heteroaryl moiety can be an N-oxide.

In certain instances, a fused heteroaryl refers to a heteroaryl ring fused to another heteroaryl ring. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocycloalkyl" or "heterocyclyl" refers to a saturated or partially unsaturated cyclic alkyl group, with one or more ring heteroatoms independently selected from boron, phosphorus, nitrogen, oxygen and sulfur. The term "heterocycloalkyl" includes heterocycloalkenyl groups (i.e., the heterocycloalkyl group having at least one double bond), bridged-heterocycloalkyl groups, fused-heterocycloalkyl groups and spiro-heterocycloalkyl groups. A heterocycloalkyl may be a single ring or multiple rings wherein the multiple rings may be fused, bridged or spiro. One or more ring carbon atoms and ring heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring carbon atom or a ring heteroatom. Any non-aromatic ring containing at least one heteroatom is considered a heterocycloalkyl, regardless of the attachment (i.e., can be bound through a carbon atom or a heteroatom).

As used herein, heterocycloalkyl has 2 to 20 ring carbon atoms (i.e., $C_{2-20}$ heterocycloalkyl), 2 to 12 ring carbon atoms (i.e., $C_{2-12}$ heterocycloalkyl), 2 to 10 ring carbon atoms (i.e., $C_{2-10}$ heterocycloalkyl), 2 to 8 ring carbon atoms (i.e., $C_{2-8}$ heterocycloalkyl), 3 to 12 ring carbon atoms (i.e., $C_{3-12}$ heterocycloalkyl), 3 to 8 ring carbon atoms (i.e., $C_{3-8}$ heterocyclyl), or 3 to 6 ring carbon atoms (i.e., $C_{3-6}$ heterocycloalkyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocycloalkyl" also includes "spiroheterocycloalkyl" when there are two positions for substitution on the same carbon atom. Examples of the spiro-heterocycloalkyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl.

Further, the term heterocycloalkyl is intended to encompass any non-aromatic ring containing at least one heteroatom, which ring is fused to one or more aryl or heteroaryl rings, regardless of the attachment to the remainder of the molecule (i.e., a heterocycloalkyl group containing a fused aromatic ring can be attached through any ring atom including a ring atom of the fused aromatic ring). Examples of the fused-heterocycloalkyl rings include, but are not limited to, 1,2,3,4-tetrahydroisoquinolinyl, 4,5,6,7-tetrahydrothieno[2,3-c]pyridinyl, indolinyl and isoindolinyl, where the heterocycloalkyl can be bound via either ring of the fused system.

"Heterocycloalkylalkyl" refers to the group "heterocycloalkyl-alkyl-."

"Oxime" refers to the group —$CR^y$(═NOH) wherein $R^y$ is hydrogen, alkyl, alkenyl, alkynyl, cycloalkyl, heterocycloalkyl, aryl, heteroalkyl or heteroaryl; each of which may be optionally substituted, as defined herein.

"Sulfonyl" refers to the group —$S(O)_2R^y$, where $R^y$ is hydrogen, alkyl, alkenyl, alkynyl, cycloalkyl, heterocycloalkyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —$S(O)R^y$, where $R^y$ is hydrogen, alkyl, alkenyl, alkynyl, cycloalkyl, heterocycloalkyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, cycloalkyl, heterocycloalkyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5 or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocycloalkyl, heteroaryl, and/or heteroalkyl) wherein at least one (e.g., 1 to 5 or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocycloalkyl, heterocycloalkylalkyl, —$NHNH_2$, ═$NNH_2$, imino, imido, hydroxy, oxo, oxime, nitro, sulfonyl, sulfinyl, alkylsulfonyl, alkylsulfinyl, thiocyanate, —S(O)OH, —$S(O)_2OH$, sulfonamido, thiol, thioxo, N-oxide or —$Si(R^y)_3$, wherein each $R^y$ is independently hydrogen, alkyl, alkenyl, alkynyl, heteroalkyl, cycloalkyl, aryl, heteroaryl or heterocycloalkyl.

In certain embodiments, "substituted" includes any of the above alkyl, alkenyl, alkynyl, cycloalkyl, heterocycloalkyl, aryl or heteroaryl groups in which one or more (e.g., 1 to 5 or 1 to 3) hydrogen atoms are independently replaced with deuterium, halo, cyano, nitro, azido, oxo, alkyl, alkenyl, alkynyl, haloalkyl, cycloalkyl, heterocycloalkyl, aryl, heteroaryl, —$NR^kR^h$, —$NR^kC$(═O)$R^h$, —$NR^kC$(═O)$NR^kR^h$, —$NR^kC$(═O)$OR^h$, —$NR^kS$(═O)$_{1-2}R^h$, —C(═O)$R^k$, —C(═O)$OR^k$, —OC(═O)$OR^k$, —OC(═O)$R^k$, —C(═O)$NR^kR^h$, —OC(═O)$NR^kR^h$, —$OR^k$, —$SR^k$, —S(═O)$R^k$, —S(═O)$_2R^k$, —OS(═O)$_{1-2}R^k$, —S(═O)$_{1-2}OR^k$, —$NR^kS$(═O)$_{1-2}NR^kR^h$, ═$NSO_2R^k$, ═$NOR^k$, —S(═O)$_{1-2}NR^kR^h$, —SFS, —$SCF_3$ or —$OCF_3$. In certain embodiments, "substituted" also means any of the above groups in which one or more (e.g., 1 to 5 or 1 to 3) hydrogen atoms are replaced with —C(═O)$R^k$, —C(═O)$OR^k$, —C(═O)$NR^kR^h$, —$CH_2SO_2R^k$, or —$CH_2SO_2NR^kR^h$. In the foregoing, $R^k$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocycloalkyl, heterocycloalkylalkyl, heteroaryl, and/or heteroarylalkyl. In certain embodiments, "substituted" also means any of the above groups in which one or more (e.g., 1 to 5 or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocycloalkyl, N-heterocycloalkyl, heterocycloalkylalkyl, heteroaryl, and/or heteroarylalkyl, or two of $R^k$ and $R^h$ and $R^i$ are taken together with the atoms to which they are attached to form a heterocycloalkyl ring optionally substituted with oxo, halo or alkyl optionally substituted with oxo, halo, amino, hydroxyl, or alkoxy.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^{3}H$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index (see e.g., A. Kerekes et. al. J. Med. Chem. 2011, 54, 201-210; R. Xu et. al. J. Label Compd. Radiopharn. 2015, 58, 308-312). An $^{8}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as $—CH_3$ being replaced for $—CD_3$). In some embodiments, the compound includes two or more deuterium atoms. In some embodiments, the compound includes 1, 2, 3, 4, 5, 6, 7, 8, 9, 10, 11, or 12 deuterium atoms. In some embodiments, all of the hydrogen atoms in a compound can be replaced or substituted by deuterium atoms. Synthetic methods for including isotopes into organic compounds are known in the art (Deuterium Labeling in Organic Chemistry by Alan F. Thomas (New York, NY., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), and prodrug of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from non-toxic inorganic and organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in Remington's Pharmaceutical Sciences, $17^{th}$ Ed., (Mack Publishing Company, Easton, 1985), p. 1418, Berge et al., J. Pharm. Sci., 1977, 66(1), 1-19 and in Stahl et al., Handbook of Pharmaceutical Salts: Properties, Selection, and Use, (Wiley, 2002).

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term "leaving group" refers to an atom or a group of atoms that is displaced in a chemical reaction as stable species taking with it the bonding electrons. The non-limiting examples of a leaving group include, halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tert-butyl-benzene)sulfonyloxy, benzenesulfonyloxy, (4-methoxy-benzene) sulfonyloxy, and the like.

The term "amide coupling conditions" refers to the reaction conditions under which an amine and a carboxylic acid couple to form an amide using a coupling reagent in presence of a base. The non-limiting examples of coupling reagents include 1-Ethyl-3-(3-dimethylaminopropyl) carbodiimide (EDC) with hydroxybenzotriazole monohydrate (HOBt), 0-(7-Azabenzotriazole-1-yl)-N,N,N,N'-tetramethyluronium hexafluorophosphate (HATU), 1-hydroxy-7-azabenzotriazole, and the like. The non-limiting examples of the base include N-methylmorpholine, pyridine, morpholine, imidazole, and the like.

The term "protecting group" refers to a moiety of a compound that masks or alters the properties of a functional group or the properties of the compound as a whole. The chemical substructure of a protective group varies widely. One function of a protective group is to serve as an intermediate in the synthesis of the parental drug substance. Chemical protective groups and strategies for protection/deprotection are well known in the art. See: "Protective Groups in Organic Chemistry", Theodora W. Greene (John Wiley & Sons, Inc., New York, 1991. Protective groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

The non-limiting examples of protective groups for a hydroxy (i.e. a "hydroxy protecting group") include methoxymethyl ether, tetrahydropyranyl ether, t-butyl ether, allyl ether, benzyl ether, t-butyldiphenylsilyl ether, acetate ester, pivalate ester, benzoate ester, benzylidene acetal, acetonide, silyl ether, and the like.

| Abbreviation | Meaning |
|---|---|
| $Amphos_2PdCl_2$ | bis(di-tert-butyl(4-dimethylaminophenyl) phosphine)dichloropalladium(II) |
| anhyd. | anhydrous |
| aq | aqueous |
| δ | Chemical shift (ppm) |
| DCE | dicholoroethane |
| DCM | dichloromethane |
| DIEA | diisopropylethylamine |
| DMAP | Dimethylaminopyridine |
| DMF | Dimethylformamide |
| DMSO | Dimethylsulfoxide |
| dppf | 1,1'-Bis(diphenylphosphino)ferrocene |
| DMAC | Dimethylacetamide |
| TEMED or TMEDA | Tetramethylethylenediamine |
| DMFDEA | N,N-dimethylformamide diethyl acetal |
| eq or equiv. | Equivalent(s) |
| Et | Ethyl |
| EtOAc | ethyl acetate |
| EtOH | ethanol |
| HATU | N-[(dimethylamino)-1H-1,2,3-triazolo-[4,5-b] pyridin-1-ylmethylene]-N-methylmethanaminium hexafluorophosphate N-oxide |
| HPLC | High performance liquid chromatography |
| LC-MS | Liquid chromatography-mass spectrometry |
| MeOH | methanol |
| MS | Mass spectrometry |
| MW or mw | microwaved |
| m/z | Mass to charge ratio |
| NBS | N-bromosuccinimide |
| NMR | Nuclear magnetic resonance spectroscopy |
| o/n | overnight |
| Ph | phenyl |
| $Pd(PPh_3)_4$ or tetrakis | tetrakis(triphenylphosphine)palladium(0) |
| Prep | preparatory |
| THF | tetrahydrofuran |
| TLC | Thin layer chromatography |

Provided herein is compound of Formula (I):

(I)

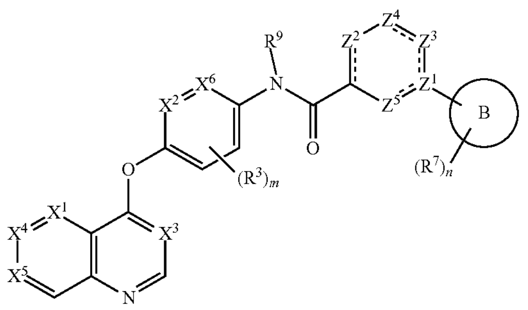

or a pharmaceutically acceptable salt or stereoisomer thereof, wherein:

ring B is a 5-membered heteroaryl having 1, 2 or 3 heteroatoms as ring members selected from N, O and S; a 9-10-membered heteroaryl having 1, 2 or 3 heteroatoms as ring members selected from N, O and S; or a 6-membered heteroaryl having 1 or 2 nitrogen atoms as ring members;

$X^1$ is N or $CR^{11}$;

$X^2$ is N, CH or $CR^3$;

$X^3$ is N or CH;

$X^4$ is N or $CR^1$;

$X^5$ is N or $CR^2$;

$X^6$ is N, CH or $CR^3$;

no more than one of $X^1$, $X^4$ and $X^5$ is N;

$Z^1$ is N, C or CH;

$Z^2$ is N, $NR^{13}$, —C(═O)— or $CR^5$;

$Z^3$ is N, $NR^{12}$, $CR^6$, —C(═O)—, —C(═S)—;

$Z^4$ is N, $NR^4$, $CR^{10}$, —C(═O)— or a bond;

$Z^5$ is N, $—COR^8$, —C(═O)— or $CR^{14}$;

one or two of $Z^1$, $Z^2$, $Z^3$ and $Z^4$ are each independently selected from N, $NR^{13}$, $NR^{12}$ and $NR^4$;

no more than two of $Z^2$, $Z^3$, $Z^4$ and $Z^5$ are —C(═O)—;

⎓ is a single bond or a double bond;

$R^1$ and $R^2$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^1$ and $R^2$ are each optionally substituted with 1, 2, 3, 4 or 5 independently selected $R^b$ substituents;

each $R^3$ is independently selected from halo, OH, CN, —COOH, —CONH($C_{1-6}$ alkyl), —$SO_2$($C_{1-6}$ alkyl), —$SO_2$NH($C_{1-6}$ alkyl), $C_1$-$C_6$ alkyl, $C_1$-$C_6$ alkoxy, $C_1$-$C_6$ haloalkoxy, $NH_2$, —NH($C_1$-$C_6$ alkyl), —N($C_1$-$C_6$ alkyl)$_2$, and $C_3$-$C_6$ cycloalkyl, wherein the $C_1$-$C_6$ alkyl, $C_1$-$C_6$ alkoxy, —NH($C_1$-$C_6$alkyl), —N($C_1$-$C_6$ alkyl)$_2$, and $C_3$-$C_6$ cycloalkyl of $R^3$ are each optionally substituted with 1, 2, or 3 independently selected $R^g$ substituents;

$R^4$, $R^{12}$ and $R^{13}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $N{=}C(NR^aR^a)_2$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^4$, $R^{12}$ and $R^{13}$ are each optionally substituted with 1, 2, 3, 4 or 5 independently selected $R^b$ substituents;

$R^5$, $R^6$ and $R^{10}$ are each independently H, halo, $C_{1-6}$ alkyl, $C_{2-6}$ alkenyl, $C_{1-6}$ alkoxy, $C_{1-6}$ alkylthio, CN, $C_{1-4}$ haloalkyl, $C_{1-4}$ haloalkoxy, OH, $C_{1-4}$alkyl-C(O)—, $C_{1-4}$alkyl-OC(O)—, —CONH($C_{1-4}$ alkyl), $NH_2$, —NH$C_{1-4}$alkyl, or —N($C_{1-4}$ alkyl)$_2$, wherein the $C_{1-6}$ alkyl, $C_{2-6}$ alkenyl, $C_{1-6}$ alkoxy, $C_{1-6}$ alkylthio, $C_{1-6}$ alkyl-C(O)— and $C_{1-4}$ alkyl of —NH($C_{1-4}$alkyl) or —N($C_{1-4}$ alkyl)$_2$ of $R^5$, $R^6$ and $R^{10}$ are each optionally substituted with 1 or 2 independently selected $R^g$ substituents;

each $R^7$ is independently selected from halo, OH, $COOR^a$, $COR^a$, $CONR^aR^a$, CN, $NH_2$, —NH($C_1$-$C_6$ alkyl), —N($C_1$-$C_6$ alkyl)$_2$, $C_1$-$C_6$ alkyl, $C_{2-6}$ alkenyl, $C_1$-$C_6$ alkoxy, $C_1$-$C_6$ haloalkyl, $C_1$-$C_6$ haloalkoxy, $CONR^aR^a$, $NR^aCOR^a$, $NR^aCONR^aR^a$, $SO_2R^a$, $NR^aS(O)_2R^a$, $NR^aS(O)_2NR^aR^a$, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene-; wherein the $C_1$-$C_6$ alkyl, $C_{1-6}$ alkenyl, $C_1$-$C_6$ alkoxy, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene- of $R^7$ are each optionally substituted with 1, 2, or 3 independently selected $R^f$ substituents;

$R^8$ is H, $C_{1-6}$ alkyl optionally substituted with 1 or 2 $R^g$ substituents or a hydroxy protecting group;

$R^g$ is H or $C_{1-6}$ alkyl optionally substituted with 1, 2, or 3 independently selected $R^9$ substituents;

$R^{11}$ is selected from H, $C_{1-6}$ alkyl, $C_{1-6}$ haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$; wherein the $C_1$-$C_6$ alkyl, $C_1$-$C_6$haloalkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$alkylene- of $R^{11}$ are each optionally substituted with 1, 2, or 3 independently selected $R^f$ substituents;

$R^{14}$ is H, halo, CN, or $C_{1-6}$ alkyl optionally substituted with 1 or 2 $R^g$ substituents;

or $R^{13}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^4$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{10}$ and $R^5$ taken together with the atoms to which they are attached form fused $C_{3-7}$ cycloalkyl, 4- to 6-membered fused heterocycloalkyl, fused 5- or 6-membered heteroaryl or fused phenyl, wherein the fused $C_{3-7}$ cycloalkyl, 4- to 6-membered fused heterocycloalkyl, 5- or 6-membered heteroaryl, or fused phenyl is each optionally substituted with 1 or 2 independently selected $R^g$ substituents and wherein one or two ring carbon atoms of the fused $C_{3-7}$ cycloalkyl or fused heterocycloalkyl are optionally replaced by a carbonyl group;

or when $Z^4$ is a bond, $R^{13}$ and $R^6$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{12}$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^6$ and $R^5$ taken together with the atoms to which they are attached form fused $C_{3-7}$ cycloalkyl, 4- to 6-membered fused heterocycloalkyl, 5- to 6-membered fused heteroaryl, or fused phenyl, wherein the fused $C_{3-7}$ cycloalkyl, 4- to 6-membered fused heterocycloalkyl, 5- to 6-membered fused heteroaryl, and fused phenyl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

or $R^{12}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^4$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^{10}$ taken together with the atoms to which they are attached form fused $C_{3-7}$ cycloalkyl, 4- to 6-membered fused heterocycloalkyl, 5- to 6-membered fused heteroaryl, or fused heteroaryl, wherein the fused $C_{3-7}$ cycloalkyl, 4- to 6-membered fused heterocycloalkyl, 5- to 6-membered fused heteroaryl, and fused heteroaryl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

each $R^a$ is independently selected from the group consisting of H, CN, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene-; wherein the $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$alkylene- of $R^a$ are each optionally substituted with 1, 2, 3, 4, or 5 independently selected $R^d$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^b$ is independently selected from the group consisting of halo, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $Si(R^c)_3$, $P(O)R^cR^c$, $P(O)(OR^c)(OR^c)$, $B(OH)_2$, $B(OR^c)_2$, and $S(O)_2NR^cR^c$; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^b$ are each further optionally substituted with 1, 2, or 3 independently selected $R^d$ substituents;

each $R^c$ is independently selected from the group consisting of H, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene-; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^c$ are each optionally substituted with 1, 2, 3, 4, or 5 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^d$ is independently selected from the group consisting of $C_1$-$C_6$ alkyl, $C_1$-$C_6$haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NRC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$; wherein the $C_1$-$C_6$ alkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^d$ are each optionally substituted with 1, 2, or 3 independently selected $R^f$ substituents;

each $R^e$ is independently selected from the group consisting of H, $C_1$-$C_6$ alkyl, $C_1$-$C_6$ alkoxy, $C_3$-$C_6$ cycloalkyl, $C_3$-$C_6$ cycloalkyl-$C_1$-$C_4$ alkylene-, $C_6$-$C_{10}$ aryl, $C_6$-$C_{10}$ aryl-$C_1$-$C_4$ alkylene-, 5- or 6-membered heteroaryl, (5- or 6-membered heteroaryl)-$C_1$-$C_4$ alkylene-, 4-7-membered heterocycloalkyl, (4-7-membered heterocycloalkyl)-$C_1$-$C_4$ alkylene-, $C_1$-$C_6$ haloalkyl, $C_1$-$C_6$ haloalkoxy, $C_2$-$C_4$ alkenyl, and $C_2$-$C_4$ alkynyl, wherein the $C_1$-$C_6$ alkyl, $C_1$-$C_6$ alkoxy, $C_3$-$C_6$ cycloalkyl, $C_6$-$C_{10}$ aryl, 5 or 6-membered heteroaryl, 4-7-membered heterocycloalkyl, $C_6$-$C_{10}$ aryl-$C_1$-$C_4$ alkylene-, (5- or 6-membered heteroaryl)-$C_1$-$C_4$ alkylene-, (4-7-membered heterocycloalkyl)-$C_1$-$C_4$ alkylene-, $C_2$-$C_4$ alkenyl, and $C_2$-$C_4$ alkynyl of $R^e$ are each optionally substituted with 1, 2, or 3 $R^f$ substituents;

or any two $R^e$ substituents together with the nitrogen atom to which they are attached form a 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo, OH, CN, COOH, $NH_2$, —NH($C_1$-$C_6$ alkyl), —N($C_1$-$C_6$ alkyl)$_2$, $C_1$-$C_6$ alkyl, vinyl, $C_1$-$C_6$ alkoxy, $C_1$-$C_6$ alkylthio, $C_1$-$C_6$haloalkyl, $C_1$-$C_6$haloalkoxy, phenyl, 5-6 membered heteroaryl, 4-6 membered heterocycloalkyl, and $C_3$-$C_6$ cycloalkyl, wherein the $C_1$-$C_6$ alkyl, $C_1$-$C_6$ alkoxy, $C_1$-$C_6$ alkylthio, phenyl, $C_3$-$C_6$ cycloalkyl, 4-6 membered heterocycloalkyl, and 5-6 membered heteroaryl of $R^f$ are each optionally substituted with 1, 2, or 3 substituents selected from halo, OH, CN, —COOH, —$NH_2$, $C_1$-$C_4$ alkyl, $C_1$-$C_4$ alkoxy, $C_1$-$C_4$ haloalkyl, $C_1$-$C_4$ haloalkoxy, phenyl, $C_3$-$C_{10}$ cycloalkyl, 5-6 membered heteroaryl, and 4-6 membered heterocycloalkyl;

each $R^g$ is independently selected from the group consisting of halo, OH, CN, COOH, —COO—$C_1$-$C_4$ alkyl, $NH_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl;

a ring nitrogen atom in Formula (I) is optionally oxidized;

the subscript m is 0, 1 or 2; and the subscript n is 0, 1, 2, 3 or 4.

In some embodiments, a compound of Formula (I) is a compound of Formula (I'). Provided herein is compound of Formula (I'):

(I')

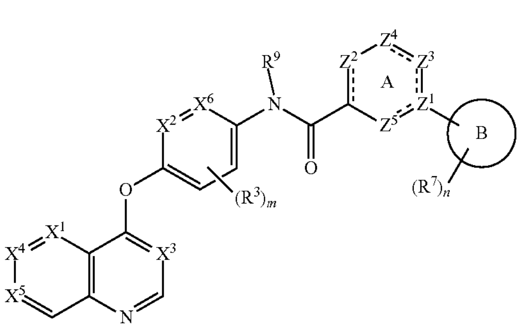

or a pharmaceutically acceptable salt or stereoisomer thereof, wherein:

ring B is 5-membered heteroaryl having 1, 2 or 3 heteroatoms as ring members selected from N, O and S; or 6-membered heteroaryl having 1 or 2 nitrogen atoms as ring members;

$X^1$ is N or $CR^{11}$;

$X^2$ is N, CH or $CR^3$;

$X^3$ is N or CH;

$X^4$ is N or $CR^1$;

$X^5$ is N or $CR^2$;

$X^6$ is N, CH or $CR^3$;

no more than one of $X^1$, $X^4$ and $X^5$ is N;

$Z^1$ is N, C or CH;

$Z^2$ is N, $NR^{13}$, —C(═O)— or $CR^5$;

$Z^3$ is N, $NR^{12}$, $CR^6$, —C(═O)—, —C(═S)—;

$Z^4$ is N, $NR^4$, $CR^{10}$, —C(═O)— or a bond;

$Z^5$ is N, —$COR^8$, —C(═O)— or $CR^{14}$;

one or two of $Z^1$, $Z^2$, $Z^3$ and $Z^4$ are each independently selected from N, $NR^{13}$, $NR^{12}$ and $NR^4$;

no more than two of $Z^2$, $Z^3$, $Z^4$ and $Z^5$ are —C(═O)—;

$\overline{\underline{\ \ }}$ is a single bond or a double bond;

$R^1$ and $R^2$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(═NR^a)R^a$, $NR^aC(O)OR^a$, $NR^aC(O)NR^aR^a$, $C(═NR^a)R^a$, $C(═NOH)R^a$, $C(═NOH)NR^a$, $C(═NCN)NR^aR^a$, $NR^aC(═NCN)NR^aR^a$, $C(═NR^a)NR^aR^a$, $NR^aC(═NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^1$ and $R^2$ are each optionally substituted with 1, 2, 3, 4 or 5 independently selected $R^b$ substituents;

each $R^3$ is independently selected from halo, OH, CN, —COOH, —CONH($C_{1-6}$ alkyl), —$SO_2$($C_{1-6}$ alkyl), —$SO_2$NH($C_{1-6}$ alkyl), $C_1$-$C_6$ alkyl, $C_1$-$C_6$ alkoxy, $C_1$-$C_6$ haloalkoxy, $NH_2$, —NH($C_1$-$C_6$ alkyl), —N($C_1$-$C_6$ alkyl)$_2$, and $C_3$-$C_6$ cycloalkyl, wherein the $C_1$-$C_6$ alkyl, $C_1$-$C_6$ alkoxy, —NH($C_1$-$C_6$alkyl), —N($C_1$-$C_6$ alkyl)$_2$, and $C_3$-$C_6$ cycloalkyl of $R^3$ are each optionally substituted with 1, 2, or 3 independently selected $R^g$ substituents;

$R^4$, $R^{12}$ and $R^{13}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $N═C(NR^aR^a)_2$, $NR^aC(═NR^a)R^a$, $NR^aC(O)OR^a$, $NR^aC(O)NR^aR^a$, $C(═NR^a)R^a$, $C(═NOH)R^a$, $C(═NOH)NR^a$, $C(═NCN)NR^aR^a$, $NR^aC(═NCN)NR^aR^a$, $C(═NR^a)NR^aR^a$, $NR^aC(═NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^4$, $R^{12}$ and $R^{13}$ are each optionally substituted with 1, 2, 3, 4 or 5 independently selected $R^b$ substituents;

$R^5$, $R^6$ and $R^{10}$ are each independently H, halo, $C_{1-6}$ alkyl, $C_{2-6}$ alkenyl, $C_{1-6}$ alkoxy, $C_{1-6}$ alkylthio, CN, $C_{1-4}$ haloalkyl, $C_{1-4}$ haloalkoxy, OH, $C_{1-4}$alkyl-C(O)—, $C_{1-4}$alkyl-OC(O)—, —CONH($C_{1-4}$ alkyl), $NH_2$, —NH$C_{1-4}$alkyl, or —N($C_{1-4}$ alkyl)$_2$, wherein the $C_{1-6}$ alkyl, $C_{2-6}$ alkenyl, $C_{1-6}$ alkoxy, $C_{1-6}$ alkylthio, $C_{1-6}$ alkyl-C(O)— and $C_{1-4}$ alkyl of —NH($C_{1-4}$alkyl) or —N($C_{1-4}$ alkyl)$_2$ of $R^5$, $R^6$ and $R^{10}$ are each optionally substituted with 1 or 2 independently selected $R^g$ substituents;

each $R^7$ is independently selected from halo, OH, $COOR^a$, $CONR^aR^a$, CN, $NH_2$, —NH($C_1$-$C_6$ alkyl), —N($C_1$-$C_6$ alkyl)$_2$, $C_1$-$C_6$ alkyl, $C_{2-6}$ alkenyl, $C_1$-$C_6$ alkoxy, $C_1$-$C_6$ haloalkyl, $C_1$-$C_6$ haloalkoxy, $CONR^aR^a$, $NR^aCOR^a$, $NR^aCONR^aR^a$, $SO_2R^a$, $NR^aS(O)_2R^a$, $NR^aS(O)_2NR^aR^a$, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene-; wherein the $C_1$-$C_6$ alkyl, $C_{1-6}$ alkenyl, $C_1$-$C_6$ alkoxy, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene- of $R^7$ are each optionally substituted with 1, 2, or 3 independently selected $R^f$ substituents;

$R^8$ is H, $C_{1-6}$ alkyl optionally substituted with 1 or 2 $R^g$ substituents or a hydroxy protecting group;

$R^g$ is H or $C_{1-6}$ alkyl optionally substituted with 1, 2, or 3 independently selected $R^9$ substituents;

$R^{11}$ is selected from H, $C_{1-6}$ alkyl, $C_{1-6}$ haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, OR, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$; wherein the $C_1$-$C_6$ alkyl, $C_1$-$C_6$haloalkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$alkylene- of $R^{11}$ are each optionally substituted with 1, 2, or 3 independently selected $R^f$ substituents;

$R^{14}$ is H, halo, CN, or $C_{1-6}$ alkyl optionally substituted with 1 or 2 $R^g$ substituents;

or $R^{13}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^4$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{10}$ and $R^5$ taken together with the atoms to which they are attached form fused $C_{3-7}$ cycloalkyl, 4- to 6-membered fused heterocycloalkyl, fused 5- or 6-membered heteroaryl or fused phenyl, wherein the fused $C_{3-7}$ cycloalkyl, 4- to 6-membered fused heterocycloalkyl, 5- or 6-membered heteroaryl, or fused phenyl is each optionally substituted with 1 or 2 independently selected $R^g$ substituents and wherein one or two ring carbon atoms of the fused $C_{3-7}$ cycloalkyl or fused heterocycloalkyl are optionally replaced by a carbonyl group;

or when $Z^4$ is a bond, $R^{13}$ and $R^6$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{12}$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^6$ and $R^5$ taken together with the atoms to which they are attached form fused $C_{3-7}$ cycloalkyl, 4- to 6-membered fused heterocycloalkyl, 5- to 6-membered fused heteroaryl, or fused phenyl, wherein the fused $C_{3-7}$ cycloalkyl, 4- to 6-membered fused heterocycloalkyl, 5- to 6-membered fused heteroaryl, and fused phenyl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

or $R^{12}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^4$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^{10}$ taken together with the atoms to which they are attached form fused $C_{3-7}$ cycloalkyl, 4- to 6-membered fused heterocycloalkyl, 5- to 6-membered fused heteroaryl, or fused heteroaryl, wherein the fused $C_{3-7}$ cycloalkyl, 4- to 6-membered fused heterocycloalkyl, 5- to 6-membered fused heteroaryl, and fused heteroaryl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

each $R^a$ is independently selected from the group consisting of H, CN, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene-; wherein the $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$alkylene- of $R^a$ are each optionally substituted with 1, 2, 3, 4, or 5 independently selected $R^d$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^b$ is independently selected from the group consisting of halo, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $Si(R^c)_3$, $P(O)R^cR^c$, $P(O)(OR^c)(OR^c)$, $B(OH)_2$, $B(OR^c)_2$, and $S(O)_2NR^cR^c$; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^b$ are each further optionally substituted with 1, 2, or 3 independently selected $R^d$ substituents;

each $R^c$ is independently selected from the group consisting of H, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene-; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^c$ are each optionally substituted with 1, 2, 3, 4, or 5 independently selected $R^f$ substituents; or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^d$ is independently selected from the group consisting of $C_1$-$C_6$ alkyl, $C_1$-$C_6$haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$; wherein the $C_1$-$C_6$ alkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^d$ are each optionally substituted with 1, 2, or 3 independently selected $R^f$ substituents;

each $R^e$ is independently selected from the group consisting of H, $C_1$-$C_6$ alkyl, $C_1$-$C_6$ alkoxy, $C_3$-$C_6$ cycloalkyl, $C_3$-$C_6$ cycloalkyl-$C_1$-$C_4$ alkylene-, $C_6$-$C_{10}$ aryl, $C_6$-$C_{10}$ aryl-$C_1$-$C_4$ alkylene-, 5- or 6-membered heteroaryl, (5- or 6-membered heteroaryl)-$C_1$-$C_4$ alkylene-, 4-7-membered heterocycloalkyl, (4-7-membered heterocycloalkyl)-$C_1$-$C_4$ alkylene-, $C_1$-$C_6$ haloalkyl, $C_1$-$C_6$ haloalkoxy, $C_2$-$C_4$ alkenyl, and $C_2$-$C_4$ alkynyl, wherein the $C_1$-$C_6$ alkyl, $C_1$-$C_6$ alkoxy, $C_3$-$C_6$ cycloalkyl, $C_6$-$C_{10}$ aryl, 5 or 6-membered heteroaryl, 4-7-membered heterocycloalkyl, $C_6$-$C_{10}$ aryl-$C_1$-$C_4$ alkylene-, (5- or 6-membered heteroaryl)-$C_1$-$C_4$ alkylene-, (4-7-membered heterocycloalkyl)-$C_1$-$C_4$ alkylene-, $C_2$-$C_4$ alkenyl, and $C_2$-$C_4$ alkynyl of $R^e$ are each optionally substituted with 1, 2, or 3 $R^f$ substituents;

or any two $R^e$ substituents together with the nitrogen atom to which they are attached form a 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo, OH, CN, COOH, $NH_2$, $-NH(C_1$-$C_6$ alkyl), $-N(C_1$-$C_6$ alkyl$)_2$, $C_1$-$C_6$ alkyl, vinyl, $C_1$-$C_6$ alkoxy, $C_1$-$C_6$ alkylthio, $C_1$-$C_6$haloalkyl, $C_1$-$C_6$haloalkoxy, phenyl, 5-6 membered heteroaryl, 4-6 membered heterocycloalkyl, and $C_3$-$C_6$ cycloalkyl, wherein the $C_1$-$C_6$ alkyl, $C_1$-$C_6$ alkoxy, $C_1$-$C_6$ alkylthio, phenyl, $C_3$-$C_6$ cycloalkyl, 4-6 membered heterocycloalkyl, and 5-6 membered heteroaryl of $R^f$ are each optionally substituted with 1, 2, or 3 substituents selected from halo, OH, CN, —COOH, $-NH_2$, $C_1$-$C_4$ alkyl, $C_1$-$C_4$ alkoxy, $C_1$-$C_4$ haloalkyl, $C_1$-$C_4$ haloalkoxy, phenyl, $C_3$-$C_{10}$ cycloalkyl, 5-6 membered heteroaryl, and 4-6 membered heterocycloalkyl;

each $R^g$ is independently selected from the group consisting of halo, OH, CN, COOH, $-COO-C_1$-$C_4$ alkyl, $NH_2$, $-NH(C_1$-$C_6$ alkyl), $-N(C_1$-$C_6$ alkyl$)_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl;

a ring nitrogen atom in Formula (I) is optionally oxidized;

the subscript m is 0, 1 or 2; and the subscript n is 0, 1, 2, 3 or 4.

In some embodiments, a compound of Formula (I) is a compound of Formula (I"). Provided herein is compound of Formula (I"):

(I")

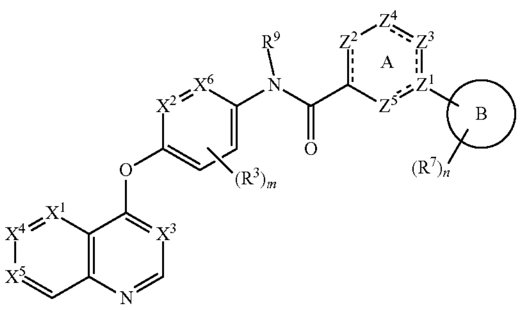

or a pharmaceutically acceptable salt or stereoisomer thereof, wherein:

ring B is 5- membered heteroaryl having 1, 2 or 3 heteroatoms as ring members selected from N, O and S; or 6-membered heteroaryl having 1 or 2 nitrogen atoms as ring members;

X is N or $CR^{11}$;

$X^2$ is N, CH or $CR^3$;

$X^3$ is N or CH;

$X^4$ is N or $CR^1$;

$X^5$ is N or $CR^2$;

$X^6$ is N, CH or $CR^3$;

no more than one of $X^1$, $X^4$ and $X^5$ is N;

$Z^1$ is N, C or CH;

$Z^2$ is N, $NR^{13}$, —C(═O)— or $CR^5$;

$Z^3$ is N, $NR^{12}$, $CR^6$, —C(═O)—, —C(═S)—;

$Z^4$ is N, $NR^4$, $CR^{10}$, —C(═O)— or a bond;

$Z^5$ is N, $—COR^B$, —C(═O)— or $CR^{14}$;

one or two of $Z^1$, $Z^2$, $Z^3$ and $Z^4$ are each independently selected from N, $NR^{13}$, $NR^{12}$ and $NR^4$;

no more than two of $Z^2$, $Z^3$, $Z^4$ and $Z^5$ are —C(═O)—;

⎓ is a single bond or a double bond;

$R^1$ and $R^2$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(═NR^a)R^a$, $NR^aC(O)OR^a$, $NR^aC(O)NR^aR^a$, $C(═NR^a)R^a$, $C(═NOH)R^a$, $C(═NOH)NR^a$, $C(═NCN)NR^aR^a$, $NR^aC(═NCN)NR^aR^a$, $C(═NR^a)NR^aR^a$, $NR^aC(═NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^1$ and $R^2$ are each optionally substituted with 1, 2, 3, 4 or 5 independently selected $R^b$ substituents;

each $R^3$ is independently selected from halo, OH, CN, —COOH, —CONH($C_{1-6}$ alkyl), $—SO_2(C_{1-6}$ alkyl), $—SO_2NH(C_{1-6}$ alkyl), $C_1$-$C_6$ alkyl, $C_1$-$C_6$ alkoxy, $C_1$-$C_6$ haloalkoxy, $NH_2$, —NH($C_1$-$C_6$ alkyl), $—N(C_1$-$C_6$ alkyl$)_2$, and $C_3$-$C_6$ cycloalkyl, wherein the $C_1$-$C_6$ alkyl, $C_1$-$C_6$ alkoxy, —NH($C_1$-$C_6$alkyl), $—N(C_1$-$C_6$ alkyl$)_2$, and $C_3$-$C_6$ cycloalkyl of $R^3$ are each optionally substituted with 1, 2, or 3 independently selected $R^g$ substituents;

$R^4$, $R^{12}$ and $R^{13}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $N═C(NR^aR^a)_2$, $NR^aC(═NR^a)R^a$, $NR^aC(O)OR^a$, $NR^aC(O)NR^aR^a$, $C(═NR^a)R^a$, $C(═NOH)R^a$, $C(═NOH)NR^a$, $C(═NCN)NR^aR^a$, $NR^aC(═NCN)NR^aR^a$, $C(═NR^a)NR^aR^a$, $NR^aC(═NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^4$, $R^{12}$ and $R^{13}$ are each optionally substituted with 1, 2, 3, 4 or 5 independently selected $R^b$ substituents;

$R^5$, $R^6$ and $R^{10}$ are each independently H, halo, $C_{1-6}$ alkyl, $C_{2-6}$ alkenyl, $C_{1-6}$ alkoxy, $C_{1-6}$ alkylthio, CN, $C_{1-4}$ haloalkyl, $C_{1-4}$ haloalkoxy, OH, $C_{1-4}$alkyl-C(O)—, $C_{1-4}$alkyl-OC(O)—, —CONH($C_{1-4}$ alkyl), $NH_2$, $—NHC_{1-4}$alkyl, or $—N(C_{1-4}$ alkyl$)_2$, wherein the $C_{1-6}$ alkyl, $C_{2-6}$ alkenyl, $C_{1-6}$ alkoxy, $C_{1-6}$ alkylthio, $C_{1-6}$ alkyl-C(O)— and $C_{1-4}$ alkyl of —NH($C_{1-4}$alkyl) or $—N(C_{1-4}$ alkyl$)_2$ of $R^5$, $R^6$ and $R^{10}$ are each optionally substituted with 1 or 2 independently selected $R^g$ substituents;

each $R^7$ is independently selected from halo, OH, $COOR^a$, $COR^a$, $CONR^aR^a$, CN, $NH_2$, —NH($C_1$-$C_6$ alkyl), $—N(C_1$-$C_6$ alkyl$)_2$, $C_1$-$C_6$ alkyl, $C_{2-6}$ alkenyl, $C_1$-$C_6$ alkoxy, $C_1$-$C_6$ haloalkyl, $C_1$-$C_6$ haloalkoxy, $CONR^aR^a$, $NR^aCOR^a$, $NR^aCONR^aR^a$, $SO_2R^a$, $NR^aS(O)_2R^a$, $NR^aS(O)_2NR^aR^a$, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene-; wherein the $C_1$-$C_6$ alkyl, $C_{1-6}$ alkenyl, $C_1$-$C_6$ alkoxy, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene- of $R^7$ are each optionally substituted with 1, 2, or 3 independently selected $R^f$ substituents;

$R^8$ is H, $C_{1-6}$ alkyl optionally substituted with 1 or 2 $R^g$ substituents or a hydroxy protecting group;

$R^9$ is H or $C_{1-6}$ alkyl optionally substituted with 1, 2, or 3 independently selected $R^g$ substituents;

$R^{11}$ is selected from H, $C_{1-6}$ alkyl, $C_{1-6}$ haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$; wherein the $C_1$-$C_6$ alkyl, $C_1$-$C_6$haloalkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$alkylene- of $R^e$ are each optionally substituted with 1, 2, or 3 independently selected $R^f$ substituents;

$R^{14}$ is H, halo, CN, or $C_{1-6}$ alkyl optionally substituted with 1 or 2 $R^g$ substituents;

or $R^{13}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^4$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{10}$ and $R^5$ taken together with the atoms to which they are attached form fused $C_{3-7}$ cycloalkyl, 4- to 6-membered fused heterocycloalkyl, fused 5- or 6-membered heteroaryl or fused phenyl, wherein the fused $C_{3-7}$ cycloalkyl, 4- to 6-membered fused heterocycloalkyl, 5- or 6-membered heteroaryl, or fused phenyl is each optionally substituted with 1 or 2 independently selected $R^g$ substituents and wherein one or two ring carbon atoms of the fused $C_{3-7}$ cycloalkyl or fused heterocycloalkyl are optionally replaced by a carbonyl group;

or when $Z^4$ is a bond, $R^{13}$ and $R^6$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{12}$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^6$ and $R^5$ taken together with the atoms to which they are attached form fused $C_{3-7}$ cycloalkyl, 4- to 6-membered fused heterocycloalkyl, 5- to 6-membered fused heteroaryl, or fused phenyl, wherein the fused $C_{3-7}$ cycloalkyl, 4- to 6-membered fused heterocycloalkyl, 5- to 6-membered fused heteroaryl, and fused phenyl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

or $R^{12}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^4$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^{10}$ taken together with the atoms to which they are attached form fused $C_{3-7}$ cycloalkyl, 4- to 6-membered fused heterocycloalkyl, 5- to 6-membered fused heteroaryl, or fused heteroaryl, wherein the fused $C_{3-7}$ cycloalkyl, 4- to 6-membered fused heterocycloalkyl, 5- to 6-membered fused heteroaryl, and fused heteroaryl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

each $R^a$ is independently selected from the group consisting of H, CN, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene-; wherein the $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$alkylene- of $R^a$ are each optionally substituted with 1, 2, 3, 4, or 5 independently selected $R^d$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^b$ is independently selected from the group consisting of halo, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR$-

$^{c}R^{c}$, C(=NOH)$R^{c}$, C(=NOH)N$R^{c}$, C(=NCN)N$R^{c}R^{c}$, N$R^{c}$C(=NCN)N$R^{c}R^{c}$, C(=N$R^{c}$)N$R^{c}R^{c}$, N$R^{c}$C(=N$R^{c}$)N$R^{c}R^{c}$, NH$R^{c}$, N$R^{c}R^{c}$, N$R^{c}$C(O)$R^{c}$, N$R^{c}$C(=N$R^{c}$)$R^{c}$, N$R^{c}$C(O)O$R^{c}$, N$R^{c}$C(O)N$R^{c}R^{c}$, N$R^{c}$S(O)$R^{c}$, N$R^{c}$S(O)$_2R^{c}$, N$R^{c}$S(O)$_2$N$R^{c}R^{c}$, S(O)$R^{c}$, S(O)N$R^{c}R^{c}$, S(O)$_2R^{c}$, S(O)$_2$N$R^{c}$C(O)$R^{c}$, Si($R^{c}$)$_3$, P(O)$R^{c}R^{c}$, P(O)(O$R^{c}$)(O$R^{c}$), B(OH)$_2$, B(O$R^{c}$)$_2$, and S(O)$_2$N$R^{c}R^{c}$; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^b$ are each further optionally substituted with 1, 2, or 3 independently selected $R^d$ substituents;

each $R^c$ is independently selected from the group consisting of H, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene-; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^c$ are each optionally substituted with 1, 2, 3, 4, or 5 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^d$ is independently selected from the group consisting of $C_1$-$C_6$ alkyl, $C_1$-$C_6$haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, NHO$R^e$, O$R^e$, S$R^e$, C(O)$R^e$, C(O)N$R^eR^e$, C(O)O$R^e$, OC(O)$R^e$, OC(O)N$R^eR^e$, NH$R^e$, N$R^eR^e$, N$R^e$C(O)$R^e$, N$R^e$C(O)N$R^eR^e$, N$R^e$C(O)O$R^e$, C(=N$R^e$)N$R^eR^e$, N$R^e$C(=N$R^e$)N$R^eR^e$, N$R^e$C(=NOH)NR$R^e$, N$R^e$C(=NCN)NR$R^e$, S(O)$R^e$, S(O)N$R^eR^e$, S(O)$_2R^e$, N$R^e$S(O)$_2R^e$, N$R^e$S(O)$_2$N$R^eR^e$, and S(O)$_2$N$R^eR^e$; wherein the $C_1$-$C_6$ alkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^d$ are each optionally substituted with 1, 2, or 3 independently selected $R^f$ substituents;

each $R^e$ is independently selected from the group consisting of H, $C_1$-$C_6$ alkyl, $C_1$-$C_6$ alkoxy, $C_3$-$C_6$ cycloalkyl, $C_3$-$C_6$ cycloalkyl-$C_1$-$C_4$ alkylene-, $C_6$-$C_{10}$ aryl, $C_6$-$C_{10}$ aryl-$C_1$-$C_4$ alkylene-, 5- or 6-membered heteroaryl, (5- or 6-membered heteroaryl)-$C_1$-$C_4$ alkylene-, 4-7-membered heterocycloalkyl, (4-7-membered heterocycloalkyl)-$C_1$-$C_4$ alkylene-, $C_1$-$C_6$ haloalkyl, $C_1$-$C_6$ haloalkoxy, $C_2$-$C_4$ alkenyl, and $C_2$-$C_4$ alkynyl, wherein the $C_1$-$C_6$ alkyl, $C_1$-$C_6$ alkoxy, $C_3$-$C_6$ cycloalkyl, $C_6$-$C_{10}$ aryl, 5 or 6-membered heteroaryl, 4-7-membered heterocycloalkyl, $C_6$-$C_{10}$ aryl-$C_1$-$C_4$ alkylene-, (5- or 6-membered heteroaryl)-$C_1$-$C_4$ alkylene-, (4-7-membered heterocycloalkyl)-$C_1$-$C_4$ alkylene-, $C_2$-$C_4$ alkenyl, and $C_2$-$C_4$ alkynyl of $R^e$ are each optionally substituted with 1, 2, or 3 $R^f$ substituents;

or any two $R^e$ substituents together with the nitrogen atom to which they are attached form a 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo, OH, CN, COOH, $NH_2$, —NH($C_1$-$C_6$ alkyl), —N($C_1$-$C_6$ alkyl)$_2$, $C_1$-$C_6$ alkyl, vinyl, $C_1$-$C_6$ alkoxy, $C_1$-$C_6$ alkylthio, $C_1$-$C_6$haloalkyl, $C_1$-$C_6$ haloalkoxy, phenyl, 5-6 membered heteroaryl, 4-6 membered heterocycloalkyl, and $C_3$-$C_6$ cycloalkyl, wherein the $C_1$-$C_6$ alkyl, $C_1$-$C_6$ alkoxy, $C_1$-$C_6$ alkylthio, phenyl, $C_3$-$C_6$ cycloalkyl, 4-6 membered heterocycloalkyl, and 5-6 membered heteroaryl of $R^f$ are each optionally substituted with 1, 2, or 3 substituents selected from halo, OH, CN, —COOH, —$NH_2$, $C_1$-$C_4$ alkyl, $C_1$-$C_4$ alkoxy, $C_1$-$C_4$ haloalkyl, $C_1$-$C_4$ haloalkoxy, phenyl, $C_3$-$C_{10}$ cycloalkyl, 5-6 membered heteroaryl, and 4-6 membered heterocycloalkyl; each $R^g$ is independently selected from the group consisting of halo, OH, CN, COOH, —COO—$C_1$-$C_4$ alkyl, $NH_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl;

a ring nitrogen atom in Formula (I'') is optionally oxidized;

the subscript m is 0, 1 or 2; and the subscript n is 0, 1, 2, 3 or 4.

In some embodiments, a compound of Formula (I) is a compound of Formula (I'''). Provided herein is a compound of Formula (I'''):

(I''')

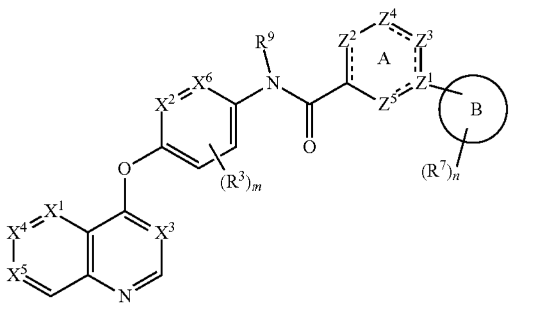

or a pharmaceutically acceptable salt or stereoisomer thereof, wherein:

ring B is 6-membered heteroaryl having 1 or 2 nitrogen atoms as ring members;

$X^1$ is N or C$R^3$;

$X^2$ is N, CH or C$R^3$;

$X^3$ is N or CH;

$X^4$ is N or C$R^1$;

$X^5$ is N or C$R^2$;

$X^6$ is N, CH or C$R^3$;

no more than one of $X^1$, $X^4$ and $X^5$ is N;

$Z^1$ is N, C or CH;

$Z^2$ is N, $NR^{13}$, —C(═O)— or $CR^5$;

$Z^3$ is N, $NR^{12}$, $CR^6$, —C(═O)—, —C(═S)—;

$Z^4$ is N, $NR^4$, $CR^{10}$, —C(═O)— or a bond;

$Z^5$ is $COR^8$, —C(═O)— or $CR^{14}$;

one or two of $Z^1$, $Z^2$, $Z^3$ and $Z^4$ are each independently selected from N, $NR^{13}$, $NR^{12}$ and $NR^4$; no more than two of $Z^2$, $Z^3$, $Z^4$ and $Z^5$ are —C(═O)—;

⎓ s a single bond or a double bond;

$R^1$ and $R^2$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{14}$ alkylene- of $R^1$ and $R^2$ are each optionally substituted with 1, 2, 3, 4 or 5 independently selected $R^b$ substituents;

each $R^3$ is independently selected from halo, OH, CN, —COOH, —CONH($C_{1-6}$ alkyl), —$SO_2$($C_{1-6}$ alkyl), —$SO_2$NH($C_{1-6}$ alkyl), $C_1$-$C_6$ alkyl, $C_1$-$C_6$ alkoxy, $C_1$-$C_6$ haloalkoxy, $NH_2$, —NH($C_1$-$C_6$ alkyl), —N($C_1$-$C_6$ alkyl)$_2$, and $C_3$-$C_6$ cycloalkyl, wherein the $C_1$-$C_6$ alkyl, $C_1$-$C_6$ alkoxy, —NH($C_1$-$C_6$alkyl), —N($C_1$-$C_6$ alkyl)$_2$, and $C_3$-$C_6$ cycloalkyl of $R^3$ are each optionally substituted with 1, 2, or 3 independently selected $R^g$ substituents;

$R^4$, $R^{12}$ and $R^{13}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{14}$ alkylene-, (4-14 membered heterocycloalkyl)-$C_{14}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $N{=}C(NR^aR^a)_2$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{14}$ alkylene- and (4-14 membered heterocycloalkyl)-$C_{14}$ alkylene- of $R^4$, $R^{12}$ and $R^{13}$ are each optionally substituted with 1, 2, 3, 4 or 5 independently selected $R^b$ substituents;

$R^5$, $R^6$ and $R^{10}$ are each independently H, halo, $C_{1-6}$ alkyl, $C_{2-6}$ alkenyl, $C_{1-6}$ alkoxy, $C_{1-6}$ alkylthio, CN, $C_{1-4}$ haloalkyl, $C_{1-4}$ haloalkoxy, OH, $C_{1-4}$alkyl-C(O)—, $C_{1-4}$alkyl-OC(O)—, —CONH($C_{1-4}$ alkyl), $NH_2$, —NH($C_{1-4}$alkyl), or —N($C_{1-4}$ alkyl)$_2$, wherein the $C_{1-6}$ alkyl, $C_{2-6}$ alkenyl, $C_{1-6}$ alkoxy, $C_{1-6}$ alkylthio, $C_{1-6}$ alkyl-C(O)— and $C_{1-4}$ alkyl of —NH($C_{1-4}$alkyl) or —N($C_{1-4}$ alkyl)$_2$ of $R^5$, $R^6$ and $R^{10}$ are each optionally substituted with 1 or 2 independently selected $R^g$ substituents;

each $R^7$ is independently selected from halo, OH, $COOR^a$, $CONR^aR^a$, CN, $NH_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ haloalkyl, $C_1$-$C_6$ haloalkoxy, $CONR^aR^a$, $NR^aCOR^a$, $NR^aCONR^aR^a$, $SO_2R^a$, $NR^aS(O)_2R^a$, $NR^aS(O)_2NR^aR^a$, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene-; wherein the $C_1$-$C_6$ alkyl, $C_{1-6}$ alkoxy, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene- of $R^7$ are each optionally substituted with 1, 2, or 3 independently selected $R^f$ substituents;

$R^8$ is H, $C_{1-6}$ alkyl optionally substituted with 1 or 2 $R^g$ substituents or a hydroxy protecting group;

$R^9$ is H or $C_{1-6}$ alkyl optionally substituted with 1, 2, or 3 independently selected $R^9$ substituents;

$R^{11}$ is selected from H, $C_{1-6}$ alkyl, $C_{1-6}$ haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$; wherein the $C_1$-$C_6$ alkyl, $C_1$-$C_6$haloalkyl, $C_6$-$C_{10}$ aryl, 5-10 membered heteroaryl, $C_3$-$C_{10}$ cycloalkyl, 4-10 membered heterocycloalkyl, $C_6$-$C_{10}$aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$alkylene- of $R^e$ are each optionally substituted with 1, 2, or 3 independently selected $R^f$ substituents;

$R^{14}$ is H, halo, CN, or $C_{1-6}$ alkyl optionally substituted with 1 or 2 $R^g$ substituents; or $R^{13}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^4$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{10}$ and $R^5$ taken together with the atoms to which they are attached form fused $C_{3-7}$ cycloalkyl, 4- to 6-membered fused heterocycloalkyl, fused 5- or 6-membered heteroaryl or fused phenyl, wherein the fused $C_{3-7}$ cycloalkyl, 4- to 6-membered fused heterocycloalkyl, 5- or 6-membered heteroaryl, or fused phenyl is each optionally substituted with 1 or 2 independently selected $R^g$ substituents and wherein one or two ring carbon atoms of the fused $C_{3-7}$ cycloalkyl or fused heterocycloalkyl are optionally replaced by a carbonyl group;

or when $Z^4$ is a bond, $R^{13}$ and $R^6$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{12}$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^6$ and $R^5$ taken together with the atoms to which they are attached form fused $C_{3-7}$ cycloalkyl, 4- to 6-membered fused heterocycloalkyl, 5- to 6-membered fused heteroaryl, or fused phenyl, wherein the fused $C_{3-7}$ cycloalkyl, 4- to 6-membered fused heterocycloalkyl, 5- to 6-membered fused heteroaryl, and fused phenyl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

or $R^{12}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^4$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^{10}$ taken together with the atoms to which they are attached form fused $C_{3-7}$ cycloalkyl, 4- to 6-membered fused heterocycloalkyl, 5- to 6-membered fused heteroaryl, or fused heteroaryl, wherein the fused $C_{3-7}$ cycloalkyl, 4- to 6-membered fused heterocycloalkyl, 5- to 6-membered fused heteroaryl, and fused heteroaryl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

each $R^a$ is independently selected from the group consisting of H, CN, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene-; wherein the $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$alkylene- of $R^a$ are each optionally substituted with 1, 2, 3, 4, or 5 independently selected $R^d$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^b$ is independently selected from the group consisting of halo, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $Si(R^c)_3$, $P(O)R^cR^c$, $P(O)(OR^c)(OR^c)$, $B(OH)_2$, $B(OR^c)_2$, and $S(O)_2NR^cR^c$; wherein the $C_1$-$C_6$ alkyl, $C_1$-$C_6$ haloalkyl, $C_1$-$C_6$ haloalkoxy, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^b$ are each further optionally substituted with 1, 2, or 3 independently selected $R^d$ substituents;

each $R^c$ is independently selected from the group consisting of H, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene-; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^c$ are each optionally substituted with 1, 2, 3, 4, or 5 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^d$ is independently selected from the group consisting of $C_1$-$C_6$ alkyl, $C_1$-$C_6$haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$; wherein the $C_1$-$C_6$ alkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^d$ are each optionally substituted with 1, 2, or 3 independently selected $R^f$ substituents;

each $R^e$ is independently selected from the group consisting of H, $C_1$-$C_6$ alkyl, $C_1$-$C_6$ alkoxy, $C_3$-$C_6$ cycloalkyl, $C_3$-$C_6$ cycloalkyl-$C_1$-$C_4$ alkylene-, $C_6$-$C_{10}$ aryl, $C_6$-$C_{10}$ aryl-$C_1$-$C_4$ alkylene-, 5- or 6-membered heteroaryl, (5- or 6-membered heteroaryl)-$C_1$-$C_4$ alkylene-, 4-7-membered heterocycloalkyl, (4-7-membered heterocycloalkyl)-$C_1$-$C_4$ alkylene-, $C_1$-$C_6$ haloalkyl, $C_1$-$C_6$ haloalkoxy, $C_2$-$C_4$ alkenyl, and $C_2$-$C_4$ alkynyl, wherein the $C_1$-$C_6$ alkyl, $C_1$-$C_6$ alkoxy, $C_3$-$C_6$ cycloalkyl, $C_6$-$C_{10}$ aryl, 5 or 6-membered heteroaryl, 4-7-membered heterocycloalkyl, $C_6$-$C_{10}$ aryl-$C_1$-$C_4$ alkylene-, (5- or 6-membered heteroaryl)-$C_1$-$C_4$ alkylene-, (4-7-membered heterocycloalkyl)-$C_1$-$C_4$ alkylene-, $C_2$-$C_4$ alkenyl, and $C_2$-$C_4$ alkynyl of $R^e$ are each optionally substituted with 1, 2, or 3 $R^f$ substituents;

or any two $R^f$ substituents together with the nitrogen atom to which they are attached form a 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo, OH, CN, COOH, $NH_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl, wherein the $C_1$-$C_6$ alkyl, $C_1$-$C_6$ alkoxy, $C_1$-$C_6$ alkylthio, phenyl, $C_3$-$C_6$ cycloalkyl, 4-6 membered heterocycloalkyl, and 5-6 membered heteroaryl of $R^f$ are each optionally substituted with 1, 2, or 3 substituents selected from halo, OH, CN, —COOH, —$NH_2$, $C_1$-$C_4$ alkyl, $C_1$-$C_4$ alkoxy, $C_1$-$C_4$ haloalkyl, $C_1$-$C_4$ haloalkoxy, phenyl, $C_3$-$C_{10}$ cycloalkyl, 5-6 membered heteroaryl, and 4-6 membered heterocycloalkyl; each $R^g$ is independently selected from the group consisting of halo, OH, CN, COOH, —COO—$C_1$-$C_4$ alkyl, $NH_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl;

a ring nitrogen atom in Formula (I''') is optionally oxidized;

the subscript m is 0, 1 or 2; and the subscript n is 0, 1, 2, 3 or 4.

Some embodiments provide for a compound of Formula (I), or a pharmaceutically acceptable salt or stereoisomer thereof, wherein

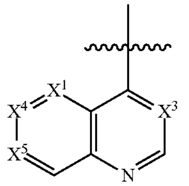

is

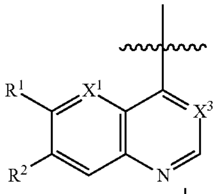

,

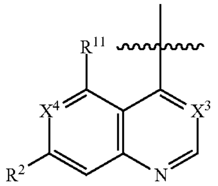

or

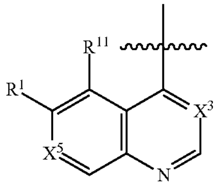

and the wavy line indicates the point of attachment to the rest of molecule.

Some embodiments provide for a compound of Formula (I), or a pharmaceutically acceptable salt or stereoisomer thereof, wherein

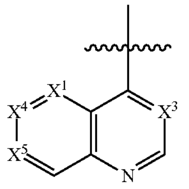

is

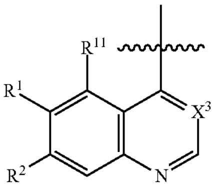

,

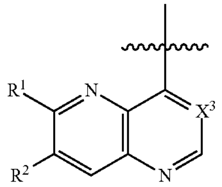

,

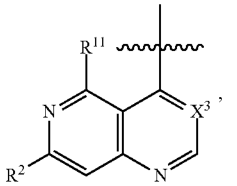

, or

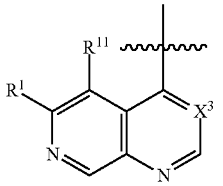

and the wavy line indicates the point of attachment to the rest of molecule.

Some embodiments provide for a compound of Formula (I), or a pharmaceutically acceptable salt or stereoisomer thereof, wherein ring B is 2-thienyl, 3-thienyl, 2-furyl, 3-furyl, 1H-pyrazol-3-yl, 1H-pyrazol-4-yl, 1H-pyrazol-5-yl or pyrazol-1-yl.

Some embodiments provide for a compound of Formula (I), or a pharmaceutically acceptable salt or stereoisomer thereof, wherein ring B is 2-pyridyl, 3-pyridyl, 4-pyridyl, or 3-pyridazinyl.

Some embodiments provide for a compound of Formula (I), or a pharmaceutically acceptable salt or stereoisomer thereof, wherein:

ring A is

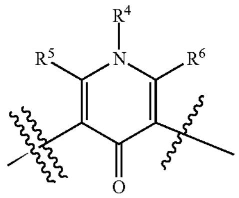
,
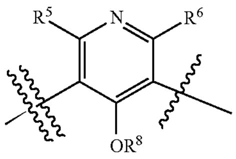
,
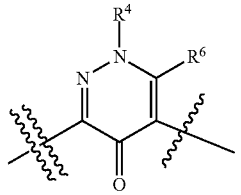
,
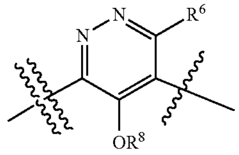
,
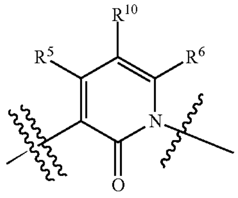
,
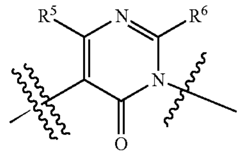
,
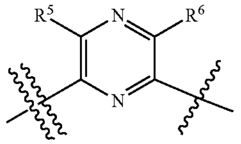
, or
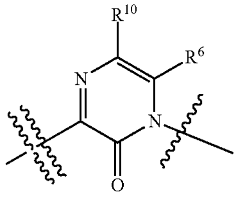
, wherein the single wavy line indicates the point of attachment to the ring B and the double wavy line indicates the point of attachment to the rest of the molecule.

In some embodiments, a compound of Formula (I) is a compound having the structure of formula (Ia):

(Ia)

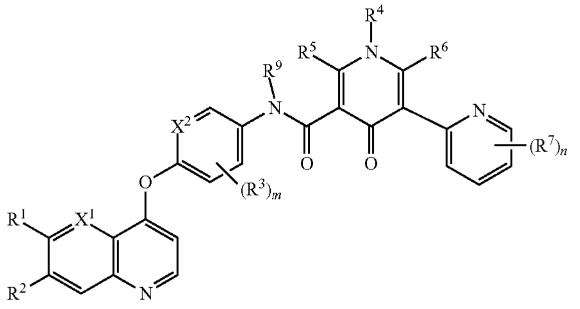

or a pharmaceutically acceptable salt or stereoisomer thereof.

In some embodiments, a compound of Formula (I) is a compound having the structure of formula (Ia-1):

(Ia-1)

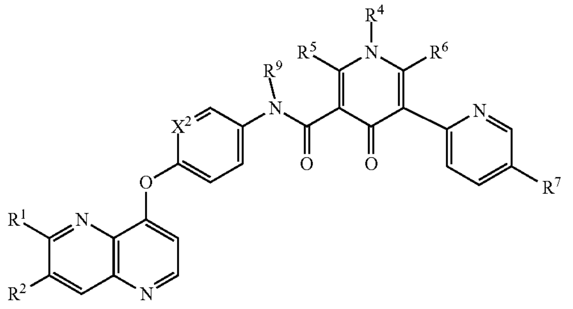

or a pharmaceutically acceptable salt or stereoisomer thereof.

In some embodiments, a compound of Formula (I) is a compound having the structure of formula (Ia-2):

(Ia-2)

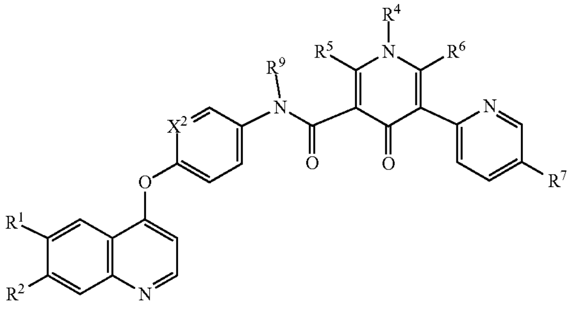

or a pharmaceutically acceptable salt or stereoisomer thereof.

In some embodiments, a compound of Formula (I) is a compound having the structure of formula (Ib):

(Ib)

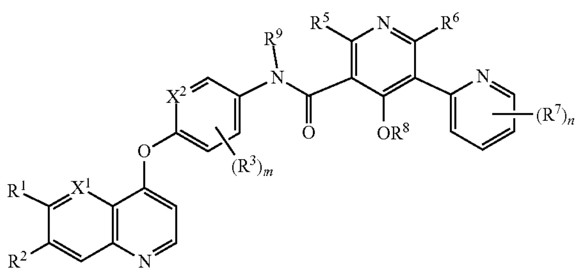

or a pharmaceutically acceptable salt or stereoisomer thereof.

In some embodiments, a compound of Formula (I) is a compound having the structure of formula (Ib-1):

(Ib-1)

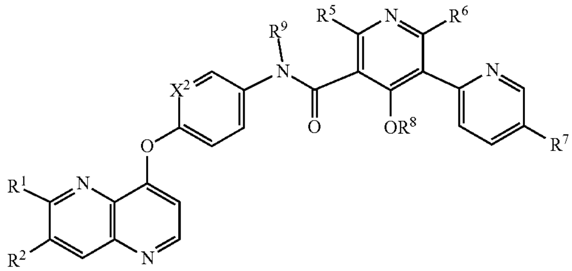

or a pharmaceutically acceptable salt or stereoisomer thereof.

In some embodiments, a compound of Formula (I) is a compound having the structure of formula (Ib-2):

(Ib-2)

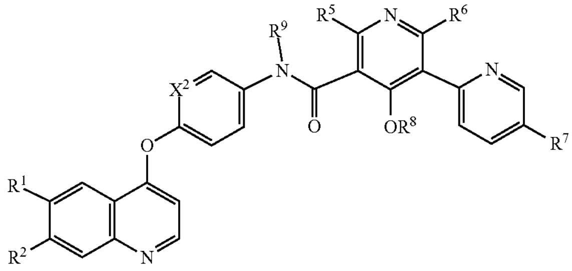

or a pharmaceutically acceptable salt or stereoisomer thereof.

In some or any embodiments described herein, a compound of Formula (I) is a compound having the structure of formula (Ic):

(Ic)

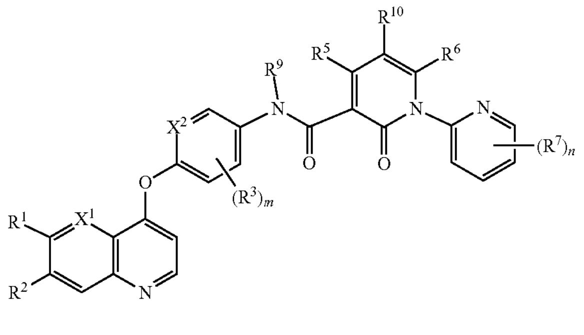

or a pharmaceutically acceptable salt or stereoisomer thereof.

In some or any embodiments described herein, a compound of Formula (I) is a compound having the structure of formula (Ic-1):

(Ic-1)

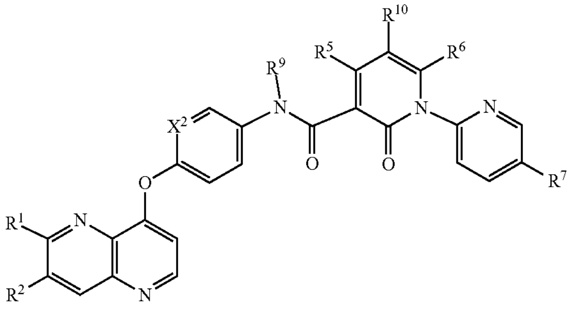

or a pharmaceutically acceptable salt or stereoisomer thereof.

In some or any embodiments described herein, a compound of Formula (I) is a compound having the structure of formula (Ic-2):

(Ic-2)

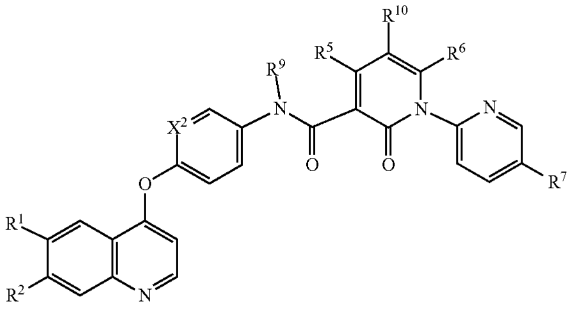

or a pharmaceutically acceptable salt or stereoisomer thereof.

In some or any embodiments described herein, a compound of Formula (I) is a compound having the structure of formula (Id):

(Id)

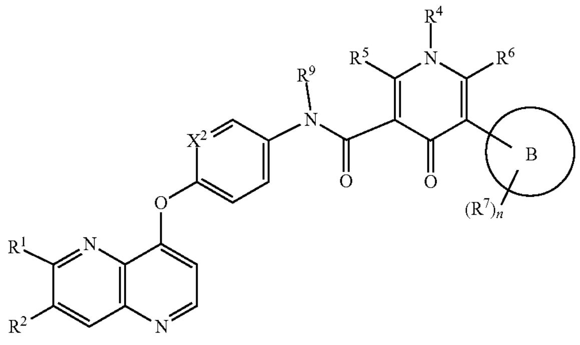

or a pharmaceutically acceptable salt or stereoisomer thereof.

In some or any embodiments described herein, a compound of Formula (I) is a compound having the structure of formula (Ie):

(Ie)

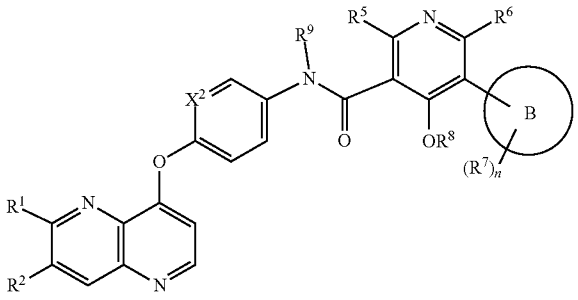

or a pharmaceutically acceptable salt or stereoisomer thereof.

In some or any embodiments described herein, a compound of Formula (I) is a compound having the structure of formula (If):

(If)

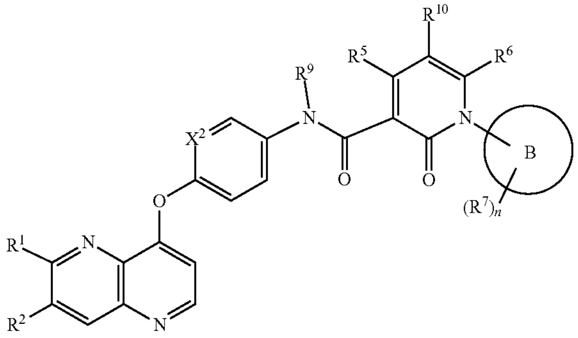

or a pharmaceutically acceptable salt or stereoisomer thereof.

In some or any embodiments described herein, a compound of Formula (I) is a compound having the structure of formula (Ij):

(Ij)

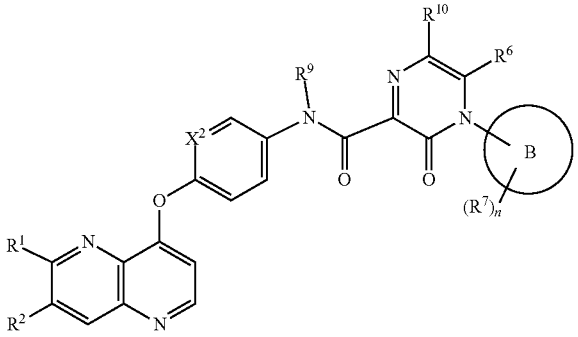

or a pharmaceutically acceptable salt or stereoisomer thereof.

In some or any embodiments described herein, a compound of Formula (I) is a compound having the structure of formula (Ik):

(Ik)

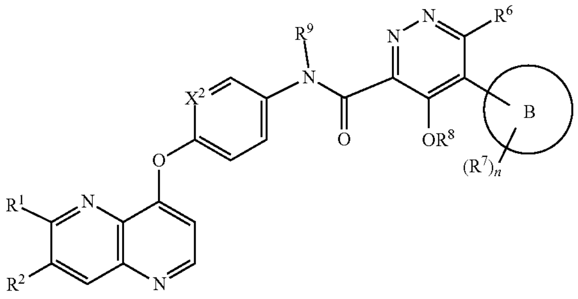

or a pharmaceutically acceptable salt or stereoisomer thereof.

In some or any embodiments described herein, a compound of Formula (I) is a compound having the structure of formula (Im):

(Im)

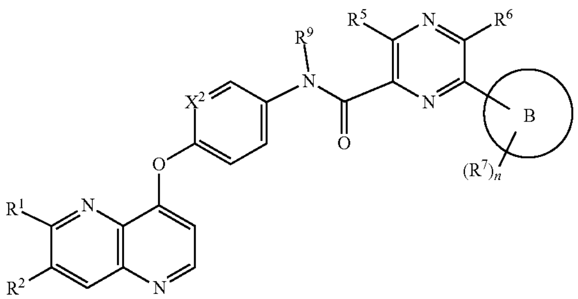

or a pharmaceutically acceptable salt or stereoisomer thereof.

Some embodiments provide a compound of any formula described herein, or a pharmaceutically acceptable salt or stereoisomer thereof, wherein ring B is 2-pyridyl, 3, pyridyl, 4-pyridyl or 5-membered heteroaryl having 1, 2 or 3 heteroatoms as ring members selected from N, O and S.

Some embodiments provide a compound of any formula described herein, or a pharmaceutically acceptable salt or stereoisomer thereof, wherein ring B is 2-thienyl, 3-thienyl, 2-furyl, 3-furyl, 2-benzofuranyl, 3-benzofuranyl, 1H-pyrazol-3-yl, 1H-pyrazol-4-yl, 1H-pyrazol-5-yl or pyrazol-1-yl.

Some embodiments provide a compound of any formula described herein, or a pharmaceutically acceptable salt or stereoisomer thereof, wherein ring B is 2-thienyl, 3-thienyl, 2-furyl, 3-furyl, 1H-pyrazol-3-yl, 1H-pyrazol-4-yl, 1H-pyrazol-5-yl or pyrazol-1-yl.

Some embodiments provide a compound of any formula described herein, or a pharmaceutically acceptable salt or stereoisomer thereof, wherein $R^1$ is H, $C_{1-6}$ alkyl, $C_{1-6}$ alkoxy, halo, $NH_2$, —NH($C_{1-6}$ alkyl), —N($C_{1-6}$ alkyl)$_2$, ($C_{1-6}$ alkyl)NHC(O)—, or ($C_{1-6}$alkyl)-$SO_2$NH—. In some of such embodiments, $C_{1-6}$ alkyl and $C_{1-6}$alkoxy of $R^1$ is optionally substituent by 1, 2, 3, 4, or 5 $R^b$ substituents.

Some embodiments provide a compound of any of the preceding formulas, or a pharmaceutically acceptable salt or stereoisomer thereof, wherein $R^2$ is H, $C_{1-6}$ alkyl, $C_{1-6}$ alkoxy, halo, OH, $NH_2$, —NH($C_{1-6}$ alkyl), —N($C_{1-6}$ alkyl)$_2$, ($C_{1-6}$ alkyl)NHC(O)—, $CF_3$, ($C_{1-6}$ alkyl)—OC(O)—, pyridyl, ($C_{1-6}$ alkyl)-$SO_2$NH— or 1H-pyrazol-4-yl optionally substituted with $R^g$. In some of such embodiments, $C_{1-6}$ alkyl, $C_{1-6}$ alkoxy of $R^2$ is optionally substituent by 1, 2, 3, 4, or 5 $R^b$ substituents.

As used herein, embodiments of "any of the preceding formulas" or "any formula described herein" refers to embodiments of formulas (I), (Ia), (Ia-1), (Ia-2), (Ib), (Ib-1), (Ic), (Ic-1), (Ic-2), (Id), (Ie), (Ij), (Ik), and/or (Im), and/or any combinations thereof.

Some embodiments provide a compound of any formula described herein, or pharmaceutically acceptable salt or stereoisomer thereof, $R^1$ and $R^2$ are each independently selected from H, $C_{1-6}$ alkoxy or $C_{1-6}$ alkoxy-$C_{1-6}$ alkoxy; or from H, methoxy or methoxyethoxy.

Some embodiments provide a compound of any formula described herein, or a pharmaceutically acceptable salt or stereoisomer thereof, wherein $X^2$ is CH or $CR^3$, wherein $R^3$ is halo.

Some embodiments provide a compound of any formula described herein, or a pharmaceutically acceptable salt or stereoisomer thereof, wherein n is 0, or wherein n is 1, 2, 3, or 4, each $R^7$ is independently selected from halo, $C_{1-6}$ alkyl, and $C_{1-6}$ alkoxy.

Some embodiments provide a compound of any formula described herein, or a pharmaceutically acceptable salt or stereoisomer thereof, wherein $R^g$ is H or methyl. In some embodiments, $R^g$ is H.

Some embodiments provide a compound of any formula described herein, or a pharmaceutically acceptable salt or stereoisomer thereof, wherein X is N.

Some embodiments provide a compound of any formula described herein, or a pharmaceutically acceptable salt or stereoisomer thereof, wherein $X^3$ is CH.

Some embodiments provide a compound of any formula described herein, or a pharmaceutically acceptable salt or stereoisomer thereof, wherein $X^2$ is CF. Some embodiments provide a compound of any formula described herein, or a pharmaceutically acceptable salt or stereoisomer thereof, wherein $X^2$ is CH.

Some embodiments provide a compound of any formula described herein, or a pharmaceutically acceptable salt or stereoisomer thereof, wherein each $R^4$ is independently selected from H, $C_{1-6}$ alkyl, $C_{1-6}$ alkoxy, OH, $NH_2$, —NH ($C_{1-6}$ alkyl), —N($C_{1-6}$ alkyl)$_2$, $C_{3-6}$ cycloalkyl, $C_{1-6}$haloalkyl, $C_{3-6}$ cycloalkyl-$C_{1-4}$ alkylene-, 4-6 membered heterocycloalkyl, (4-6 membered heterocycloalkyl)-$C_{1-4}$ alkylene-, 5-6 membered heteroaryl, (5-6 membered heteroaryl)-$C_{1-4}$ alkylene-, and N═C[N($C_{1-6}$ alkyl)($C_{1-6}$ alkyl)]$_2$, wherein the $C_{1-6}$ alkyl, $C_{1-6}$ alkoxy, —NH($C_{1-6}$ alkyl), —N($C_{1-6}$ alkyl)$_2$, $C_{3-6}$ cycloalkyl, $C_{3-6}$ cycloalkyl-$C_{1-4}$ alkylene-, 4-6 membered heterocycloalkyl, (4-6 membered heterocycloalkyl)-$C_{1-4}$ alkylene-, 5-6 membered heteroaryl, (5-6 membered heteroaryl)-$C_{1-4}$ alkylene-, and N═C[N ($C_{1-6}$ alkyl)($C_{1-6}$ alkyl)]2 of $R^4$ are each optionally substituted with 1 or 2 independently selected $R^b$ or $R^g$ substituents. In some embodiments, $R^4$ is selected from H or methyl.

Some embodiments provide a compound of any formula described herein, or a pharmaceutically acceptable salt or stereoisomer thereof, wherein $R^{12}$ and $R^{13}$ are independently selected from H, $C_{1-6}$ alkyl, $C_{1-6}$ alkoxy, OH, $NH_2$, —NH ($C_{1-6}$ alkyl), —N($C_{1-6}$ alkyl)$_2$, $C_{3-6}$ cycloalkyl, $C_{1-6}$haloalkyl, $C_{3-6}$ cycloalkyl-$C_{1-4}$ alkylene-, 4-6 membered heterocycloalkyl, (4-6 membered heterocycloalkyl)-$C_{1-4}$ alkylene-, 5-6 membered heteroaryl, (5-6 membered heteroaryl)-$C_{1-4}$ alkylene-, and N═C[N($C_{1-6}$ alkyl)($C_{1-6}$ alkyl)]$_2$, wherein the $C_{1-6}$ alkyl, $C_{1-6}$ alkoxy, —NH($C_{1-6}$ alkyl), —N($C_{1-6}$ alkyl)$_2$, $C_{3-6}$ cycloalkyl, $C_{3-6}$ cycloalkyl-$C_{1-4}$ alkylene-, 4-6 membered heterocycloalkyl, (4-6 membered heterocycloalkyl)-$C_{1-4}$ alkylene-, 5-6 membered heteroaryl, (5-6 membered heteroaryl)-$C_{1-4}$ alkylene-, and N═C[N ($C_{1-6}$ alkyl)($C_{1-6}$ alkyl)]2 of $R^4$ are each optionally substituted with 1 or 2 independently selected $R^g$ substituents.

Some embodiments provide a compound of any formula described herein, or a pharmaceutically acceptable salt or stereoisomer thereof, wherein $R^5$, $R^6$, and $R^{10}$ are each independently selected from H, $CH_3$, propen-2-yl, Br, Cl, CN, methoxy, 2-fluoroethyl, isopropyl, $CH_3$C(O)—, OH, t-butyl, ethyl, hydroxymethyl, isopropylthio, and methoxymethyl. In some embodiments, $R^5$ and $R^6$ are each independently selected from H or methyl. In some embodiments, $R^{10}$ is selected from H, CN, halo, or $CH_3$C(O)—.

Some embodiments provide a compound of any formula described herein, or a pharmaceutically acceptable salt or stereoisomer thereof, wherein each $R^8$ is independently H or $C_{1-6}$ alkyl. In some embodiments, $Z^5$ is $COR^8$ wherein $R^8$ is H or $C_{1-6}$ alkyl; or $R^8$ is H. In some embodiments, $Z^5$ is —C(═O)—.

Some embodiments provide a compound of any formula described herein, or a pharmaceutically acceptable salt or stereoisomer thereof, wherein $R^{14}$ is H or halo.

Some embodiments provide a compound of any formula described herein, or a pharmaceutically acceptable salt or stereoisomer thereof, wherein $X^6$ is CH or $CR^3$, wherein $R^3$ is halo.

Any of the embodiments described above are applicable to Formula (I) and sub-formulas thereof in any combination. As used herein, "Formula (I) and sub-formulas thereof" refers to Formula (I), (I'), (I"), (I'"), (Ia), (Ia-1), (Ia-2), (Ib), (Ib-1), (Ib-2), (Ic), (Ic-1), (Ic-2), (Id), (Ie), (If), (Ij), (Ik), (Im), and/or any combinations thereof.

In some embodiments, provided is a compound, or a pharmaceutically acceptable salt or stereoisomer thereof, selected from Table 1A. In some embodiments, provided is a compound, or a pharmaceutically acceptable salt or stereoisomer thereof, selected from Table 1B. In some embodiments, provided is a compound, or a pharmaceutically acceptable salt or stereoisomer thereof, selected from Table 1C. In some embodiments, provided is a compound, or a pharmaceutically acceptable salt or stereoisomer thereof, selected from Table 1A and/or Table 1B and/or Table 1C.

TABLE 1A

| Compound No. | Structure | Compound Name |
|---|---|---|
| 41 | 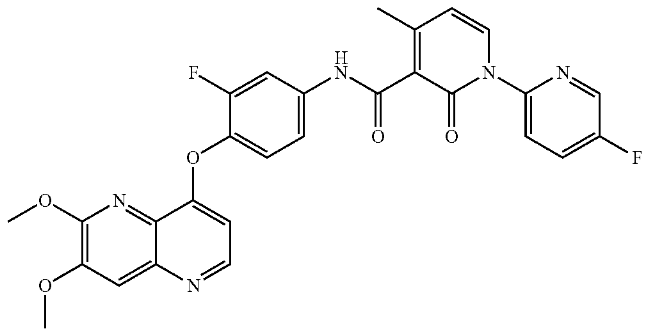 [SMILES: COc1cc2nccc(Oc3ccc(NC(=O)c4c(C)ccn(-c5ccc(F)cn5)c4=O)cc3F)c2nc1OC] | N-[4-[(6,7-dimethoxy-1,5-naphthyridin-4-yl)oxy]-3-fluorophenyl]-1-(5-fluoropyridin-2-yl)-4-methyl-2-oxopyridine-3-carboxamide |
| 42 | 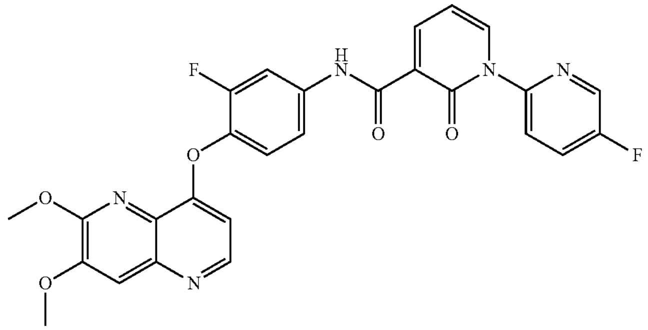 [SMILES: COc1cc2nccc(Oc3ccc(NC(=O)c4cccn(-c5ccc(F)cn5)c4=O)cc3F)c2nc1OC] | N-[4-[(6,7-dimethoxy-1,5-naphthyridin-4-yl)oxy]-3-fluorophenyl]-1-(5-fluoropyridin-2-yl)-2-oxopyridine-3-carboxamide |
| 43 | 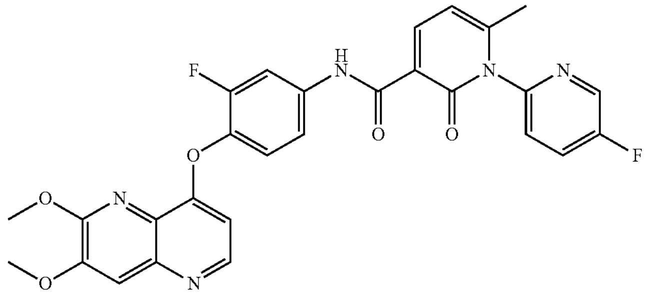 [SMILES: COc1cc2nccc(Oc3ccc(NC(=O)c4ccc(C)n(-c5ccc(F)cn5)c4=O)cc3F)c2nc1OC] | N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide |
| 44 | 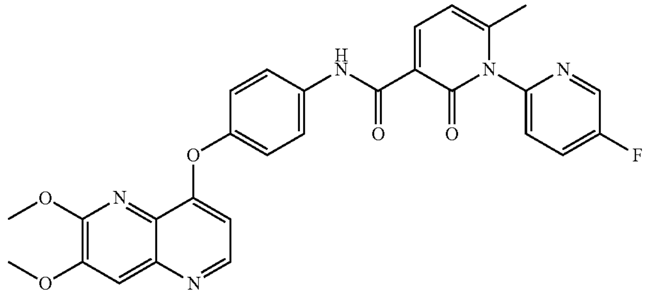 [SMILES: COc1cc2nccc(Oc3ccc(NC(=O)c4ccc(C)n(-c5ccc(F)cn5)c4=O)cc3)c2nc1OC] | N-[4-[(6,7-dimethoxy-1,5-naphthyridin-4-yl)oxy]phenyl]-1-(5-fluoropyridin-2-yl)-6-methyl-2-oxopyridine-3-carboxamide |
| 45 | 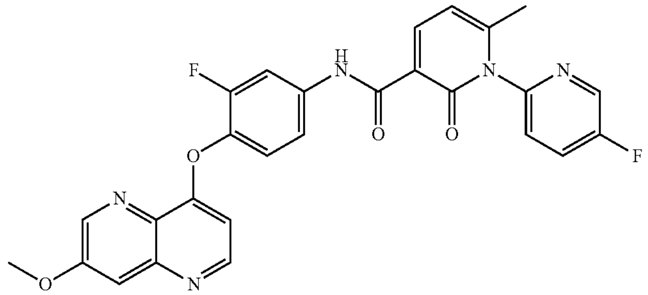 [SMILES: COc1cnc2c(Oc3ccc(NC(=O)c4ccc(C)n(-c5ccc(F)cn5)c4=O)cc3F)ccnc2c1] | N-[3-fluoro-4-[(7-methoxy-1,5-naphthyridin-4-yl)oxy]phenyl]-1-(5-fluoropyridin-2-yl)-6-methyl-2-oxopyridine-3-carboxamide |

TABLE 1A-continued

| Compound No. | Structure | Compound Name |
| --- | --- | --- |
| 46 | 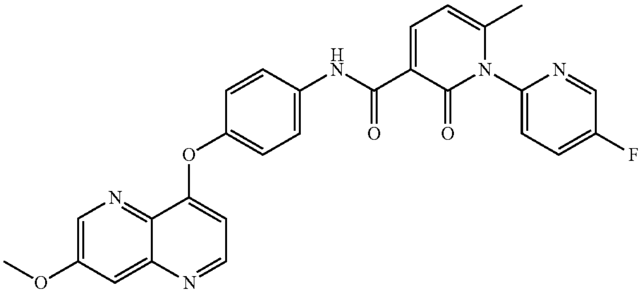 [SMILES: COc1cnc2c(Oc3ccc(NC(=O)c4ccc(C)n(-c5ccc(F)cn5)c4=O)cc3)ccnc2c1] | 1-(5-fluoropyridin-2-yl)-N-[4-[(7-methoxy-1,5-naphthyridin-4-yl)oxy]phenyl]-6-methyl-2-oxopyridine-3-carboxamide |
| 47 | 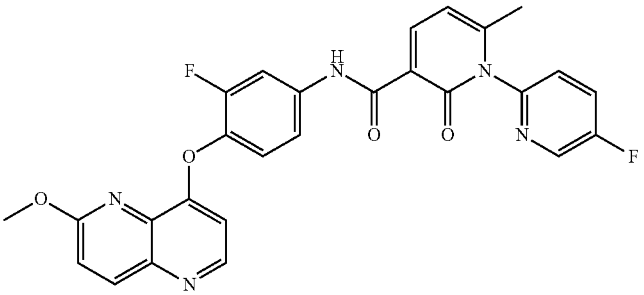 | N-[3-fluoro-4-[(6-methoxy-1,5-naphthyridin-4-yl)oxy]phenyl]-1-(5-fluoropyridin-2-yl)-6-methyl-2-oxopyridine-3-carboxamide |
| 48 | 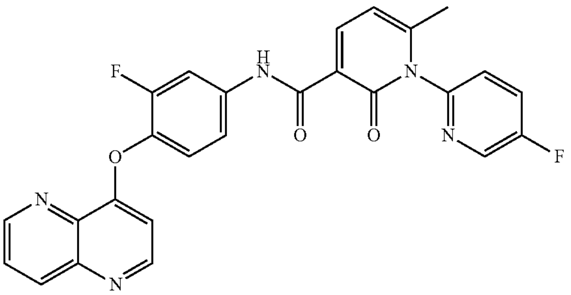 [SMILES: Cc1ccc(C(=O)Nc2ccc(Oc3ccnc4cccnc34)c(F)c2)c(=O)n1-c1ccc(F)cn1] | N-[3-fluoro-4-(1,5-naphthyridin-4-yloxy)phenyl]-1-(5-fluoropyridin-2-yl)-6-methyl-2-oxopyridine-3-carboxamide |
| 49 | 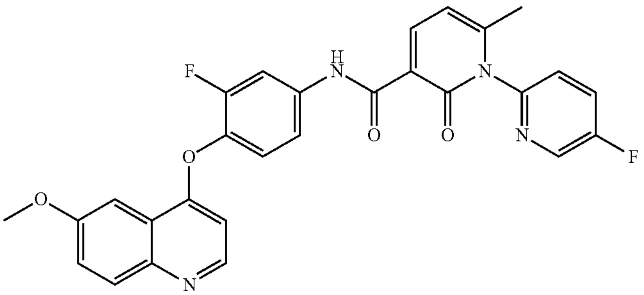 [SMILES: COc1ccc2nccc(Oc3ccc(NC(=O)c4ccc(C)n(-c5ccc(F)cn5)c4=O)cc3F)c2c1] | N-[3-fluoro-4-(6-methoxyquinolin-4-yl)oxyphenyl]-1-(5-fluoropyridin-2-yl)-6-methyl-2-oxopyridine-3-carboxamide |
| 50 | 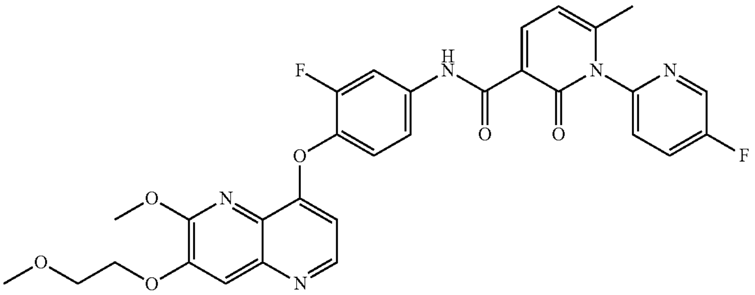 [SMILES: COCCOc1cc2nccc(Oc3ccc(NC(=O)c4ccc(C)n(-c5ccc(F)cn5)c4=O)cc3F)c2nc1OC] | N-[3-fluoro-4-[[6-methoxy-7-(2-methoxy ethoxy)-1,5-naphthyridin-4-yl]oxy]phenyl]-1-(5-fluoropyridin-2-yl)-6-methyl-2-oxopyridine-3-carboxamide |

TABLE 1A-continued

| Compound No. | Structure | Compound Name |
|---|---|---|
| 51 | 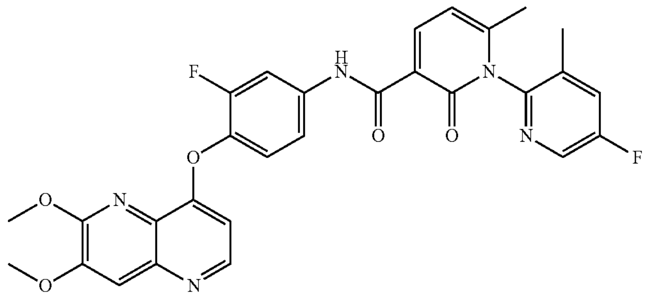 [SMILES: COc1cc2nccc(Oc3ccc(NC(=O)c4ccc(C)n(-c5ncc(F)cc5C)c4=O)cc3F)c2nc1OC] | N-[4-[(6,7-dimethoxy-1,5-naphthyridin-4-yl)oxy]-3-fluorophenyl]-1-(5-fluoro-3-methylpyridin-2-yl)-6-methyl-2-oxopyridine-3-carboxamide |
| 52 | 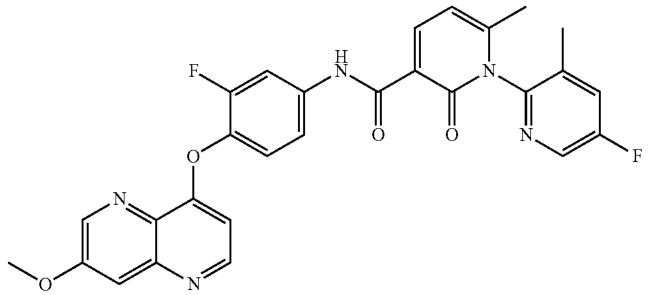 [SMILES: COc1cnc2c(Oc3ccc(NC(=O)c4ccc(C)n(-c5ncc(F)cc5C)c4=O)cc3F)ccnc2c1] | N-[3-fluoro-4-[(7-methoxy-1,5-naphthyridin-4-yl)oxy]phenyl]-1-(5-fluoro-3-methylpyridin-2-yl)-6-methyl-2-oxopyridine-3-carboxamide |
| 53 | 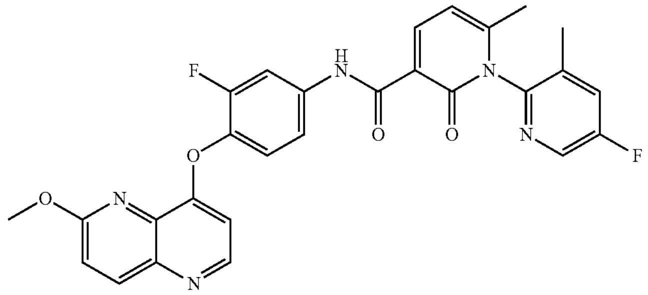 | N-[3-fluoro-4-[(6-methoxy-l,5-naphthyridin-4-yl)oxy]phenyl]-1-(5-fluoro-3-methylpyridin-2-yl)-6-methyl-2-oxopyridine-3-carboxamide |
| 54 | 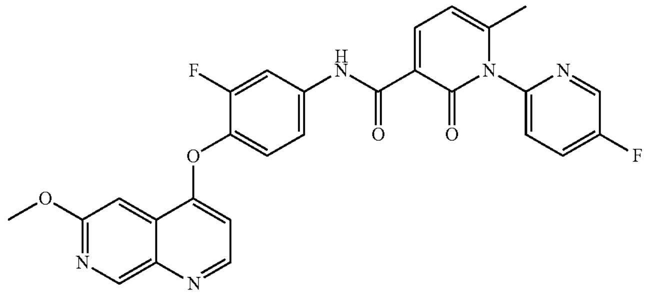 [SMILES: COc1cc2c(Oc3ccc(NC(=O)c4ccc(C)n(-c5ccc(F)cn5)c4=O)cc3F)ccnc2cn1] | N-[4-[(6-methoxy-l,7-naphthyridin-4-yl)oxy]-3-fluorophenyl]-1-(5-fluoropyridin-2-yl)-6-methyl-2-oxopyridine-3-carboxamide |
| 54A | 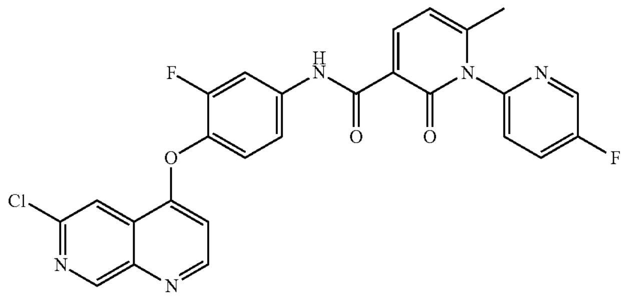 [SMILES: Cc1ccc(C(=O)Nc2ccc(Oc3ccnc4cnc(Cl)cc34)c(F)c2)c(=O)n1-c1ccc(F)cn1] | N-[3-fluoro-4-[(6-chloro-l,7-naphthyridin-4-yl)oxy]phenyl]-l-(5-fluoropyridin-2-yl)-6-methyl-2-oxopyridine-3-carboxamide |

TABLE 1A-continued

| Compound No. | Structure | Compound Name |
|---|---|---|
| 55 | 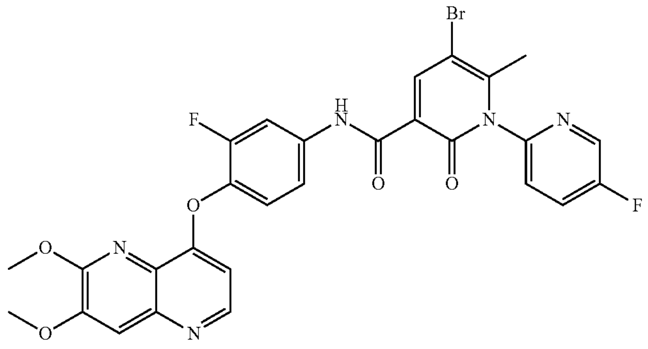 [SMILES: COc1cc2nccc(Oc3ccc(NC(=O)c4cc(Br)c(C)n(-c5ccc(F)cn5)c4=O)cc3F)c2nc1OC] | 5-bromo-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide |
| 56 | 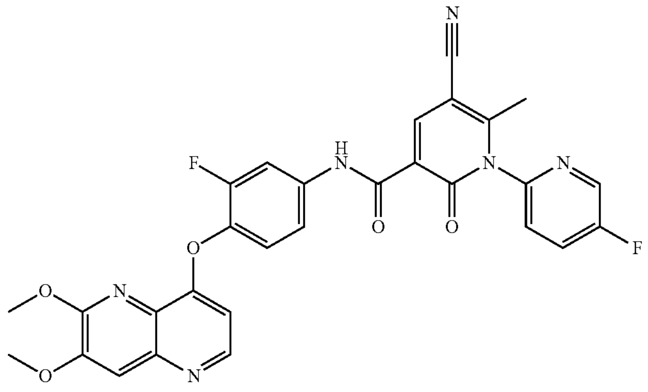 [SMILES: COc1cc2nccc(Oc3ccc(NC(=O)c4cc(C#N)c(C)n(-c5ccc(F)cn5)c4=O)cc3F)c2nc1OC] | 5-cyano-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide |
| 59 | 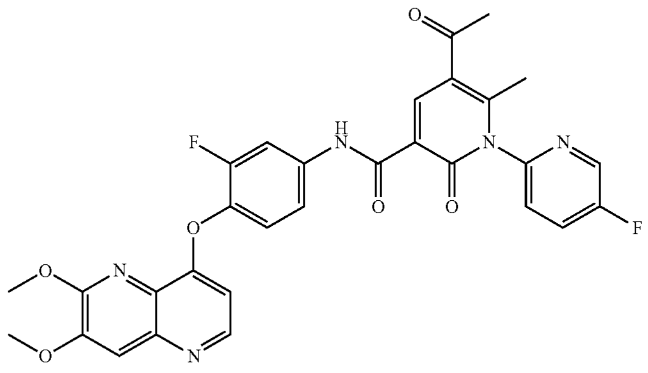 [SMILES: COc1cc2nccc(Oc3ccc(NC(=O)c4cc(C(C)=O)c(C)n(-c5ccc(F)cn5)c4=O)cc3F)c2nc1OC] | 5-acetyl-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide |
| 68 | 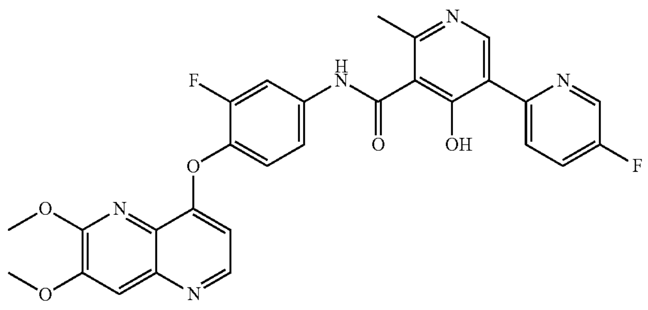 [SMILES: COc1cc2nccc(Oc3ccc(NC(=O)c4c(C)ncc(-c5ccc(F)cn5)c4O)cc3F)c2nc1OC] | N-[4-[(6,7-dimethoxy-1,5-naphthyridin-4-yl)oxy]-3-fluorophenyl]-5-(5-fluoropyridin-2-yl)-4-hydroxy-2-methylpyridine-3-carboxamide |

TABLE 1A-continued

| Compound No. | Structure | Compound Name |
|---|---|---|
| 69 | 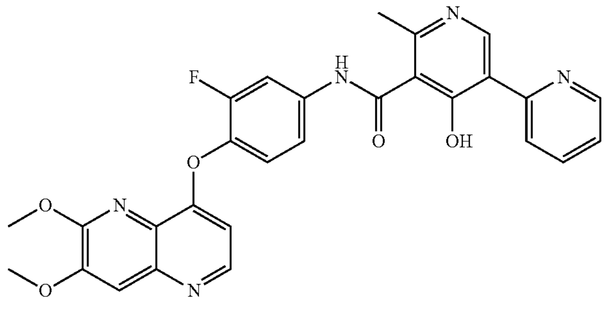 [SMILES: COc1cc2nccc(Oc3ccc(NC(=O)c4c(C)ncc(-c5ccccn5)c4O)cc3F)c2nc1OC] | N-[4-[(6,7-dimethoxy-1,5-naphthyridin-4-yl)oxy]-3-fluorophenyl]-4-hydroxy-2-methyl-5-pyridin-2-ylpyridine-3-carboxamide |
| 70 | 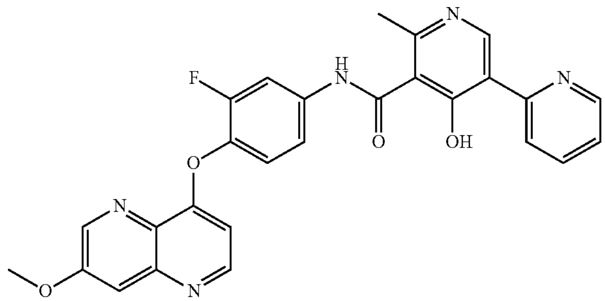 [SMILES: COc1cnc2c(Oc3ccc(NC(=O)c4c(C)ncc(-c5ccccn5)c4O)cc3F)ccnc2c1] | N-[3-fluoro-4-[(7-methoxy-1,5-naphthyridin-4-yl)oxy]phenyl]-4-hydroxy-2-methyl-5-pyridin-2-ylpyridine-3-carboxamide |
| 71 | 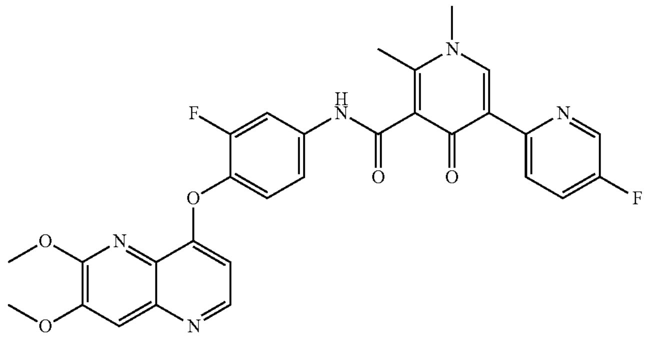 [SMILES: COc1cc2nccc(Oc3ccc(NC(=O)c4c(C)n(C)cc(-c5ccc(F)cn5)c4=O)cc3F)c2nc1OC] | N-[4-[(6,7-dimethoxy-1,5-naphthyridin-4-yl)oxy]-3-fluorophenyl]-5-(5-fluoropyridin-2-yl)-1,2-dimethyl-4-oxopyridine-3-carboxamide |
| 72 | 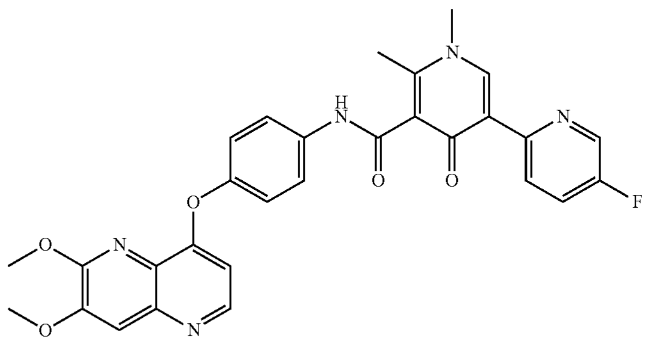 [SMILES: COc1cc2nccc(Oc3ccc(NC(=O)c4c(C)n(C)cc(-c5ccc(F)cn5)c4=O)cc3)c2nc1OC] | N-[4-[(6,7-dimethoxy-1,5-naphthyridin-4-yl)oxy]phenyl]-5-(5-fluoropyridin-2-yl)-1,2-dimethyl-4-oxopyridine-3-carboxamide |

TABLE 1A-continued

| Compound No. | Structure | Compound Name |
|---|---|---|
| 73 | 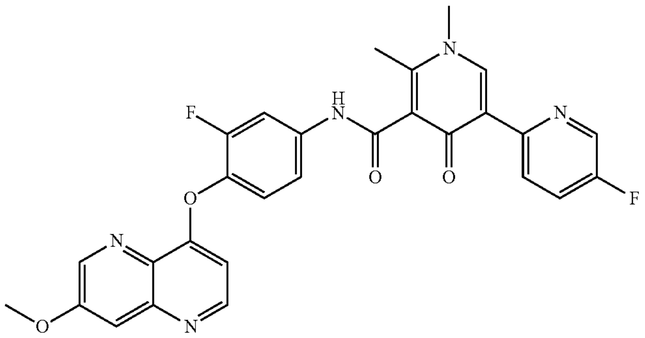 [SMILES: COc1cnc2c(Oc3ccc(NC(=O)c4c(C)n(C)cc(-c5ccc(F)cn5)c4=O)cc3F)ccnc2c1] | N-[3-fluoro-4-[(7-methoxy-1,5-naphthyridin-4-yl)oxy]phenyl]-5-(5-fluoropyridin-2-yl)-1,2-dimethyl-4-oxopyridine-3-carboxamide |
| 85 | 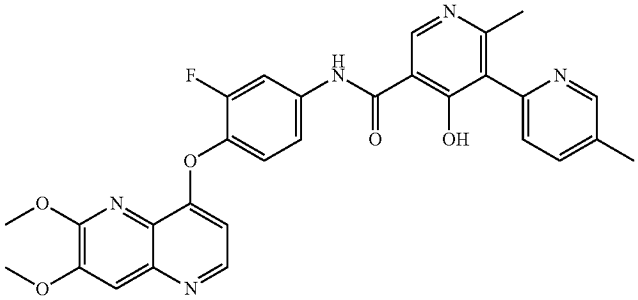 | N-[4-[(6,7-dimethoxy-1,5-naphthyridin-4-yl)oxy]-3-fluorophenyl]-5-(5-fluoropyridin-2-yl)-4-hydroxy-6-methylpyridine-3-carboxamide |

or a pharmaceutically acceptable salt, a stereoisomer, or a mixture of stereoisomers thereof.

TABLE 1B

| Compound No. | Structure | Compound Name |
|---|---|---|
| 86 | 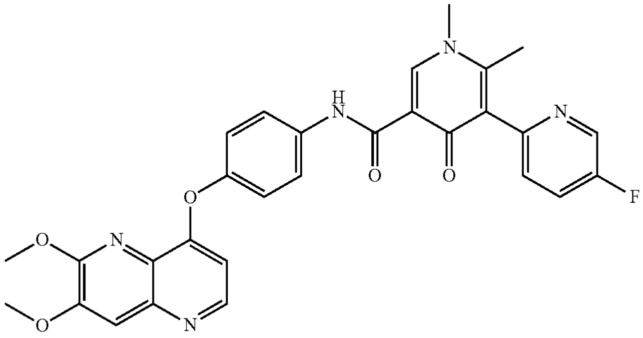 [SMILES: COc1cc2nccc(Oc3ccc(NC(=O)c4cn(C)c(C)c(-c5ccc(F)cn5)c4=O)cc3)c2nc1OC] | N-[4-[(6,7-dimethoxy-1,5-naphthyridin-4-yl)oxy]phenyl]-5-(5-fluoropyridin-2-yl)-1,6-dimethyl-4-oxopyridine-3-carboxamide |
| 89 | 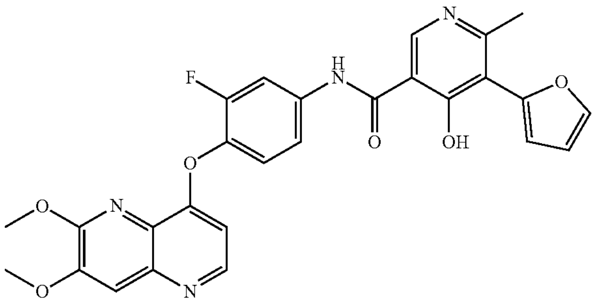 | N-[4-[(6,7-dimethoxy-1,5-naphthyridin-4-yl)oxy]-3-fluorophenyl]-5-(furan-2-yl)-4-hydroxy-6-methylpyridine-3-carboxamide |

TABLE 1B-continued

| Compound No. | Structure | Compound Name |
|---|---|---|
| 90 | 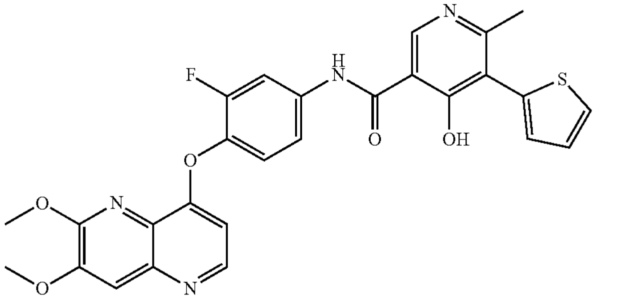 [SMILES: COc1cc2nccc(Oc3ccc(NC(=O)c4cnc(C)c(-c5cccs5)c4O)cc3F)c2nc1OC] | N-[4-[(6,7-dimethoxy-1,5-naphthyridin-4-yl)oxy]-3-fluorophenyl]-4-hydroxy-6-methyl-5-thiophen-2-ylpyridine-3-carboxamide |
| 91 | 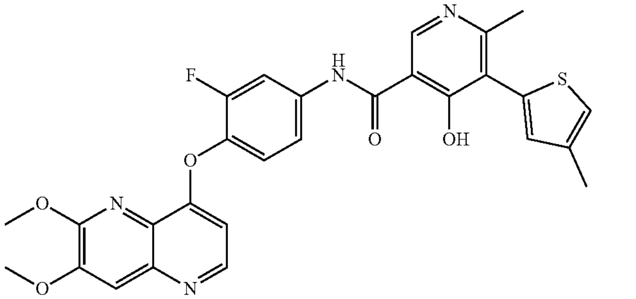 [SMILES: COc1cc2nccc(Oc3ccc(NC(=O)c4cnc(C)c(-c5cc(C)cs5)c4O)cc3F)c2nc1OC] | N-[4-[(6,7-dimethoxy-1,5-naphthyridin-4-yl)oxy]-3-fluorophenyl]-4-hydroxy-6-methyl-5-(4-methylthiophen-2-yl)pyridine-3-carboxamide |
| 92 | 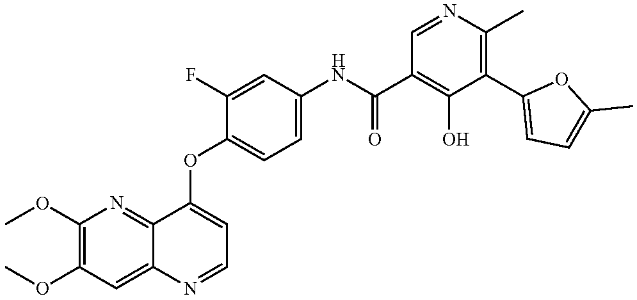 | N-[4-[(6,7-dimethoxy-1,5-naphthyridin-4-yl)oxy]-3-fluorophenyl]-4-hydroxy-6-methyl-5-(5-methylfuran-2-yl)pyridine-3-carboxamide |
| 93 | 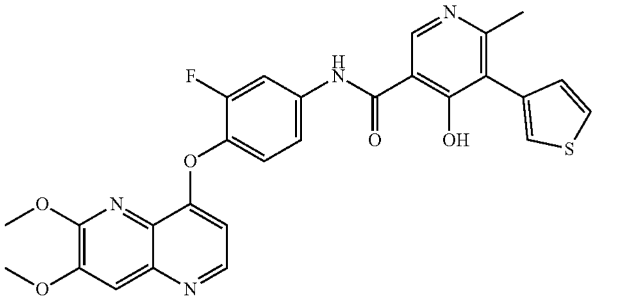 [SMILES: COc1cc2nccc(Oc3ccc(NC(=O)c4cnc(C)c(-c5ccoc5)c4O)cc3F)c2nc1OC] | N-[4-[(6,7-dimethoxy-1,5-naphthyridin-4-yl)oxy]-3-fluorophenyl]-4-hydroxy-6-methyl-5-thiophen-3-ylpyridine-3-carboxamide |
| 94 | 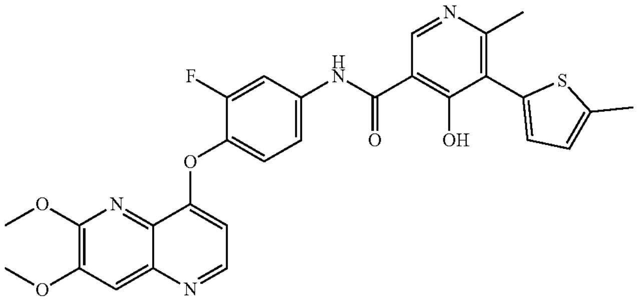 | N-[4-[(6,7-dimethoxy-1,5-naphthyridin-4-yl)oxy]-3-fluorophenyl]-4-hydroxy-6-methyl-5-(5-methylthiophen-2-yl)pyridine-3-carboxamide |

TABLE 1B-continued

| Compound No. | Structure | Compound Name |
|---|---|---|
| 95 | 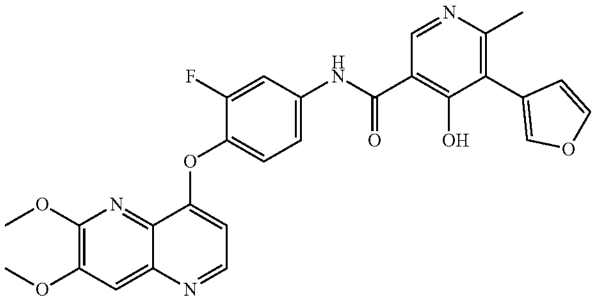 | N-[4-[(6,7-dimethoxy-1,5-naphthyridin-4-yl)oxy]-3-fluorophenyl]-5-(furan-3-yl)-4-hydroxy-6-methylpyridine-3-carboxamide |
| 96 | 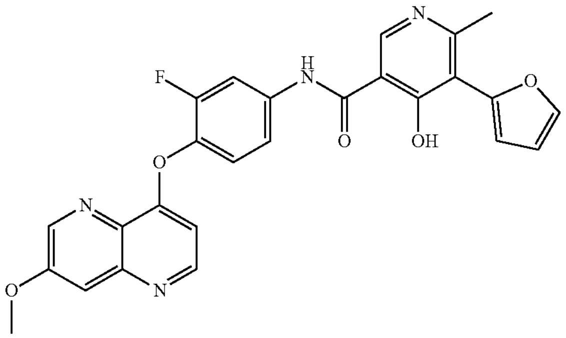 [SMILES: COc1cnc2c(Oc3ccc(NC(=O)c4cnc(C)c(-c5ccco5)c4O)cc3F)ccnc2c1] | N-[3-fluoro-4-[(7-methoxy-1,5-1,5-naphthyridin-4-yl)oxy]phenyl]-5-(furan-2-yl)-4-hydroxy-6-methylpyridine-3-carboxamide |
| 97 | 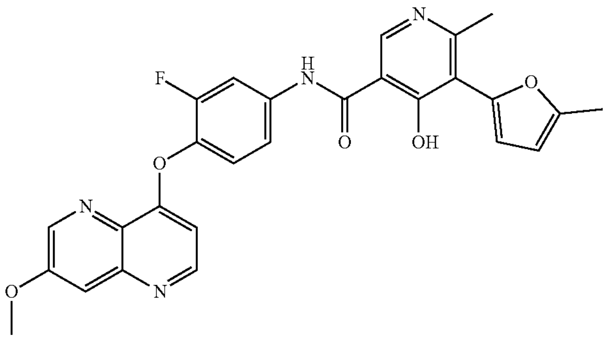 [SMILES: COc1cnc2c(Oc3ccc(NC(=O)c4cnc(C)c(-c5ccc(C)o5)c4O)cc3F)ccnc2c1] | N-[3-fluoro-4-[(7-methoxy-1,5-naphthyridin-4-yl)oxy]phenyl]-4-hydroxy-6-methyl-5-(5-methylfuran-2-yl)pyridine-3-carboxamide |
| 98 | 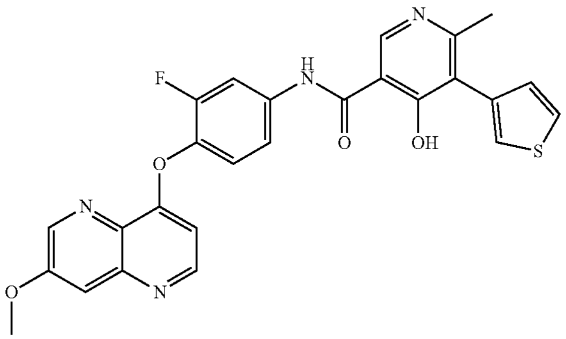 [SMILES: COc1cnc2c(Oc3ccc(NC(=O)c4cnc(C)c(-c5ccsc5)c4O)cc3F)ccnc2c1] | N-[3-fluoro-4-[(7-methoxy-1,5-naphthyridin-4-yl)oxy]phenyl]-4-hydroxy-6-methyl-5-thiophen-3-ylpyridine-3-carboxamide |

TABLE 1B-continued

| Compound No. | Structure | Compound Name |
|---|---|---|
| 99 | 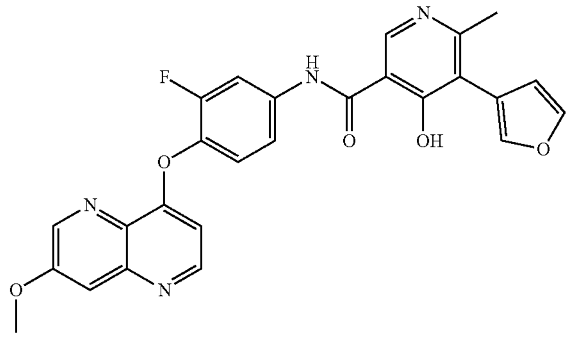 [SMILES: COc1cnc2c(Oc3ccc(NC(=O)c4cnc(C)c(-c5ccoc5)c4O)cc3F)ccnc2c1] | N-[3-fluoro-4-[(7-methoxy-1,5-naphthyridin-4-yl)oxy]phenyl]-5-(furan-3-yl)-4-hydroxy-6-methylpyridine-3-carboxamide |
| 100 | 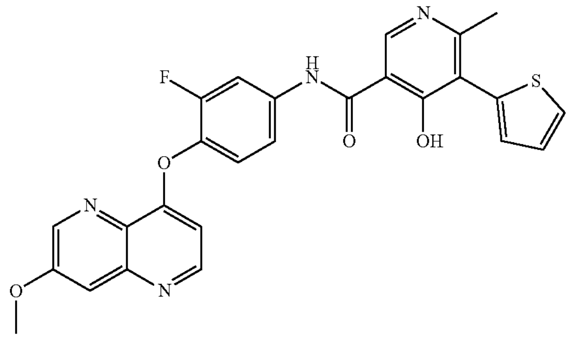 | N-[3-fluoro-4-[(7-methoxy-1,5-naphthyridin-4-yl)oxy]phenyl]-4-hydroxy-6-methyl-5-thiophen-2-ylpyridine-3-carboxamide |
| 101 | 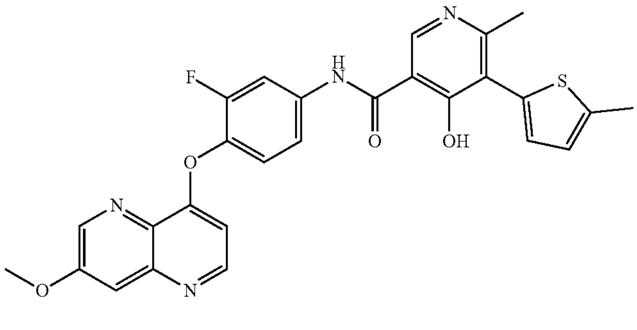 | N-[3-fluoro-4-[(7-methoxy-1,5-naphthyridin-4-yl)oxy]phenyl]-4-hydroxy-6-methyl-5-(5-methylthiophen-2-yl)pyridine-3-carboxamide |
| 102 | 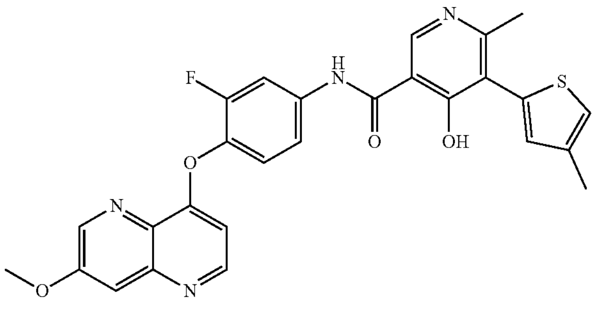 [SMILES: COc1cnc2c(Oc3ccc(NC(=O)c4cnc(C)c(-c5cc(C)cs5)c4O)cc3F)ccnc2c1] | N-[3-fluoro-4-[(7-methoxy-1,5-naphthyridin-4-yl)oxy]phenyl]-4-hydroxy-6-methyl-5-(4-methylthiophen-2-yl)pyridine-3-carboxamide |

TABLE 1B-continued

| Compound No. | Structure | Compound Name |
|---|---|---|
| 103 | 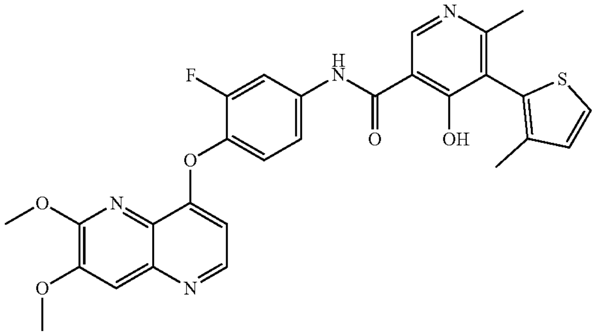 [SMILES: COc1cc2nccc(Oc3ccc(NC(=O)c4cnc(C)c(-c5sccc5C)c4O)cc3F)c2nc1OC] | N-[4-[(6,7-dimethoxy-1,5-naphthyridin-4-yl)oxy]-3-fluorophenyl]-4-hydroxy-6-methyl-5-(3-methylthiophen-2-yl)pyridine-3-carboxamide |
| 104 | 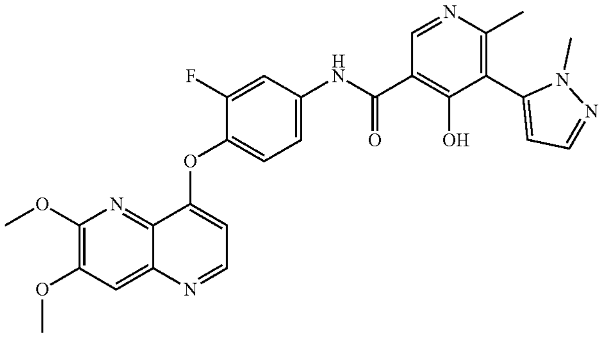 [SMILES: COc1cc2nccc(Oc3ccc(NC(=O)c4cnc(C)c(-c5ccnn5C)c4O)cc3F)c2nc1OC] | N-[4-[(6,7-dimethoxy-1,5-naphthyridin-4-yl)oxy]-3-fluorophenyl]-4-hydroxy-6-methyl-5-(2-methylpyrazol-3-yl)pyridine-3-carboxamide |
| 105 | 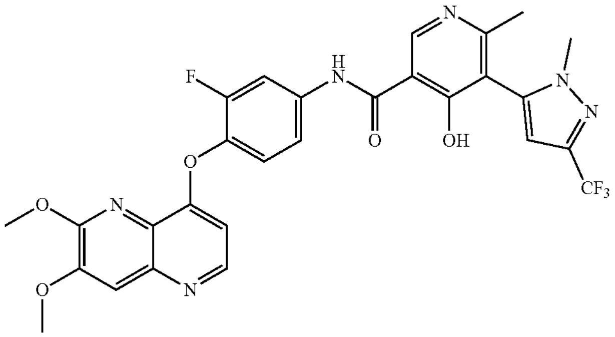 [SMILES: COc1cc2nccc(Oc3ccc(NC(=O)c4cnc(C)c(-c5cc(C(F)(F)F)nn5C)c4O)cc3F)c2nc1OC] | N-[4-[(6,7-dimethoxy-1,5-naphthyridin-4-yl)oxy]-3-fluorophenyl]-4-hydroxy-6-methyl-5-[2-methyl-5-(trifluoromethyl)pyrazol-3-yl]pyridine-3-carboxamide |
| 106 | 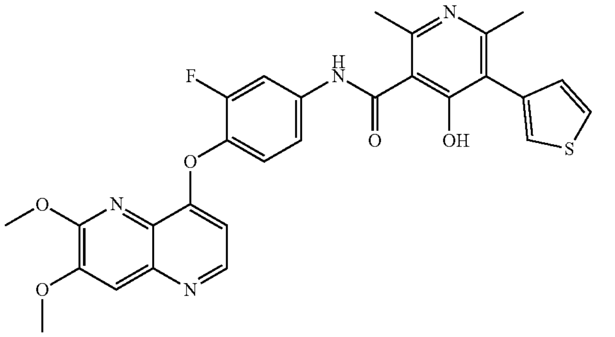 [SMILES: COc1cc2nccc(Oc3ccc(NC(=O)c4c(C)nc(C)c(-c5ccsc5)c4O)cc3F)c2nc1OC] | N-[4-[(6,7-dimethoxy-1,5-naphthyridin-4-yl)oxy]-3-fluorophenyl]-4-hydroxy-2,6-dimethyl-5-thiophen-3-ylpyridine-3-carboxamide |

TABLE 1B-continued

| Compound No. | Structure | Compound Name |
|---|---|---|
| 107 | 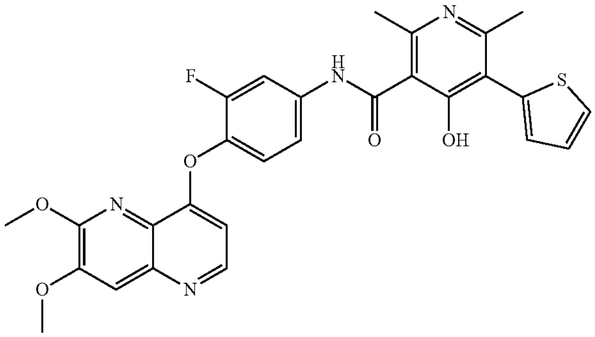 | N-[4-[(6,7-dimethoxy-1,5-naphthyridin-4-yl)oxy]-3-fluorophenyl]-4-hydroxy-2,6-dimethyl-5-thiophen-2-ylpyridine-3-carboxamide |
| 108 | 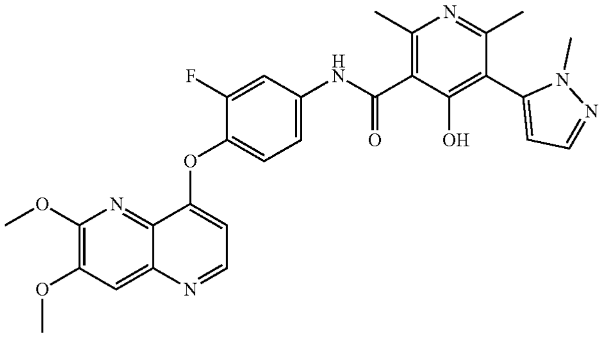 [SMILES: COc1cc2nccc(Oc3ccc(NC(=O)c4c(C)nc(C)c(-c5ccnn5C)c4O)cc3F)c2nc1OC] | N-[4-[(6,7-dimethoxy-1,5-naphthyridin-4-yl)oxy]-3-fluorophenyl]-4-hydroxy-2,6-dimethyl-5-(2-methylpyrazol-3-yl)pyridine-3-carboxamide |
| 109 | 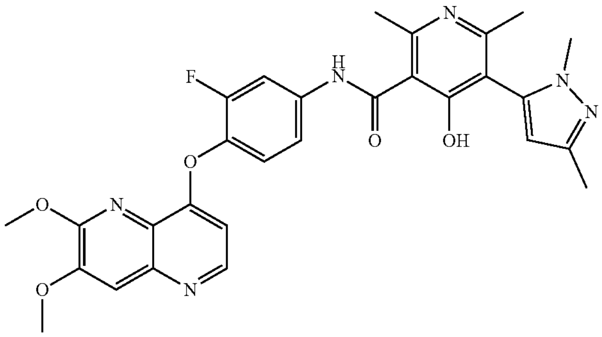 [SMILES: COc1cc2nccc(Oc3ccc(NC(=O)c4c(C)nc(C)c(-c5cc(C)nn5C)c4O)cc3F)c2nc1OC] | N-[4-[(6,7-dimethoxy-1,5-naphthyridin-4-yl)oxy]-3-fluorophenyl]-5-(2,5-dimethylpyrazol-3-yl)-4-hydroxy-2,6-dimethylpyridine-3-carboxamide |
| 110 | 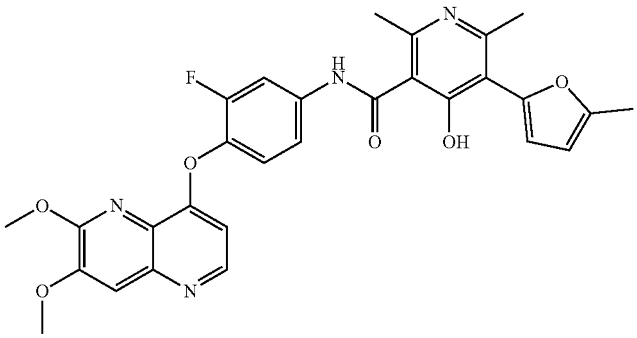 | N-[4-[(6,7-dimethoxy-1,5-naphthyridin-4-yl)oxy]-3-fluorophenyl]-4-hydroxy-2,6-dimethyl-5-(5-methylfuran-2-yl)pyridine-3-carboxamide |

TABLE 1B-continued

| Compound No. | Structure | Compound Name |
|---|---|---|
| 111 | 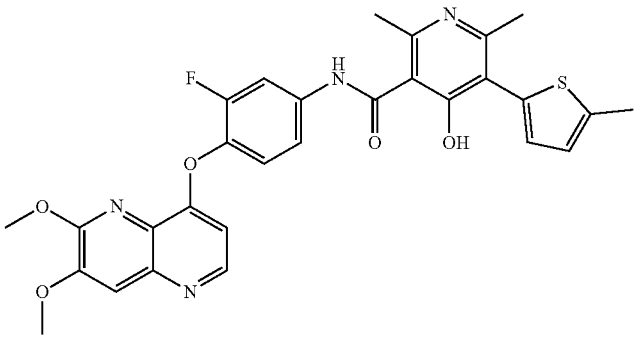 | N-[4-[(6,7-dimethoxy-1,5-naphthyridin-4-yl)oxy]-3-fluorophenyl]-4-hydroxy-2,6-dimethyl-5-(5-methylthiophen-2-yl)pyridine-3-carboxamide |
| 112 | 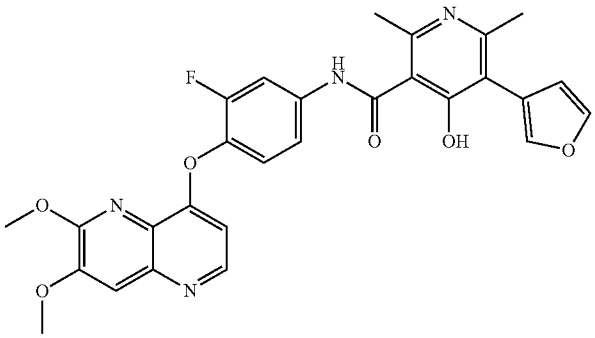 | N-[4-[(6,7-dimethoxy-1,5-naphthyridin-4-yl)oxy]-3-fluorophenyl]-5-(furan-3-yl)-4-hydroxy-2,6-dimethylpyridine-3-carboxamide |
| 115 | 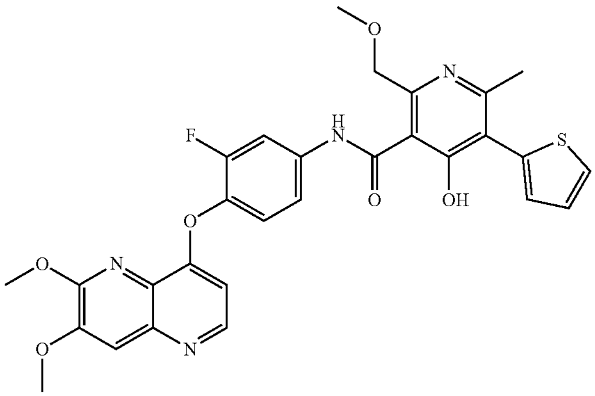 | N-[4-[(6,7-dimethoxy-1,5-naphthyridin-4-yl)oxy]-3-fluorophenyl]-4-hydroxy-2-(methoxymethyl)-6-methyl-5-thiophen-2-ylpyridine-3-carboxamide |
| 116 | 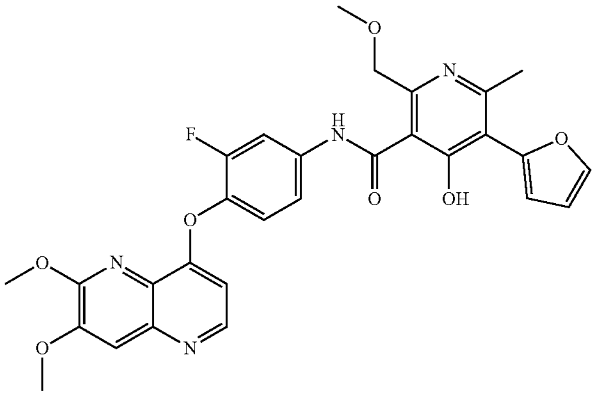 [SMILES: COCc1nc(C)c(-c2ccco2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(furan-2-yl)-4-hydroxy-2-(methoxymethyl)-6-methylpyridine-3-carboxamide |

TABLE 1B-continued

| Compound No. | Structure | Compound Name |
| --- | --- | --- |
| 117 | 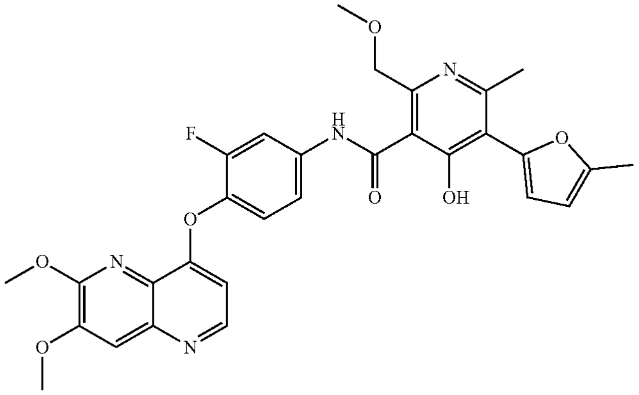 | N-[4-[(6,7-dimethoxy-1,5-naphthyridin-4-yl)oxy]-3-fluorophenyl]-4-hydroxy-2-(methoxymethyl)-6-methyl-5-(5-methylfuran-2-yl)pyridine-3-carboxamide |
| 118 | 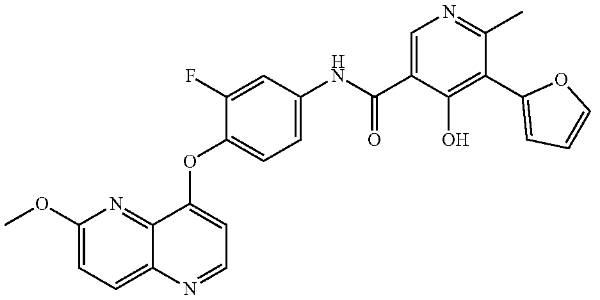 | N-[3-fluoro-4-[(6-methoxy-1,5-naphthyridin-4-yl)oxy]phenyl]-5-(furan-2-yl)-4-hydroxy-6-methylpyridine-3-carboxamide |
| 119 | 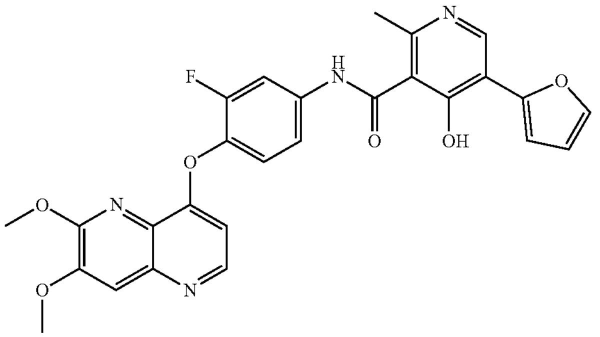 [SMILES: COc1cc2nccc(Oc3ccc(NC(=O)c4c(C)ncc(-c5ccco5)c4O)cc3F)c2nc1OC] | N-[4-[(6,7-dimethoxy-1,5-naphthyridin-4-yl)oxy]-3-fluorophenyl]-5-(furan-2-yl)-4-hydroxy-2-methylpyridine-3-carboxamide |
| 120 | 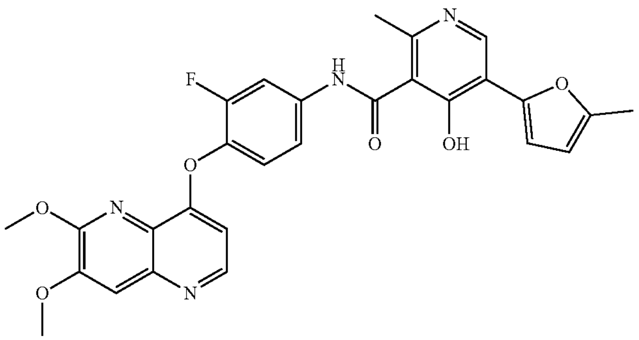 | N-[4-[(6,7-dimethoxy-1,5-naphthyridin-4-yl)oxy]-3-fluorophenyl]-4-hydroxy-2-methyl-5-(5-methylfuran-2-yl)pyridine-3-carboxamide |

TABLE 1B-continued

| Compound No. | Structure | Compound Name |
|---|---|---|
| 121 | 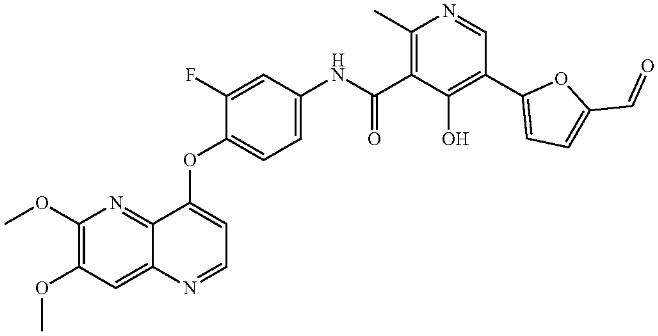 [SMILES: COc1cc2nccc(Oc3ccc(NC(=O)c4c(C)ncc(-c5ccc(C=O)o5)c4O)cc3F)c2nc1OC] | N-[4-[(6,7-dimethoxy-1,5-naphthyridin-4-yl)oxy]-3-fluorophenyl]-5-(5-formylfuran-2-yl)-4-hydroxy-2-methylpyridine-3-carboxamide |
| 122 | 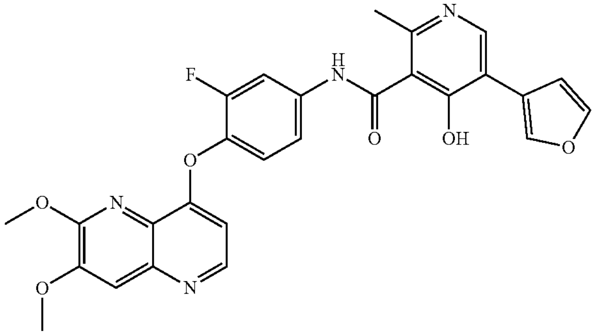 [SMILES: COc1cc2nccc(Oc3ccc(NC(=O)c4c(C)ncc(-c5ccoc5)c4O)cc3F)c2nc1OC] | N-[4-[(6,7-dimethoxy-1,5-naphthyridin-4-yl)oxy]-3-fluorophenyl]-5-(furan-3-yl)-4-hydroxy-2-methylpyridine-3-carboxamide |
| 123 | 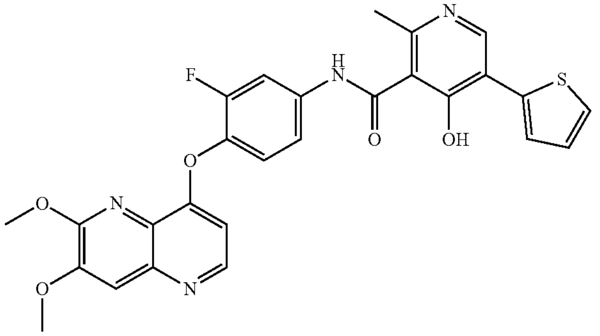 | N-[4-[(6,7-dimethoxy-1,5-naphthyridin-4-yl)oxy]-3-fluorophenyl]-4-hydroxy-2-methyl-5-thiophen-2-ylpyridine-3-carboxamide |
| 124 | 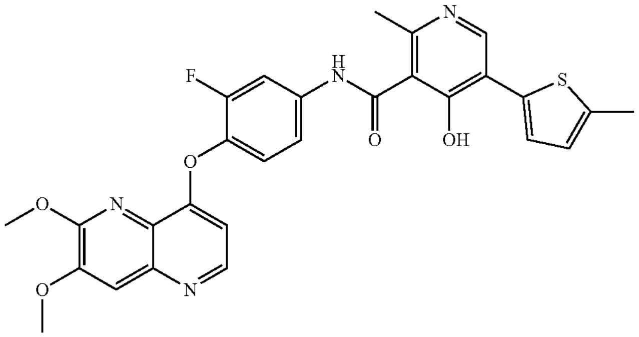 | N-[4-[(6,7-dimethoxy-1,5-naphthyridin-4-yl)oxy]-3-fluorophenyl]-4-hydroxy-2-methyl-5-(5-methylthiophen-2-yl)pyridine-3-carboxamide |

TABLE 1B-continued

| Compound No. | Structure | Compound Name |
|---|---|---|
| 125 | 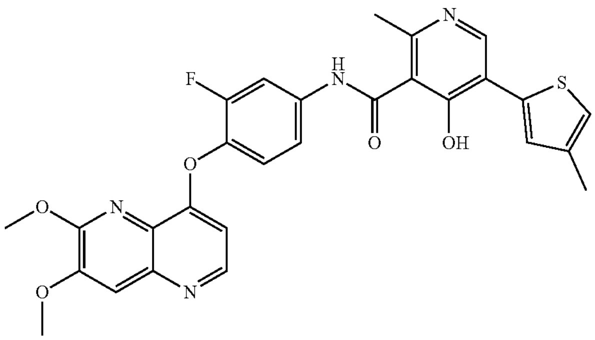 [SMILES: COc1cc2nccc(Oc3ccc(NC(=O)c4c(C)ncc(-c5cc(C)cs5)c4O)cc3F)c2nc1OC] | N-[4-[(6,7-dimethoxy-1,5-naphthyridin-4-yl)oxy]-3-fluorophenyl]-4-hydroxy-2-methyl-5-(4-methylthiophen-2-yl)pyridine-3-carboxamide |
| 126 | 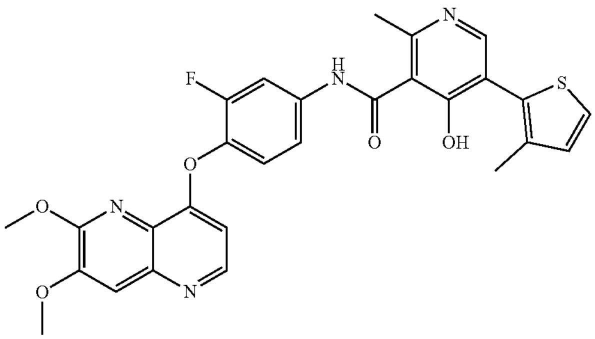 [SMILES: COc1cc2nccc(Oc3ccc(NC(=O)c4c(C)ncc(-c5sccc5C)c4O)cc3F)c2nc1OC] | N-[4-[(6,7-dimethoxy-1,5-naphthyridin-4-yl)oxy]-3-fluorophenyl]-4-hydroxy-2-methyl-5-(3-methylthiophen-2-yl)pyridine-3-carboxamide |
| 127 | 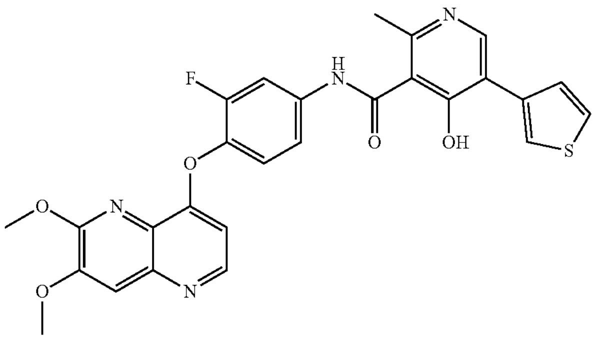 | N-[4-[(6,7-dimethoxy-1,5-naphthyridin-4-yl)oxy]-3-fluorophenyl]-4-hydroxy-2-methyl-5-thiophen-3-ylpyridine-3-carboxamide |
| 128 | 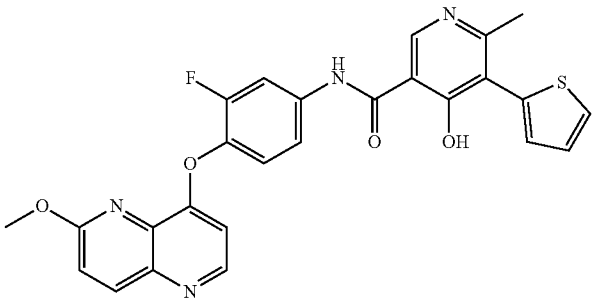 [SMILES: COc1ccc2nccc(Oc3ccc(NC(=O)c4cnc(C)c(-c5cccs5)c4O)cc3F)c2n1] | N-[3-fluoro-4-[(6-methoxy-1,5-naphthyridin-4-yl)oxy]phenyl]-4-hydroxy-6-methyl-5-thiophen-2-ylpyridine-3-carboxamide |

TABLE 1B-continued

| Compound No. | Structure | Compound Name |
|---|---|---|
| 129 | 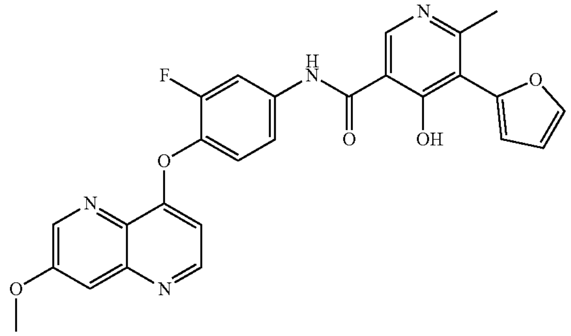 [SMILES: COc1cnc2c(Oc3ccc(NC(=O)c4cnc(C)c(-c5ccco5)c4O)cc3F)ccnc2c1] | 5-(furan-2-yl)-4-hydroxy-N-[4-[(7-methoxy-1,5-naphthyridin-4-yl)oxy]phenyl]-6-methylpyridine-3-carboxamide |
| 135 | 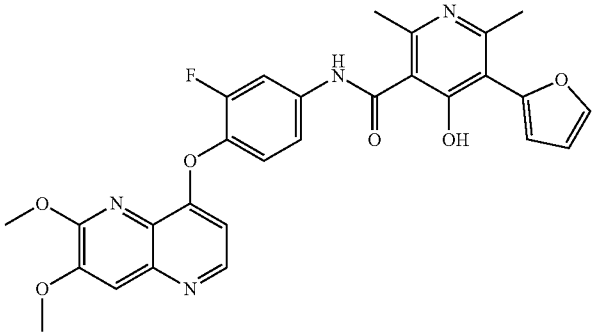 [SMILES: COc1cc2nccc(Oc3ccc(NC(=O)c4c(C)nc(C)c(-c5ccco5)c4O)cc3F)c2nc1OC] | N-[4-[(6,7-dimethoxy-1,5-naphthyridin-4-yl)oxy]-3-fluorophenyl]-5-(furan-2-yl)-4-hydroxy-2,6-dimethylpyridine-3-carboxamide |
| 136 | 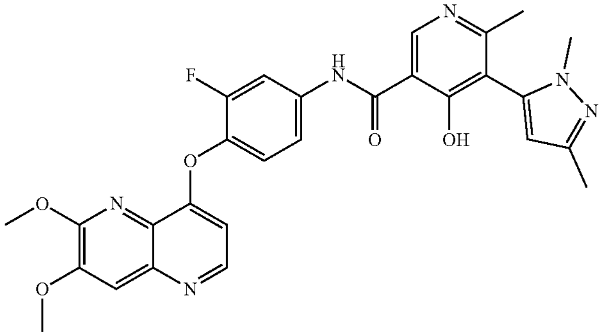 [SMILES: COc1cc2nccc(Oc3ccc(NC(=O)c4cnc(C)c(-c5cc(C)nn5C)c4O)cc3F)c2nc1OC] | N-[4-[(6,7-dimethoxy-1,5-naphthyridin-4-yl)oxy]-3-fluorophenyl]-5-(2,5-dimethylpyrazol-3-yl)-4-hydroxy-6-methylpyridine-3-carboxamide |
| 137 | 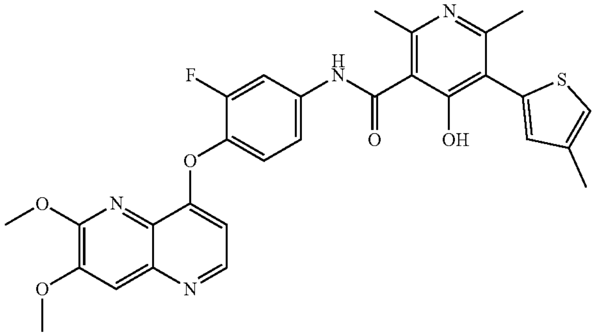 [SMILES: COc1cc2nccc(Oc3ccc(NC(=O)c4c(C)nc(C)c(-c5cc(C)cs5)c4O)cc3F)c2nc1OC] | N-[4-[(6,7-dimethoxy-1,5-naphthyridin-4-yl)oxy]-3-fluorophenyl]-4-hydroxy-2,6-dimethyl-5-(4-methylthiophen-2-yl)pyridine-3-carboxamide |

TABLE 1B-continued

| Compound No. | Structure | Compound Name |
|---|---|---|
| 138 | 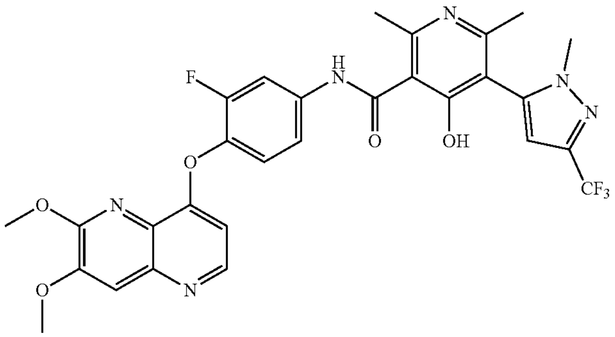 [SMILES: COc1cc2nccc(Oc3ccc(NC(=O)c4c(C)nc(C)c(-c5cc(C(F)(F)F)nn5C)c4O)cc3F)c2nc1OC] | N-[4-[(6,7-dimethoxy-1,5-naphthyridin-4-yl)oxy]-3-fluorophenyl]-4-hydroxy-2,6-dimethyl-5-[2-methyl-5-(trifluoromethyl)pyrazol-3-yl]pyridine-3-carboxamide |
| 139 | 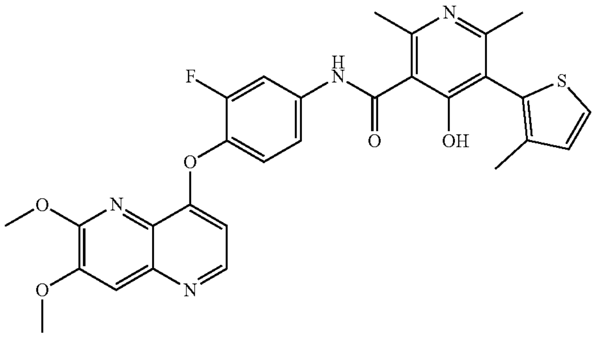 [SMILES: COc1cc2nccc(Oc3ccc(NC(=O)c4c(C)nc(C)c(-c5sccc5C)c4O)cc3F)c2nc1OC] | N-[4-[(6,7-dimethoxy-1,5-naphthyridin-4-yl)oxy]-3-fluorophenyl]-4-hydroxy-2,6-dimethyl-5-(3-methylthiophen-2-yl)pyridine-3-carboxamide |
| 140 | 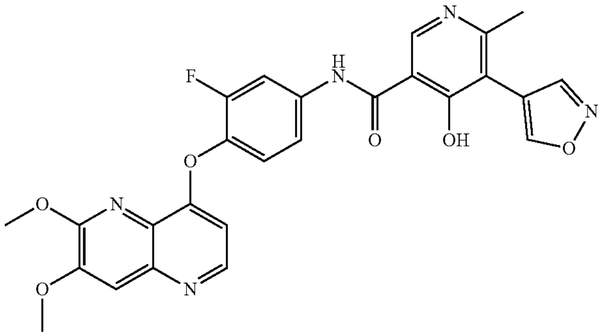 [SMILES: COc1cc2nccc(Oc3ccc(NC(=O)c4cnc(C)c(-c5cnoc5)c4O)cc3F)c2nc1OC] | N-[4-[(6,7-dimethoxy-1,5-naphthyridin-4-yl)oxy]-3-fluorophenyl]-4-hydroxy-6-methyl-5-(1,2-oxazol-4-yl)pyridine-3-carboxamide |
| 141 | 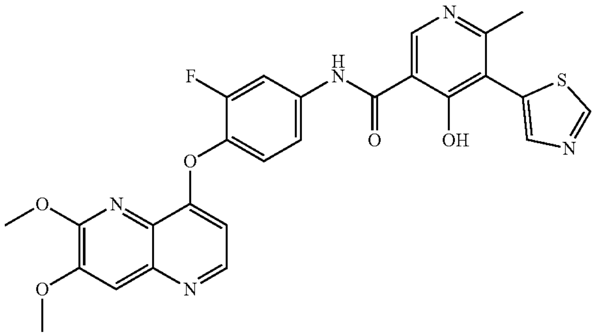 [SMILES: COc1cc2nccc(Oc3ccc(NC(=O)c4cnc(C)c(-c5cncs5)c4O)cc3F)c2nc1OC] | N-[4-[(6,7-dimethoxy-1,5-naphthyridin-4-yl)oxy]-3-fluorophenyl]-4-hydroxy-6-methyl-5-(1,3-thiazol-5-yl)pyridine-3-carboxamide |

TABLE 1B-continued

| Compound No. | Structure | Compound Name |
|---|---|---|
| 142 | 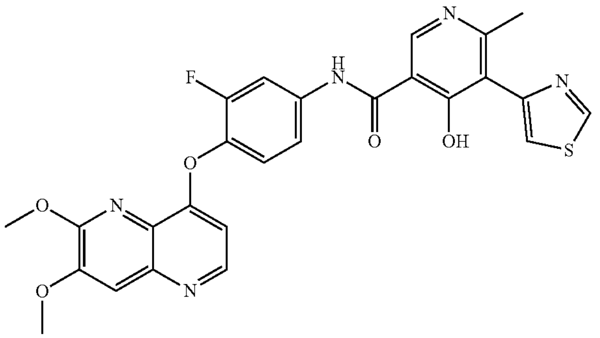 [SMILES: COc1cc2nccc(Oc3ccc(NC(=O)c4cnc(C)c(-c5cscn5)c4O)cc3F)c2nc1OC] | N-[4-[(6,7-dimethoxy-1,5-naphthyridin-4-yl)oxy]-3-fluorophenyl]-4-hydroxy-6-methyl-5-(l,3-thiazol-4-yl)pyridine-3-carboxamide |
| 143 | 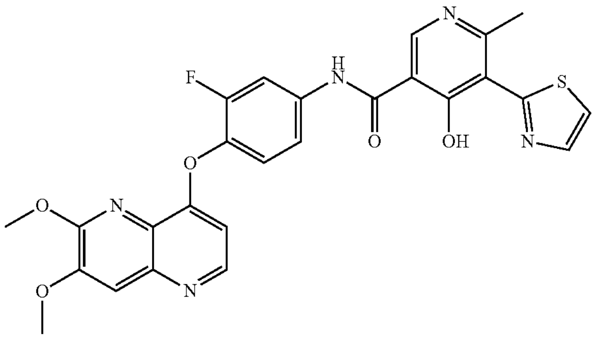 [SMILES: COc1cc2nccc(Oc3ccc(NC(=O)c4cnc(C)c(-c5nccs5)c4O)cc3F)c2nc1OC] | N-[4-[(6,7-dimethoxy-1,5-naphthyridin-4-yl)oxy]-3-fluorophenyl]-4-hydroxy-6-methyl-5-(l,3-thiazol-2-yl)pyridine-3-carboxamide |
| 147 | 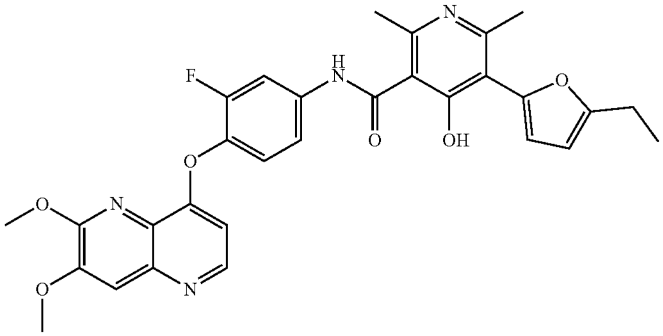 [SMILES: CCc1ccc(-c2c(C)nc(C)c(C(=O)Nc3ccc(Oc4ccnc5cc(OC)c(OC)nc45)c(F)c3)c2O)o1] | N-[4-[(6,7-dimethoxy-1,5-naphthyridin-4-yl)oxy]-3-fluorophenyl]-5-(5-ethylfuran-2-yl)-4-hydroxy-2,6-dimethylpyridine-3-carboxamide |
| 148 | 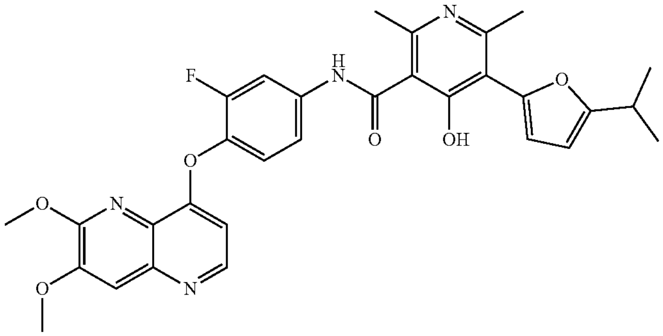 [SMILES: COc1cc2nccc(Oc3ccc(NC(=O)c4c(C)nc(C)c(-c5ccc(C(C)C)o5)c4O)cc3F)c2nc1OC] | N-[4-[(6,7-dimethoxy-1,5-naphthyridin-4-yl)oxy]-3-fluorophenyl]-4-hydroxy-2,6-dimethyl-5-(5-propan-2-ylfuran-2-yl)pyridine-3-carboxamide |

TABLE 1B-continued

| Compound No. | Structure | Compound Name |
|---|---|---|
| 151 | 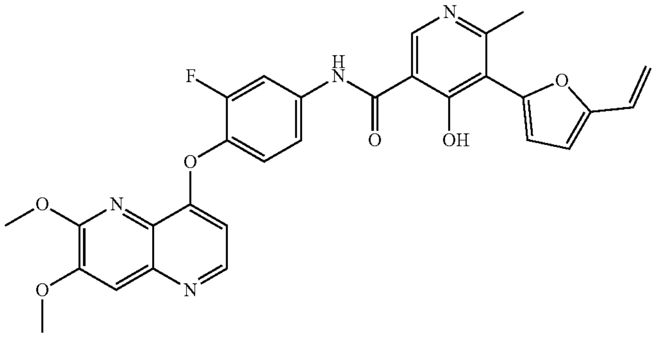 [SMILES: C=Cc1ccc(-c2c(C)ncc(C(=O)Nc3ccc(Oc4ccnc5cc(OC)c(OC)nc45)c(F)c3)c2O)o1] | N-[4-[(6,7-dimethoxy-1,5-naphthyridin-4-yl)oxy]-3-fluorophenyl]-5-(5-ethenylfuran-2-yl)-4-hydroxy-6-methylpyridine-3-carboxamide |
| 152 | 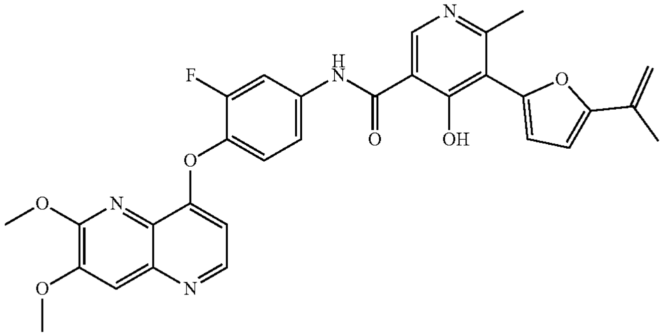 [SMILES: C=C(C)c1ccc(-c2c(C)ncc(C(=O)Nc3ccc(Oc4ccnc5cc(OC)c(OC)nc45)c(F)c3)c2O)o1] | N-[4-[(6,7-dimethoxy-1,5-naphthyridin-4-yl)oxy]-3-fluorophenyl]-4-hydroxy-6-methyl-5-(5-prop-1-en-2-ylfuran-2-yl)pyridine-3-carboxamide |
| 153 | 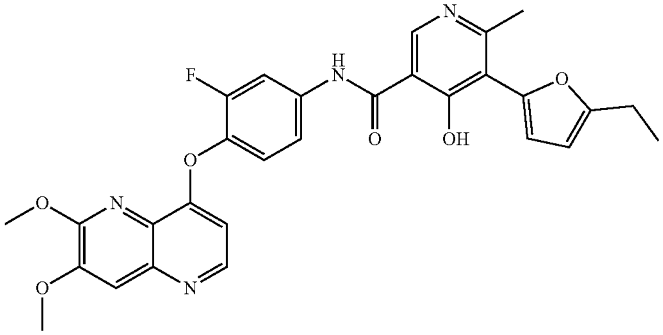 [SMILES: CCc1ccc(-c2c(C)ncc(C(=O)Nc3ccc(Oc4ccnc5cc(OC)c(OC)nc45)c(F)c3)c2O)o1] | N-[4-[(6,7-dimethoxy-1,5-naphthyridin-4-yl)oxy]-3-fluorophenyl]-5-(5-ethylfuran-2-yl)-4-hydroxy-6-methylpyridine-3-carboxamide |
| 154 | 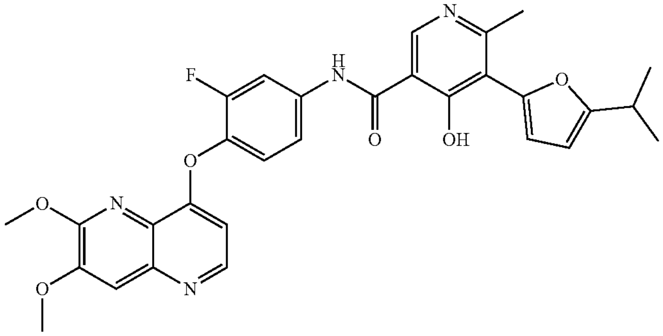 [SMILES: COc1cc2nccc(Oc3ccc(NC(=O)c4cnc(C)c(-c5ccc(C(C)C)o5)c4O)cc3F)c2nc1OC] | N-[4-[(6,7-dimethoxy-1,5-naphthyridin-4-yl)oxy]-3-fluorophenyl]-4-hydroxy-6-methyl-5-(5-propan-2-ylfuran-2-yl)pyridine-3-carboxamide |

TABLE 1B-continued

| Compound No. | Structure | Compound Name |
|---|---|---|
| 155 | 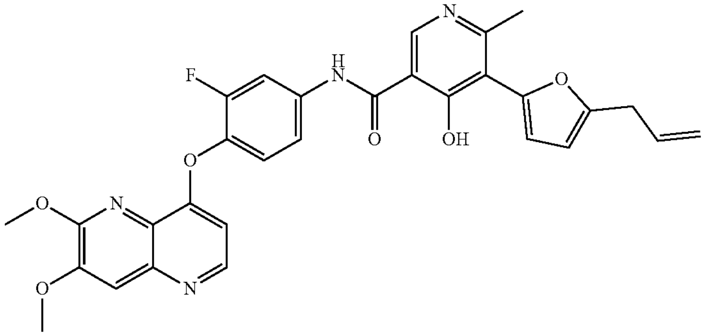 [SMILES: C=CCc1ccc(-c2c(C)ncc(C(=O)Nc3ccc(Oc4ccnc5cc(OC)c(OC)nc45)c(F)c3)c2O)o1] | N-[4-[(6,7-dimethoxy-1,5-naphthyridin-4-yl)oxy]-3-fluorophenyl]-4-hydroxy-6-methyl-5-(5-prop-2-enylfuran-2-yl)pyridine-3-carboxamide |
| 160 | 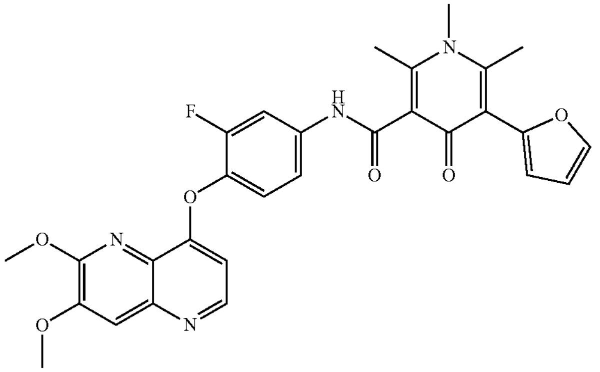 [SMILES: COc1cc2nccc(Oc3ccc(NC(=O)c4c(C)n(C)c(C)c(-c5ccco5)c4=O)cc3F)c2nc1OC] | N-[4-[(6,7-dimethoxy-1,5-naphthyridin-4-yl)oxy]-3-fluorophenyl]-5-(furan-2-yl)-1,2,6-trimethyl-4-oxopyridine-3-carboxamide |

or a pharmaceutically acceptable salt, a stereoisomer, or a mixture of stereoisomers thereof.

TABLE 1C

| Compound No. | Structure | Compound Name |
|---|---|---|
| 155A | 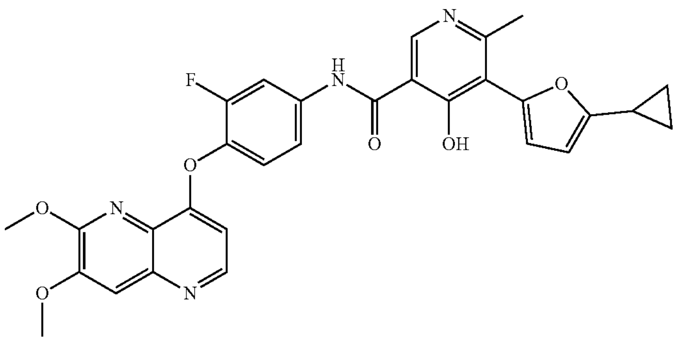 [SMILES: COc1cc2nccc(Oc3ccc(NC(=O)c4cnc(C)c(-c5ccc(C6CC6)o5)c4O)cc3F)c2nc1OC] | 5-(5-cyclopropylfuran-2-yl)-N-[4-[(6,7-dimethoxy-1,5-naphthyridin-4-yl)oxy]-3-fluorophenyl]-4-hydroxy-6-methylpyridine-3-carboxamide |

TABLE 1C-continued

| Compound No. | Structure | Compound Name |
|---|---|---|
| 155B | 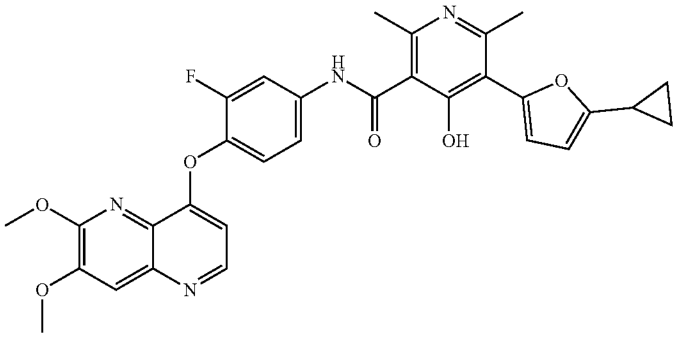 [SMILES: COc1cc2nccc(Oc3ccc(NC(=O)c4c(C)nc(C)c(-c5ccc(C6CC6)o5)c4O)cc3F)c2nc1OC] | 5-(5-cyclopropylfuran-2-yl)-N-[4-[(6,7-dimethoxy-1,5-naphthyridin-4-yl)oxy]-3-fluorophenyl]-4-hydroxy-2,6-dimethylpyridine-3-carboxamide |
| 161 | 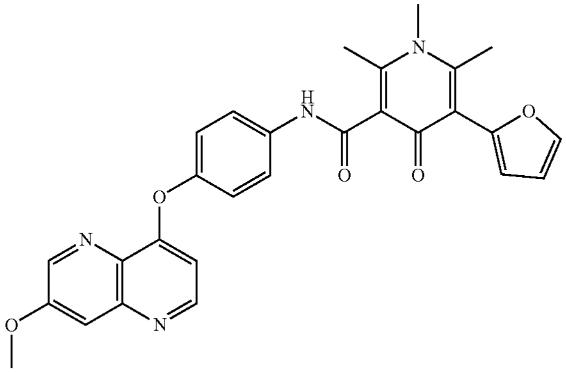 | 5-(furan-2-yl)-N-[4-[(7-methoxy-1,5-naphthyridin-4-yl)oxy]phenyl]-1,2,6-trimethyl-4-oxopyridine-3-carboxamide |
| 162 | 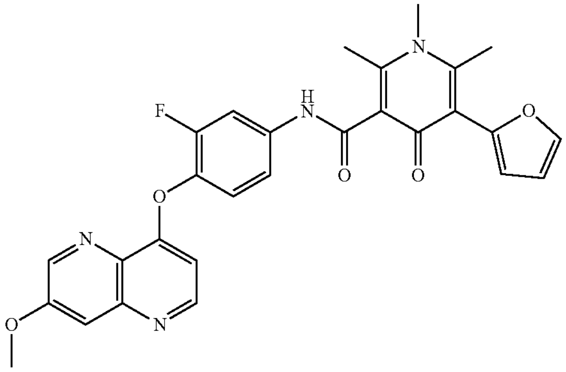 | N-[3-fluoro-4-[(7-methoxy-1,5-naphthyridin-4-yl)oxy]phenyl]-5-(furan-2-yl)-1,2,6-trimethyl-4-oxopyridine-3-carboxamide |
| 163 | 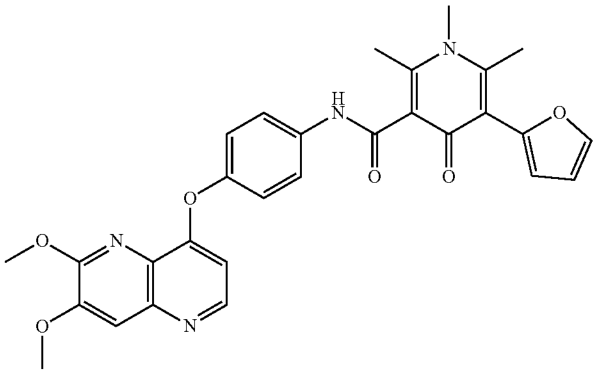 [SMILES: COc1cc2nccc(Oc3ccc(NC(=O)c4c(C)n(C)c(C)c(-c5ccco5)c4=O)cc3)c2nc1OC] | N-[4-[(6,7-dimethoxy-1,5-naphthyridin-4-yl)oxy]-2,5-difluorophenyl]-5-(furan-2-yl)-1,2,6-trimethyl-4-oxopyridine-3-carboxamide |

TABLE 1C-continued

| Compound No. | Structure | Compound Name |
|---|---|---|
| 164 | 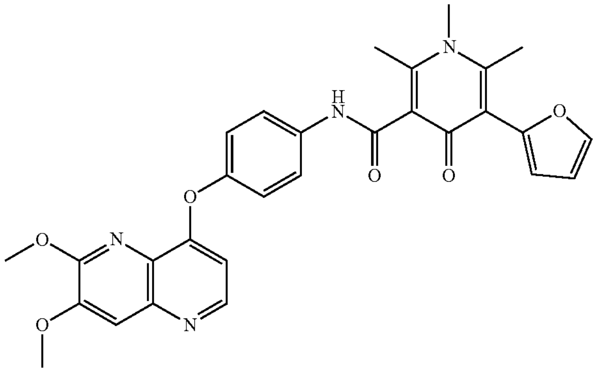 [SMILES: COc1cc2nccc(Oc3ccc(NC(=O)c4c(C)n(C)c(C)c(-c5ccco5)c4=O)cc3)c2nc1OC] | N-[4-[(6,7-dimethoxy-1,5-naphthyridin-4-yl)oxy]phenyl]-5-(furan-2-yl)-1,2,6-trimethyl-4-oxopyridine-3-carboxamide |
| 165 | 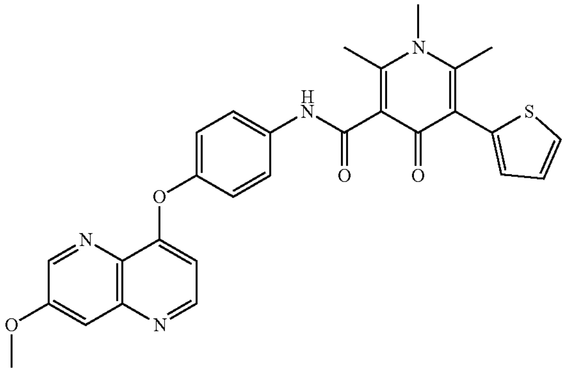 [SMILES: COc1cnc2c(Oc3ccc(NC(=O)c4c(C)n(C)c(C)c(-c5cccs5)c4=O)cc3)ccnc2c1] | N-[4-[(7-methoxy-1,5-naphthyridin-4-yl)oxy]phenyl]-1,2,6-trimethyl-4-oxo-5-thiophen-2-ylpyridine-3-carboxamide |
| 166 | 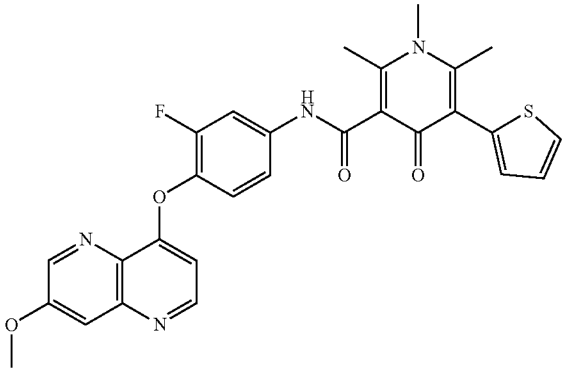 [SMILES: COc1cnc2c(Oc3ccc(NC(=O)c4c(C)n(C)c(C)c(-c5cccs5)c4=O)cc3F)ccnc2c1] | N-[3-fluoro-4-[(7-methoxy-1,5-naphthyridin-4-yl)oxy]phenyl]-1,2,6-trimethyl-4-oxo-5-thiophen-2-ylpyridine-3-carboxamide |
| 167 | 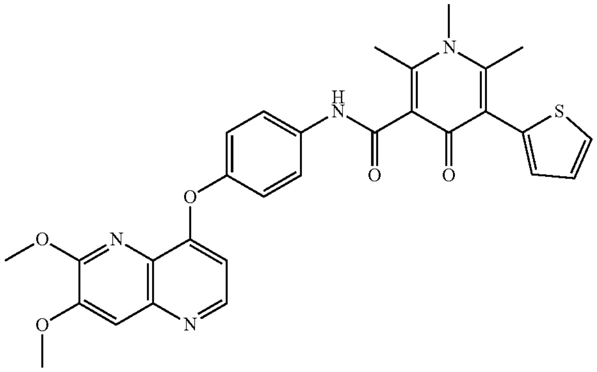 | N-[4-[(6,7-dimethoxy-1,5-naphthyridin-4-yl)oxy]phenyl]-1,2,6-trimethyl-4-oxo-5-thiophen-2-ylpyridine-3-carboxamide |

TABLE 1C-continued

| Compound No. | Structure | Compound Name |
|---|---|---|
| 168 | 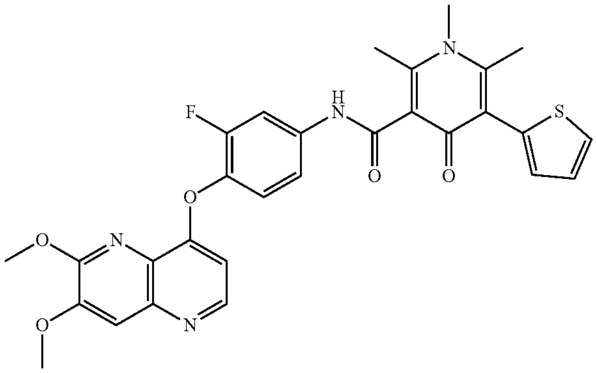 [SMILES: COc1cc2nccc(Oc3ccc(NC(=O)c4c(C)n(C)c(C)c(-c5cccs5)c4=O)cc3F)c2nc1OC] | N-[4-[(6,7-dimethoxy-1,5-naphthyridin-4-yl)oxy]-3-fluorophenyl]-1,2,6-trimethyl-4-oxo-5-thiophen-2-ylpyridine-3-carboxamide |
| 195 | 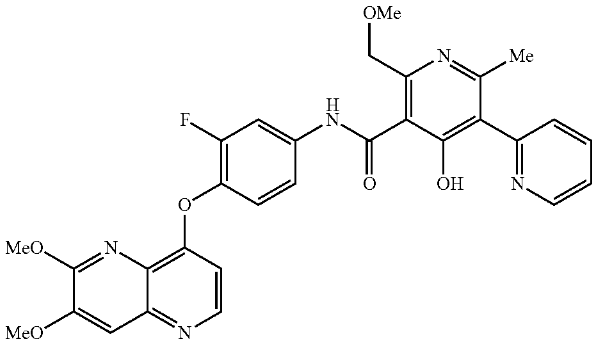 [SMILES: COCc1nc(C)c(-c2ccccn2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-hydroxy-2-(methoxymethyl)-6-methyl-5-pyridin-2-ylpyridine-3-carboxamide |
| 196 | 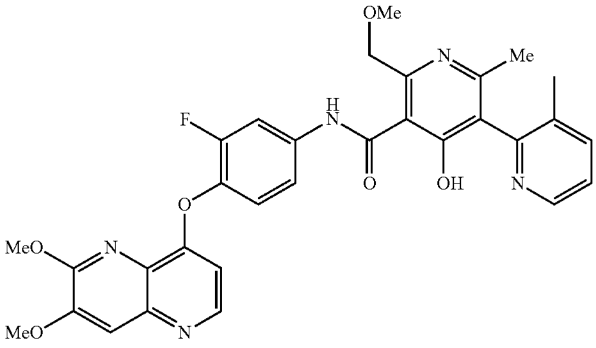 [SMILES: COCc1nc(C)c(-c2ncccc2C)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-hydroxy-2-(methoxymethyl)-6-methyl-5-(3-methylpyridin-2-yl)pyridine-3-carboxamide |
| 197 | 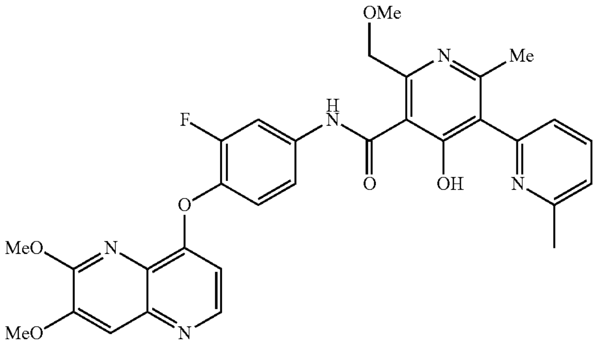 [SMILES: COCc1nc(C)c(-c2cccc(C)n2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-hydroxy-2-(methoxymethyl)-6-methyl-5-(6-methylpyridin-2-yl)pyridine-3-carboxamide |

TABLE 1C-continued

| Compound No. | Structure | Compound Name |
| --- | --- | --- |
| 198 | 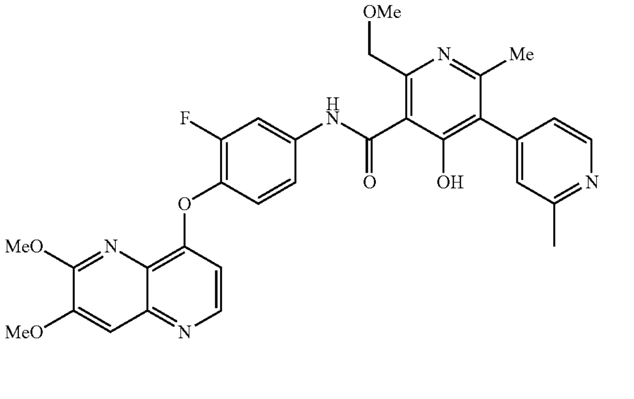 [SMILES: COCc1nc(C)c(-c2ccnc(C)c2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-hydroxy-2-(methoxymethyl)-6-methyl-5-(2-methylpyridin-4-yl)pyridine-3-carboxamide |
| 200 | 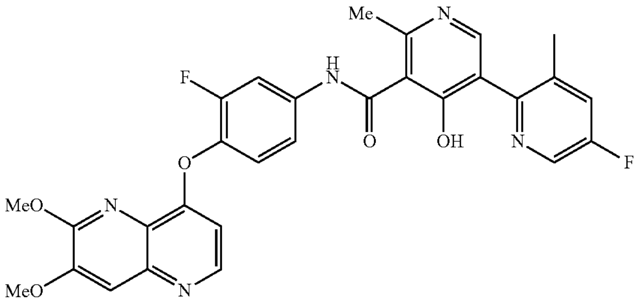 [SMILES: COc1cc2nccc(Oc3ccc(NC(=O)c4c(C)ncc(-c5ncc(F)cc5C)c4O)cc3F)c2nc1OC] | N-[4-[(6,7-dimethoxy-1,5-naphthyridin-4-yl)oxy]-3-fluorophenyl]-5-(5-fluoro-3-methylpyridin-2-yl)-4-hydroxy-2-methylpyridine-3-carboxamide |
| 212 | 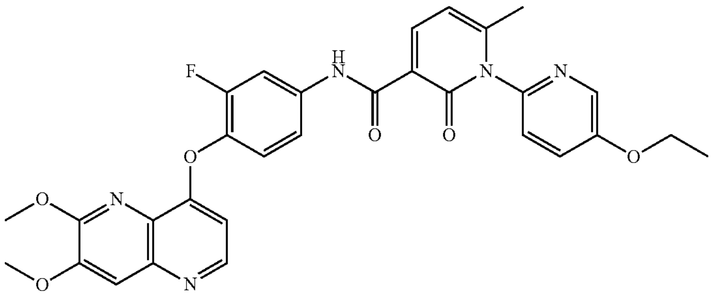 [SMILES: CCOc1ccc(-n2c(C)ccc(C(=O)Nc3ccc(Oc4ccnc5cc(OC)c(OC)nc45)c(F)c3)c2=O)nc1] | N-[4-[(6,7-dimethoxy-1,5-naphthyridin-4-yl)oxy]-3-fluorophenyl]-1-(5-ethoxy-pyridin-2-yl)-6-methyl-2-oxopyridine-3-carboxamide |
| 213 | 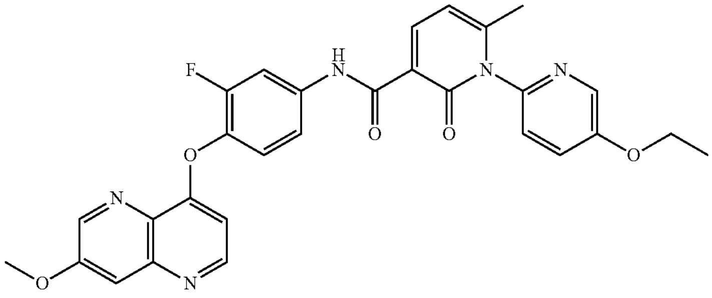 [SMILES: CCOc1ccc(-n2c(C)ccc(C(=O)Nc3ccc(Oc4ccnc5cc(OC)cnc45)c(F)c3)c2=O)nc1] | 1-(5-ethoxy-pyridin-2-yl)-N-[3-fluoro-4-[(7-methoxy-1,5-naphthyridin-4-yl)oxy]phenyl]-6-methyl-2-oxopyridine-3-carboxamide |

TABLE 1C-continued

| Compound No. | Structure | Compound Name |
|---|---|---|
| 214 | 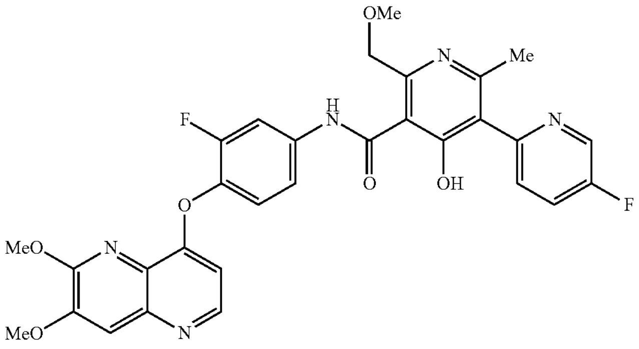 [SMILES: COCc1nc(C)c(-c2ccc(F)cn2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(5-fluoropyridin-2-yl)-4-hydroxy-2-(methoxymethyl)-6-methylpyridine-3-carboxamide |
| 215 | 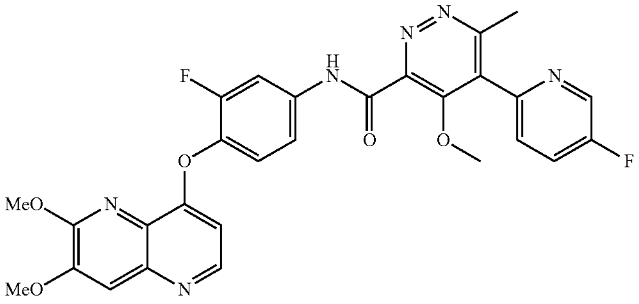 [SMILES: COc1cc2nccc(Oc3ccc(NC(=O)c4nnc(C)c(-c5ccc(F)cn5)c4OC)cc3F)c2nc1OC] | N-[4-[(6,7-dimethoxy-1,5-naphthyridin-4-yl)oxy]-3-fluorophenyl]-5-(5-fluoropyridin-2-yl)-4-methoxy-6-methylpyridazine-3-carboxamide |
| 216 | 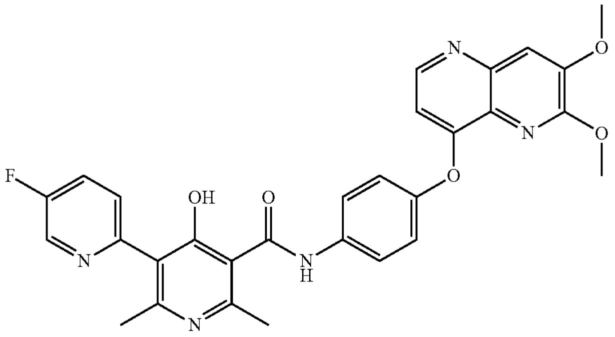 [SMILES: COc1cc2nccc(Oc3ccc(NC(=O)c4c(C)nc(C)c(-c5ccc(F)cn5)c4O)cc3)c2nc1OC] | N-[4-[(6,7-dimethoxy-1,5-naphthyridin-4-yl)oxy]phenyl]-5-(5-fluoropyridin-2-yl)-4-hydroxy-2,6-dimethylpyridine-3-carboxamide |
| 217 | 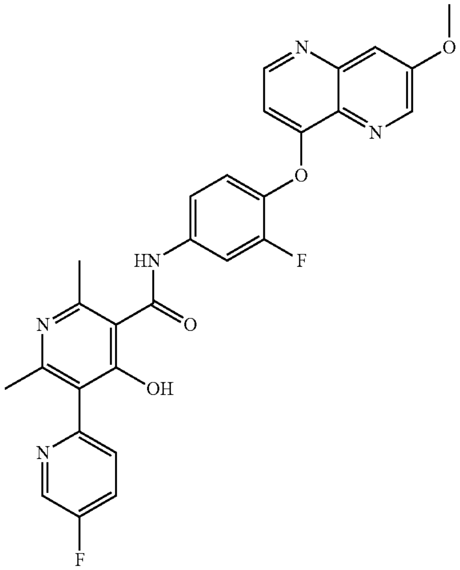 | N-[3-fluoro-4-[(7-methoxy-1,5-naphthyridin-4-yl)oxy]phenyl]-5-(5-fluoropyridin-2-yl)-4-hydroxy-2,6-dimethylpyridine-3-carboxamide |

TABLE 1C-continued

| Compound No. | Structure | Compound Name |
|---|---|---|
| 218 | 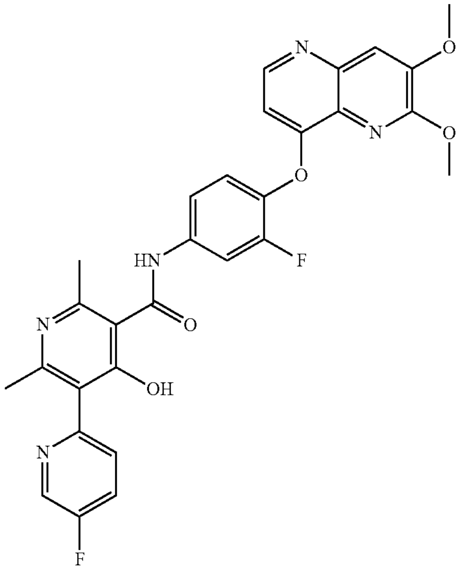 | N-[4-[(6,7-dimethoxy-1,5-naphthyridin-4-yl)oxy]-3-fluorophenyl]-5-(5-fluoropyridin-2-yl)-4-hydroxy-2,6-dimethylpyridine-3-carboxamide |
| 219 | 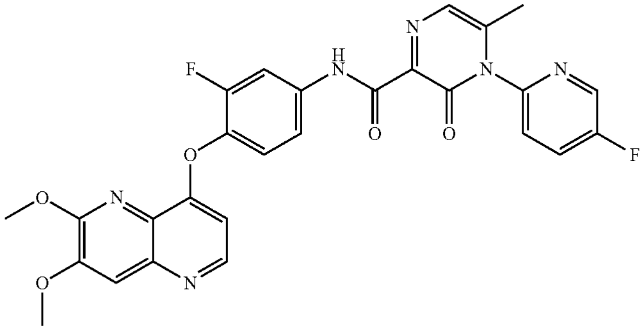 [SMILES: COc1cc2nccc(Oc3ccc(NC(=O)c4ncc(C)n(-c5ccc(F)cn5)c4=O)cc3F)c2nc1OC] | N-[4-[(6,7-dimethoxy-1,5-naphthyridin-4-yl)oxy]-3-fluorophenyl]-4-(5-fluoropyridin-2-yl)-5-methyl-3-oxopyrazine-2-carboxamide |
| 220 | 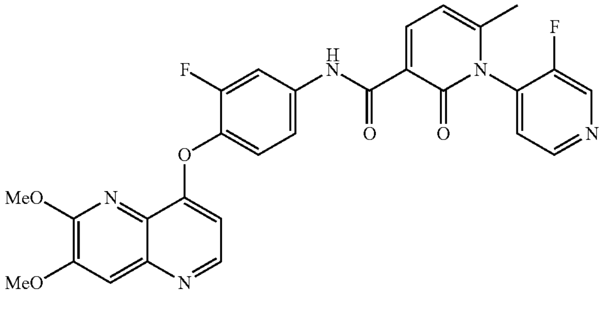 [SMILES: COc1cc2nccc(Oc3ccc(NC(=O)c4ccc(C)n(-c5ccncc5F)c4=O)cc3F)c2nc1OC] | N-[4-[(6,7-dimethoxy-1,5-naphthyridin-4-yl)oxy]-3-fluorophenyl]-1-(3-fluoropyridin-4-yl)-6-methyl-2-oxopyridine-3-carboxamide |
| 221 | 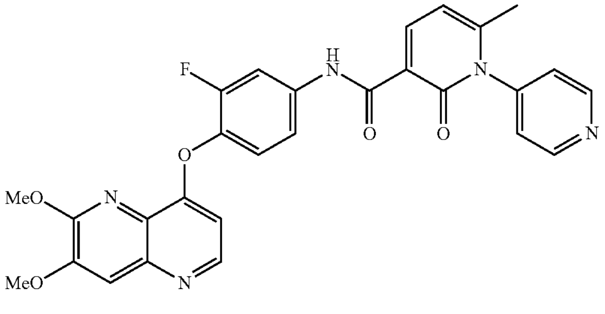 [SMILES: COc1cc2nccc(Oc3ccc(NC(=O)c4ccc(C)n(-c5ccncc5)c4=O)cc3F)c2nc1OC] | N-[4-[(6,7-dimethoxy-1,5-naphthyridin-4-yl)oxy]-3-fluorophenyl]-6-methyl-2-oxo-1-pyridin-4-ylpyridine-3-carboxamide |

TABLE 1C-continued

| Compound No. | Structure | Compound Name |
|---|---|---|
| 222 | 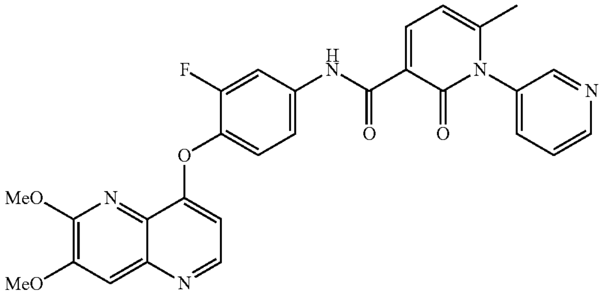 [SMILES: COc1cc2nccc(Oc3ccc(NC(=O)c4ccc(C)n(-c5cccnc5)c4=O)cc3F)c2nc1OC] | N-[4-[(6,7-dimethoxy-1,5-naphthyridin-4-yl)oxy]-3-fluorophenyl]-6-methyl-2-oxo-1-pyridin-3-ylpyridine-3-carboxamide |
| 223 | 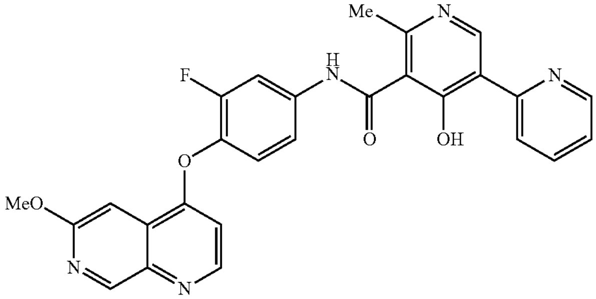 [SMILES: COc1cc2c(Oc3ccc(NC(=O)c4c(C)ncc(-c5ccccn5)c4O)cc3F)ccnc2cn1] | N-[3-fluoro-4-[(6-methoxy-1,7-naphthyridin-4-yl)oxy]phenyl]-4-hydroxy-2-methyl-5-pyridin-2-ylpyridine-3-carboxamide |
| 224 | 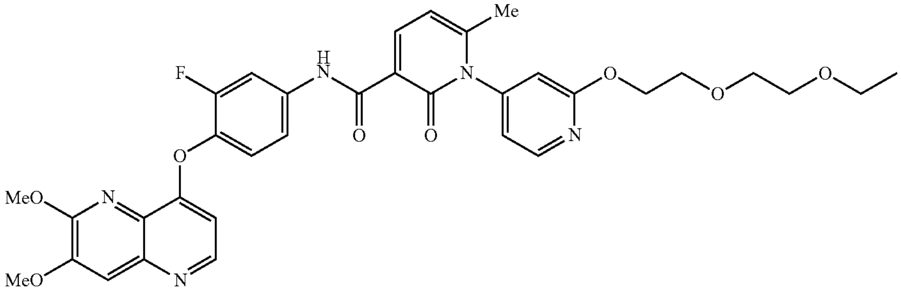 [SMILES: CCOCCOCCOc1cc(-n2c(C)ccc(C(=O)Nc3ccc(Oc4ccnc5cc(OC)c(OC)nc45)c(F)c3)c2=O)ccn1] | N-[4-[(6,7-dimethoxy-1,5-naphthyridin-4-yl)oxy]-3-fluorophenyl]-1-[2-[2-(2-ethoxyethoxy)ethoxy]pyridin-4-yl]-6-methyl-2-oxopyridine-3-carboxamide |
| 225 | 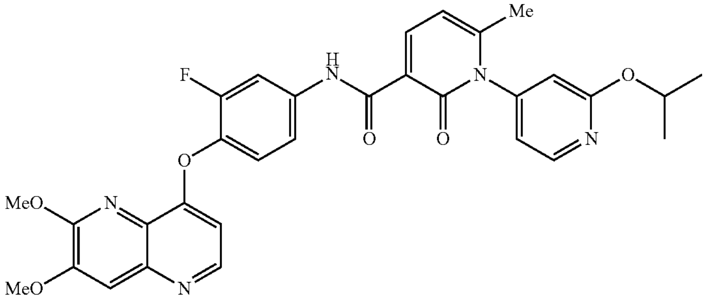 [SMILES: COc1cc2nccc(Oc3ccc(NC(=O)c4ccc(C)n(-c5ccnc(OC(C)C)c5)c4=O)cc3F)c2nc1OC] | N-[4-[(6,7-dimethoxy-1,5-naphthyridin-4-yl)oxy]-3-fluorophenyl]-6-methyl-2-oxo-1-(2-propan-2-yloxypyridin-4-yl)pyridine-3-carboxamide |
| 226 | 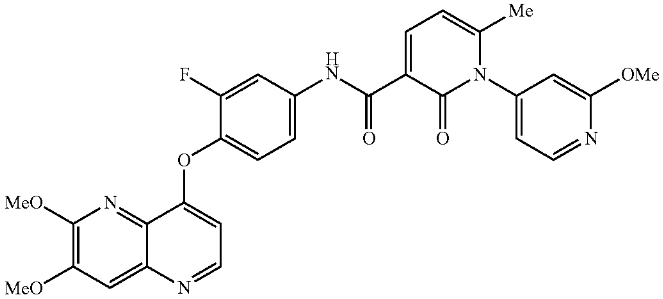 [SMILES: COc1cc(-n2c(C)ccc(C(=O)Nc3ccc(Oc4ccnc5cc(OC)c(OC)nc45)c(F)c3)c2=O)ccn1] | N-[4-[(6,7-dimethoxy-1,5-naphthyridin-4-yl)oxy]-3-fluorophenyl]-1-(2-methoxypyridin-4-yl)-6-methyl-2-oxopyridine-3-carboxamide |

TABLE 1C-continued

| Compound No. | Structure | Compound Name |
|---|---|---|
| 227 | 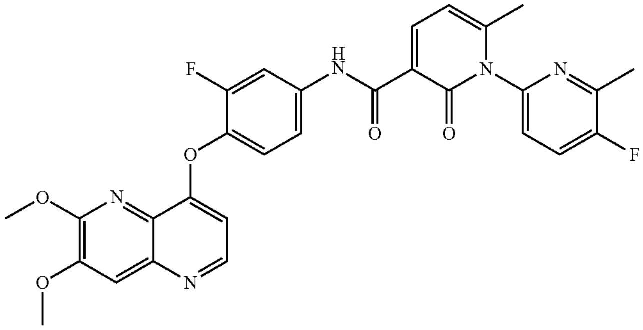 [SMILES: COc1cc2nccc(Oc3ccc(NC(=O)c4ccc(C)n(-c5ccc(F)c(C)n5)c4=O)cc3F)c2nc1OC] | N-[4-[(6,7-dimethoxy-1,5-naphthyridin-4-yl)oxy]-3-fluorophenyl]-1-(5-fluoro-6-methylpyridin-2-yl)-6-methyl-2-oxopyridine-3-carboxamide |
| 228 | 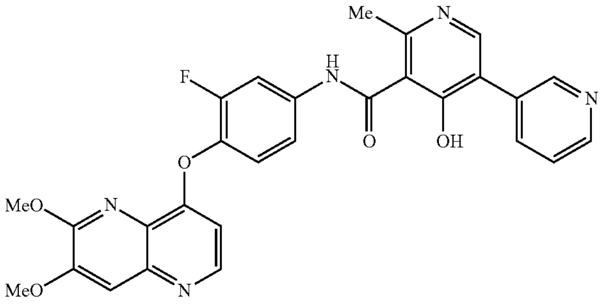 [SMILES: COc1cc2nccc(Oc3ccc(NC(=O)c4c(C)ncc(-c5cccnc5)c4O)cc3F)c2nc1OC] | N-[4-[(6,7-dimethoxy-1,5-naphthyridin-4-yl)oxy]-3-fluorophenyl]-4-hydroxy-2-methyl-5-pyridin-3-ylpyridine-3-carboxamide |
| 229 | 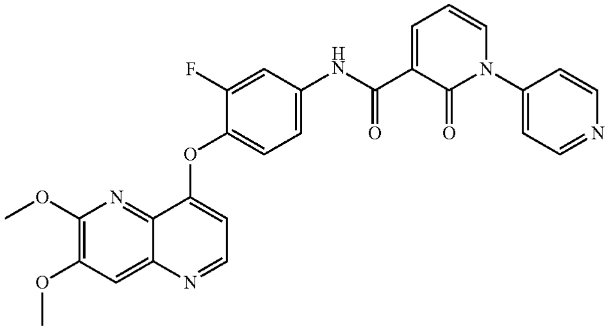 [SMILES: COc1cc2nccc(Oc3ccc(NC(=O)c4cccn(-c5ccncc5)c4=O)cc3F)c2nc1OC] | N-[4-[(6,7-dimethoxy-1,5-naphthyridin-4-yl)oxy]-3-fluorophenyl]-2-oxo-1-pyridin-4-ylpyridine-3-carboxamide |
| 230 | 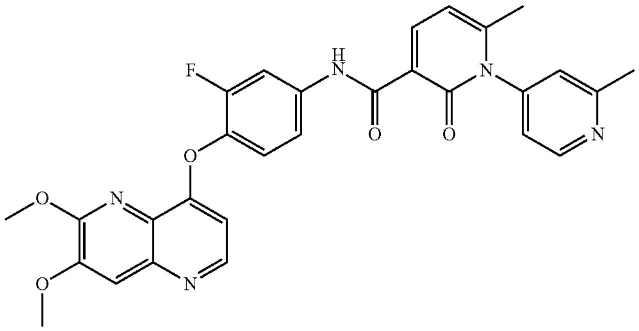 | N-[4-[(6,7-dimethoxy-1,5-naphthyridin-4-yl)oxy]-3-fluorophenyl]-6-methyl-1-(2-methylpyridin-4-yl)-2-oxopyridine-3-carboxamide |

TABLE 1C-continued

| Compound No. | Structure | Compound Name |
|---|---|---|
| 231 | 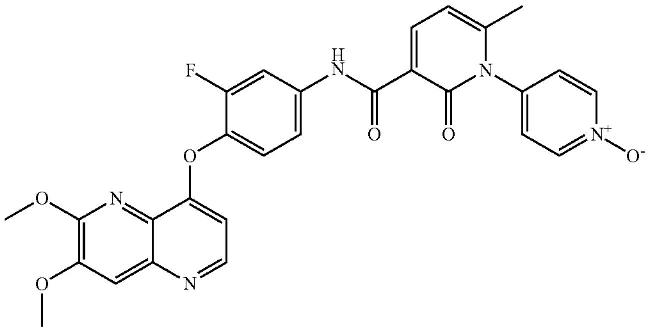 [SMILES: COc1cc2nccc(Oc3ccc(NC(=O)c4ccc(C)n(-c5cc[n+]([O-])cc5)c4=O)cc3F)c2nc1OC] | N-[4-[(6,7-dimethoxy-1,5-naphthyridin-4-yl)oxy]-3-fluorophenyl]-6-methyl-1-(1-oxidopyridin-1-ium-4-yl)-2-oxopyridine-3-carboxamide |
| 232 | 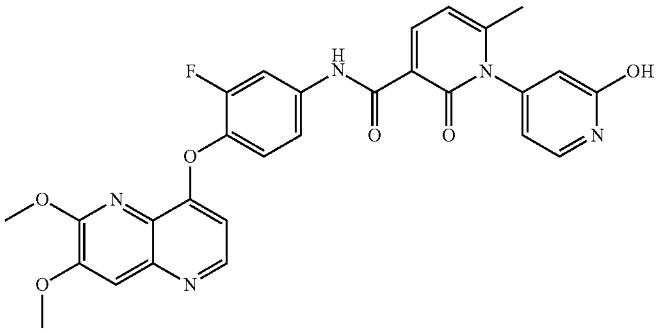 [SMILES: COc1cc2nccc(Oc3ccc(NC(=O)c4ccc(C)n(-c5ccnc(O)c5)c4=O)cc3F)c2nc1OC] | N-[4-[(6,7-dimethoxy-1,5-naphthyridin-4-yl)oxy]-3-fluorophenyl]-1-(2-hydroxypyridin-4-yl)-6-methyl-2-oxopyridine-3-carboxamide |
| 233 | 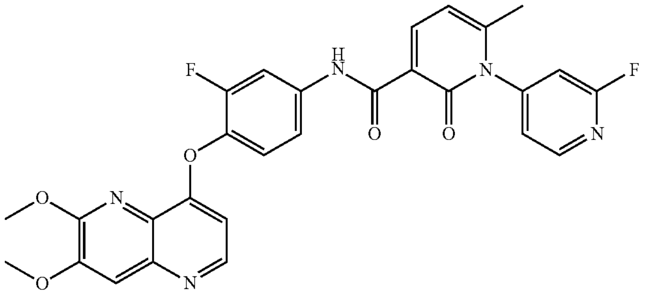 [SMILES: COc1cc2nccc(Oc3ccc(NC(=O)c4ccc(C)n(-c5ccnc(F)c5)c4=O)cc3F)c2nc1OC] | N-[4-[(6,7-dimethoxy-1,5-naphthyridin-4-yl)oxy]-3-fluorophenyl]-1-(2-fluoropyridin-4-yl)-6-methyl-2-oxopyridine-3-carboxamide |
| 234 | 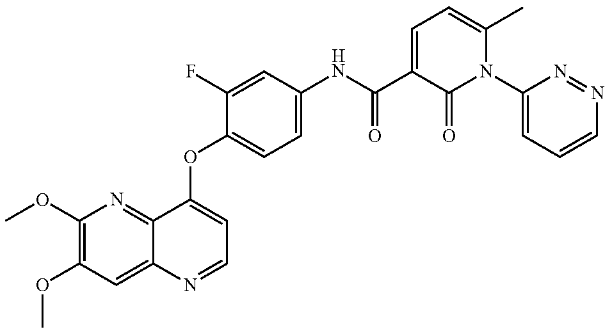 [SMILES: COc1cc2nccc(Oc3ccc(NC(=O)c4ccc(C)n(-c5cccnn5)c4=O)cc3F)c2nc1OC] | N-[4-[(6,7-dimethoxy-1,5-naphthyridin-4-yl)oxy]-3-fluorophenyl]-6-methyl-2-oxo-1-pyridazin-3-ylpyridine-3-carboxamide |

TABLE 1C-continued

| Compound No. | Structure | Compound Name |
|---|---|---|
| 235 | 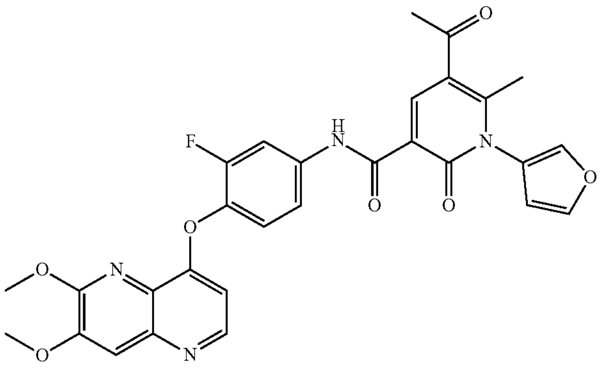 [SMILES: COc1cc2nccc(Oc3ccc(NC(=O)c4cc(C(C)=O)c(C)n(-c5ccoc5)c4=O)cc3F)c2nc1OC] | 5-acetyl-N-[4-[(6,7-dimethoxy-1,5-naphthyridin-4-yl)oxy]-3-fluorophenyl]-1-(furan-3-yl)-6-methyl-2-oxopyridine-3-carboxamide |
| 236 | 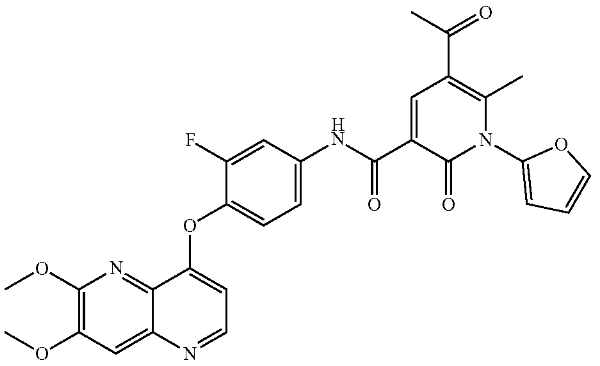 [SMILES: COc1cc2nccc(Oc3ccc(NC(=O)c4cc(C(C)=O)c(C)n(-c5ccco5)c4=O)cc3F)c2nc1OC] | 5-acetyl-N-[4-[(6,7-dimethoxy-1,5-naphthyridin-4-yl)oxy]-3-fluorophenyl]-1-(furan-2-yl)-6-methyl-2-oxopyridine-3-carboxamide |
| 237 | 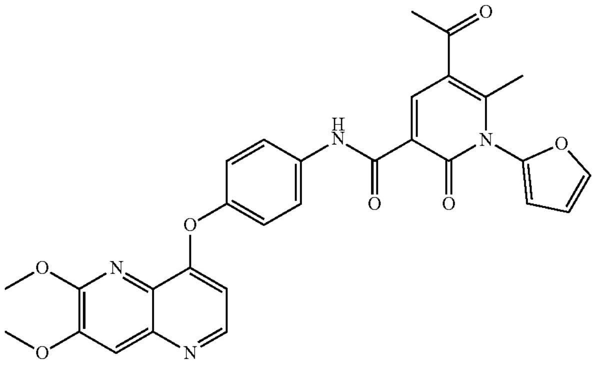 [SMILES: COc1cc2nccc(Oc3ccc(NC(=O)c4cc(C(C)=O)c(C)n(-c5ccco5)c4=O)cc3)c2nc1OC] | 5-acetyl-N-[4-[(6,7-dimethoxy-1,5-naphthyridin-4-yl)oxy]phenyl]-1-(furan-2-yl)-6-methyl-2-oxopyridine-3-carboxamide |
| 238 | 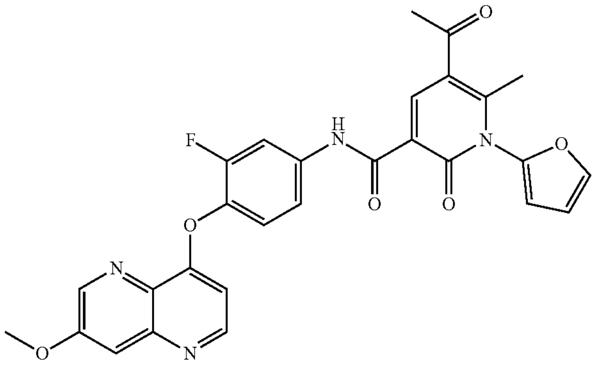 [SMILES: COc1cnc2c(Oc3ccc(NC(=O)c4cc(C(C)=O)c(C)n(-c5ccco5)c4=O)cc3F)ccnc2c1] | 5-acetyl-N-[3-fluoro-4-[(7-methoxy-1,5-naphthyridin-4-yl)oxy]phenyl]-1-(furan-2-yl)-6-methyl-2-oxopyridine-3-carboxamide |

TABLE 1C-continued

| Compound No. | Structure | Compound Name |
|---|---|---|
| 239 | 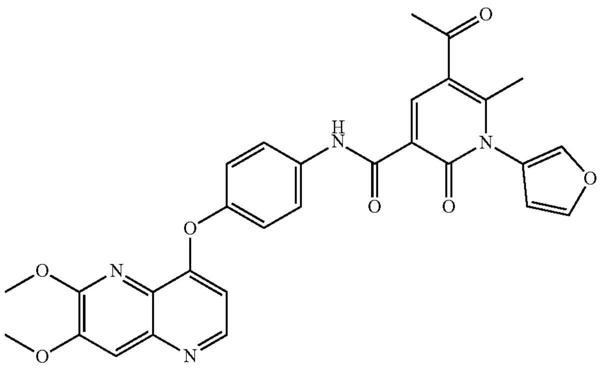 [SMILES: COc1cc2nccc(Oc3ccc(NC(=O)c4cc(C(C)=O)c(C)n(-c5ccoc5)c4=O)cc3)c2nc1OC] | 5-acetyl-N-[4-[(6,7-dimethoxy-1,5-naphthyridin-4-yl)oxy]phenyl]-1-(furan-3-yl)-6-methyl-2-oxopyridine-3-carboxamide |
| 240 | 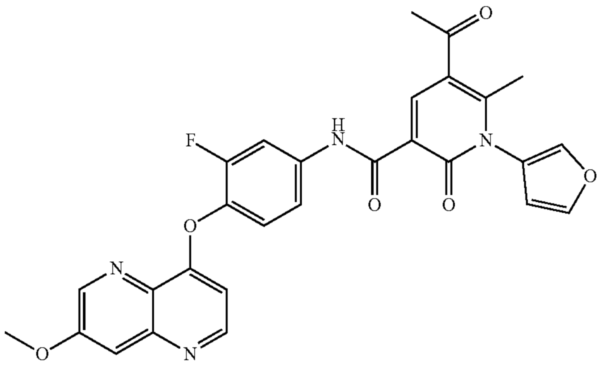 [SMILES: COc1cnc2c(Oc3ccc(NC(=O)c4cc(C(C)=O)c(C)n(-c5ccoc5)c4=O)cc3F)ccnc2c1] | 5-acetyl-N-[3-fluoro-4-[(7-methoxy-1,5-naphthyridin-4-yl)oxy]phenyl]-1-(furan-3-yl)-6-methyl-2-oxopyridine-3-carboxamide |
| 241 | 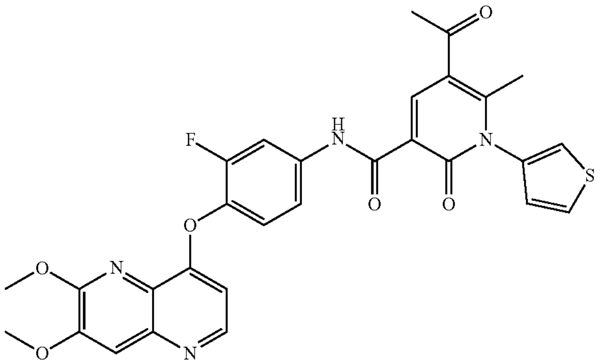 [SMILES: COc1cc2nccc(Oc3ccc(NC(=O)c4cc(C(C)=O)c(C)n(-c5ccsc5)c4=O)cc3F)c2nc1OC] | 5-acetyl-N-[4-[(6,7-dimethoxy-1,5-naphthyridin-4-yl)oxy]-3-fluorophenyl]-6-methyl-2-oxo-1-thiophen-3-ylpyridine-3-carboxamide |
| 242 | 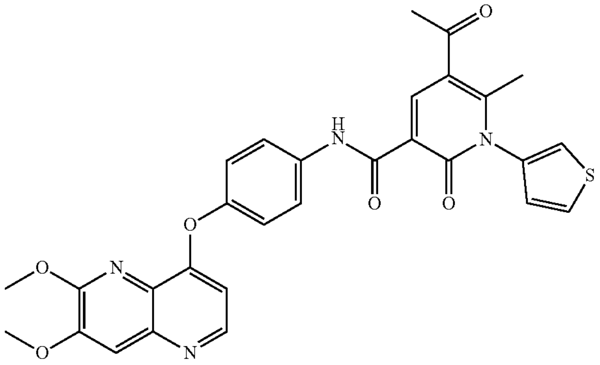 [SMILES: COc1cc2nccc(Oc3ccc(NC(=O)c4cc(C(C)=O)c(C)n(-c5ccsc5)c4=O)cc3)c2nc1OC] | 5-acetyl-N-[4-[(6,7-dimethoxy-1,5-naphthyridin-4-yl)oxy]phenyl]-6-methyl-2-oxo-1-thiophen-3-ylpyridine-3-carboxamide |

TABLE 1C-continued

| Compound No. | Structure | Compound Name |
| --- | --- | --- |
| 243 | 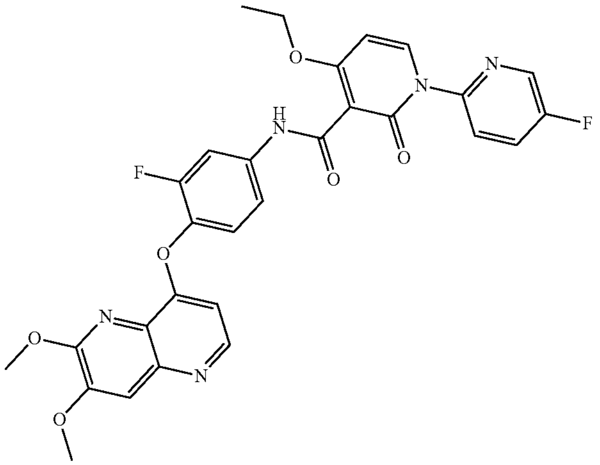 [SMILES: CCOc1ccn(-c2ccc(F)cn2)c(=O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-ethoxy-1-(5-fluoropyridin-2-yl)-2-oxopyridine-3-carboxamide |
| 244 | 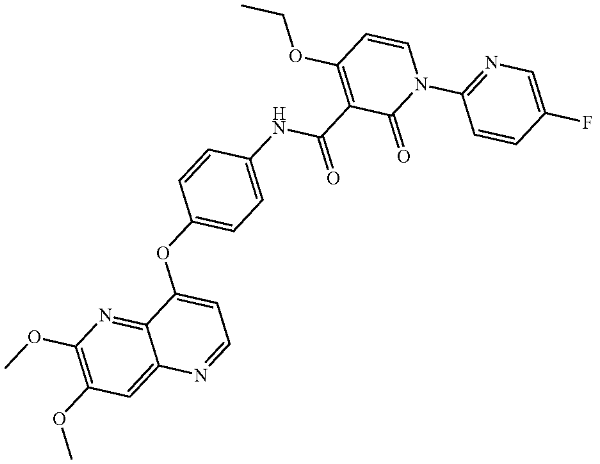 [SMILES: CCOc1ccn(-c2ccc(F)cn2)c(=O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-4-ethoxy-1-(5-fluoropyridin-2-yl)-2-oxopyridine-3-carboxamide |
| 245 | 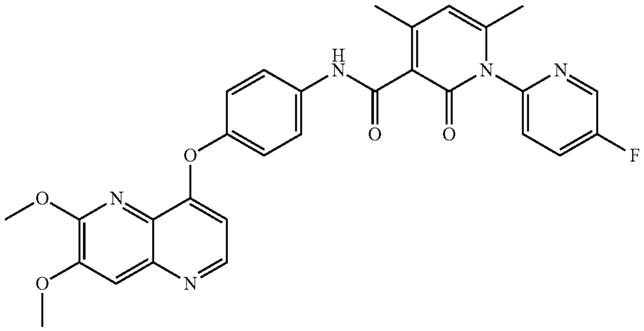 [SMILES: COc1cc2nccc(Oc3ccc(NC(=O)c4c(C)cc(C)n(-c5ccc(F)cn5)c4=O)cc3)c2nc1OC] | N-[4-[(6,7-dimethoxy-1,5-naphthyridin-4-yl)oxy]phenyl]-1-(5-fluoropyridin-2-yl)-4,6-dimethyl-2-oxopyridine-3-carboxamide |
| 246 | 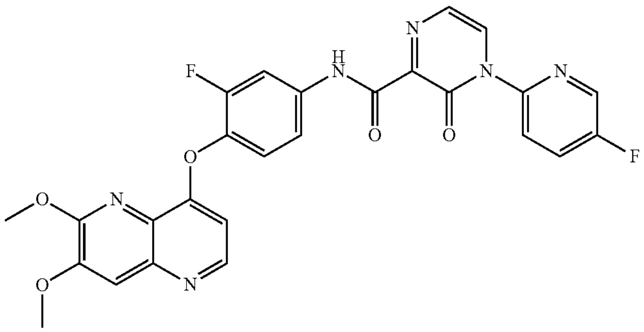 [SMILES: COc1cc2nccc(Oc3ccc(NC(=O)c4nccn(-c5ccc(F)cn5)c4=O)cc3F)c2nc1OC] | N-[4-[(6,7-dimethoxy-1,5-naphthyridin-4-yl)oxy]-3-fluorophenyl]-4-(5-fluoropyridin-2-yl)-3-oxopyrazine-2-carboxamide |

TABLE 1C-continued

| Compound No. | Structure | Compound Name |
|---|---|---|
| 247 | 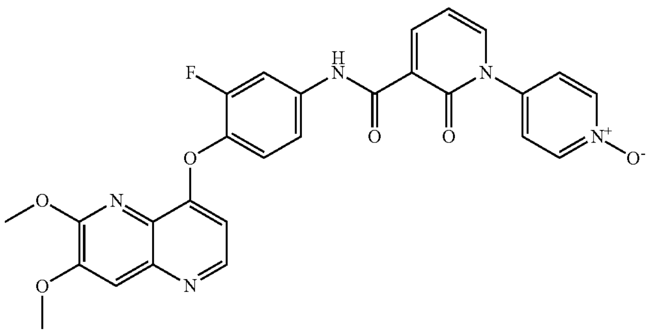 [SMILES: COc1cc2nccc(Oc3ccc(NC(=O)c4cccn(-c5cc[n+]([O-])cc5)c4=O)cc3F)c2nc1OC] | N-[4-[(6,7-dimethoxy-1,5-naphthyridin-4-yl)oxy]-3-fluorophenyl]-1-(1-oxidopyridin-1-ium-4-yl)-2-oxopyridine-3-carboxamide |
| 248 | 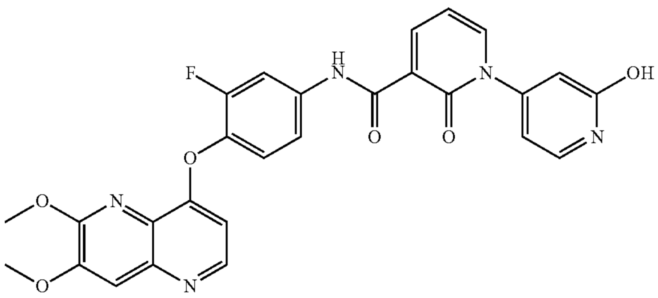 [SMILES: COc1cc2nccc(Oc3ccc(NC(=O)c4cccn(-c5ccnc(O)c5)c4=O)cc3F)c2nc1OC] | N-[4-[(6,7-dimethoxy-1,5-naphthyridin-4-yl)oxy]-3-fluorophenyl]-1-(2-hydroxypyridin-4-yl)-2-oxopyridine-3-carboxamide |
| 254 | 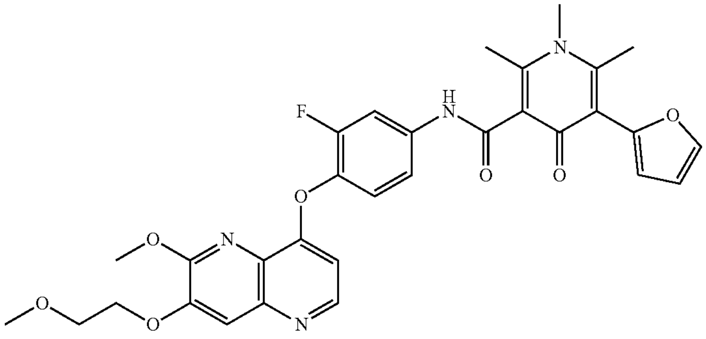 [SMILES: COCCOc1cc2nccc(Oc3ccc(NC(=O)c4c(C)n(C)c(C)c(-c5ccco5)c4=O)cc3F)c2nc1OC] | N-[3-fluoro-4-[[6-methoxy-7-(2-methoxy-ethoxy)-1,5-naphthyridin-4-yl]oxy]phenyl]-5-(furan-2-yl)-1,2,6-trimethyl-4-oxopyridine-3-carboxamide |
| 255 | 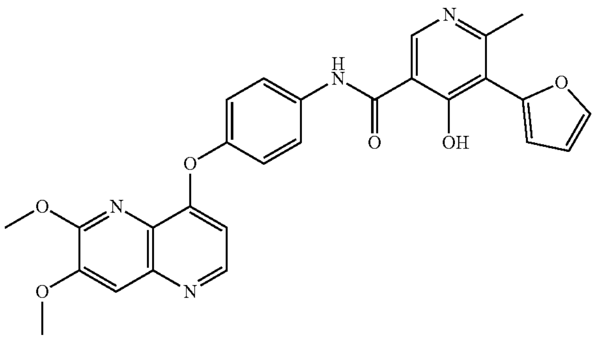 | N-[4-[(6,7-dimethoxy-1,5-naphthyridin-4-yl)oxy]phenyl]-5-(furan-2-yl)-4-hydroxy-6-methylpyridine-3-carboxamide |

TABLE 1C-continued

| Compound No. | Structure | Compound Name |
|---|---|---|
| 256 | 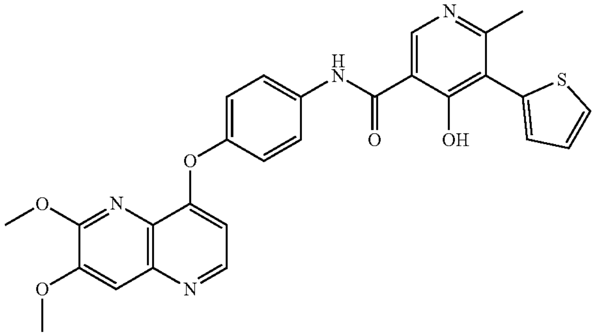 [SMILES: COc1cc2nccc(Oc3ccc(NC(=O)c4cnc(C)c(-c5cccs5)c4O)cc3)c2nc1OC] | N-[4-[(6,7-dimethoxy-1,5-naphthyridin-4-yl)oxy]phenyl]-4-hydroxy-6-methyl-5-thiophen-2-ylpyridine-3-carboxamide |
| 257 | 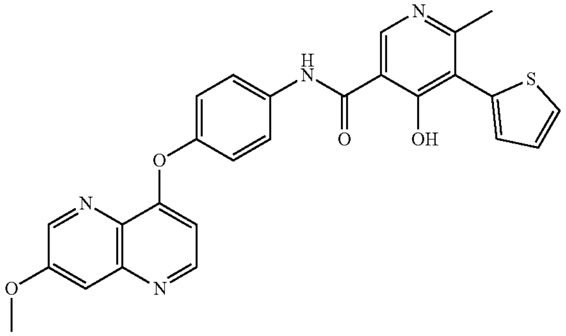 [SMILES: COc1cnc2c(Oc3ccc(NC(=O)c4cnc(C)c(-c5cccs5)c4O)cc3)ccnc2c1] | 4-hydroxy-N-[4-[(7-methoxy-1,5-naphthyridin-4-yl)oxy]phenyl]-6-methyl-5-thiophen-2-ylpyridine-3-carboxamide |
| 258 | 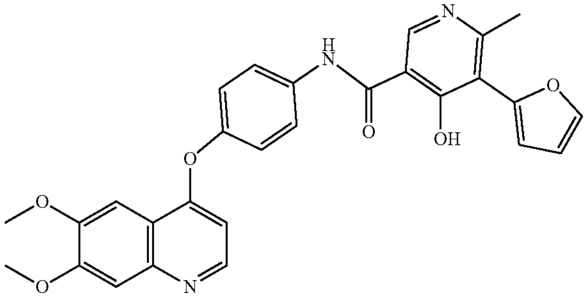 [SMILES: COc1cc2nccc(Oc3ccc(NC(=O)c4cnc(C)c(-c5ccco5)c4O)cc3)c2cc1OC] | N-[4-(6,7-dimethoxy-quinolin-4-yl) oxyphenyl]-5-(furan-2-yl)-4-hydroxy-6-methylpyridine-3-carboxamide |
| 259 | 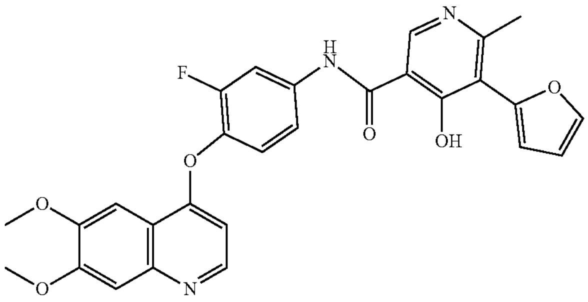 [SMILES: COc1cc2nccc(Oc3ccc(NC(=O)c4cnc(C)c(-c5ccco5)c4O)cc3F)c2cc1OC] | N-[4-(6,7-dimethoxy-quinolin-4-yl)oxy-3-fluorophenyl]-5-(furan-2-yl)-4-hydroxy-6-methylpyridine-3-carboxamide |

TABLE 1C-continued

| Compound No. | Structure | Compound Name |
|---|---|---|
| 260 | 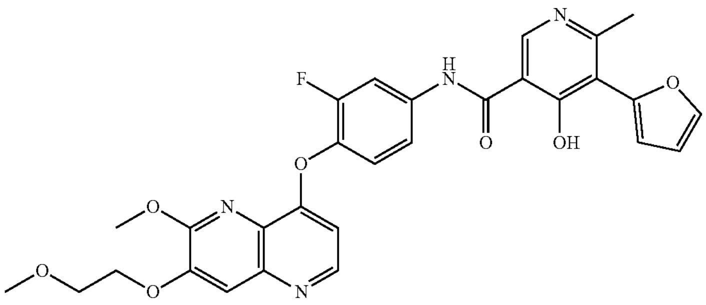 [SMILES: COCCOc1cc2nccc(Oc3ccc(NC(=O)c4cnc(C)c(-c5ccco5)c4O)cc3F)c2nc1OC] | N-[3-fluoro-4-[[6-methoxy-7-(2-methoxy-ethoxy)-1,5-naphthyridin-4-yl]oxy]phenyl]-5-(furan-2-yl)-4-hydroxy-6-methylpyridine-3-carboxamide |
| 261 | 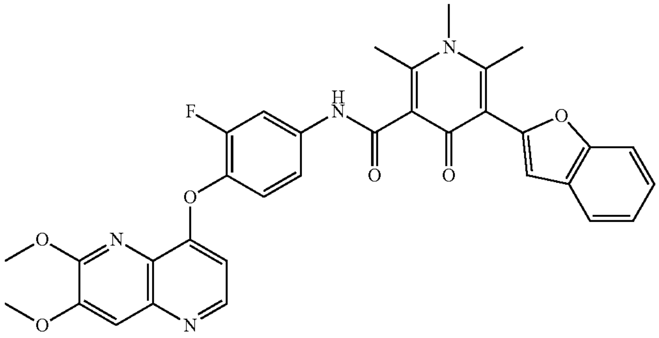 [SMILES: COc1cc2nccc(Oc3ccc(NC(=O)c4c(C)n(C)c(C)c(-c5cc6ccccc6o5)c4=O)cc3F)c2nc1OC] | 5-(1-benzofuran-2-yl)-N-[4-[(6,7-dimethoxy-1,5-naphthyridin-4-yl)oxy]-3-fluorophenyl]-1,2,6-trimethyl-4-oxopyridine-3-carboxamide |
| 262 | 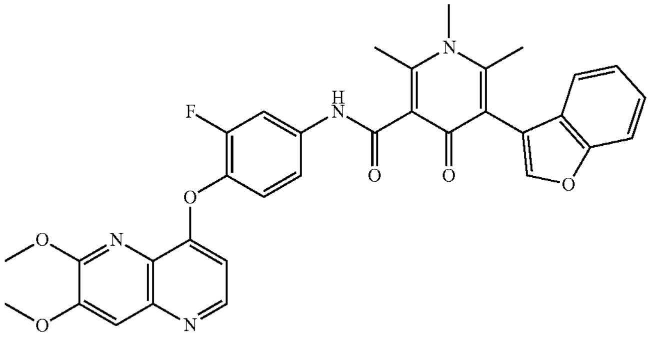 [SMILES: COc1cc2nccc(Oc3ccc(NC(=O)c4c(C)n(C)c(C)c(-c5coc6ccccc56)c4=O)cc3F)c2nc1OC] | 5-(1-benzofuran-3-yl)-N-[4-[(6,7-dimethoxy-1,5-naphthyridin-4-yl)oxy]-3-fluorophenyl]-1,2,6-trimethyl-4-oxopyridine-3-carboxamide |
| 263 | 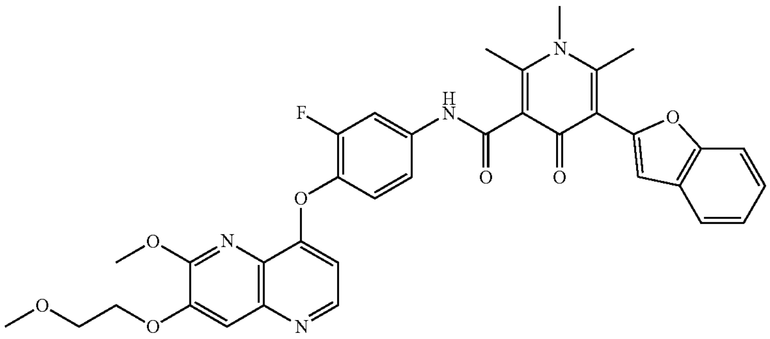 [SMILES: COCCOc1cc2nccc(Oc3ccc(NC(=O)c4c(C)n(C)c(C)c(-c5cc6ccccc6o5)c4=O)cc3F)c2nc1OC] | 5-(1-benzofuran-2-yl)-N-[3-fluoro-4-[[6-methoxy-7-(2-methoxy-ethoxy)-1,5-naphthyridin-4-yl]oxy]phenyl]-1,2,6-trimethyl-4-oxopyridine-3-carboxamide |

TABLE 1C-continued

| Compound No. | Structure | Compound Name |
|---|---|---|
| 264 | 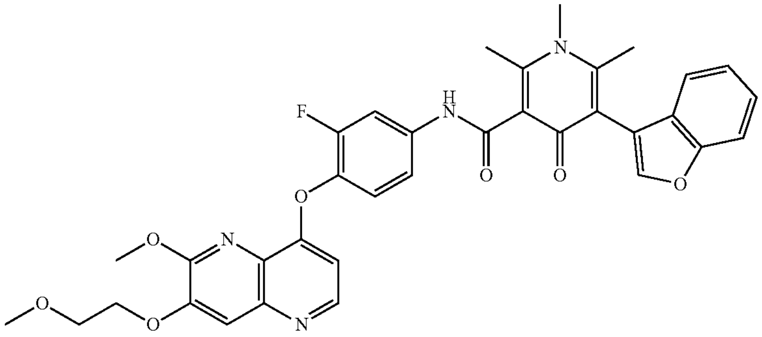 [SMILES: COCCOc1cc2nccc(Oc3ccc(NC(=O)c4c(C)n(C)c(C)c(-c5coc6ccccc56)c4=O)cc3F)c2nc1OC] | 5-(1-benzofuran-3-yl)-N-[3-fluoro-4-[[6-methoxy-7-(2-methoxy-ethoxy)-1,5-naphthyridin-4-yl]oxy]phenyl]-1,2,6-trimethyl-4-oxopyridine-3-carboxamide |
| 265 | 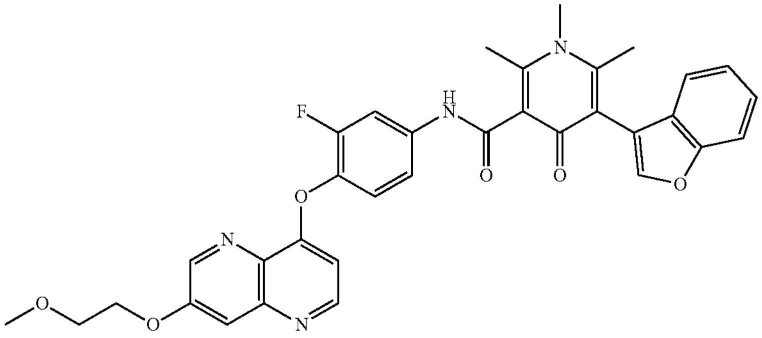 [SMILES: COCCOc1cnc2c(Oc3ccc(NC(=O)c4c(C)n(C)c(C)c(-c5coc6ccccc56)c4=O)cc3F)ccnc2c1] | 5-(1-benzofuran-3-yl)-N-[3-fluoro-4-[[7-(2-methoxy-ethoxy)-1,5-naphthyridin-4-yl]oxy]phenyl]-1,2,6-trimethyl-4-oxopyridine-3-carboxamide |
| 266 | 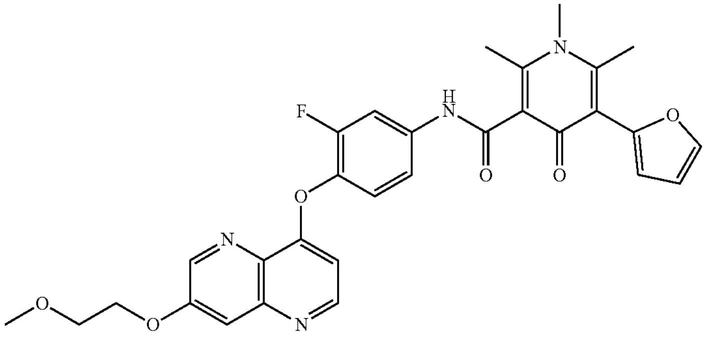 [SMILES: COCCOc1cnc2c(Oc3ccc(NC(=O)c4c(C)n(C)c(C)c(-c5ccco5)c4=O)cc3F)ccnc2c1] | N-[3-fluoro-4-[[7-(2-methoxy-ethoxy)-1,5-naphthyridin-4-yl]oxy]phenyl]-5-(furan-2-yl)-1,2,6-trimethyl-4-oxopyridine-3-carboxamide |
| 269 | 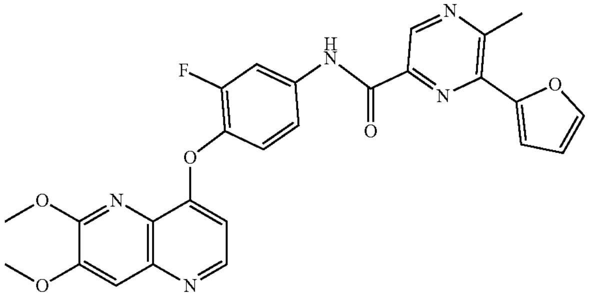 [SMILES: COc1cc2nccc(Oc3ccc(NC(=O)c4cnc(C)c(-c5ccco5)n4)cc3F)c2nc1OC] | N-[4-[(6,7-dimethoxy-1,5-naphthyridin-4-yl)oxy]-3-fluorophenyl]-6-(furan-2-yl)-5-methylpyrazine-2-carboxamide |

TABLE 1C-continued

| Compound No. | Structure | Compound Name |
|---|---|---|
| 275 | 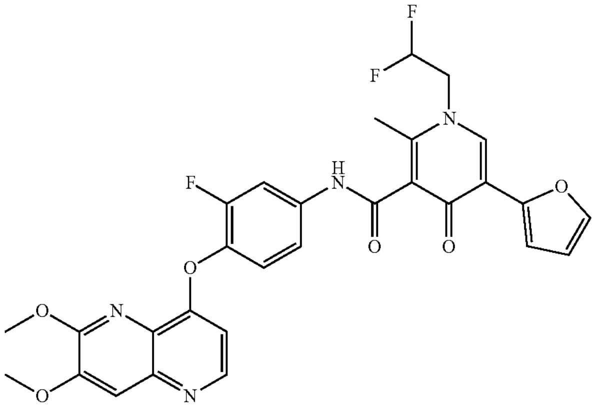 [SMILES: COc1cc2nccc(Oc3ccc(NC(=O)c4c(C)n(CC(F)F)cc(-c5ccco5)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(furan-2-yl)-2-methyl-4-oxopyridine-3-carboxamide |
| 297 | 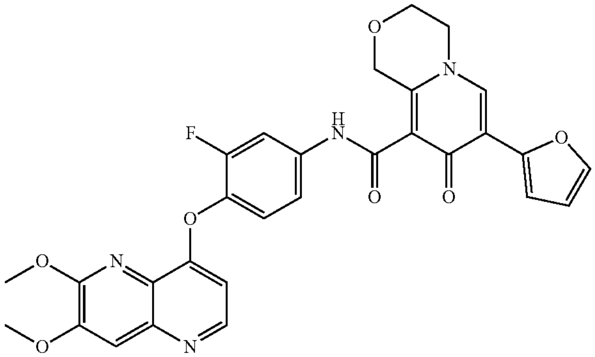 [SMILES: COc1cc2nccc(Oc3ccc(NC(=O)c4c5n(cc(-c6ccco6)c4=O)CCOC5)cc3F)c2nc1OC] | N-[4-[(6,7-dimethoxy-1,5-naphthyridin-4-yl)oxy]-3-fluorophenyl]-7-(furan-2-yl)-8-oxo-3,4-dihydro-1H-pyrido[2,1-c][1,4]oxazine-9-carboxamide |
| 298 | 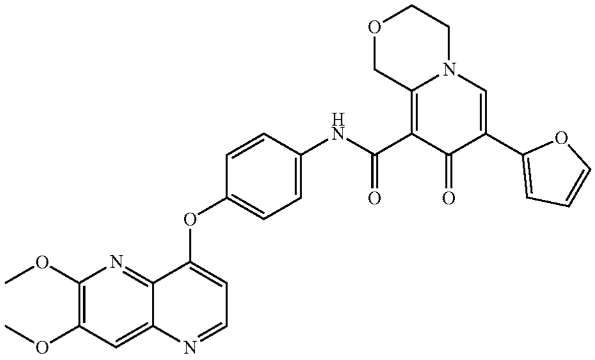 | N-[4-[(6,7-dimethoxy-1,5-naphthyridin-4-yl)oxy]phenyl]-7-(furan-2-yl)-8-oxo-3,4-dihydro-1H-pyrido[2,1-c][1,4]oxazine-9-carboxamide |
| 299 | 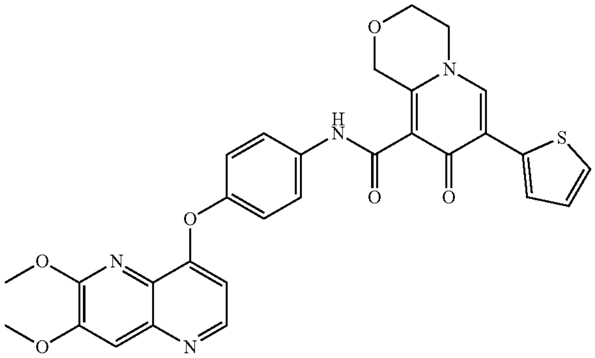 [SMILES: COc1cc2nccc(Oc3ccc(NC(=O)c4c5n(cc(-c6cccs6)c4=O)CCOC5)cc3)c2nc1OC] | N-[4-[(6,7-dimethoxy-1,5-naphthyridin-4-yl)oxy]phenyl]-8-oxo-7-thiophen-2-yl-3,4-dihydro-1H-pyrido[2,1-c][1,4]oxazine-9-carboxamide |

TABLE 1C-continued

| Compound No. | Structure | Compound Name |
|---|---|---|
| 300 | 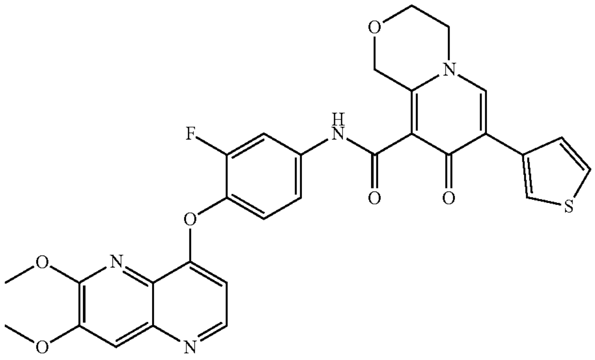 [SMILES: COc1cc2nccc(Oc3ccc(NC(=O)c4c5n(cc(-c6ccsc6)c4=O)CCOC5)cc3F)c2nc1OC] | N-[4-[(6,7-dimethoxy-1,5-naphthyridin-4-yl)oxy]-3-fluorophenyl]-8-oxo-7-thiophen-3-yl-3,4-dihydro-1H-pyrido[2,1-c][1,4]oxazine-9-carboxamide |
| 301 | 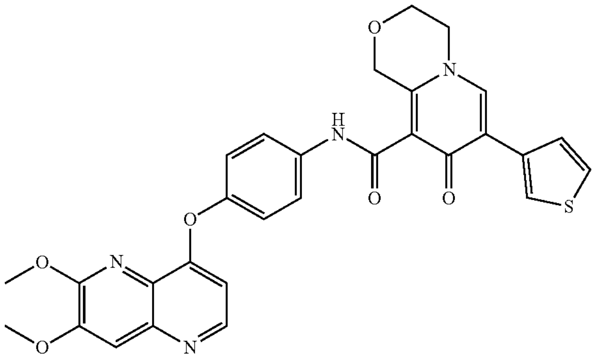 [SMILES: COc1cc2nccc(Oc3ccc(NC(=O)c4c5n(cc(-c6ccsc6)c4=O)CCOC5)cc3)c2nc1OC] | N-[4-[(6,7-dimethoxy-1,5-naphthyridin-4-yl)oxy]phenyl]-8-oxo-7-thiophen-3-yl-3,4-dihydro-1H-pyrido[2,1-c][1,4]oxazine-9-carboxamide |
| 302 | 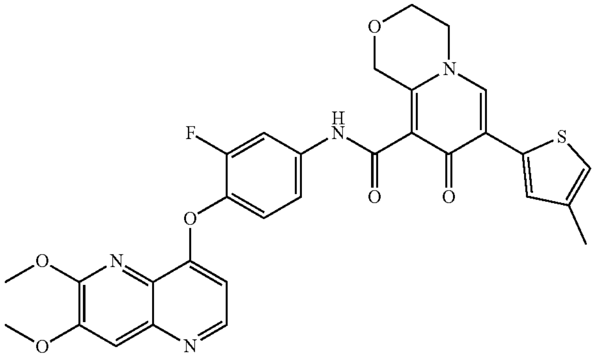 [SMILES: COc1cc2nccc(Oc3ccc(NC(=O)c4c5n(cc(-c6cc(C)cs6)c4=O)CCOC5)cc3F)c2nc1OC] | N-[4-[(6,7-dimethoxy-1,5-naphthyridin-4-yl)oxy]-3-fluorophenyl]-7-(4-methylthiophen-2-yl)-8-oxo-3,4-dihydro-1H-pyrido[2,1-c][1,4]oxazine-9-carboxamide |
| 303 | 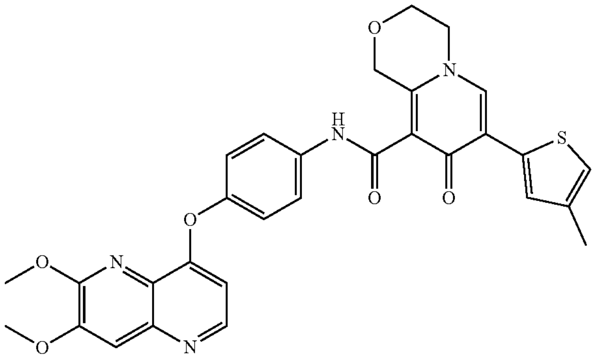 [SMILES: COc1cc2nccc(Oc3ccc(NC(=O)c4c5n(cc(-c6cc(C)cs6)c4=O)CCOC5)cc3)c2nc1OC] | N-[4-[(6,7-dimethoxy-1,5-naphthyridin-4-yl)oxy]phenyl]-7-(4-methylthiophen-2-yl)-8-oxo-3,4-dihydro-1H-pyrido [2,1-c][1,4] oxazine-9-carboxamide |

TABLE 1C-continued

| Compound No. | Structure | Compound Name |
|---|---|---|
| 304 | 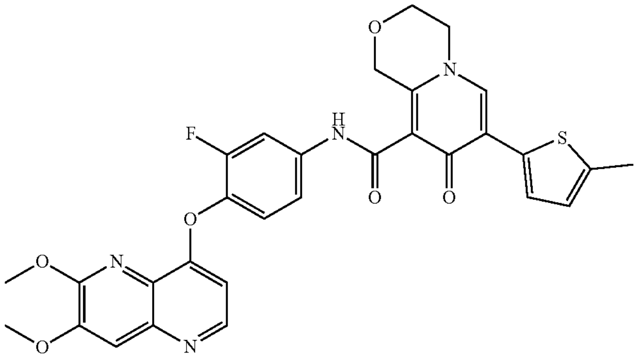 | N-[4-[(6,7-dimethoxy-1,5-naphthyridin-4-yl)oxy]-3-fluorophenyl]-7-(5-methylthiophen-2-yl)-8-oxo-3,4-dihydro-1H-pyrido[2,1-c][1,4]oxazine-9-carboxamide |
| 305 | 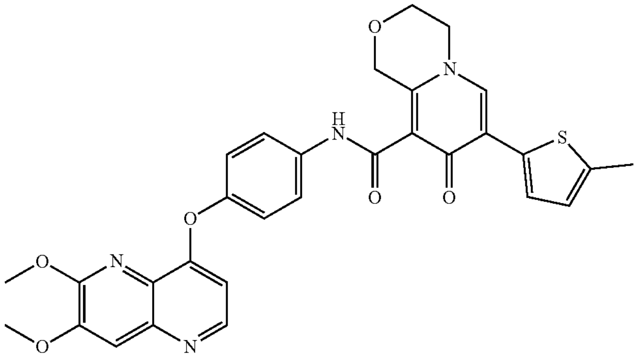 | N-[4-[(6,7-dimethoxy-1,5-naphthyridin-4-yl)oxy]phenyl]-7-(5-methylthiophen-2-yl)-8-oxo-3,4-dihydro-1H-pyrido[2,1-c][1,4]oxazine-9-carboxamide |
| 306 | 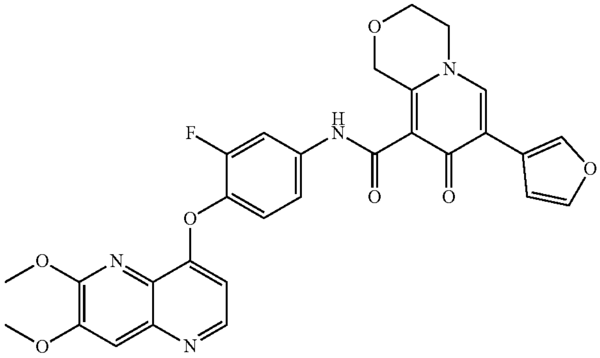 [SMILES: COc1cc2nccc(Oc3ccc(NC(=O)c4c5n(cc(-c6ccoc6)c4=O)CCOC5)cc3F)c2nc1OC] | N-[4-[(6,7-dimethoxy-1,5-naphthyridin-4-yl)oxy]-3-fluorophenyl]-7-(furan-3-yl)-8-oxo-3,4-dihydro-1H-pyrido[2,1-c][1,4]oxazine-9-carboxamide |
| 307 | 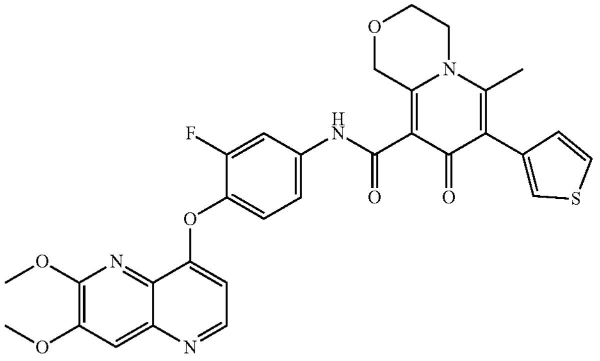 [SMILES: COc1cc2nccc(Oc3ccc(NC(=O)c4c5n(c(C)c(-c6ccsc6)c4=O)CCOC5)cc3F)c2nc1OC] | N-[4-[(6,7-dimethoxy-1,5-naphthyridin-4-yl)oxy]-3-fluorophenyl]-6-methyl-8-oxo-7-thiophen-3-yl-3,4-dihydro-1H-pyrido[2,1-c][1,4]oxazine-9-carboxamide |

TABLE 1C-continued

| Compound No. | Structure | Compound Name |
|---|---|---|
| 308 | 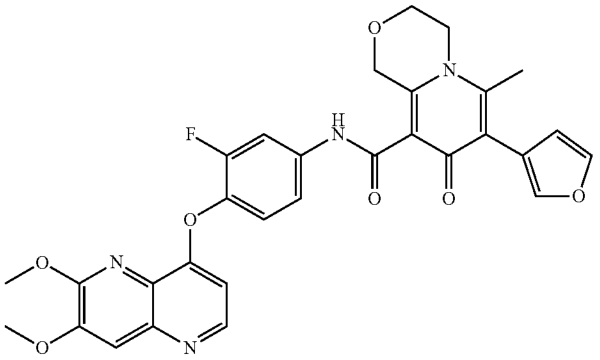 [SMILES: COc1cc2nccc(Oc3ccc(NC(=O)c4c5n(c(C)c(-c6ccoc6)c4=O)CCOC5)cc3F)c2nc1OC] | N-[4-[(6,7-dimethoxy-1,5-naphthyridin-4-yl)oxy]-3-fluorophenyl]-7-(furan-3-yl)-6-methyl-8-oxo-3,4-dihydro-1H-pyrido[2,1-c][1,4]oxazine-9-carboxamide |
| 309 | 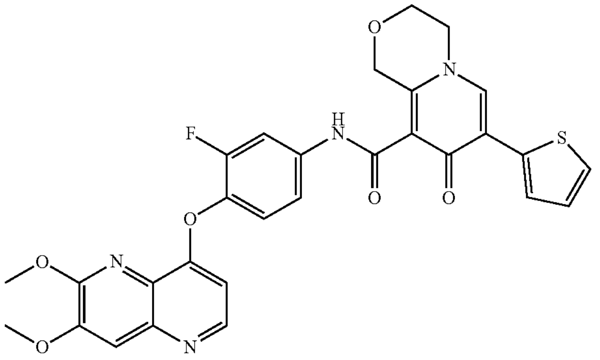 | N-[4-[(6,7-dimethoxy-1,5-naphthyridin-4-yl)oxy]-3-fluorophenyl]-8-oxo-7-thiophen-2-yl-3,4-dihydro-1H-pyrido[2,1-c][1,4]oxazine-9-carboxamide |
| 310 | 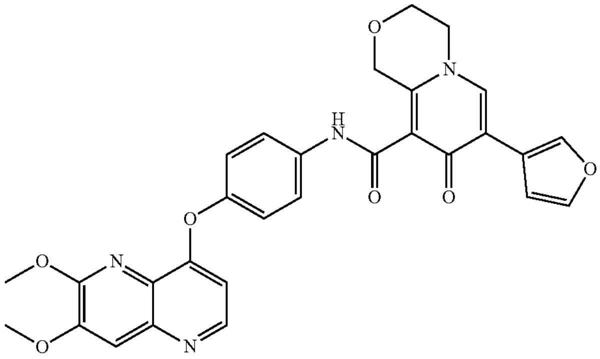 [SMILES: COc1cc2nccc(Oc3ccc(NC(=O)c4c5n(cc(-c6ccoc6)c4=O)CCOC5)cc3)c2nc1OC] | N-[4-[(6,7-dimethoxy-1,5-naphthyridin-4-yl)oxy]phenyl]-7-(furan-3-yl)-8-oxo-3,4-dihydro-1H-pyrido[2,1-c][1,4]oxazine-9-carboxamide |
| 311 | 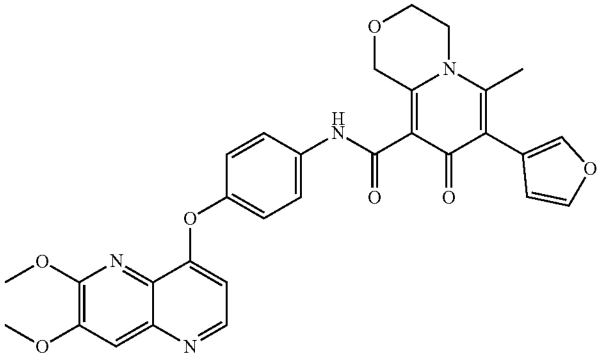 [SMILES: COc1cc2nccc(Oc3ccc(NC(=O)c4c5n(c(C)c(-c6ccoc6)c4=O)CCOC5)cc3)c2nc1OC] | N-[4-[(6,7-dimethoxy-1,5-naphthyridin-4-yl)oxy]phenyl]-7-(furan-3-yl)-6-methyl-8-oxo-3,4-dihydro-1H-pyrido[2,1-c][1,4]oxazine-9-carboxamide |

TABLE 1C-continued

| Compound No. | Structure | Compound Name |
|---|---|---|
| 312 | 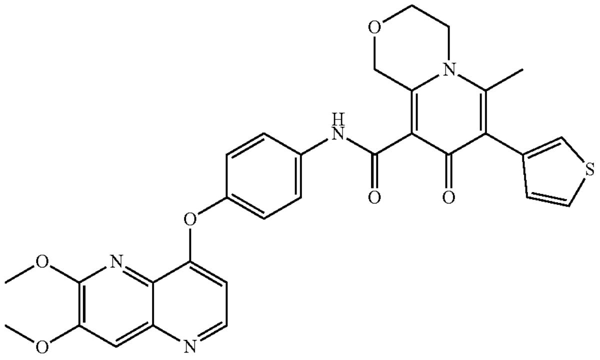 [SMILES: COc1cc2nccc(Oc3ccc(NC(=O)c4c5n(c(C)c(-c6ccsc6)c4=O)CCOC5)cc3)c2nc1OC] | N-[4-[(6,7-dimethoxy-1,5-naphthyridin-4-yl)oxy]phenyl]-6-methyl-8-oxo-7-thiophen-3-yl-3,4-dihydro-1H-pyrido[2,1-c][1,4]oxazine-9-carboxamide |
| 313 | 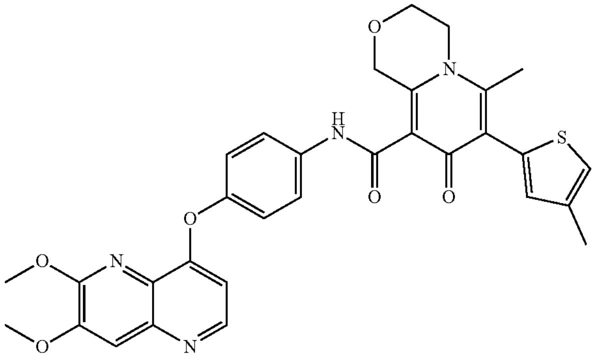 [SMILES: COc1cc2nccc(Oc3ccc(NC(=O)c4c5n(c(C)c(-c6cc(C)cs6)c4=O)CCOC5)cc3)c2nc1OC] | N-[4-[(6,7-dimethoxy-1,5-naphthyridin-4-yl)oxy]phenyl]-6-methyl-7-(4-methylthiophen-2-yl)-8-oxo-3,4-dihydro-1H-pyrido[2,1-c][1,4]oxazine-9-carboxamide |
| 314 | 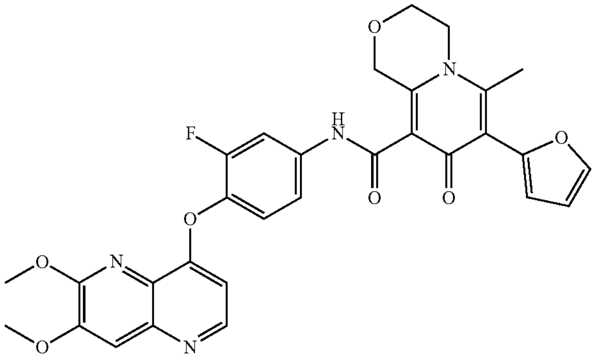 | N-[4-[(6,7-dimethoxy-1,5-naphthyridin-4-yl)oxy]-3-fluorophenyl]-7-(furan-2-yl)-6-methyl-8-oxo-3,4-dihydro-1H-pyrido[2,1-c][1,4]oxazine-9-carboxamide |
| 315 | 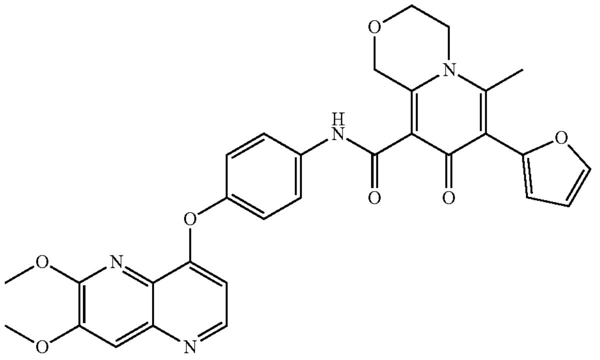 [SMILES: COc1cc2nccc(Oc3ccc(NC(=O)c4c5n(c(C)c(-c6ccco6)c4=O)CCOC5)cc3)c2nc1OC] | N-[4-[(6,7-dimethoxy-1,5-naphthyridin-4-yl)oxy]phenyl]-7-(furan-2-yl)-6-methyl-8-oxo-3,4-dihydro-1H-pyrido[2,1-c][1,4]oxazine-9-carboxamide |

TABLE 1C-continued

| Compound No. | Structure | Compound Name |
|---|---|---|
| 316 | 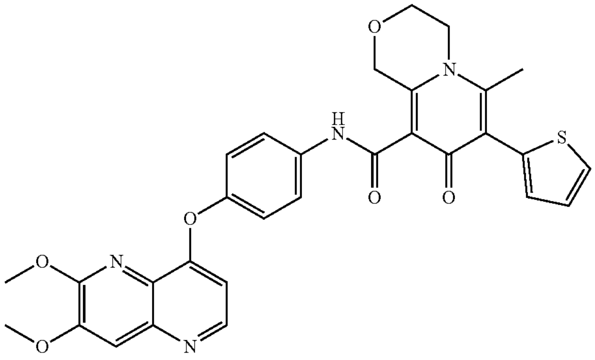 [SMILES: COc1cc2nccc(Oc3ccc(NC(=O)c4c5n(c(C)c(-c6cccs6)c4=O)CCOC5)cc3)c2nc1OC] | N-[4-[(6,7-dimethoxy-1,5-naphthyridin-4-yl)oxy]phenyl]-6-methyl-8-oxo-7-thiophen-2-yl-3,4-dihydro-1H-pyrido[2,1-c][1,4]oxazine-9-carboxamide |
| 317 | 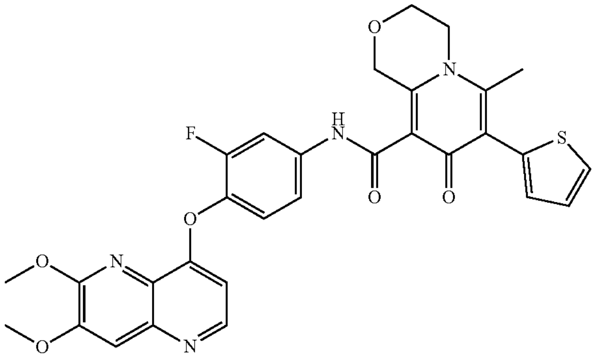 [SMILES: COc1cc2nccc(Oc3ccc(NC(=O)c4c5n(c(C)c(-c6cccs6)c4=O)CCOC5)cc3F)c2nc1OC] | N-[4-[(6,7-dimethoxy-1,5-naphthyridin-4-yl)oxy]-3-fluorophenyl]-6-methyl-8-oxo-7-thiophen-2-yl-3,4-dihydro-1H-pyrido[2,1-c][1,4]oxazine-9-carboxamide |
| 318 | 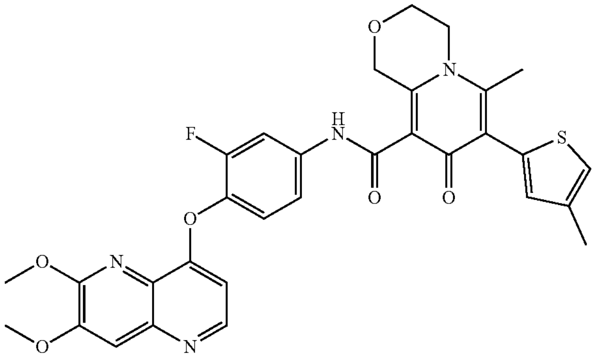 [SMILES: COc1cc2nccc(Oc3ccc(NC(=O)c4c5n(c(C)c(-c6cc(C)cs6)c4=O)CCOC5)cc3F)c2nc1OC] | N-[4-[(6,7-dimethoxy-1,5-naphthyridin-4-yl)oxy]-3-fluorophenyl]-6-methyl-7-(4-methylthiophen-2-yl)-8-oxo-3,4-dihydro-1H-pyrido[2,1-c][1,4]oxazine-9-carboxamide |
| 324 | 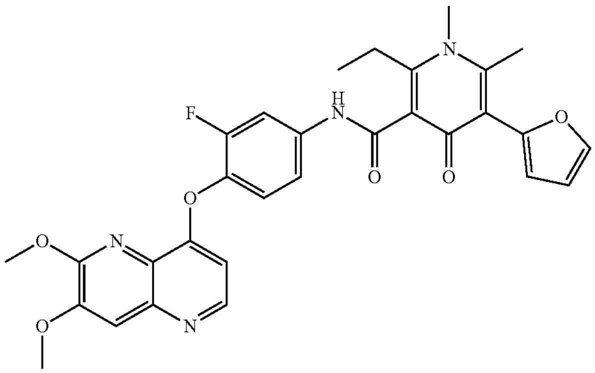 [SMILES: CCc1c(C(=O)Nc2ccc(Oc3ccnc4cc(OC)c(OC)nc34)c(F)c2)c(=O)c(-c2ccco2)c(C)n1C] | N-[4-[(6,7-dimethoxy-1,5-naphthyridin-4-yl)oxy]-3-fluorophenyl]-2-ethyl-5-(furan-2-yl)-1,6-dimethyl-4-oxopyridine-3-carboxamide |

TABLE 1C-continued

| Compound No. | Structure | Compound Name |
| --- | --- | --- |
| 325 | 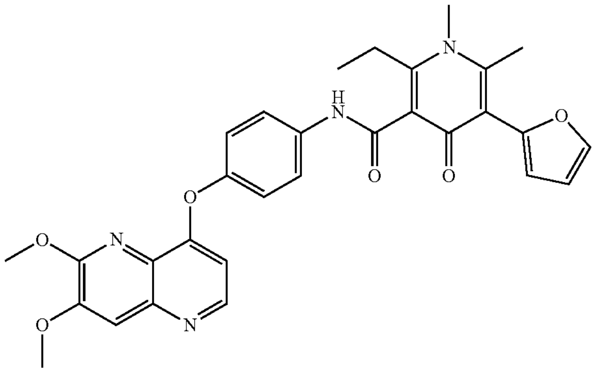 [SMILES: CCc1c(C(=O)Nc2ccc(Oc3ccnc4cc(OC)c(OC)nc34)cc2)c(=O)c(-c2ccco2)c(C)n1C] | N-[4-[(6,7-dimethoxy-1,5-naphthyridin-4-yl)oxy]phenyl]-2-ethyl-5-(furan-2-yl)-1,6-dimethyl-4-oxopyridine-3-carboxamide |
| 326 | 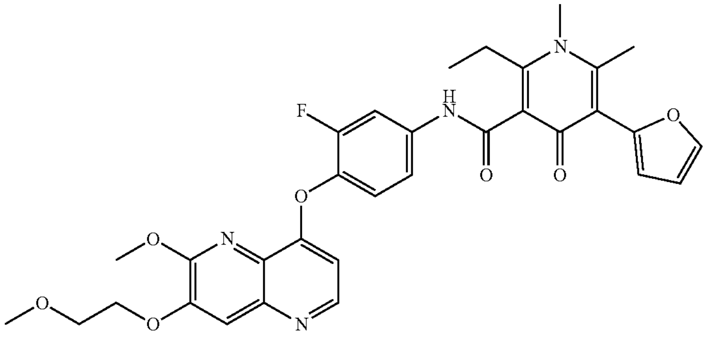 [SMILES: CCc1c(C(=O)Nc2ccc(Oc3ccnc4cc(OCCOC)c(OC)nc34)c(F)c2)c(=O)c(-c2ccco2)c(C)n1C] | 2-ethyl-N-[3-fluoro-4-[[6-methoxy-7-(2-methoxyethoxy)-1,5-naphthyridin-4-yl]oxy]phenyl]-5-(furan-2-yl)-1,6-dimethyl-4-oxopyridine-3-carboxamide |
| 327 | 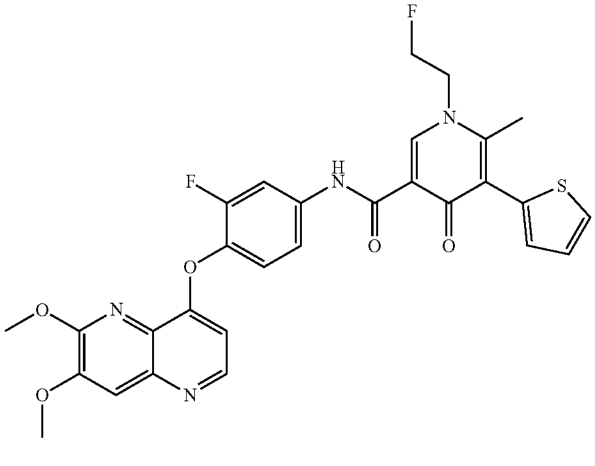 [SMILES: COc1cc2nccc(Oc3ccc(NC(=O)c4cn(CCF)c(C)c(-c5cccs5)c4=O)cc3F)c2nc1OC] | N-[4-[(6,7-dimethoxy-1,5-naphthyridin-4-yl)oxy]-3-fluorophenyl]-1-(2-fluoroethyl)-6-methyl-4-oxo-5-thiophen-2-ylpyridine-3-carboxamide |

TABLE 1C-continued

| Compound No. | Structure | Compound Name |
| --- | --- | --- |
| 328 | 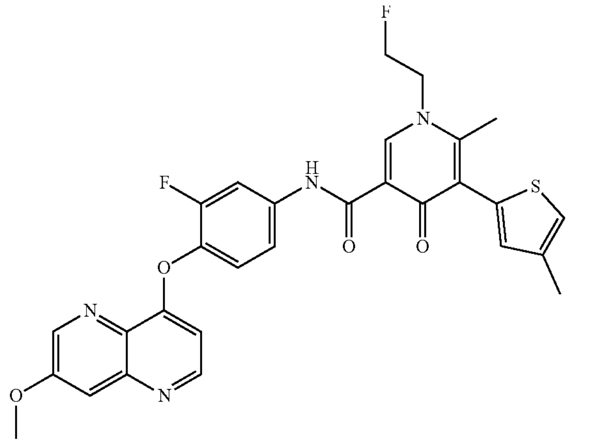 [SMILES: COc1cnc2c(Oc3ccc(NC(=O)c4cn(CCF)c(C)c(-c5cc(C)cs5)c4=O)cc3F)ccnc2c1] | 1-(2-fluoroethyl)-N-[3-fluoro-4-[(7-methoxy-1,5-naphthyridin-4-yl)oxy]phenyl]-6-methyl-5-(4-methylthiophen-2-yl)-4-oxopyridine-3-carboxamide |
| 329 | 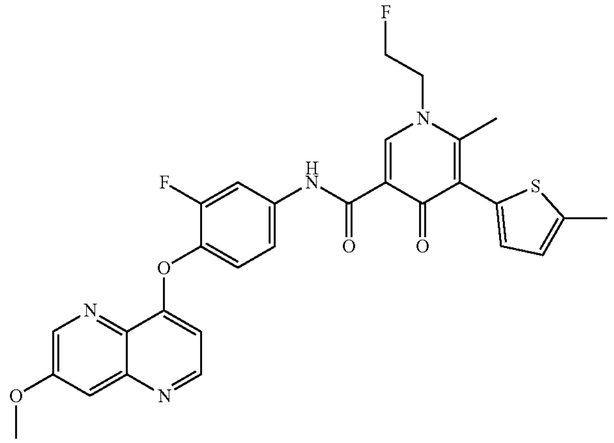 [SMILES: COc1cnc2c(Oc3ccc(NC(=O)c4cn(CCF)c(C)c(-c5ccc(C)s5)c4=O)cc3F)ccnc2c1] | 1-(2-fluoroethyl)-N-[3-fluoro-4-[(7-methoxy-1,5-naphthyridin-4-yl)oxy]phenyl]-6-methyl-5-(5-methylthiophen-2-yl)-4-oxopyridine-3-carboxamide |
| 330 | 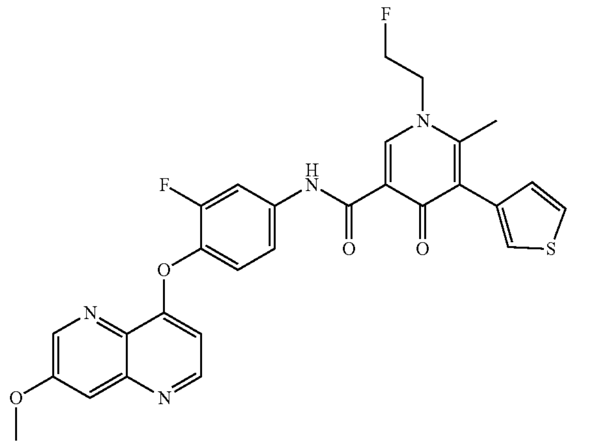 [SMILES: COc1cnc2c(Oc3ccc(NC(=O)c4cn(CCF)c(C)c(-c5ccsc5)c4=O)cc3F)ccnc2c1] | 1-(2-fluoroethyl)-N-[3-fluoro-4-[(7-methoxy-1,5-naphthyridin-4-yl)oxy]phenyl]-6-methyl-4-oxo-5-thiophen-3-ylpyridine-3-carboxamide |

TABLE 1C-continued

| Compound No. | Structure | Compound Name |
|---|---|---|
| 331 | 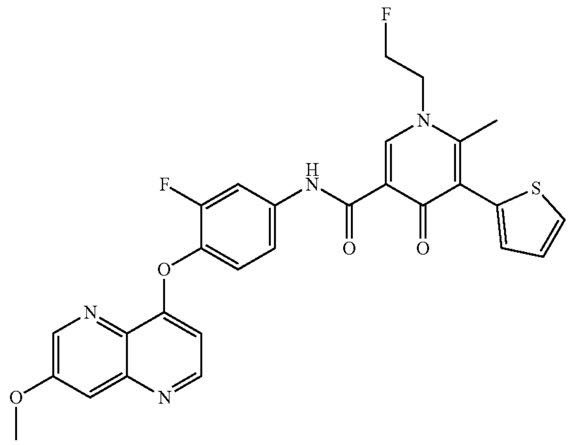 [SMILES: COc1cnc2c(Oc3ccc(NC(=O)c4cn(CCF)c(C)c(-c5cccs5)c4=O)cc3F)ccnc2c1] | 1-(2-fluoroethyl)-N-[3-fluoro-4-[(7-methoxy-1,5-naphthyridin-4-yl)oxy]phenyl]-6-methyl-4-oxo-5-thiophen-2-ylpyridine-3-carboxamide |
| 332 | 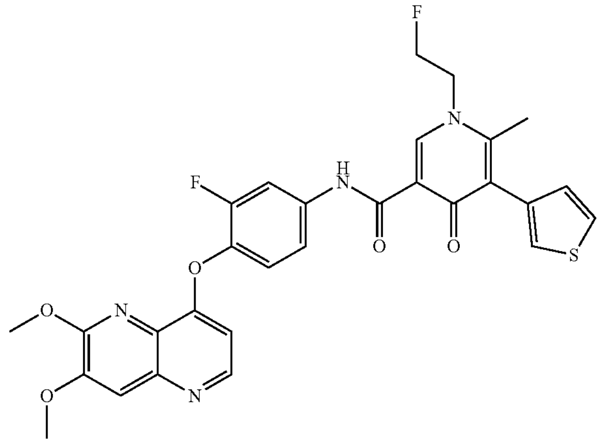 [SMILES: COc1cc2nccc(Oc3ccc(NC(=O)c4cn(CCF)c(C)c(-c5ccsc5)c4=O)cc3F)c2nc1OC] | N-[4-[(6,7-dimethoxy-1,5-naphthyridin-4-yl)oxy]-3-fluorophenyl]-1-(2-fluoroethyl)-6-methyl-4-oxo-5-thiophen-3-ylpyridine-3-carboxamide |
| 333 | 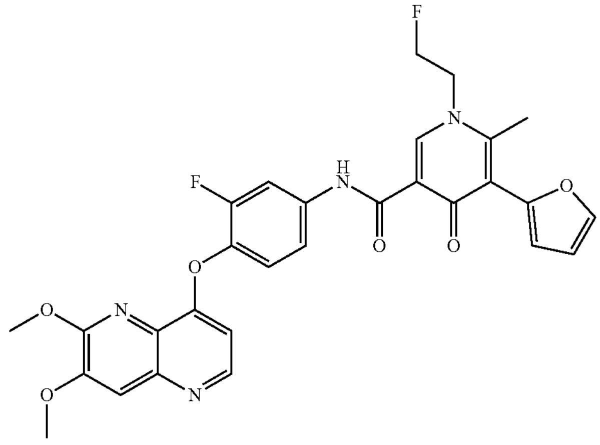 | N-[4-[(6,7-dimethoxy-1,5-naphthyridin-4-yl)oxy]-3-fluorophenyl]-1-(2-fluoroethyl)-5-(furan-2-yl)-6-methyl-4-oxopyridine-3-carboxamide |

TABLE 1C-continued

| Compound No. | Structure | Compound Name |
| --- | --- | --- |
| 334 | 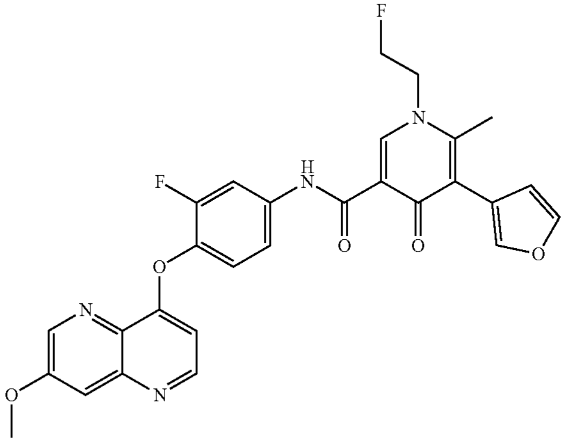 [SMILES: COc1cnc2c(Oc3ccc(NC(=O)c4cn(CCF)c(C)c(-c5ccoc5)c4=O)cc3F)ccnc2c1] | 1-(2-fluoroethyl)-N-[3-fluoro-4-[(7-methoxy-1,5-naphthyridin-4-yl)oxy]phenyl]-5-(furan-3-yl)-6-methyl-4-oxopyridine-3-carboxamide |
| 337 | 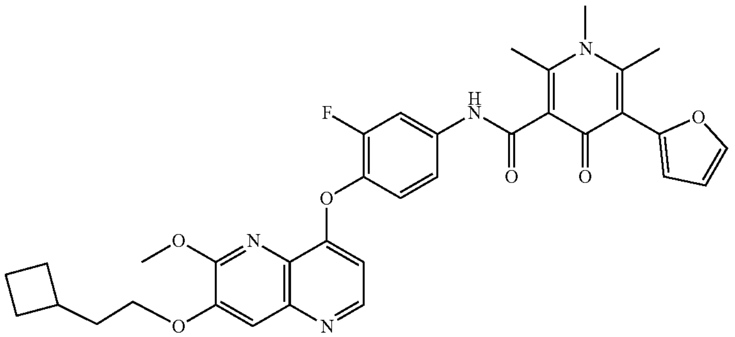 [SMILES: COc1nc2c(Oc3ccc(NC(=O)c4c(C)n(C)c(C)c(-c5ccco5)c4=O)cc3F)ccnc2cc1OCCC1CCC1] | N-[4-[[7-(2-cyclobutyl-ethoxy)-6-methoxy-1,5-naphthyridin-4-yl]oxy]-3-fluorophenyl]-5-(furan-2-yl)-1,2,6-trimethyl-4-oxopyridine-3-carboxamide |

or a pharmaceutically acceptable salt, a stereoisomer, or a mixture of stereoisomers thereof.

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Provided herein is a method of modulating in vivo activity of a protein kinase in a subject, the method comprising administering to the subject a therapeutically effective amount of a compound of Formula (I) or a subformula thereof (e.g., formula (Ia), (Ia-1), (Ia-2), (Ib), (Ib-1), (Ic), (Ic-1), (Ic-2), (Id), (Ie), (Ij), (Ik), and/or (Im), and/or any combinations thereof), or a pharmaceutically acceptable salt or stereoisomer thereof, or a pharmaceutical composition described herein.

Provided herein is a method of treating a disease, disorder, or syndrome in a subject, the method comprising administering to the subject in need thereof a therapeutically effective amount of a compound of Formula (I) or a subformula thereof (e.g., formula (Ia), (Ta-1), (Ia-2), (Tb), (Ib-1), (Ic), (Ic-1), (Ic-2) (Id), (Ie), (Ij), (Ik), and/or (Im), and/or any combinations thereof), or a pharmaceutically acceptable salt or stereoisomer thereof, or a pharmaceutical composition described herein, wherein the disease, disorder, or syndrome is mediated at least in part by modulating in vivo activity of a protein kinase. In some instances, the protein kinase is AXL, KDR, Mer, or Met.

Provided herein are methods for treating cancer.

"Cancer" includes tumor types such as tumor types including breast, colon, renal, lung, squamous cell myeloid leukemia, hemangiomas, melanomas, astrocytomas, and glioblastomas as well as other cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia, renal cell carcinoma), bladder and urethra (squamous cell carcinoma, transitional cell carcinoma, adenocarcinoma), prostate (adenocarcinoma, sarcoma, small cell carcinoma of the prostate), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; as well as cancers of the thyroid including medullary thyroid cancer. Thus, the term "cancerous cell," as provided herein, includes a cell afflicted by any one of the above-identified conditions.

In one embodiment, the cancer is selected from ovarian cancer, prostate cancer, lung cancer, medullary thyroid cancer, liver cancer, gastrointestinal cancer, pancreatic cancer, bone cancer, hematologic cancer, skin cancer, kidney cancer, breast cancer, colon cancer, and fallopian tube cancer.

In another embodiment, the disease or disorder is ovarian cancer.

In another embodiment, the disease or disorder is prostate cancer.

In another embodiment, the disease or disorder is lung cancer.

In another embodiment, the disease or disorder is medullary thyroid cancer.

In another embodiment, the disease or disorder is liver cancer.

In another embodiment, the disease or disorder is gastrointestinal cancer.

In another embodiment, the disease or disorder is pancreatic cancer.

In another embodiment, the disease or disorder is bone cancer.

In another embodiment, the disease or disorder is hematologic cancer.

In another embodiment, the disease or disorder is skin cancer.

In another embodiment, the disease or disorder is kidney cancer.

In another embodiment, the disease or disorder is breast cancer.

In another embodiment, the disease or disorder is colon cancer. In another embodiment, the disease or disorder is fallopian cancer. In another embodiment, the disease or disorder is liver cancer, wherein the liver cancer is hepatocellular carcinoma, cholangiocarcinoma, hepatoblastoma, angiosarcoma, hepatocellular adenoma, or hemagioma.

In another embodiment, the disease or disorder is gastrointestinal cancer, wherein the gastrointestinal cancer is cancer of the esophagus which is squamous cell carcinoma, adenocarcinoma, or leiomyosarcoma; cancer of the stomach which is carcinoma, or lymphoma; cancer of the pancreas, which is ductal adenocarcinoma, insulinoma, gucagonoma, gastrinoma, carcinoid tumors, or vipoma; cancer of the small bowel, which is adenocarcinoma, lymphoma, carcinoid tumors, Karposi's sarcoma, leiomyoma, hemagioma, lipoma, or cancer of the large bowel, which is adenocarcinoma, tubular adenoma, villous adenoma, hamartoma, or leiomyoma.

In another embodiment, the disease or disorder is cancer of the pancreas, wherein the cancer of the pancreas is ductal adenocarcinoma, insulinoma, gucagonoma, gastrinoma, carcinoid tumors, or vipoma.

In another embodiment, the disease or disorder is bone cancer, wherein the bone cancer is osteosarcoma, fibrosarcoma, malignant fibrous histiocytoma, chondrosarcoma, Ewing's sarcoma, malignant reticulum cell sarcoma, multiple myeloma, malignant giant cell tumor chordoma, osteocartiliginous exostoses, chondroblastoma, chondromyxofibroma, or osteoid osteoma.

In another embodiment, the disease or disorder is hematologic cancer, wherein the hematologic cancer is myeloid leukemia, acute lymphoblastic leukemia, chronic lymphocytic leukemia, myeloproliferative diseases, multiple myeloma, or myelodysplastic syndrome.

In another embodiment, the disease or disorder is skin cancer, wherein the skin cancer is malignant melanoma, basal cell carcinoma, squamous cell carcinoma, or Karposi's sarcoma.

In another embodiment, the disease or disorder is a renal tumor or renal cell carcinoma.

In another embodiment, the disease or disorder is breast cancer.

In another embodiment, the disease or disorder is a colon cancer tumor.

In another embodiment, the disease or disorder is fallopian tube carcinoma.

Combination Therapies

A compound as disclosed herein can be administered as a single therapy or in combination ("co-administered") with one or more additional therapies for the treatment of a disease or disorder, for instance a disease or disorder associated with hyper-proliferation such as cancer. Therapies that may be used in combination with a compound disclosed herein include: (i) surgery; (ii) radiotherapy (for example, gamma radiation, neutron beam radiotherapy, electron beam radiotherapy, proton therapy, brachytherapy, and systemic radioactive isotopes); (iii) endocrine therapy; (iv) adjuvant therapy, immunotherapy, CAR T- cell therapy; and (v) other chemotherapeutic agents.

The term "co-administered" ("co-administering") refers to either simultaneous administration, or any manner of separate sequential administration, of a compound as described herein, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

In one embodiment, the treatment method includes the co-administration of a compound as disclosed herein, or a pharmaceutically acceptable salt, stereoisomer, or mixture of stereoisomers thereof, and at least one immunotherapy. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor- Infiltrating Lymphocyte (TIL) Vaccine with Interleukin-2 (IL-2) or Lymphokine- Activated Killer (LAK) Cell Therapy.

Further examples of therapeutic antibodies that cam be used include, but are not limited to, trastuzumab; abciximab; daclizumab; BEC2; IMC-C22; vitaxin; Campath 1H/LDP-03; Smart M195; epratuzumab; bectumomab; visilizumab; CM3, a humanized ani-ICAM3 antibody: IDEC-1 14; ibritumomab tiuxetan; IDEC-131; IDEC-151; IDEC-152; SMART anti-CD3; eculizumab; adalimumab; certolizumab; IDEC-1 51; MDX-CD4; CD20-sreptdavidin; CDP571; LDP02; OrthoClone OKT4A; ruplizumab; natalizumab; and lerdelimumab.

Immunotherapies that can be used in combination with a compound as disclosed herein include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IF A); QS-21; DETOX; Levamisole; and Dinitrophenyl (DNP), and combinations thereof, such as, for example, combinations of, interleukins, for example, IL-2 with other cytokines, such as IFN-alpha.

In certain embodiments of each of the aforementioned aspects, as well as other aspects and embodiments described elsewhere herein, the immunotherapeutic agent is an agent that modulates immune responses, for example, a checkpoint inhibitor or a checkpoint agonist. In some embodiments, the immunotherapeutic agent is an antibody modulator that targets PD-1, PD-L1, PD-L2, CEACAM (e g., CEACAM-1, -3 and/or -5), CTLA-4, TIM-3, LAG-3, VISTA, BTLA, TIGIT, LAIR1, CD160, 2B4, TCGBF beta, OX40, 41BB, LIGHT, CD40, GITR, TCGBF-beta, TIM-3, SIRP-alpha, VSIG8, BTLA, SIGLEC7, SIGLEC9, ICOS, B7H13, 13714, FAS, and/or BTNL2 among ithers known in the art. In some embodiments, the immunotherapeutic agent is an agent that increases natural killer (NK) cell activity. In some embodiments, the immunotherapeutic agent is an agent that inhibits suppression of an immune response. In some embodiments, the immunotherapeutic agent is an agent that inhibits suppressor cells or suppressor cell activity. In some embodiments, the immunotherapeutic agent is an agent or therapy that inhibits Treg activity. In some embodiments, the immunotherapeutic agent is an agent that inhibits the activity of inhibitory immune checkpoint receptors.

In some embodiments, the immunotherapeutic agent includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g., SL AMF7), HVEM, LIGHT, CD2, CD27, CD28, CDS, IC7AM-1, LFA-1 (CD11a/CD18), ICOS (CD278), 4-1BB (C137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In one embodiment, the treatment method includes the co-administration of a compound as disclosed herein or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $1^{131}$, $1^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agents" include chemical compounds useful in the treatment of cancer. Examples of chemotherapeutic agents include erlotinib, bortezomib, disulfiram, epigallocatechin gallate, salinosporamide A, carfilzomib, 17-AAG (geldanamycin), radicicol, lactate dehydrogenase A (LDH-A), fulvestrant, sunitib, letrozole, imatinib mesylate, fmasunate, oxaliplatin, 5-FET (5-fluorouracil), leucovorin, Rapamycin, Lapatinib, Lonafamib (SCH 66336), sorafenib, Bayer Labs), gefitinib, AG1478; alkylating agents such as thiotepa and CYTOXAN®; cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; cally statin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5 alpha-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancrati statin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma II and calicheamicin omega I (Angew Chem. Inti. Ed. Engl. 1994 33: 183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin, morpholino-doxorubicin, cyanomorpholino- doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6- mercaptopurine, thiamiprine, thioguanine; pyrimidine analogs such as ancitabine, azacitidine, azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Ore.); razoxane; rhizoxin; sizofuran; spirogermanium; tenuazonic acid; triaziquone; 2,2',2"-trichlorotriethylamine; trichothecenes especially T-2 toxin, verracurin A, roridin A and anguidine); urethan; vindesine; dacarbazine; mannomustine; mitobronitol; mitolactol; pipobroman; gacytosine; arabinoside "Ara-C"); cyclophosphamide; thiotepa; taxoids, e.g., paclitaxel, ABRAXANE® (Cremophor-free), albumin-engineered nanoparticle formulations of paclitaxel (American Pharmaceutical Partners, Schaumberg, Ill.), and docetaxel/doxetaxel; chloranmbucil; gemcitabine; 6-thioguanine; mercaptopurine; methotrexate; platinum analogs such as cisplatin and carboplatin; vinblastine; etoposide (VP-16); ifosfamide; mitoxantrone; vincristine; vinorelbine; novantrone; teniposide; edatrexate; daunomycin; aminopterin; capecitabine; ibandronate; CPT-11; topoisomerase inhibitor RFS 2000; difluorom ethyl ornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including tamoxifen citrate), raloxifene, droloxifene, iodoxyfene, 4-hydroxytamoxifen, trioxifene, keoxifene, LY117018, onapristone, and toremifme citrate; (ii) aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretinoic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LEIRTOTECAN®; ABARELIX®; and (ix) pharmaceutically acceptable salts, acids and derivatives of any of the above.

Chemotherapeutic agents also include antibodies, as described above, including alemtuzumab, bevacizumab; cetuximab; panitumumab, rituximab, pertuzumab, tositumomab, and the antibody drug conjugate, gemtuzumab ozogamicin. Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nivolumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-8744695, Wyeth Research and Abbott Laboratories) which is a recombinant exclusively human-sequence, full-length $IgG_1$ λ antibody genetically modified to recognize interleukin- 12 p40 protein. Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone- 17-valerate, aclometasone dipropionate, betamethasone valerate, betamethasone dipropionate, prednicarbate, clobetasone-1 7-butyrate, clobetasol-1 7-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF alpha) blockers such as etanercept, infliximab, adalimumab, certolizumab pegol, golimumab (Simponi), Interleukin 1 (IL-1) blockers such as anakinra, T cell costimulation blockers such as abatacept, Interleukin 6 (IL-6) blockers such as tocilizumab; Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/132 blockers such as Anti-lymphotoxin alpha (LTa); miscellaneous investigational agents such as thioplatin, PS-341, phenylbutyrate, ET- I8-OCH3, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol); beta-lapachone; lapachol; colchicines; betulinic acid; acetylcamptothecin, scopolectin, and 9-aminocamptothecin); podophyllotoxin; tegafur; bexarotene; bisphosphonates such as clodronate, etidronate, NE-58095, zoledronic acid/zoledronate, alendronate, pamidronate, tiludronate, or risedronate; and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifamib (R11577); orafenib, ABT510; Bcl-2 inhibitor such as oblimersen sodium pixantrone; farnesyltransferase inhibitors such as lonafamib (SCH 6636); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin combined with 5-FU and leucovorin. Chemotherapeutic agents also include Poly ADP ribose polymerase (PARP) inhibitors: olaparib, rucaprib niraparib, talzoparib.

In some embodiments, compounds as disclosed herein can be used in combination therapy with any of the kinase inhibitors disclosed herein for the treatment of diseases such as cancer. Exemplary kinase inhibitors include imatinib, baricitinib gefitinib, erlotinib, sorafenib, dasatinib, sunitinib, lapatinib, nilotinib, pirfenidone, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, abemaciclib, acalabrutinib, alectinib, binimetinib, brigatinib, encorafenib, erdafitinib, everolimus, fostamatinib, gilter, larotrectinib, lorlatinib, netarsudil, osimertinib, pemigatinib, pexidartinib, ribociclib, temsirolimus, XL-092, XL-147, XL-765, XL-499, and XL-880. In some embodiments, a compound as described herein can be used in combination with a HSP90 inhibitor (e.g., XL888), liver X receptor (LXR) modulators, retinoid-related orphan receptor gamma (RORγ) modulators, checkpoint inhibitors such as a CK1 inhibitor or aCK1α inhibitor, a Wnt pathway inhibitor (e.g., SST-215), or a mineralocorticoid receptor inhibitor, (e.g., esaxerenone) or XL-888 for the treatment of a disease disclosed herein such as cancer. In some embodiments, the compounds as disclosed herein can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, 1NS—R, IGF-1R, IR—R, PDGFαR, PDGFβ/R, CSFIR, KIT, FLK-II, KDR/FLK-1, FLK-4, flt-1, FGFR1, FGFR2, FGFR3, FGFR4, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYR, FRK, JAK (JAK1 and or JAK2), ABL, ALK, CDK7, CDK12, KRAS, and B-Raf.

In some embodiments, non-limiting examples of inhibitors that can be combined with the compounds of the present disclosure for treatment of cancer and infections include an FGFR inhibitor (FGFR1, FGFR2, FGFR3 or FGFR4, e.g., pemigatinib, an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, vandetanib, ramucirumab, lenvatinib, ziv-aflibercept), a PARP inhibitor (e.g. olaparib, rucaparib, veliparib or niraparib), a JAK inhibitor (e.g., ruxolitinib, baricitinib, itacitinib), an IDO inhibitor (e.g., epacadostat, NLG919, or BMS-986205, MK7162), an LSD1 inhibitor, a TDO inhibitor, a PI3K-delta inhibitor (e.g., parsaclisib), a PI3K-gamma inhibitor such as PI3K-gamma selective inhibitor, a Pim inhibitor, a CSF1R inhibitor, a TAM receptor tyrosine kinases (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors, or combinations thereof.

In some embodiments, for treatment of cancer, compounds as disclosed herein can be used in combination with inhibitors of PD-1 or inhibitors of PD-L1, e.g., an anti-PD-1 monoclonal antibody or an anti -PD-L 1 monoclonal antibody, for example, nivolumab (Opdivo), pembrolizumab (Keytruda, MK-3475), atezolizumab, avelumab, cemiplimab, spartalizumab, camrelizumab, cetrelimab, toripalimab, sintilimab, AB122, JTX-4014, BGB-108, BCD-100, BAT1306, LZM009, AK105, HLX10, and TSR-042, AMP-224, AMP- 514, PDR001, durvalumab, pidilizumab (Imfinzi®, CT-011), CK-301, BMS 936559, and MPDL3280A. In some embodiments, the anti-PD-1 monoclonal antibody is nivolumab, pembrolizumab, pidilizumab, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab.

In some embodiments, for treatment of cancer, compounds as disclosed herein can be used in combination with inhibitors of PD-L1. Antibodies that bind to human PD-L1 include atezolizumab, avelumab, durvalumab, tislelizumab, BMS-935559, MEDI4736, FAZ053, KN035, CS1001, CBT-502, A167, STI-A101, CK-301, BGB-A333, MSB-2311, HLX20, KN035, AUNP12, CA-170, BMS-986189 and LY3300054. In some embodiments, the anti-PD-L1 monoclonal antibody is BMS-935559, MEDI4736, MPDL3280A, or MSB0010718C. In some embodiments, the anti-PD-L1 monoclonal antibody is atezolizumab, avelumab, durvalumab.

CTLA-4 inhibitors, e.g., an anti-CTLA-4 antibody, for example, ipilimumab (Yervoy), tremelimumab and AGEN1884; and phosphatidylserine inhibitors, for example, bavituximab (PGN401); antibodies to cytokines (IL-10, TGF-b, and the like); other anti-cancer agents such as cemiplimab. In some embodiments, the inhibitor of an immune checkpoint molecule is an inhibitor of PD-L1 and CTLA-4, e.g., an anti-PD -L1/CTLA-4 bispecific antibody or an anti-PD-1/CTLA-4 bispecific antibody. Bispecific antibodies that bind to PD-L1 and CTLA-4 include AK104.

In some embodiments, the compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGF(i receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104. In some embodiments, the bispecific antibody binds to PD-L1 and CD137. In some embodiments, the bispecific antibody that binds to PD-L1 and CD 137 is MCLA-145.

Pharmaceutical Compositions and Modes of Administration

Compounds provided herein are usually administered in the form of pharmaceutical compositions. Thus, provided herein are also pharmaceutical compositions that comprise one or more of the compounds described herein or a pharmaceutically acceptable salt, a stereoisomer, or a mixture of stereoisomers thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, a stereoisomer, or a mixture of stereoisomers thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, a stereoisomer, or a mixture of stereoisomers thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, a stereoisomer, or a mixture of stereoisomers thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Preparation of compounds as disclosed herein can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, $6^{th}$ Ed. (Wiley, 2007); Petursson et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula I or any subformulas as disclosed herein and certain intermediates can be prepared, for example, using a process as illustrated in Schemes 1-4. The variables employed in the Schemes below are as defined throughout the specification.

Scheme 1.

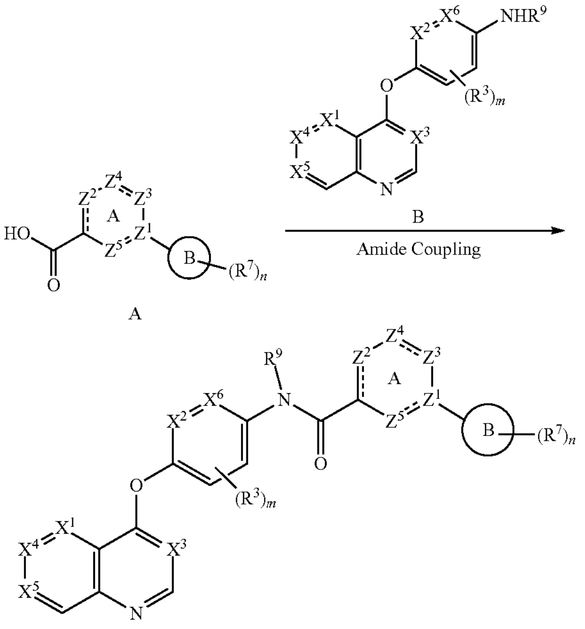

I

As shown in Scheme 1, a compound of formula I can be synthesized from carboxylic acid A and aniline B by standard methods to form amide bonds using coupling agents appropriate for this transformation that are well known in the art such as HATU in the presence of a base such as DIEA in organic solvents such as DMF at room or elevated temperatures, wherein Q is a leaving group (including, but not limiting to, Br, Cl, I, triflate, and the like).

Scheme 2

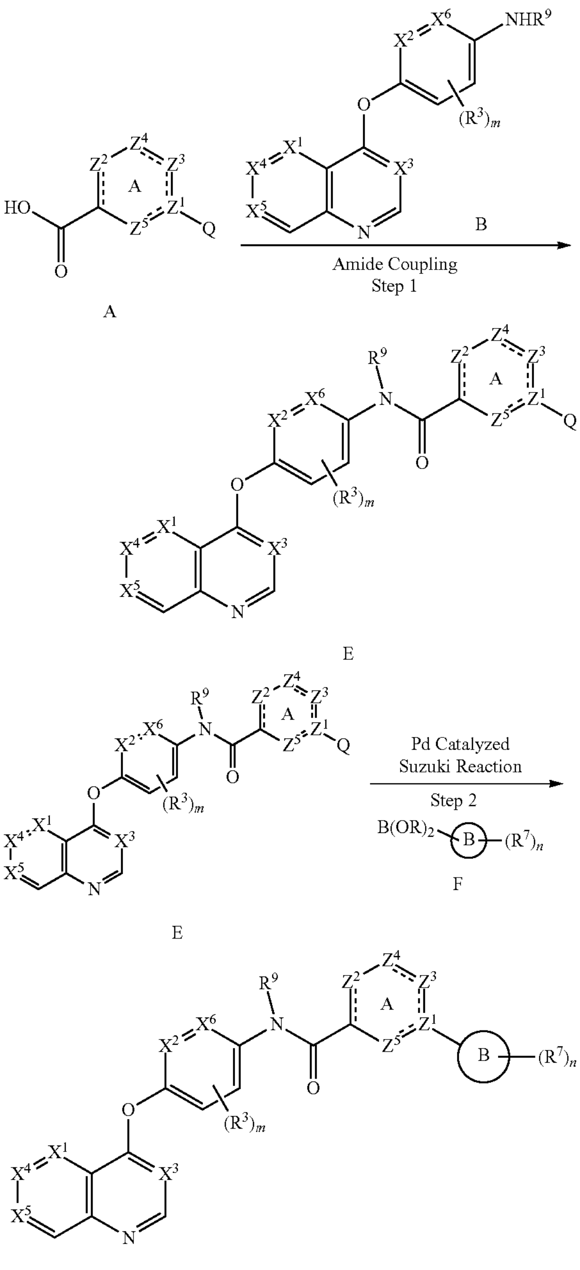

I

As shown in Scheme 2, a compound of formula I can be made from a two-step process starting from bromocarboxylic acid D, where Q is a leaving group, including Cl, Br, I or triflate, and aniline B which are coupled together by standard methods to form amide bonds using coupling agents appropriate for this transformation that are well known in the art such as HATU in the presence of a base such as DIEA in organic solvents such as DMF at room or elevated temperatures to form a compound of formula E. In a second step, compounds of formula E can be converted to compounds of formula I by coupling with boron acid or ester compounds of the formula F using coupling chemistry known to those skilled in the art. Typical procedures to accomplish this type of coupling involve the use palladium-containing complexes as a catalyst in the presence of an inorganic base such as tripotassium phosphate in a mixture of water and a water-miscible solvent such as dioxane.

Scheme 3.

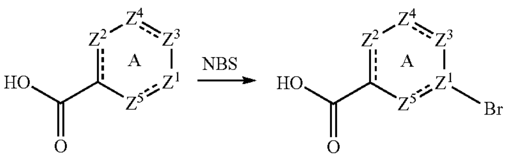

F D

As shown in Scheme 3, a compound of formula D (Q=Br) can be prepared from carboxylic acid F through treatment with NBS in an appropriate solvent typically at room temperature.

Scheme 4.

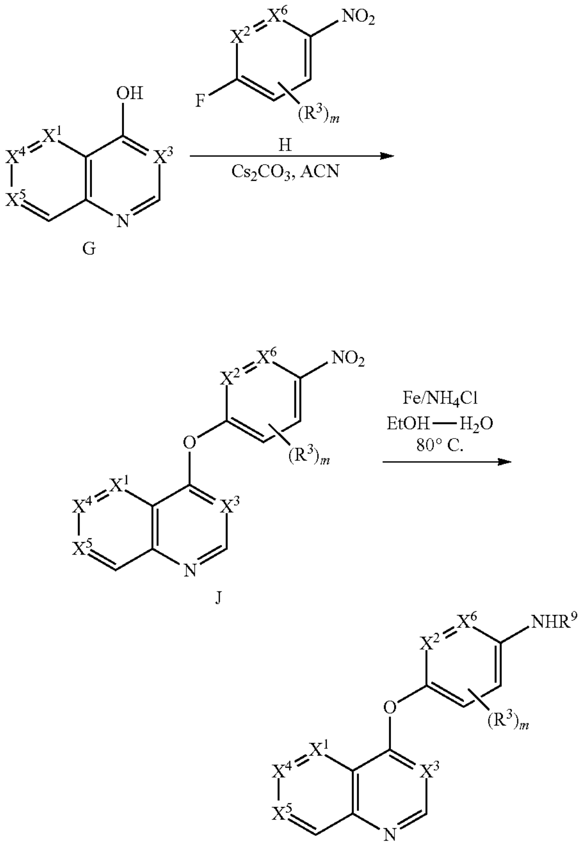

G J B

As shown in Scheme 4, a compound of formula J can be prepared by reacting a compound of formula G with a compound of formula H in the presence of a base such as cesium carbonate in an appropriate organic solvent, typically at room temperature. A compound of formula B can be made from a compound of formula J by reducing the nitro group with a mixture of ammonium chloride and iron typically in a solvent mixture of water and an alcohol such as methanol or ethanol at elevated temperatures.

Scheme 5.

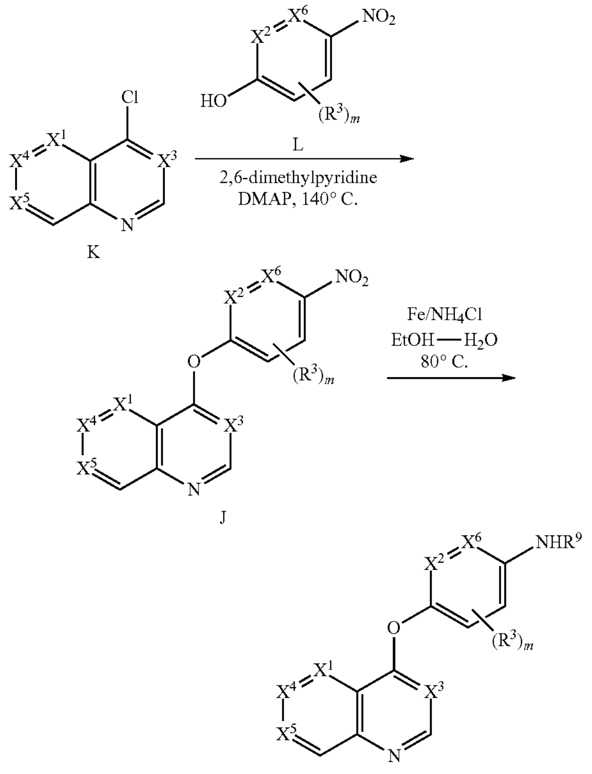

K J B

As shown in Scheme 5, a compound of formula J can also be synthesized by reacting a compound of formula K with a compound of formula L in an appropriate solvent such as 2,6-dimethylpyridine in the presence of a catalytic amount of dimethylaminopyridine at elevated temperatures. A compound of formula B can be prepared from a compound of formula J by reducing the nitro group with a mixture of ammonium chloride and iron typically in a solvent mixture of water and an alcohol such as methanol or ethanol at elevated temperatures.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Synthetic Examples

The following examples are provided for the purpose of further illustration and are not intended to limit the scope of the claimed invention. The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Procedure A:
4-((1,5-Naphthyridin-4-yl)oxy)anilines (6)

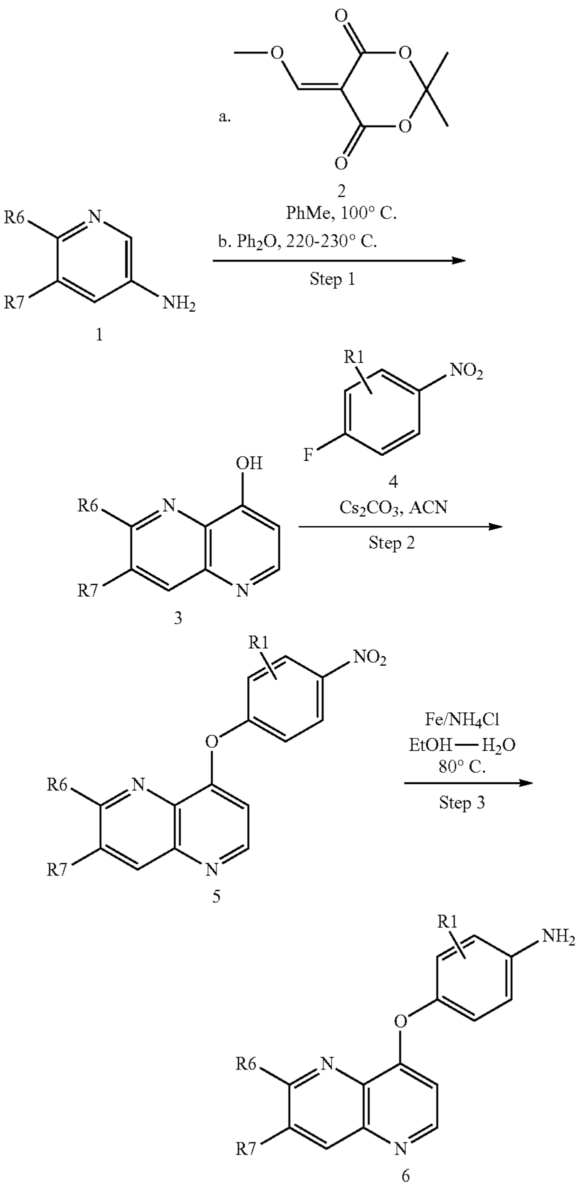

Step 1: A mixture of Compound 1 (32 mmol) and Compound 2 (5.92 g, 32 mmol) in toluene (50 ml) was stirred at 105° C. for 1.5 h and cooled to room temperature. Hexane (50 ml) was added and the suspension filtered to give a brown solid. This solid was mixed with $Ph_2O$ (50 mL) and the resulting mixture was stirred at 220-230° C. for 1 h, cooled to room temperature and poured into $Et_2O$ (100 mL). The resulting suspension was filtered, washed with $Et_2O$ and dried to give Compound 3 typically as a brown solid (25-85% yield).

Step 2: A mixture of Compound 3 (4.8 mmol), Compound 4 (6.8 mmol), and $Cs_2CO_3$ (6.6 g, 20 mmol) in acetonitrile (20 mL) was stirred at room temperature overnight. EtOAc (80 mL) was added and the resulting mixture filtered. The filtrate was evaporated and residue purified by silica gel column chromatography to give Compound 5 (20-50%).

Step 3: A mixture of Compound 5 (1.8 mmol), $NH_4Cl$ (500 mg, 9.3 mmol), and Fe (260 mg, 4.6 mmol) in MeOH/water (20/5 mL) was refluxed for 1 h and then cooled to room temperature. The resulting mixture was filtered through Celite and filtrate concentrated to remove MeOH. To residue was added aq saturated $NaHCO_3$ (6 mL) and the resulting aqueous mixture was extracted with EtOAc. The organic extract was dried over anhyd. $Na_2SO_4$ and evaporated give Compound 6 typically as a brown solid (50-100% yield).

The following intermediates were made following General Procedure A for the synthesis of 4-((1,5-Naphthyridin-4-yl)oxy)anilines 6:

I-1

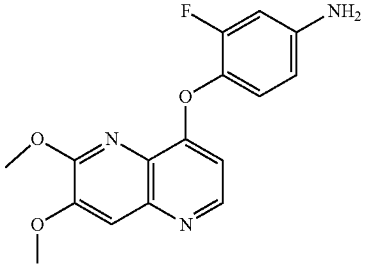

I-2

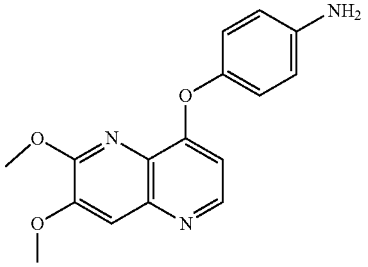

I-3

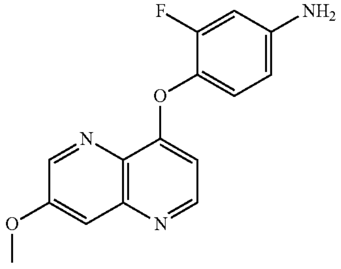

-continued

I-4

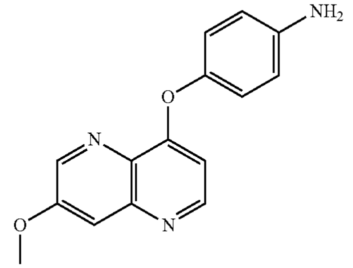

I-5

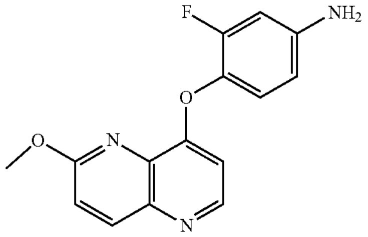

I-6

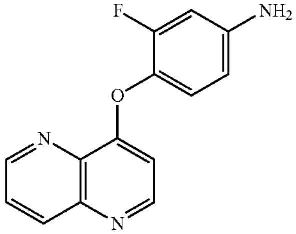

I-8

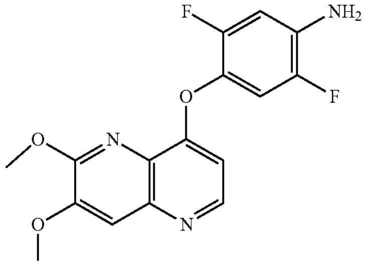

4-((6,7-Dimethoxy-1,5-naphthyridin-4-yl)oxy)-3-fluoroaniline (I-1): MS for $C_{16}H_{14}FN_3O_3$: m/z 316 (MH+).

4-((6,7-Dimethoxy-1,5-naphthyridin-4-yl)oxy)aniline (I-2): MS for $C_{16}H_{15}N_3O_3$: m/z 298 (MH+).

3-Fluoro-4-((7-methoxy-1,5-naphthyridin-4-yl)oxy)aniline (I-3): MS for $C_{15}H_{12}FN_3O_2$: m/z 286 (MH+).

4-((7-Methoxy-1,5-naphthyridin-4-yl)oxy)aniline (I-4): MS for $C_{15}H_{13}N_3O_2$: m/z 268 (MH+).

3-Fluoro-4-((6-methoxy-1,5-naphthyridin-4-yl)oxy)aniline (I-5): MS for $C_{15}H_{12}FN_3O_2$: m/z 286.0 (MH+).

4-((1,5-Naphthyridin-4-yl)oxy)-3-fluoroaniline (I-6): MS for $C_{14}H_{10}FN_3O$: m/z 256 (MH+).

4-((6,7-Dimethoxy-1,5-naphthyridin-4-yl)oxy)-2,5-difluoroaniline (I-8): MS for $C_{16}H_{13}F_2N_3O_3$: m/z 334.0 ($MH^+$).

General Procedure B: 4-(Quinolin-4-yloxy)aniline (10)

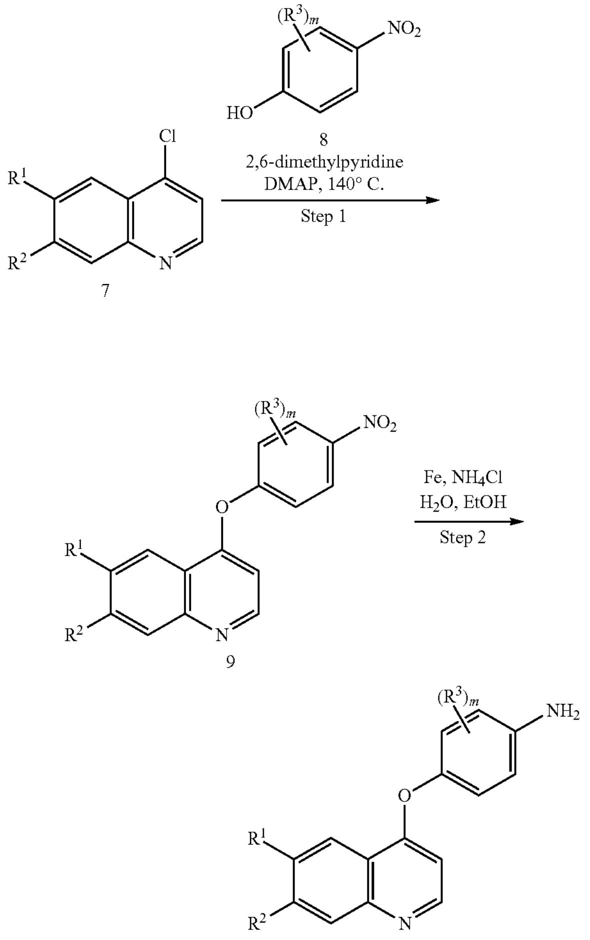

10

Step 1: To a mixture of Compound 7 (44.7 mmol, 1 eq) and Compound 8 (62.5 mmol, 1.4 eq) in 2,6-dimethylpyridine (50 ml) was added DMAP (1.10 g, 9.0 mmol, 0.2 eq). The mixture was stirred at 140° C. for 36 h. The reaction was cooled to room temperature, MeOH (32 g) was added, followed by aq $K_2CO_3$ (4 g in water (62 g)). The resulting mixture was stirred at 0° C. for 2 h. The resulting precipitate was filtered and washed with water (200 ml) to give Compound 9 as a yellow solid (50-60% yield).

Step 2: To a mixture of Compound 9 (6.1 mmol, 1 eq) in EtOH (40 ml) and water (8 ml) was added Fe (1.71 g, 30.6 mmol, 5.0 eq) and $NH_4Cl$ (2.62 g, 49.0 mmol, 8.0 eq). The mixture was stirred at 85° C. for 3 h. The reaction was filtered, and the filtrate was dried over anhyd. $Na_2SO_4$ and concentrated to give crude product. To this crude product was added EtOAc (150 mL) and DCM (150 mL). The resulting mixture was filtered, and the filtrate was concentrated to give Compound 10 as a yellow solid (50-70% yield).

The following intermediate was made following General Procedure B for the synthesis of 4-(quinolin-4-yloxy)anilines 10:

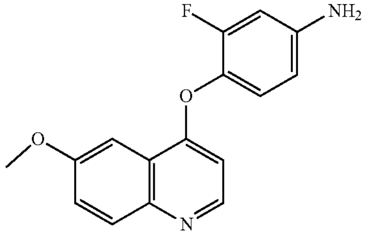

I-7

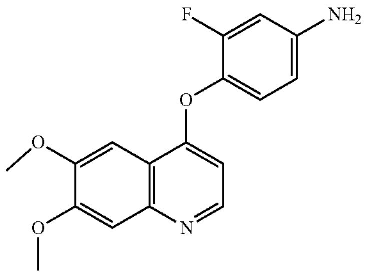

I-9

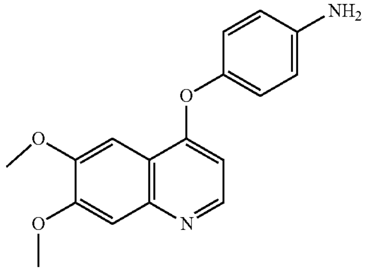

I-10

3-Fluoro-4-((6-methoxyquinolin-4-yl)oxy)aniline (I-7): MS for $C_{16}H_{13}FN_2O_2$: m/z 285.0 (MH+).

4-((6,7-Dimethoxyquinolin-4-yl)oxy)-3-fluoroaniline (I-9): MS for $C_{17}H_{15}FN_2O_3$: m/z 315 ($MH^+$).

4-((6,7-Dimethoxyquinolin-4-yl)oxy)aniline (I-10): MS for $C_{17}H_{16}N_2O_3$: m/z 297.2 ($MH^+$).

General Procedure C: Suzuki Reaction

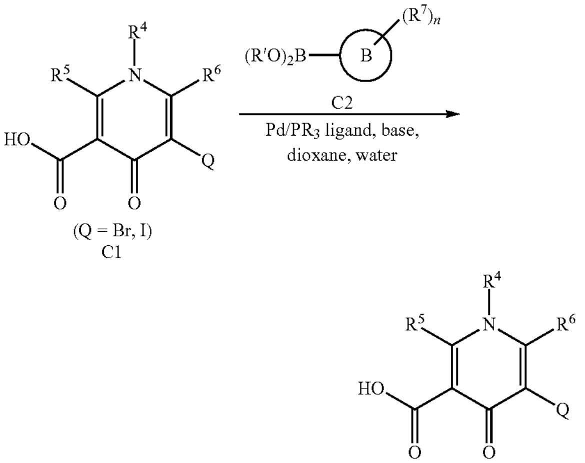

C3

A mixture of the Compound C1 (1 eq), boronic acid/ester C2 (1-5 eq), catalytic Pd/$PR_3$ complex such as, but not limited to, $Pd(PPh_3)_4$ (5-10 mol %), $Pd(dppf)Cl_2$ (mol10-20%), $Pd(Amphos)_2Cl_2$ (10-20 mol %)/SPhos (1 eq), and a base (2-5 eq) such as, but not limited to, $Cs_2CO_3$, $K_2CO_3$, $Na_2CO_3$, $K_3PO_4$, KF, in dioxane/water (1/1 to 5/1) (1.5-5 mL/mmol of C1) was degassed and purged with nitrogen 3 times. The resulting mixture was stirred at 80-160° C., with or without microwave irradiation, under an atmosphere of nitrogen until the starting material C1 was consumed (0.5-20 hr) as monitored by LC-MS and/or TLC. The reaction mixture was then concentrated under reduced pressure. To the resulting residue was added water and resulting mixture was washed with EtOAc, followed by DCM. The aqueous phase was acidified with aq 2 N HCl to pH 2-5. If a suspension resulted, the mixture was filtered, the solid washed with water and dried under reduced pressure to give crude Compound C3. If a filterable solid did not result, the acidic aqueous phase was extracted with an organic solvent such as, but not limited to, EtOAc or DCM. The combined organic extracts were dried over anhyd $Na_2SO_4$ or $MgSO_4$ and concentrated to provide crude Compound C3. Crude Compound C3 was either purified by silica gel chromatography or used directly in subsequent steps without further purification (9-97% yield).

General Procedure D: HATU Coupling

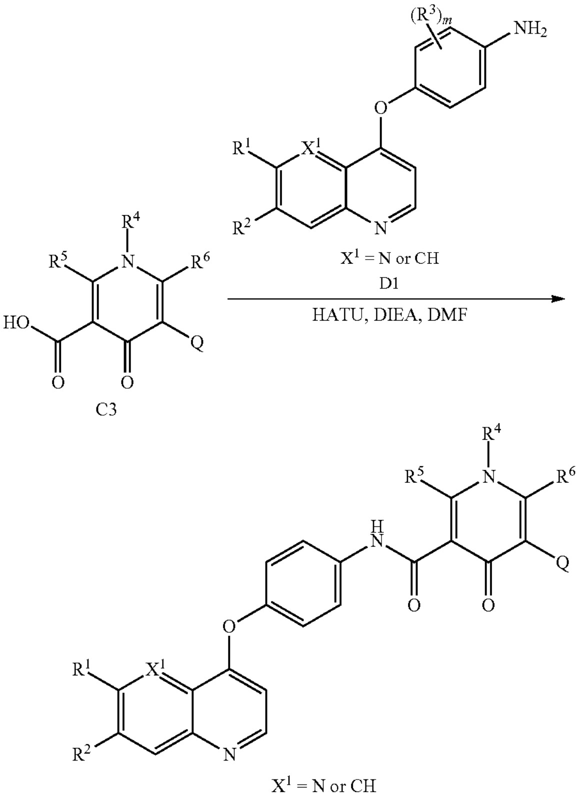

D2

To a solution of Compound C3 (1 eq) in DMF (2-5 mL/mmol of C3) was added the aniline D1 (0.7-1.1 eq), HATU (1.1-2 eq), and DIEA (3-5 eq). The mixture was stirred (room temperature to 40° C.) until Compound C3 was consumed based on LC-MS and/or TLC (4-15 h). The reaction was quenched with water and extracted with EtOAc twice. The combined organic extracts were washed with aq saturated NaCl (3-5 times), dried over anhyd $Na_2SO_4$ and concentrated under reduced pressure. The resulting residue was purified by flash silica gel chromatography to give the Compound D2 (6-63% yield).

Example 1: 6-Methoxy-5-(2-methoxyethoxy)pyridin-3-amine (13)

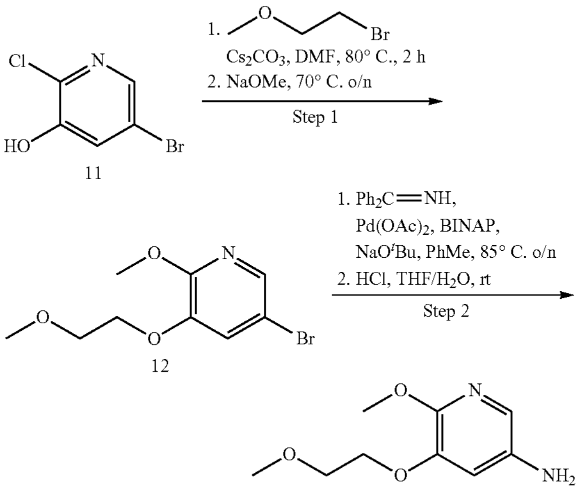

11

12

13

Step 1: 2,3-Dimethoxy-8-(4-nitrophenoxy)-1,5-naphthyridine (12): A mixture of Compound 11 (2.10 g, 10.0 mmol), 1-bromo-2-methoxyethane (1.50 g, 10.8 mmol), and $Cs_2CO_3$, (6.6 g, 20.2 mmol) in DMF was stirred at 80° C. for 2 h, quenched with water and extracted with EtOAc (2x), The combined extracts were washed with aq saturated NaCl, dried over $Na_2SO_4$ and evaporated to give the crude intermediate product as an off-white solid (2.68 g, MS for $C_9H_9BrClNO_2$, found 268 (MH+)). This intermediate product (2.68 g, 10.0 mmol) was mixed with NaOMe (3.0 g, 55.5 mmol) in MeOH (40 mL) and heated at 70° C. overnight. The reaction mixture was concentrated to remove MeOH and the resulting residue was partitioned between water and EtOAc. The EtOAc phase was washed with aq saturated NaCl, dried over $Na_2SO_4$ and evaporated to give crude Compound 12 as an oil (3.0 g) which was used in the next step without further purification. MS for $C_9H_{12}BrNO_3$: m/z 262/264 (MH+).

Step 2: 6-Methoxy-5-(2-methoxyethoxy)pyridin-3-amine (13): Compound 12 (3.0 g, crude) was mixed with diphenylmethanimine (3.6 g, 20 mmol), $Pd(OAc)_2$ (360 mg, 1.61 mmol), BINAP (1.3 g, 2.08 mmol) and NaO'Bu (1.6 g, 16.7 mmol) in toluene (60 ml). The resulting mixture was degassed with argon and stirred at 85° C. overnight. The reaction mixture was partitioned between water and EtOAc. The organic phase was separated and evaporated to dryness under reduced pressure. To the residue was added THF (40 mL) and aqueous 2M HCl (40 mL) and resulting mixture was stirred at room temperature overnight. The pH of the reaction mixture was adjusted to pH 10 with $NaHCO_3$ and extracted with EtOAc. The extract was concentrated and the resulting residue subjected to chromatography on silica gel(0-90% EtOAc in hexanes) to afford Compound 13 as a brown oil (1.4 g, 71% yield from Compound 11). MS for $C9H_{14}N_2O_3$: m/z 199 (MH+).

The following compounds can be made by adapting the procedure used to make Compound 13 in Example 1:

13-1

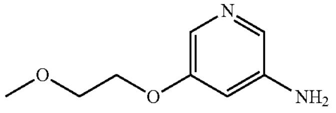

13-2

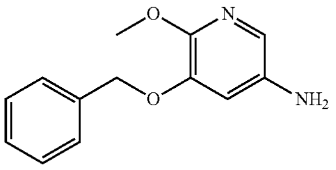

5-(2-Methoxyethoxy)pyridin-3-amine (13-1): Step 1 was replaced with the following method: To a mixture of 5-bromopyridin-3-ol (2 g, 11.5 mmol, 1 eq) and 1-bromo-2-methoxy-ethane (2.4 g, 17 mmol, 11.5 eq) in DMF (20 ml) was added $Cs_2CO_3$ (4.9 g, 14.9 mmol, 1.3 eq). The mixture was stirred at 80° C. for 12 h. The reaction mixture was diluted with EtOAc (10 mL) and washed with water (5×30 ml) washed with aq saturated NaCl (30 mL), dried over anhyd $Na_2SO_4$ and concentrated under reduced pressure to give 3-bromo-5-(2-methoxyethoxy)pyridine as a yellow solid (4.2 g, crude) which was used to replace Compound 12 in Step 2. $^1H$ NMR (400 MHz, DMSO-$d_6$) δ 7.55 (d, 1H), 7.47 (d, 1H), 6.50 (t, 1H), 5.30 (s, 2H), 4.06-4.00 (m, 2H), 3.65-3.59 (m, 2H), 3.33-3.23 (m, 3H).

5-(Benzyloxy)-6-methoxypyridin-3-amine (13-2): 1-Bromo-2-methoxyethane was replaced by 4-methoxybenzyl chloride. MS for $C_3H_{14}N_2O_2$: m/z 231.0 (MH+).

Example 2: 3-Fluoro-4-((6-methoxy-7-(2-methoxyethoxy)-1,5-naphthyridin-4-yl)oxy)aniline (17)

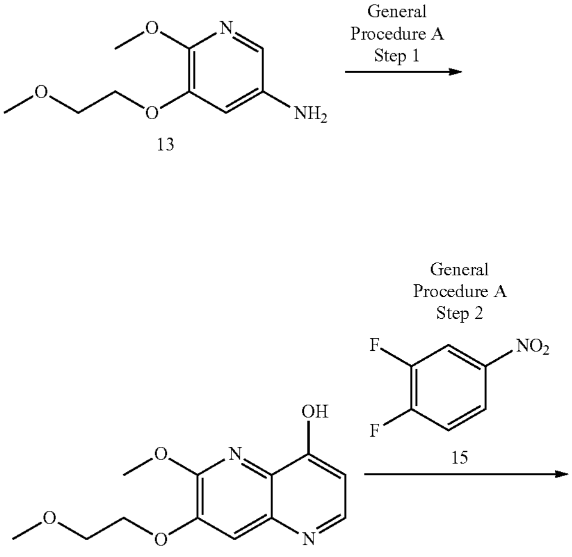

13

15

14

-continued

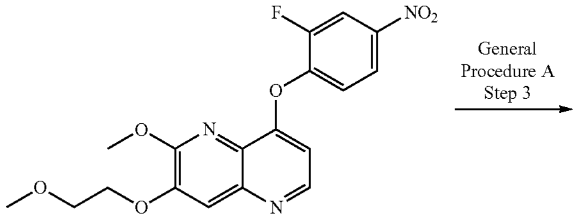

16

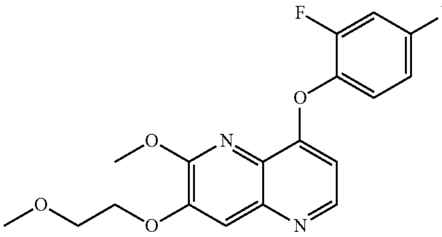

17

3-Fluoro-4-((6-methoxy-7-(2-methoxyethoxy)-1,5-naphthyridin-4-yl)oxy)aniline (17): Compound 17 was made from Compound 13 following the three step procedure outlined in General Procedure A for the synthesis of 4-((1,5-naphthyridin-4-yl)oxy)anilines 6. $^1$H NMR (400 MHz, DMSO-d6) δ 8.47 (d, 1H), 7.64 (s, 1H), 7.05 (t, 1H), 6.61-6.50 (m, 2H), 6.46 (dd, 1H), 5.47 (s, 2H), 4.31 (t, 2H), 4.04 (s, 3H), 3.76 (t, 2H), 3.34 (s, 3H); MS for $C_{18}H_{18}FN_3O_4$: m/z 360.2 (MH+).

The following compounds can be made by adapting the procedure used to make Compound 17 in Example 2:

17-1

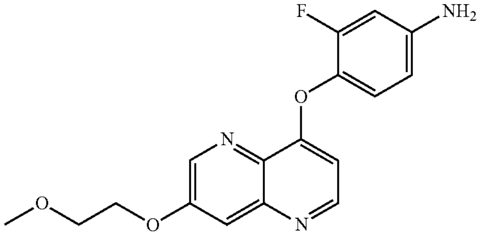

17-2

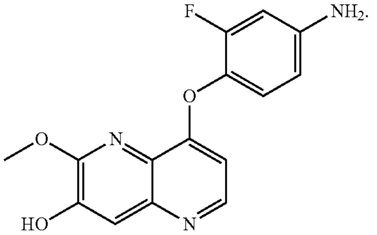

Example 3: 4-((6-Chloro-1,7-naphthyridin-4-yl)oxy)-3-fluoroaniline (24)

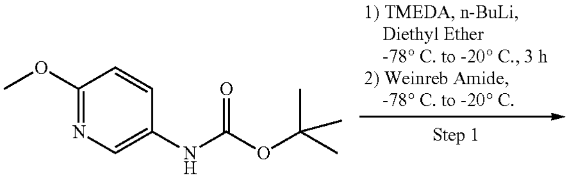

18

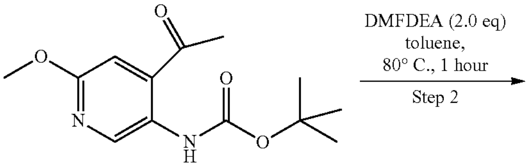

19

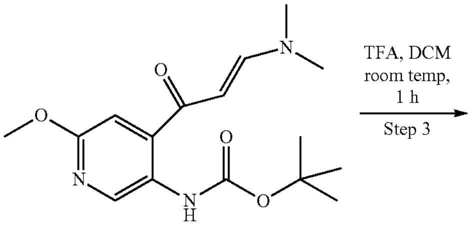

20

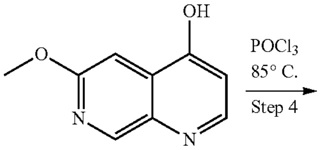

21

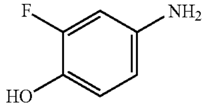

23

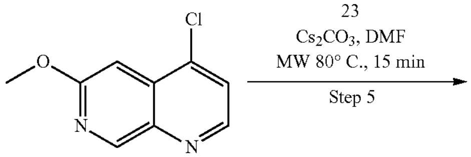

22

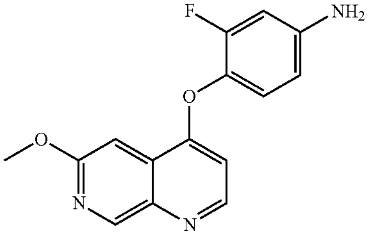

24

Step 1: tert-Butyl (4-acetyl-6-methoxypyridin-3-yl)carbamate (19): Compound 18 (2.5 g, 11 mmol) was added to an oven dried round bottom flask equipped with a magnetic stir bar under nitrogen. Anhydrous diethyl ether (50 ml) was added to the flask under nitrogen followed by TMEDA (5.0 mL, 3.0 eq). The homogenous mixture was cooled to −78° C. and stirred for 15 min under nitrogen. N-Butyl lithium (10 ml, 2.5M in hexanes) was added to the mixture dropwise.

After addition was complete, the mixture was warmed up to −20° C. and stirred at that temperature for 2 h. After 2 h, the mixture was cooled to −78° C., Weinreb amide was added to the mixture, after which the mixture was allowed to warm up to −20° C. and stirred under nitrogen for 2 h. The mixture was quenched at low temperature with water. EtOAc was used to extract the aqueous layer. The combined organic extracts were dried over anhyd. $Na_2SO_4$ and concentrated under reduced pressure. The residue was absorbed onto silica gel and purified by flash chromatography (EtOAc: hexanes) to give Compound 19 as an off white solid (745 mg, 25% yield). $^1H$ NMR (400 MHz, $CDCl_3$) δ 9.61 (bs, 1H), 9.20 (s, 1H), 7.10 (s, 1H), 3.97 (s, 3H), 2.64 (s, 3H), 1.54 (s, 9H).

Step 2: tert-Butyl (E)-(4-(3-(dimethylamino)acryloyl)-6-methoxypyridin-3-yl)carbamate (20): Compound 19 (745 mg, 2.79 mmol) was dissolved in toluene and DMFDEA (1.46 mL, 2.0 eq) was added to the resulting solution. The reaction mixture was heated at 80° C. Upon completion of the reaction, the solution was concentrated under reduced pressure to remove toluene. EtOAc was added to the residue and the mixture was absorbed onto silica gel under reduced pressure and purified by flash chromatography (EtOAc: hexanes) to give Compound 20 as an orange solid (800 mg, 89% yield). $^1H$ NMR (400 MHz, $CDCl_3$) δ 9.50 (bs, 1H), 9.03 (s, 1H), 7.79 (d, 1H), 6.95 (s, 1H), 5.56 (d, 1H), 3.97 (s, 3H), 3.21 (s, 3H), 2.96 (s, 3H), 1.51 (s, 9H); MS for $C_{16}H_{23}N_3O_4$: m/z 322 (MH+).

Step 3: 6-Methoxy-1,7-naphthyridin-4-ol (21): Compound 20 (800 mg, 2.49 mmol) was dissolved in DCM (12.45 ml, 0.2M) and trifluoroacetic acid (3.81 mL, 20 eq) was added dropwise. The resulting mixture was stirred at room temperature for 1 h. Upon completion of the reaction, the reaction mixture was concentrated under reduced pressure to remove trifluoroacetic acid. The residual solid was suspended in EtOAc and a small amount of aq saturated $NaHCO_3$ solution was added dropwise until the solid dissolved into the organic layer. The phases were separated and solid NaCl was added to the aq layer. The resulting mixture was extracted with DCM. The combined organic extracts were dried over anhyd. $Na_2SO_4$ and concentrated under reduced pressure to give crude Compound 21 (435 mg, 99.2% yield) which used for the next step without further purification. $^1H$ NMR (400 MHz, DMSO-$d_6$) δ 8.76 (s, 1H), 7.97 (d, 1H), 7.24 (s, 1H), 6.02 (d, 1H), 3.91 (s, 3H); MS for $C_9H_8N_2O_2$: m/z 177 (MH+).

Step 4: 4-Chloro-6-methoxy-1,7-naphthyridine (22): Compound 21 (435 mg, 2.47 mmol) was suspended in $POCl_3$ (6.5 mL) and the mixture was heated at 80° C. for 2 h. Upon completion of reaction, excess $POCl_3$ was mostly removed by concentrating under reduced pressure. EtOAc was added to the residue, and the resulting mixture was cooled in an ice bath. Aqueous saturated $NaHCO_3$ was added dropwise until all the residual $POCl_3$ was consumed. The organic phase was separated from the aqueous phase and concentrated under reduced pressure. DCM was added to the resulting residue. The resulting solution was dried over anhyd. $Na_2SO_4$ and concentrated under reduced pressure to give Compound 22 as an off while solid (353 mg, 73% yield) which used in the next step without further purification. $^1H$ NMR (400 MHz, DMSO-$d_6$) δ 9.24 (s, 1H), 8.79 (d, 1H), 7.92 (d, 1H), 7.28 (s, 1H), 4.03 (s, 3H); MS for $C9H7ClN_2O$: m/z 195 (MH+).

Step 5: 3-Fluoro-4-((6-methoxy-1,7-naphthyridin-4-yl)oxy)aniline (23): Compound 22 (353 mg, 1.81 mmol), was dissolved in anhydrous DMF (9 mL, 0.2 M) in a 20 mL microwave tube. $Cs_2CO_3$ (1.77 g, 3.0 eq) was added to the mixture followed by Compound 23 (461 mg, 2.0 eq). The mixture was degassed with nitrogen for 5 min, then sealed and heated at 85° C. under microwave irradiation for 15 min. Upon completion of the reaction, the mixture was diluted with DCM and filtered. The filtrate was washed with water and concentrated under reduced pressure. The resulting residue was diluted with DCM again and washed with water again. The phases were separated and the organic phase was dried over anhyd. $Na_2SO_4$ and concentrated under reduced pressure. The resulting residue was absorbed onto silica gel and purified by flash column chromatography to give Compound 24 as a light brown solid (402 mg, 77.7% yield). $^1H$ NMR (400 MHz, DMSO-$d_6$) δ 9.15 (s, 1H), 8.62 (d, 1H), 7.39 (s, 1H), 7.10 (t, 1H), 6.66 (d, 1H), 6.56 (d, 1H), 6.48 (d, 1H), 5.54 (s, 2H), 4.01 (s, 3H); MS for $C_{15}H_{12}FN_3O_2$: m/z 286 (MH+).

The following compound was made using the same 5 step synthesis used to make Compound 24 in Example 3:

24A

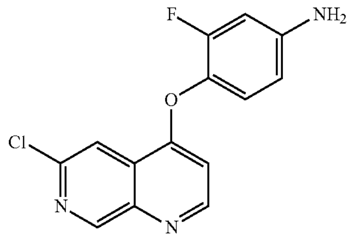

4-((6-Chloro-1,7-naphthyridin-4-yl)oxy)-3-fluoroaniline (24A): Compound 18 was replaced with tert-butyl (6-chloropyridin-3-yl)carbamate. $^1H$ NMR (400 MHz, DMSO-$d_6$) δ 9.29 (s, 1H), 8.85 (d, 1H), 8.25 (s, 1H), 7.13 (t, 1H), 6.85 (d, 1H), 6.57 (d, 1H), 6.48 (d, 1H), 5.71 (s, 2H); MS for $C14H_9ClFN_3O$: m/z 290 (MH+).

Example 4: Ethyl 3-((5-fluoropyridin-2-yl)amino)-3-oxopropanoate (27)

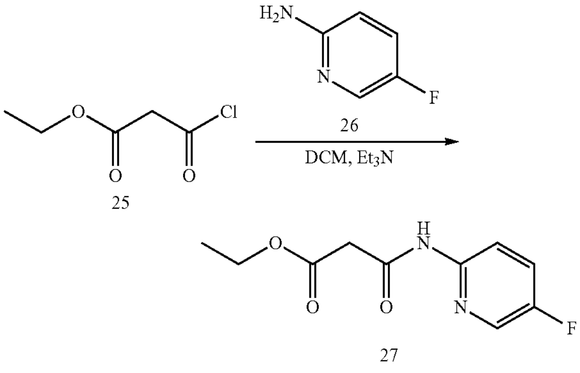

26

25

27

A solution of Compound 25 (1 g, 6.64 mmol, 0.83 mL, 1 eq) in DCM (5 ml) was added dropwise to a stirred solution of Compound 26 (745 mg, 6.64 mmol, 1 eq) and $Et_3N$ (0.92 mL, 6.64 mmol) in DCM (20 ml) at −70° C. under nitrogen. Once addition of the Compound 25 solution was complete, the resulting reaction mixture was allowed to warm up to 15° C. for 12 h. The reaction mixture was concentrated in vacuo and the resulting residue was dissolved in EtOAc (30 mL), washed successively with water (2×15 ml) and aq saturated NaCl (2×15 mL), dried over anhyd. $Na_2SO_4$ and concentrated under vacuum to give Compound 27 as a yellow solid (1.0 g, 66.6% yield). 1H NMR (400 MHz, $CDCl_3$) δ 9.64 (br s, 1H), 8.22 (br dd, 1H), 8.15 (d, 1H), 7.40-7.50 (m, 1H), 4.27 (q, 2H), 3.50 (s, 2H), 1.35-1.30 (m, 3H).

The following compounds were made in a manner similar to Compound 27 in Example 4:

27-2

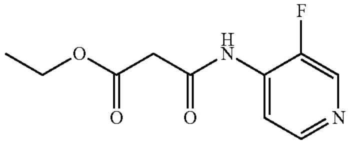

27-3

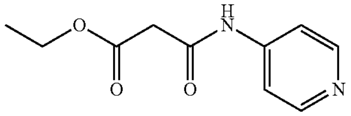

27-4

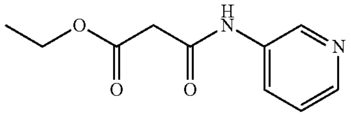

27-5

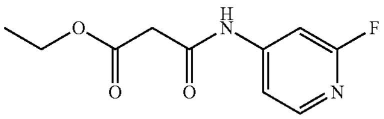

27-6

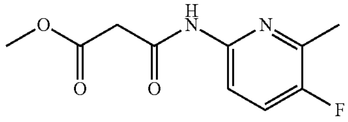

27-7

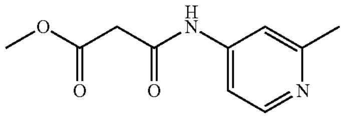

27-8

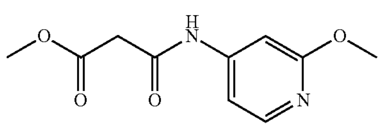

27-9

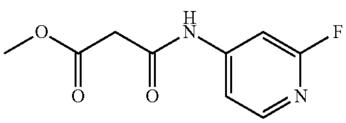

27-10

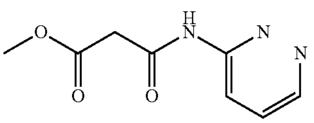

27-11

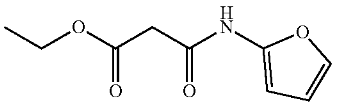

-continued 27-12

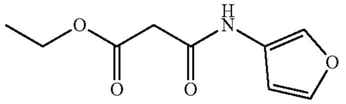

27-13

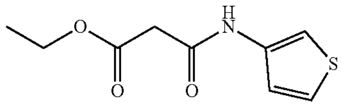

Ethyl 3-((3-fluoropyridin-4-yl)amino)-3-oxopropanoate (27-2): Compound 26 was replaced with 3-fluoropyridin-4-amine. $^1$H NMR (400 MHz, $CDCl_3$) δ 9.99 (s, 1H), 8.51-8.40 (m, 1H), 8.41-8.29 (m, 2H), 4.31 (q, 2H), 3.56 (s, 2H), 1.35 (t, 3H); MS for $C_{10}H_{11}FN_2O_3$: m/z 227.0 (MH+).

Ethyl 3-oxo-3-(pyridin-4-ylamino)propanoate (27-3): Compound 26 was replaced with pyridin-4-amine. $^1$H NMR (400 MHz, DMSO-$d_6$) δ 10.57 (s, 1H), 8.44 (d, 2H), 7.54 (d, 2H), 4.13 (q, 2H), 3.51 (s, 2H), 1.20 (t, 3H); MS for $C_{10}H_{12}N_2O_3$: m/z 209.0 (MH+).

Ethyl 3-oxo-3-(pyridin-3-ylamino)propanoate (27-4): Compound 26 was replaced with pyridin-3-amine. $^1$H NMR (400 MHz, DMSO-$d_6$) δ 10.40 (s, 1H), 8.71 (d, 1H), 8.29 (dd, 1H), 8.05-7.96 (m, 1H), 7.36 (dd, 1H), 4.13 (q, 2H), 3.49 (s, 2H), 1.21 (t, 3H); MS for $C_{10}H_{12}N_2O_3$: m/z 209.0 (MH+).

Ethyl 3-((2-fluoropyridin-4-yl)amino)-3-oxopropanoate (27-5): Compound 26 was replaced with 2-fluoropyridin-4-amine. $^1$H NMR (400 MHz, $CDCl_3$) δ 9.88 (s, 1H), 8.13 (d, 1H), 7.41 (d, 1H), 7.32-7.21 (m, 1H), 4.36-4.24 (m, 2H), 3.53 (s, 2H), 1.36 (t, 3H).

Methyl 3-((5-fluoro-6-methylpyridin-2-yl)amino)-3-oxopropanoate (27-6): Compound 26 was replaced with 5-fluoro-6-methylpyridin-2-amine and Compound 25 was replaced by methyl 3-chloro-3-oxopropanoate. MS for $C_{10}H_{11}FN_2O_3$: m/z 227 (MH+).Methyl 3-((2-methylpyridin-4-yl)amino)-3-oxopropanoate (27-7): Compound 26 was replaced with 2-methylpyridin-4-amine and Compound 25 was replaced by methyl 3-chloro-3-oxopropanoate. $^1$H NMR (400 MHz, DMSO-$d_6$) δ 10.58 (s, 1H), 8.31 (d, 1H), 7.44 (d, 1H), 7.35 (dd, 1H), 3.65 (s, 3H), 3.53 (s, 2H), 2.41 (s, 3H); MS for $C_{10}H_{12}N_2O_3$: m/z 208.9 (MH+).

Methyl 3-((2-methoxypyridin-4-yl)amino)-3-oxopropanoate (27-8): Compound 26 was replaced with 2-methoxypyridin-4-amine and Compound 25 was replaced by methyl 3-chloro-3-oxopropanoate. $^1$H NMR (400 MHz, $CDCl_3$) δ 9.45 (br s, 1H), 8.08 (d, 1H), 7.11 (d, 1H), 7.03 (dd, 1H), 3.94 (s, 3H), 3.82 (s, 3H), 3.51 (s, 2H); MS for $C_{10}H_{12}N_2O_4$: m/z 224.9 (MH+).

Methyl 3-((2-fluoropyridin-4-yl)amino)-3-oxopropanoate (27-9): Compound 26 was replaced with 2-fluoropyridin-4-amine and Compound 25 was replaced by methyl 3-chloro-3-oxopropanoate. MS for $C9H_9FN_2O_3$: m/z 212.9 (MH+).

Methyl 3-oxo-3-(pyridazin-3-ylamino)propanoate (27-10): Compound 26 was replaced with pyridazin-3-amine and Compound 25 was replaced by methyl 3-chloro-3-oxopropanoate. MS for $C_8H_9N_3O_3$: m/z 195.9 (MH+).

Ethyl 3-(furan-2-ylamino)-3-oxopropanoate (27-11): Compound 26 was replaced with furan-2-amine. MS for $C9H_{11}NO_4$: m/z 198 (MH+).

Ethyl 3-(furan-3-ylamino)-3-oxopropanoate (27-12): Compound 26 was replaced with furan-3-amine. MS for $C9H_{11}NO_4$: m/z 198 (MH+).

Ethyl 3-oxo-3-(thiophen-3-ylamino)propanoate (27-13): Compound 26 was replaced with thiophen-3-amine. MS for $C_9H_{11}NO_3S$: m/z 214 (MH+).

Example 5: Ethyl 3-((5-fluoro-3-methylpyridin-2-yl)amino)-3-oxopropanoate (29)

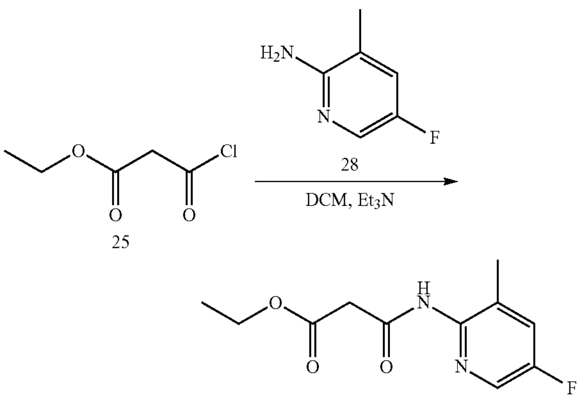

28

25

29

Compound 29 was synthesized using an analogous method to the synthesis of Compound 27 in Example 4, replacing Compound 26 with Compound 28. $^1$H NMR ($CDCl_3$) δ: 9.49 (s, 1H), 8.10 (d, 1H), 7.30 (dd, 1H), 4.22 (q, 2H), 3.53 (s, 2H), 2.28 (s, 3H), 1.28 (t, 3H). MS for $C_{11}H_{13}FN_2O_3$: m/z 241 (MH+).

Example 6: Ethyl 3-((5-fluoropyridin-2-yl)amino)-3-oxopropanoate 5'-fluoro-6-methyl-2-oxo-2H-[1,2'-bipyridine]-3-carboxylic acid (31)

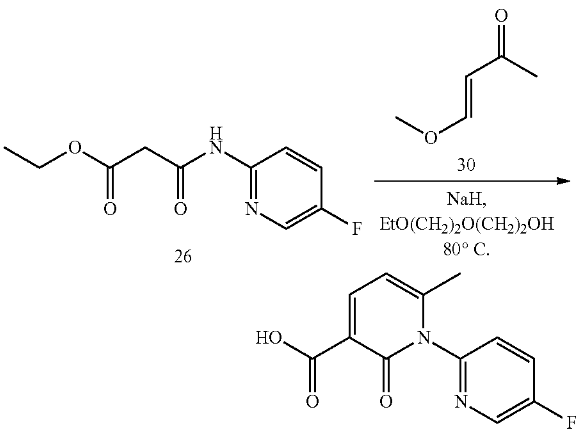

30

26

31

To a flask containing 2-(2-ethoxyethoxy)ethan-1-ol (6 ml) at room temperature was added NaH (60% in oil, 380 mg, 9.94 mmol). The mixture was stirred at room temperature for 10 min until all NaH was dissolved. To this mixture were added Compound 26 (1.41 g, 6.63 mmol) and Compound 30 (995 mg, 9.95 mmol). The resulting mixture was stirred at 80° C. for 1 h. After the mixture was cooled to room temperature, 1 N HCl was added until pH 3. The mixture was filtered and the solid was dried under vacuum to give Compound 31 (600 mg, 36%). $^1$H NMR (400 MHz, DMSO-$d_6$) δ 13.87 (s, 1H), 8.72 (d, 1H), 8.43 (d, 1H), 8.10 (td, 1H), 7.80 (dd, 1H), 6.79 (d, 1H), 2.08 (s, 3H); MS for C12$H_9FN_2O_3$: m/z 249 (MH+).

The following compounds were made in a manner similar to Compound 31 in Example 6:

31-2

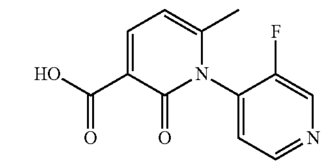

31-3

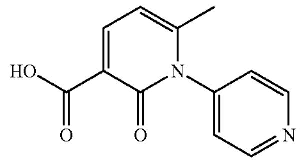

31-4

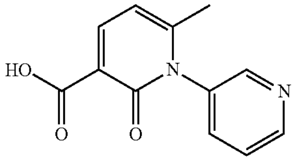

31-6

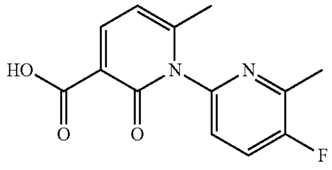

31-7

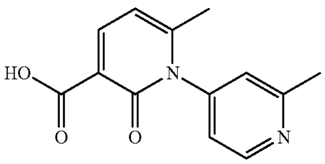

31-8

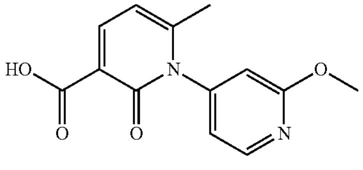

31-10

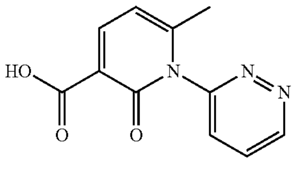

3'-Fluoro-6-methyl-2-oxo-2H-[1,4'-bipyridine]-3-carboxylic acid (31-2): Compound 27 was replaced with Compound 27-2. $^1$H NMR (400 MHz, $CDCl_3$) δ 13.34 (s, 1H), 8.82 (s, 1H), 8.72 (d, 1H), 8.55 (dd, 1H), 7.35 (t, 1H), 6.61 (d, 1H), 2.21 (s, 3H); MS for $C_{12}H_9FN_2O_3$: m/z 249.0 (MH+).

6-Methyl-2-oxo-2H-[1,4'-bipyridine]-3-carboxylic acid (31-3): Compound 27 was replaced with Compound 27-3. $^1$H NMR (400 MHz, DMSO-$d_6$) δ 13.92 (s, 1H), 8.85 (d, 2H), 8.43 (d, 1H), 7.59 (d, 2H), 6.82 (d, 1H), 2.11 (s, 3H); MS for $C_{12}H_{10}N_2O_3$: m/z 231.0 (MH+).

6-Methyl-2-oxo-2H-[1,3'-bipyridine]-3-carboxylic acid (31-4): Compound 27 was replaced with Compound 27-4. $^1$H NMR (400 MHz, DMSO-$d_6$) δ 14.00 (s, 1H), 8.75 (d, 1H), 8.74-8.63 (m, 1H), 8.43 (dd, 1H), 8.02-7.92 (m, 1H), 7.67 (dd, 1H), 6.83 (d, 1H), 2.11 (s, 3H); MS for $C_{12}H_{10}N_2O_3$: m/z 231.0 (MH+).

5'-Fluoro-6,6'-dimethyl-2-oxo-2H-[1,2'-bipyridine]-3-carboxylic acid (31-6): Compound 27 was replaced with Compound 27-6. MS for $C13H_{11}FN_2O_3$: m/z 263 (MH+).

2',6-Dimethyl-2-oxo-2H-[1,4'-bipyridine]-3-carboxylic acid (31-7): Compound 27 was replaced with Compound 27-7. $^1H$ NMR (400 MHz, DMSO-$d_6$) δ 13.97 (br s, 1H), 8.69 (d, 1H), 8.42 (d, 1H), 7.42 (s, 1H), 7.37 (br d, 1H), 6.81 (d, 1H), 2.56 (s, 3H), 2.11 (s, 3H); MS for $C13H_{12}N_2O_3$: m/z 245 (MH+).

2'-Methoxy-6-methyl-2-oxo-2H-[1,4'-bipyridine]-3-carboxylic acid (31-8): Compound 27 was replaced with Compound 27-8. $^1H$ NMR: (400 MHz, DMSO-$d_6$) δ 8.41 (s, 1H), 8.39 (d, 1H), 7.13 (dd, 1H), 7.07 (d, 1H), 6.80 (d, 1H), 3.93 (s, 3H), 2.13 (s, 3H); MS for $Cl3H_{12}N_2O_4$: m/z 260.9 (MH+).

6-Methyl-2-oxo-1-(pyridazin-3-yl)-1,2-dihydropyridine-3-carboxylic acid (31-10): Compound 27 was replaced with Compound 27-10. $^1H$ NMR: (400 MHz, DMSO-$d_6$) δ 9.45-9.49 (m, 1H), 8.47 (d, 1H), 8.08-8.12 (m, 2H), 6.83 (d, 1H), 2.08 (s, 3H); MS for $C_{11}H_9N_3O_3$: m/z 231.9 (MH+).

Example 6a: 5'-Ethoxy-6-methyl-2-oxo-2H-[1,2'-bipyridine]-3-carboxylic acid (31a)

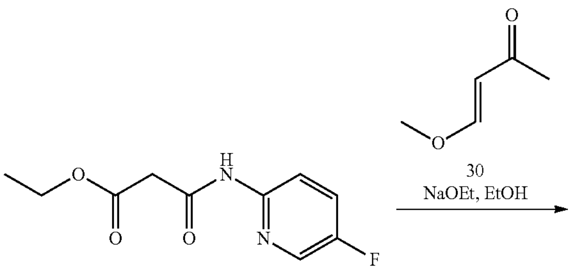

27

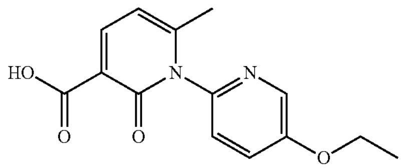

31a

5'-Ethoxy-6-methyl-2-oxo-2H-[1,2'-bipyridine]-3-carboxylic acid (31a): To a mixture of Compound 27 (4.4 mmol, 1 eq) and Compound 30 (6.6 mmol, 1.5 eq) in EtOH (15 ml) was added NaOEt (210 mg, 3.0 mmol, 3 eq). The mixture was stirred at 80° C. for 10 h. The reaction was cooled to room temperature, concentrated, and extracted with DCM. The organic phase was washed with aq 1 N HCl and concentrated. To the resulting residue was added aq saturated $NaHCO_3$. The resulting mixture was stirred and filtered to give crude Compound 31a (520 mg, 43% yield) which was used in the next step without further purification. MS for $C14H_{14}N_2O_4$: m/z 275 (MH+).

Example 6b: 5-Acetyl-1-(furan-3-yl)-6-methyl-2-oxo-1,2-dihydropyridine-3-carboxylic acid (6b-3)

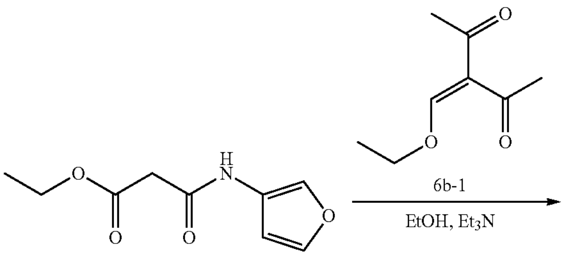

27-12

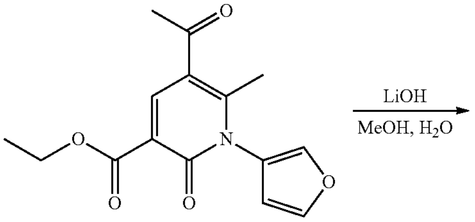

6b-2

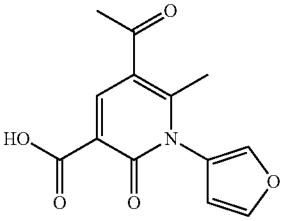

6b-3

Step 1: Ethyl 5-acetyl-1-(furan-3-yl)-6-methyl-2-oxo-1,2-dihydropyridine-3-carboxylate (6b-2): A mixture of Compound 27-12 (590 mg, 3.0 mmol), Compound 6b-1 (0.47 ml, 3.0 mmol), triethylamine (1.30 mL, 9.0 mmol) and EtOH (10 ml) was stirred at room temperature. After 6 d, the resulting mixture was concentrated in vacuo, dissolved in EtOAc (10 mL), and washed with aq saturated $NaHCO_3$ (6 mL). The aqueous layer was extracted with EtOAc (2×5 mL) and the combined organic layers were dried over anhyd. $Na_2SO_4$ and concentrated under vacuum to give Compound 6b-2 which was used in the next step without further purification. MS for $C15H_{15}NO_5$: m/z 290 (MH+).

Step 2: 5-Acetyl-1-(furan-3-yl)-6-methyl-2-oxo-1,2-dihydropyridine-3-carboxylic acid (6b-3): A mixture of crude Compound 6b-2 from the previous step (~3.0 mmol, 1 eq), LiGH monohydrate (190 mg, 4.5 mmol), MeOH (6 mL) and water (2 mL) was stirred at room temperature for 1 h. After concentrating the reaction mixture in vacuo, water (1 mL) was added and the resulting solution was washed with EtOAc (2×3 mL). The aqueous layer was acidified with 1N HCl and extracted with EtOAc (2×3 mL). The combined organic layers were concentrated in vacuo and purified by prep HPLC to give Compound 6b-3 as beige solid (22 mg). MS for $C_{13}H_{11}NO_5$: m/z 262 (MH+).

The following compounds were made using the same 2 step synthesis used to make Compound 6b-3 in Example 6b:

6b-4

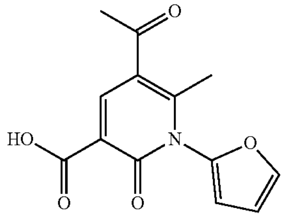

6b-5

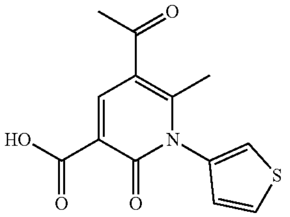

5-Acetyl-1-(furan-2-yl)-6-methyl-2-oxo-1,2-dihydropyridine-3-carboxylic acid (6b-4): Compound 27-12 was replaced with Compound 27-11. MS for $C_{13}H_{11}NO_5$: m/z 262 (MH+).

5-Acetyl-6-methyl-2-oxo-1-(thiophen-3-yl)-1,2-dihydropyridine-3-carboxylic acid (6b-5): Compound 27-12 was replaced with Compound 27-13. MS for $C_{13}H_{11}NO_4S$: m/z 278 (MH+).

Example 7: 5'-Fluoro-3',6-dimethyl-2-oxo-2H-[1,2'-bipyridine]-3-carboxylic acid (32)

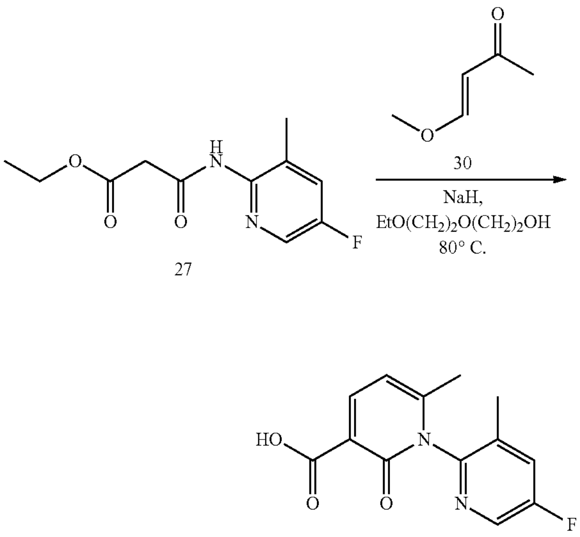

27

32

Compound 32 was synthesized using an analogous method to the synthesis of Compound 31 in Example 6, replacing Compound 26 with Compound 29. $^1H$ NMR (DMSO-$d_6$) δ: 13.76 (s, 1H), 8.56 (d, 1H), 8.47 (d, 1H), 8.04 (dd, 1H), 6.83 (d, 1H), 2.11 (s, 3H), 2.05 (s, 3H). MS for $C_{13}H_{11}FN_2O_3$: m/z 263 (MH+).

Example 8: 5'-Fluoro-4-methyl-2-oxo-2H-[1,2'-bipyridine]-3-carboxylic acid (35)

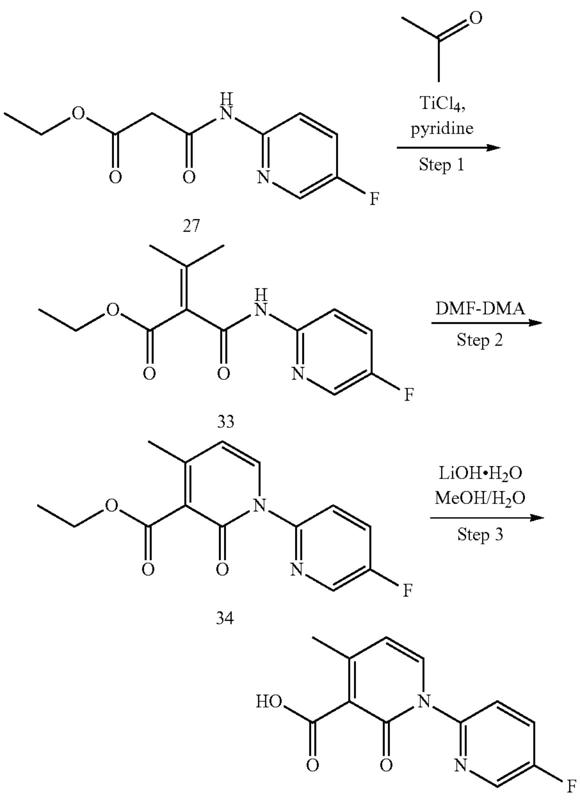

27

33

34

35

Step 1: Ethyl 2-((5-fluoropyridin-2-yl)carbamoyl)-3-methylbut-2-enoate (33): A solution of Compound 27 (500 mg, 2.21 mmol, 1 eq) in THF (6 mL) in a round-bottom flask was cooled to 0° C. in an ice bath. To the cooled solution was added $TiCl_4$ (461.19 mg, 2.43 mmol, 1.1 eq) by syringe (1M solution in THF, 2.4 mL, 2.43 mmol) dropwise over 30 min. The resulting mixture was stirred with cooling for 30 min at 0° C., after which acetone (0.33 mL, 4.42 mmol, 2 eq) was added. The reaction mixture was stirred for 30 min at 0° C. before dropwise addition of anhydrous pyridine (0.71 mL, 8.84 mmol, 4 eq). The reaction was allowed to warm gradually to 25° C. for 24 h, then poured into ice water and extracted with EtOAc (3×30 mL). The combined organic extracts were washed with aq saturated NaCl, dried over anhyd. $MgSO_4$ and concentrated to dryness. The crude residue was purified by silica gel chromatography (petroleum ether/EtOAc=5/1) to give Compound 33 as a colorless oil (110 mg, 16.82% yield, 90% purity). $^1H$ NMR (400 MHz, $CDCl_3$) δ 8.51 (br s, 1H), 8.31 (br dd, 1H), 8.14 (d, 1H), 7.52-7.42 (m, 1H), 4.25 (q, 2H), 2.19 (s, 3H), 2.06 (s, 3H), 1.29 (t, 3H).

Step 2: Ethyl 5'-fluoro-4-methyl-2-oxo-2H-[1,2'-bipyridine]-3-carboxylate (34): A solution of Compound 33 (80 mg, 0.3 mmol, 1 eq) in DMF-DMA (3 mL) was heated at 80° C. for 12 h. The mixture was concentrated under vacuum to give crude Compound 34 as a yellow solid (80 mg) which was used without further purification.

Step 3: 5'-Fluoro-4-methyl-2-oxo-2H-[1,2'-bipyridine]-3-carboxylic acid (35): To a solution of Compound 34 (80 mg, 0.29 mmol, 1 eq) in MeOH (5 mL) was added LiOH monohydrate (61 mg, 1.45 mmol, 5 eq) in $H_2O$ (1 mL). The mixture was stirred at 40° C. for 2 h, followed by stirring at 45° C. for 12 h. Water (20 mL) was added to the reaction mixture which was then washed with EtOAc (25 mL). The aqueous layer was acidified with 2N HCl to pH 5 and extracted with EtOAc (3×20 mL). The combined organic extracts were dried over anhyd. $Na_2SO_4$ and concentrated in vacuo to give crude Compound 35 as a yellow solid (40 mg). $^1H$ NMR (400 MHz, $CDCl_3$) δ 8.46 (d, 1H), 7.97 (d, 1H), 7.92 (dd, 1H), 7.70-7.60 (m, 1H), 6.55 (d, 1H), 2.85 (s, 3H).

Example 9: 5-Bromo-5'-fluoro-6-methyl-2-oxo-2H-[1,2'-bipyridine]-3-carboxylic acid (36)

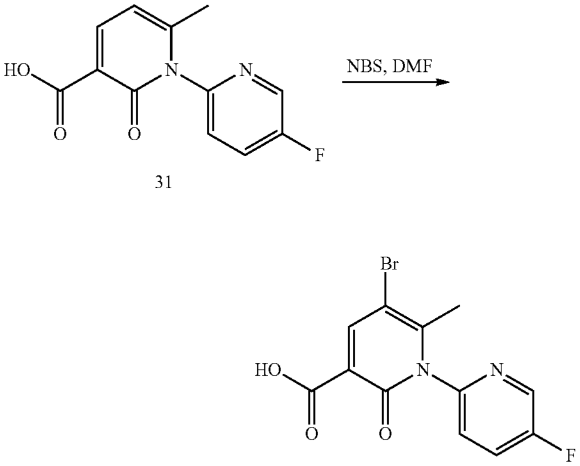

31

36

To a mixture of Compound 31 (660 mg, 2.66 mmol, 1 eq) in DMF (7 mL) was added NBS (568 mg, 3.19 mmol, 1.2 eq) under nitrogen. The mixture was stirred at 25° C. for 12 h. The reaction 5 mixture was concentrated in vacuo, water (30 mL) was added and the mixture extracted with DCM (2×20 mL). The combined organic extracts were concentrated in vacuo to give crude Compound 36 as a yellow solid (940 mg). $^1H$ NMR (400 MHz, $CDCl_3$) δ 13.44 (s, 1H), 8.71 (s, 1H), 8.57 (d, 1H), 7.74 (m, 1H), 7.41 (dd, 1H), 2.28 (s, 3H); MS for $C_{12}H_8BrFN_2O_3$: m/z 328.9 (MH+).

Example 10: 5'-Fluoro-2-oxo-2H-[1,2'-bipyridine]-3-carboxylic acid (40)

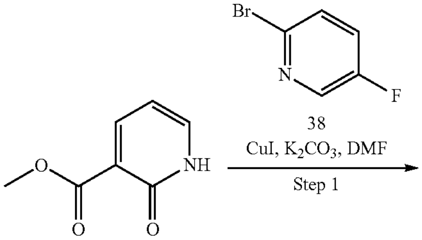

37

-continued

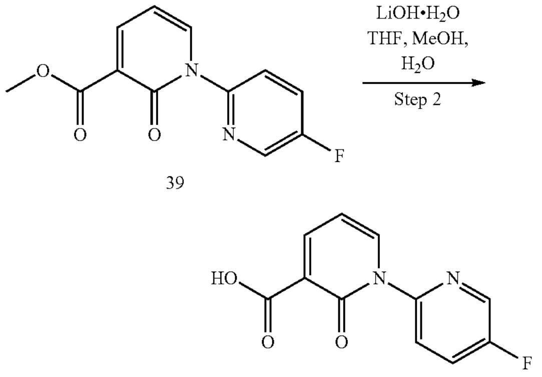

39

40

Step 1: Methyl 5'-fluoro-2-oxo-2H-[1,2'-bipyridine]-3-carboxylate (39): To a mixture of Compound 37 (1 g, 6.53 mmol, 1 eq), CuI (125 mg, 0.66 mmol, 0.1 eq) and $K_2CO_3$ (903 mg, 6.53 mmol, 1 eq) in DMF (10 ml) was added Compound 38 (2.30 g, 13.07 mmol, 2 eq) and the resulting mixture was stirred at 150° C. for 6 h under nitrogen. The resulting gray suspension of Compound 39 in DMF was used in the next step without isolation. MS for $C_{12}H_9FN_2O_3$: m/z 248.9 (MH+).

Step 2: 5'-Fluoro-2-oxo-2H-[1,2'-bipyridine]-3-carboxylic acid (40): To the suspension of Compound 39 in DMF from the previous step (6.53 mmol) was added THF (7.5 mL), MeOH (15 mL) and water (1.5 mL) followed by the addition of LiOH monohydrate (548 mg, 13.06 mmol, 2 eq). The mixture was stirred at 15° C. for 1 h. The reaction mixture was then concentrated in vacuo. The 20 resulting residue was diluted with water (10 mL) and washed with EtOAc (2×10 mL). The aqueous phase was acidified with HCl solution (2M) to pH -5. The resulting solid was filtered and dried under reduced pressure to give Compound 40 as a yellow solid (620 mg, 41% yield) which was used in subsequent steps without further purification. $^1H$ NMR (400 MHz, DMSO-$d_6$) δ 13.92 (br s, 1H), 8.69 (br s, 1H), 8.50 (br d, 1H), 8.32 (br d, 1H), 8.06 (br s, 1H), 7.94 (br s, 1H), 6.82 (br s, 1H); MS for $C_{11}H_7FN_2O_3$: m/z 234.9 (MH+).

Example 11: N-[4-[(6,7-Dimethoxy-1,5-naphthyridin-4-yl)oxy]-3-fluorophenyl]-1-(5-fluoropyridin-2-yl)-4-methyl-2-oxopyridine-3-carboxamide (41)

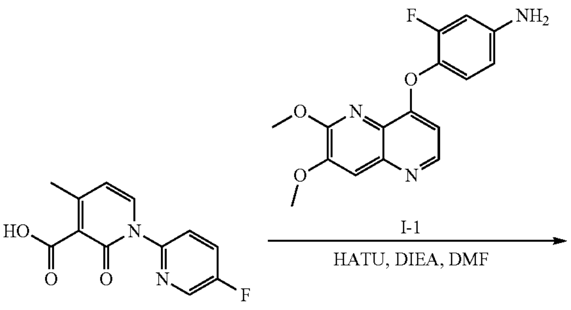

35

-continued

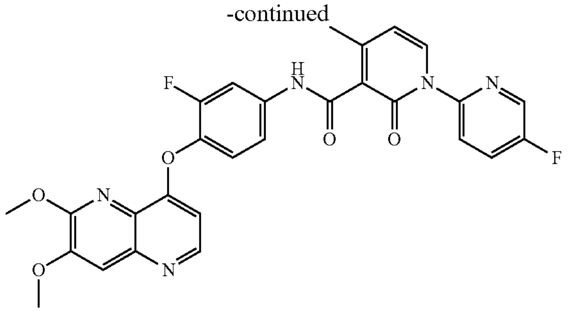

41

Using a method similar to General Procedure D, to a solution of Compound 35 (40 mg, 0.16 mmol, 1 eq) in DMF (3 mL) was added Intermediate I-1 (45.73 mg, 0.145 mmol, 0.9 eq), HATU (73.53 mg, 0.19 mmol, 1.2 eq) and DIEA (0.084 mL, 0.48 mmol, 3 eq). The mixture was heated at 40° C. for 3 h. Water (20 mL) was added and the resulting mixture was extracted with DCM (3×25 mL). The combined organic extracts were dried over anhyd. $Na_2SO_4$ and concentrated in vacuo. The resulting crude product was purified by silica gel chromatography (DCM/MeOH=10/1) to give Compound 41 as a yellow solid (35.7 mg, 38.58% yield). $^1H$ NMR (400 MHz, $CDCl_3$) δ 11.84 (s, 1H), 8.52 (d, 1H), 8.47 (d, 1H), 7.92 (d, 1H), 7.86 (dd, 1H), 7.83 (d, 1H), 7.66 (dd, 1H), 7.52 (s, 1H), 7.33 (br d, 1H), 7.18 (t, 1H), 6.74 (d, 1H), 6.45 (d, 1H), 4.13 (s, 3H), 4.03 (s, 3H), 2.85 (s, 3H); MS for $C_{28}H_{21}F_2N_5O_5$: m/z 568 $[M+Na]^+$.

The following compounds were made following methods analogous to that used to synthesize Compound 41 in Example 11 from Compound 35 and Intermediate I-1. The temperatures of the reactions can vary from room temperature to 40° C. Reaction times can vary from 2-4 h. EtOAc can replace DCM as the extraction solvent.

N-[4-[(6,7-Dimethoxy-1,5-naphthyridin-4-yl)oxy]-3-fluorophenyl]-1-(5-fluoropyridin-2-yl)-2-oxopyridine-3-carboxamide (42): Compound 35 was replaced with Compound 40. $^1H$ NMR (400 MHz, DMSO-$d_6$) δ 11.91 (br s, 1H), 8.69 (br s, 1H), 8.57 (br d, 2H), 8.24 (br s, 1H), 8.10-7.92 (m, 3H), 7.65 (br s, 1H), 7.46 (br d, 1H), 7.34 (br d, 1H), 6.88-6.74 (m, 2H), 3.95 (br d, 6H); MS for $C_{27}H_{19}F_2N_5O_5$: m/z 532.1 (MH+).

N-[4-[(6,7-Dimethoxy-1,5-naphthyridin-4-yl)oxy]-3-fluorophenyl]-1-(5-fluoropyridin-2-yl)-6-methyl-2-oxopyridine-3-carboxamide (43): Compound 35 was replaced with Compound 31. $^1H$ NMR (400 MHz, DMSO-$d_6$) δ 11.86 (s, 1H), 8.73 (d, 1H), 8.54 (t, 2H), 8.11 (td, 1H), 8.00 (dd, 1H), 7.80 (dd, 1H), 7.65 (s, 1H), 7.45 (d, 1H), 7.31 (t, 1H), 6.83 (d, 1H), 6.73 (d, 1H), 3.96 (s, 3H), 3.93 (s, 3H), 2.07 (d, 3H); MS for $C_{28}H_{21}F_2N_5O_5$: m/z 546.2 (MH+).

N-[4-[(6,7-Dimethoxy-1,5-naphthyridin-4-yl)oxy]phenyl]-1-(5-fluoropyridin-2-yl)-6-methyl-2-oxopyridine-3-carboxamide (44): Intermediate I-1 was replaced with Intermediate I-2, and Compound 35 was replaced with Compound 31. $^1H$ NMR (400 MHz, DMSO-$d_6$) δ 11.68 (s, 1H), 8.66 (d, 1H), 8.46 (dd, 2H), 8.04 (td, 1H), 7.76-7.67 (m, 3H), 7.57 (s, 1H), 7.15-7.06 (m, 2H), 6.74 (d, 1H), 6.65 (d, 1H), 3.89 (s, 3H), 3.85 (s, 3H), 1.99 (s, 3H); MS for $C_{28}H_{22}FN_5O_5$: m/z 528.2 (MH+).

N-[3-Fluoro-4-[(7-methoxy-1,5-naphthyridin-4-yl)oxy]phenyl]-1-(5-fluoropyridin-2-yl)-6-methyl-2-oxopyridine-3-carboxamide (45): Intermediate I-1 was replaced with Intermediate I-3, and Compound 35 was replaced with Compound 31. $^1H$ NMR (400 MHz, DMSO-$d_6$) δ 11.90 (s, 1H), 8.77-8.73 (m, 2H), 8.71 (d, 1H), 8.54 (d, 1H), 8.11 (td, 1H), 8.05 (dd, 1H), 7.84-7.75 (m, 2H), 7.55-7.47 (m, 1H), 7.40 (t, 1H), 6.78-6.70 (m, 2H), 4.00 (s, 3H), 2.07 (s, 3H); MS for $C_{27}H_{19}F_2N_5O_4$: m/z 516.2 (MH+).

1-(5-Fluoropyridin-2-yl)-N-[4-[(7-methoxy-1,5-naphthyridin-4-yl)oxy]phenyl]-6-methyl-2-oxopyridine-3-carboxamide (46): Intermediate I-1 was replaced with Intermediate I-4, and Compound 35 was replaced with Compound 31. $^1H$ NMR (400 MHz, DMSO-$d_6$) δ 11.78 (s, 1H), 8.76-8.71 (m, 2H), 8.70 (d, 1H), 8.54 (d, 1H), 8.11 (td, 1H), 7.86-7.76 (m, 4H), 7.28-7.20 (m, 2H), 6.77-6.69 (m, 2H), 4.00 (s, 3H), 2.07 (s, 3H); MS for $C_{27}H_{20}FN_5O_4$: m/z 498.2 (MH+).

N-[3-Fluoro-4-[(6-methoxy-1,5-naphthyridin-4-yl)oxy]phenyl]-1-(5-fluoropyridin-2-yl)-6-methyl-2-oxopyridine-3-carboxamide (47): Intermediate I-1 was replaced with Intermediate I-5, and Compound 35 was replaced with Compound 31. $^1H$ NMR (400 MHz, DMSO-$d_6$) δ 11.87 (s, 1H), 8.73 (d, 1H), 8.62 (d, 1H), 8.53 (d, 1H), 8.29 (d, 1H), 8.11 (td, 1H), 8.02 (dd, 1H), 7.80 (dd, 1H), 7.51-7.43 (m, 1H), 7.33 (dd, 2H), 6.97 (d, 1H), 6.76-6.70 (m, 1H), 3.92 (s, 3H), 2.07 (s, 3H); MS for $C_{27}H_{19}F_2N_5O_4$: m/z 516.2 (MH+).

N-[3-Fluoro-4-(1,5-naphthyridin-4-yloxy)phenyl]-1-(5-fluoropyridin-2-yl)-6-methyl-2-oxopyridine-3-carboxamide (48): Intermediate I-1 was replaced with Intermediate I-6, and Compound 35 was replaced with Compound 31. $^1H$ NMR (400 MHz, DMSO-$d_6$) δ 11.91 (s, 1H), 9.02 (dd, 1H), 8.79 (d, 1H), 8.74 (d, 1H), 8.55 (d, 1H), 8.45 (dd, 1H), 8.12 (td, 1H), 8.06 (dd, 1H), 7.87 (dd, 1H), 7.81 (dd, 1H), 7.56-7.49 (m, 1H), 7.43 (t, 1H), 6.91 (dd, 1H), 6.74 (d, 1H), 2.07 (s, 3H); MS for $C_{26}H_{17}F_2N_5O_3$: m/z 486.2 (MH+).

N-[3-Fluoro-4-(6-methoxyquinolin-4-yl)oxyphenyl]-1-(5-fluoropyridin-2-yl)-6-methyl-2-oxopyridine-3-carboxamide (49): Intermediate I-1 was replaced with Intermediate I-7, and Compound 35 was replaced with Compound 31. $^1H$ NMR (400 MHz, DMSO-$d_6$) δ 11.92 (s, 1H), 8.74 (d, 1H), 8.54 (d, 2H), 8.17-8.02 (m, 2H), 7.96 (d, 1H), 7.81 (dd, 1H), 7.59 (d, 1H), 7.54 (dd, 1H), 7.51-7.41 (m, 2H), 6.74 (d, 1H), 6.61 (d, 1H), 3.94 (s, 3H), 2.08 (s, 3H).); MS for $C_{28}H_{20}F_2N_4O_4$: m/z 515.2 (MH+).

N-[3-Fluoro-4-[[6-methoxy-7-(2-methoxyethoxy)-1,5-naphthyridin-4-yl]oxy]phenyl]-1-(5-fluoropyridin-2-yl)-6-methyl-2-oxopyridine-3-carboxamide (50): Intermediate I-1 was replaced 5 with Compound 17, and Compound 35 was replaced with Compound 31. $^1H$ NMR (400 MHz, DMSO-d6) δ 11.80 (s, 1H), 8.66 (d, 1H), 8.49-8.39 (m, 2H), 8.04 (td, 1H), 7.94 (dd, 1H), 7.73 (dd, 1H), 7.60 (s, 1H), 7.38 (d, 1H), 7.24 (t, 1H), 6.75 (d, 1H), 6.66 (d, 1H), 4.24 (t, 2H), 3.87 (s, 3H), 3.68 (t, 2H), 3.27 (s, 3H), 2.00 (s, 3H); MS for $C_{30}H_{25}F_2N_5O_6$: m/z 590.2 (MH+).

N-[4-[(6,7-Dimethoxy-1,5-naphthyridin-4-yl)oxy]-3-fluorophenyl]-1-(5-fluoro-3-methylpyridin-2-yl)-6-methyl-2-oxopyridine-3-carboxamide (51): Compound 35 was replaced with Compound 32. $^1H$ NMR ($CDCl_3$) δ: 11.81 (s, 1H), 8.68 (d, 1H), 8.52 (d, 1H), 8.42 (d, 1H), 7.94 (dd, 1H), 7.57 (dd, 1H), 7.53 (s, 1H), 7.33 (ddd, 1H), 7.16 (t, 1H), 6.75 (dd, 1H), 6.54 (d, 1H), 4.11 (s, 3H), 4.03 (s, 3H), 2.22 (s, 3H), 2.07 (s, 3H). MS for $C_{29}H_{23}F_2N_5O_5$: m/z 560 (MH+).

N-[3-Fluoro-4-[(7-methoxy-1,5-naphthyridin-4-yl)oxy]phenyl]-1-(5-fluoro-3-methylpyridin-2-yl)-6-methyl-2-oxopyridine-3-carboxamide (52): Compound 35 was replaced with Compound 32 and Intermediate I-1 was replaced with Intermediate I-3. $^1H$ NMR ($CDCl_3$) δ: 11.86 (s, 1H), 8.78 (d, 1H), 8.68 (d, 1H), 8.66 (d, 1H), 8.42 (d, 1H), 7.97 (dd, 1H), 7.67 (d, 1H), 7.57 (dd, 1H), 7.38 (ddd, 1H), 7.25 (t, 1H), 6.63 (dd, 1H), 6.54 (d, 1H), 4.01 (s, 3H), 2.21 (s, 3H), 2.07 (s, 3H). MS for $C_{28}H_{21}F_2N_5O_4$: m/z 530 [MH]+.

N-[3-Fluoro-4-[(6-methoxy-1,5-naphthyridin-4-yl)oxy]phenyl]-1-(5-fluoro-3-methylpyridin-2-yl)-6-methyl-2-oxopyridine-3-carboxamide (53): Compound 35 was replaced with Compound 32 and Intermediate I-1 was replaced with Intermediate I-5. $^1$H NMR (Chloroform-d) δ: 11.82 (s, 1H), 8.67 (d, 1H), 8.57 (d, 1H), 8.42 (d, 1H), 8.20 (d, 1H), 7.94 (dd, 1H), 7.56 (dd, 1H), 7.34 (ddd, 1H), 7.21-7.11 (m, 2H), 6.84 (dd, 1H), 6.54 (d, 1H), 4.02 (s, 3H), 2.21 (s, 3H), 2.06 (s, 3H). MS for $C_{28}H_{21}F_2N_5O_4$: m/z 530 [MH]+.

N-[3-Fluoro-4-[(6-methoxy-1,7-naphthyridin-4-yl)oxy]phenyl]-1-(5-fluoropyridin-2-yl)-6-methyl-2-oxopyridine-3-carboxamide (54): Compound 35 was replaced with Compound 31 and Intermediate I-1 was replaced with Compound 24. $^1$H NMR (400 MHz, DMSO-d$_6$) δ 11.86 (s, 1H), 9.11 (s, 1H), 8.67 (d, 1H), 8.58 (d, 1H), 8.47 (d, 1H), 8.14-7.91 (m, 2H), 7.74 (dd, 1H), 7.58-7.30 30 (m, 3H), 6.68 (t, 2H), 3.95 (s, 3H), 2.01 (s, 3H); MS for $C_{27}H_{19}F_2N_5O_4$: m/z 516.0 (MH+).

N-[4-[(6-Chloro-1,7-naphthyridin-4-yl)oxy]-3-fluorophenyl]-1-(5-fluoropyridin-2-yl)-6-methyl-2-oxopyridine-3-carboxamide (54A): Compound 35 was replaced with Compound 31 and Intermediate I-1 was replaced with Compound 24A. $^1$H NMR (400 MHz, DMSO-d$_6$) δ 11.87 (s, 1H), 9.25 (s, 1H), 8.80 (d, 1H), 8.67 (d, 1H), 8.48 (d, 1H), 8.22 (s, 1H), 8.03 (ddd, 2H), 7.74 (dd, 1H), 7.59-7.32 (m, 2H), 6.87 (d, 1H), 6.67 (d, 1H), 2.01 (s, 3H); MS for $C_{26}H_{16}ClF_2N_5O_3$: m/z 520 (MH+).

Example 12: 5-Bromo-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide (55)

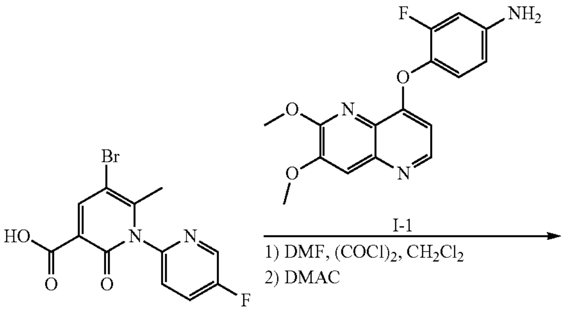

36

-continued

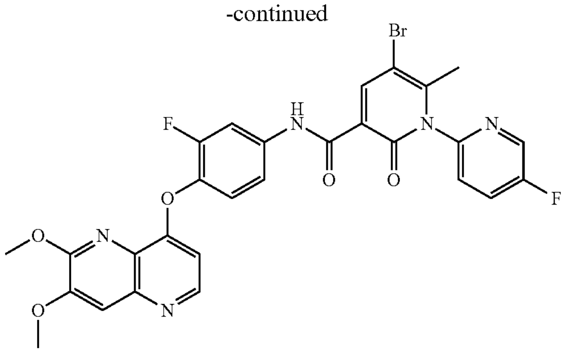

55

To a solution of Compound 36 (250 mg, 0.76 mmol, 1 eq) in DCM (5 ml) was added $(COCl)_2$ (1.47 mL, 17 mmol, 22 eq) and DMF (0.006 mL, 0.076 mmol, 0.1 eq). The reaction mixture was stirred at 20° C. for 0.5 h. The mixture was concentrated in vacuo to give the acid chloride of 10 Compound 36 as a brown solid (260 mg, 98.45% yield). To a solution of this acid chloride (210 mg, 0.61 mmol, 1.2 eq) in DMAC (2 mL) was added Intermediate I-1 (160 mg, 0.51 mmol, 1 eq). The mixture was stirred at 25° C. for 3 h. The reaction mixture was poured into water (20 mL) and extracted with DCM (3×20 mL). The combined organic extracts were washed with aq saturated NaCl (10 mL) and concentrated in vacuo. The resulting residue was purified by flash silica gel 15 chromatography (ISCO®; 4 g SepaFlash® Silica Flash Column, Eluent of 0-50% EtOAc/Petroleum ether gradient @30 mL/min) followed by further purification by prep-TLC (dichloromethane: methanol=20:1, $R_f$=0.4) to give Compound 55 as a white solid (28.0 mg, 8.8% yield). $^1$H NMR (400 MHz, DMSO-d$_6$) δ 11.66 (s, 1H), 8.75 (br s, 1H), 8.58 (s, 1H), 8.54 (d, 1H), 8.14 (m, 1H), 7.99 (br d, 1H), 7.85-7.76 (m, 1H), 7.65 (s, 1H), 7.48 (br d, 1H), 7.31 (t, 1H), 6.83 (d, 1H), 3.96 (s, 3H), 3.91 (s, 3H), 2.17 (s, 3H); MS for $C_{28}H_{20}BrF_2N_5O_5$: m/z 624.0 (MH+).

Example 13: 5-Cyano-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide (56)

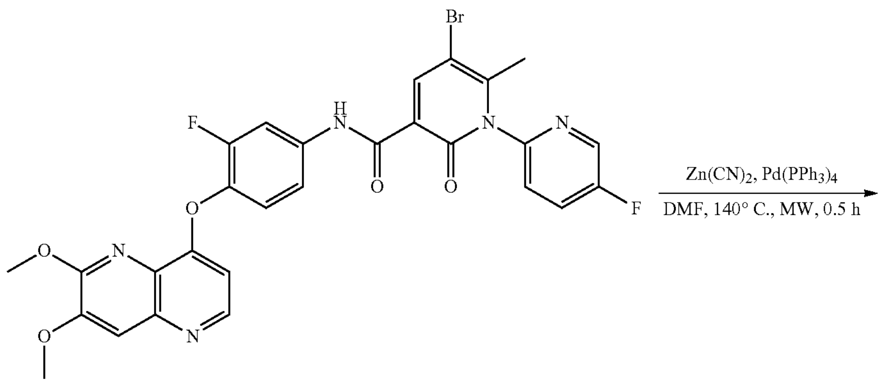

55

-continued

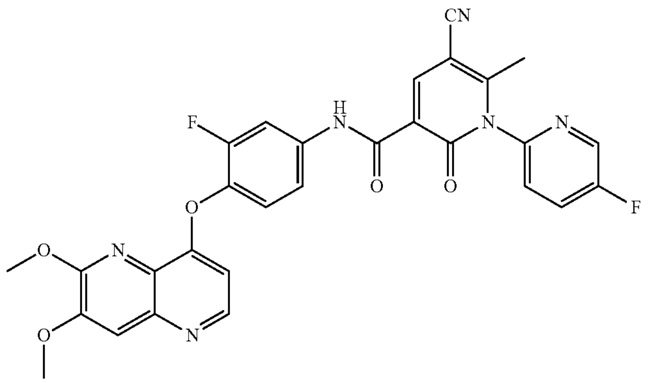

56

A mixture of Compound 55 (150 mg, 0.24 mmol, 1 eq), $Zn(CN)_2$ (90 mg, 0.77 mmol, 0.049 mL, 3.2 eq) and $Pd(PPh_3)_4$(28 mg, 0.024 mmol, 0.1 eq) in DMF (4 mL) under nitrogen was stirred at 140° C. under microwave irradiation for 0.5 h. The reaction mixture was cooled to room temperature, followed by the addition of saturated $FeSO_4$ solution. The resulting mixture was extracted with EtOAc (3x50 mL). The combined organic extracts were washed with water, aq saturated NaCl, dried over anhyd. $Na_2SO_4$ and concentrated. The resulting residue was purified by column chromatography ($SiO_2$, DCM:MeOH=20:1, $R_f$=0.4) followed by further purification by prep-HPLC (column: Venusil ASB Phenyl 150 * 30 mm*5 um; mobile phase: [water (0.05% HCl)-ACN]; B %: 35%-65%, 9 min) to give Compound 56 as a yellow solid (17.5 mg, 17.5% yield). $^1$H NMR (400 MHz, DMSO-$d_6$) δ 11.31 (br s, 1H), 8.77 (m, 2H), 8.67 (br s, 1H), 8.17 (br s, 1H), 8.05 (br d, 1H), 7.88-7.72 (m, 2H), 7.57 (m, 1H), 7.46 (m, 1H), 7.09 (m, 1H), 4.02 (br d, 6H), 2.28 (br s, 3H); MS for $C_{29}H_{20}F_2N_6O_5$: m/z 571.2 (MH+).

Example 14: 5-Acetyl-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide (59)

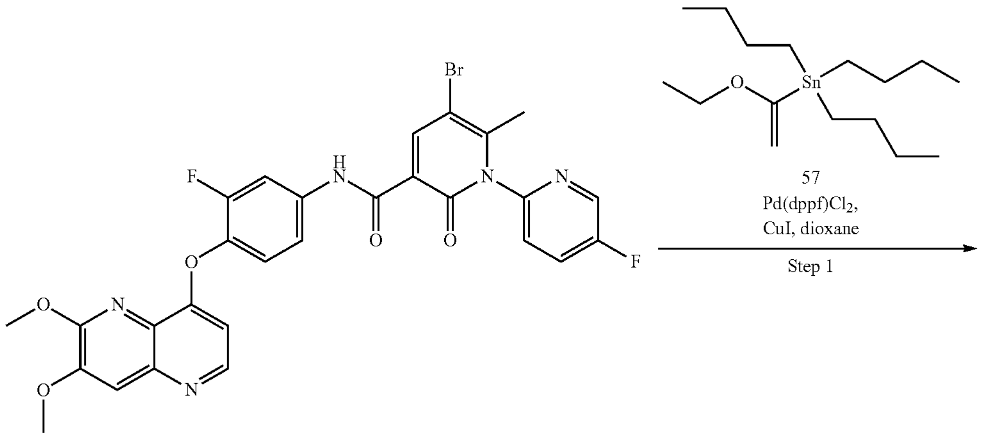

55

-continued

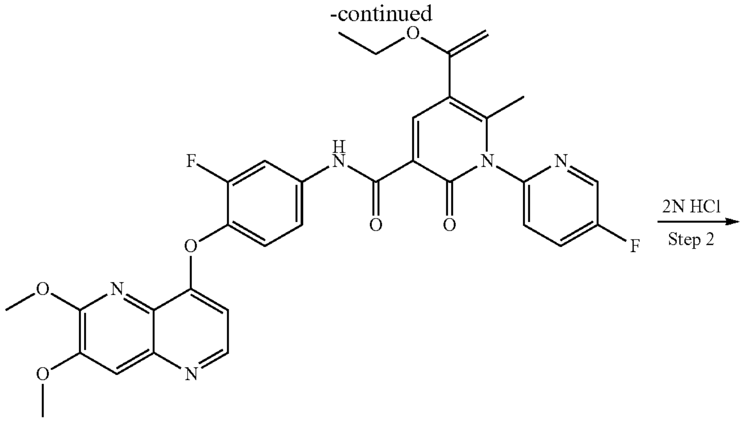

58

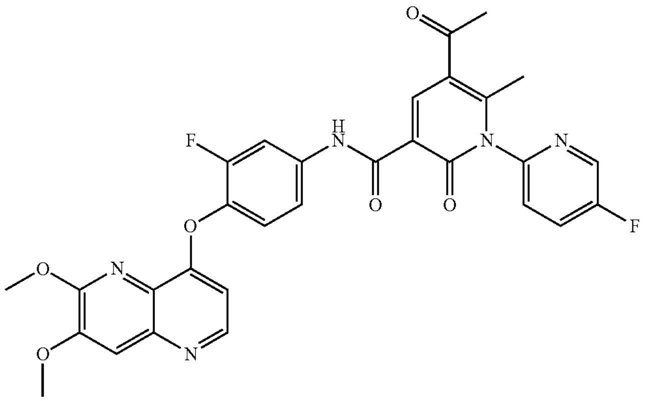

59

Step 1: N-(4-((6,7-Dimethoxy-1,5-naphthyridin-4-yl)oxy)-3-fluorophenyl)-5-(1-ethoxyvinyl)-5'-fluoro-6-methyl-2-oxo-2H-[1,2'-bipyridine]-3-carboxamide (58): To a solution of Compound 55 (220 mg, 0.35 mmol, 1 eq) in dioxane (4 ml) was added Pd(dppf)$Cl_2$ (26 mg, 0.035 mmol, 0.1 eq), CuI (13 mg, 0.070 mmol, 0.2 eq) and Compound 57 (445 mg, 1.23 mmol, 0.42 mL, 3.5 eq). The reaction mixture was allowed to stir at 100° C. for 12 h under nitrogen. Aq saturated KF (20 ml) was added and the mixture was stirred at 25° C. for 1 h. Ammonium hydroxide (1 ml) was added and the resulting mixture was extracted with EtOAc (3×30 mL). The combined organic extracts were washed with aq saturated NaCl (10 mL), dried over anhyd. $Na_2SO_4$ and concentrated under reduced pressure. The resulting residue was purified by flash silica gel chromatography (ISCO®; 12 g SepaFlash® Silica Flash Column, Eluent of 0-5% MeOH/DCM gradient @30 mL/min) to give Compound 58 as a yellow solid (200 mg, 49.42% yield). MS for $C_{32}H_{27}F_2N_5O_6$: m/z 616.2 (MH+).

Step 2: 5-Acetyl-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide (59): Compound 58 (100 mg, 0.16 mmol, 1 eq) in HCl (2 M, 0.081 mL, 1 eq) was stirred at 25° C. for 2 h. The reaction mixture was extracted with DCM (3×20 mL). The combined organic extracts were dried over anhyd. $Na_2SO_4$ and concentrated in vacuo. The resulting residue was purified by prep-TLC ($SiO_2$, DCM: MeOH=20:1, Rf=0.2) followed by further purification by prep-HPLC (column: Boston Green ODS 150 * 30 mm * 5 um; mobile phase: [water (0.075% TFA)-ACN]; B %: 25%-55%, 8 min) to give Compound 59 as a white solid (38.3 mg, 41% yield). $^1$H NMR (400 MHz, $CDCl_3$) δ 11.46 (s, 1H), 9.13 (s, 1H), 8.61 (d, 1H), 8.53 (d, 1H), 7.91 (m, 1H), 7.76 (m, 1H), 7.52 (s, 1H), 7.39 (dd, 1H), 7.31 (m, 1H), 7.16 (br t, 1H), 6.76 (d, 1H), 4.10 (s, 3H), 4.03 (s, 3H), 2.68 (s, 3H), 2.43 (s, 3H); MS for $C_{30}H_{23}F_2N_5O_6$: m/z 588.1 (MH+).

Example 15A: 5-(4-Fluorophenyl)-2-methyl-4-oxo-1,4-dihydropyridine-3-carboxylic acid (15A-3)

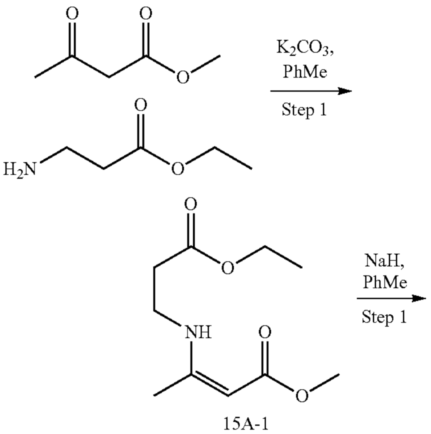

15A-1

-continued

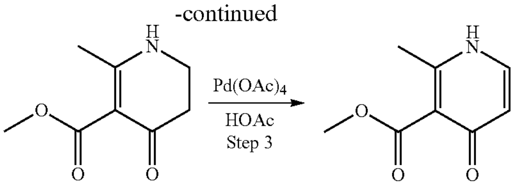

15A-2

15A-3

Step 1: Methyl 3-((3-ethoxy-3-oxopropyl)amino)but-2-enoate (15A-1): A mixture of 3-aminopropionic acid ethyl ester hydrochloride (15.6 g, 101 mmol), methyl 3-oxobutanoate (10.8 mL, 101 mmol) and anhyd. $K_2CO_3$ (28.0 g, 203 mmol) in toluene (200 mL) was refluxed with a Dean-Stark trap overnight. The reaction mixture was cooled and diluted with EtOAc (150 mL), filtered and the filtrate was concentrated under reduced pressure to give crude Compound 15A-1 (21 g), which was used in the next step without further purification.

Step 2: Methyl 2-methyl-4-oxo-1,4,5,6-tetrahydropyridine-3-carboxylate (15A-2): To a solution of crude Compound 15A-1 (21 g, 95 mmol) in 200 mL of toluene was added sodium hydride (6.0 g, 60% dispersion in oil, 150 mmol) and the resulting yellow suspension was refluxed overnight. The mixture was concentrated to remove solvent and the residue was treated carefully with water (100 mL), acidified to pH 2 with 6 M HCl and then washed with $Et_2O$ (3x). The aqueous phase was basified with $NaHCO_3$ and extracted with EtOAc (5×). The combined EtOAc extracts were dried over anhyd. $Na_2SO_4$ and concentrated to give Compound 15A-2 (7.6 g, 46% yield) which was used without further purification. MS for $C_8H_{11}NO_3$: m/z 170 (MH+).

Step 3: Methyl 2-methyl-4-oxo-1,4-dihydropyridine-3-carboxylate (15A-3): A mixture of Compound 15A-2 (3.6 g, 21 mmol) and lead tetraacetate (20 g, 58 mmol) in 30 mL of acetic acid was stirred at 100° C. overnight and concentrated under reduced pressure to remove acetic acid. The resulting residue was purified by silica gel chromatography (5-15% MeOH in DCM) to give Compound 15A-3 as a red oil (2.0 g, 56%). MS for $C_8H_9NO_3$: m/z 168 (MH+).

Example 15: Ethyl 5-bromo-4-hydroxy-2-methylnicotinate (61)

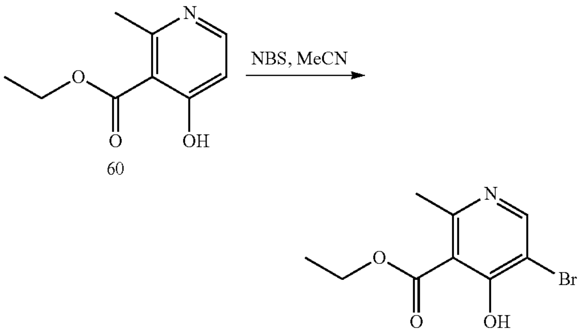

60

61

Compound 60 can be made using the same method used to make Compound 15A-3 in Example 15A. To a solution of Compound 60 (13.7 g, 80.7 mmol) in acetonitrile (250 ml) was added NBS (14.4 g, 80.7 mmol) in portions over a period of 10 min at room temperature. The reaction was allowed to proceed for 1 hour, and the product precipitated from the reaction mixture. The precipitate was collected by vacuum filtration to yield Compound 61 as a white solid (10.9 g, 52% yield). $^1$H NMR (400 MHz, $CDCl_3$) δ 8.14 (s, 1H), 4.37 (q, 2H), 2.52 (s, 3H), 1.38 (t, 3H); MS for $C_9H_{10}BrNO_3$: m/z 260.0 (MH+).

The following compounds were made in a manner similar to Compound 61 using NBS as a brominating agent in an appropriate solvent. If the desired product did not precipitate from the reaction mixture, water was added to aid the precipitation. If no filterable solid resulted, the reaction mixture was diluted with DCM, washed with water, washed with aq saturated NaCl, dried over anhyd $Na_2SO_4$ and concentrated to give the desired product:

61-2

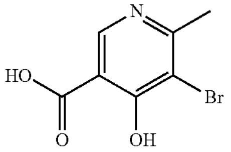

61-3

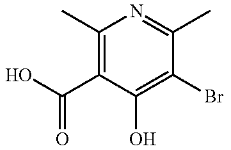

61-4

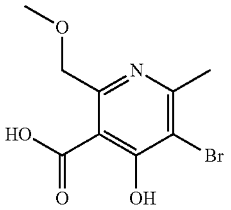

61-5

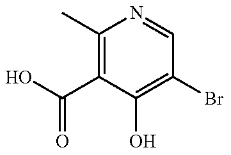

5-Bromo-4-hydroxy-6-methylnicotinic acid (61-2): Compound 60 was replaced with 4-hydroxy-6-methylnicotinic acid. MS for $C_7H_6BrNO_3$: m/z 232/234 (MH+).

5-Bromo-4-hydroxy-2,6-dimethylnicotinic acid (61-3): Compound 60 was replaced with 4-hydroxy-2,6-dimethylnicotinic acid. MS for $C_8H_8BrNO_3$: m/z 246 (MH+).

5-Bromo-4-hydroxy-2-(methoxymethyl)-6-methylnicotinic acid (61-4): MS for $C_9H_{10}BrNO_4$: m/z 276 (MH+). See Example 26 for the synthesis of 4-hydroxy-2-(methoxymethyl)-6-methylnicotinic acid (Compound 132).

5-Bromo-4-hydroxy-2-methylnicotinic acid (61-5): MS for $C_7H_6BrNO_3$: m/z 232.0 (MH+). In addition to the direct bromination of 4-hydroxy-2-methylnicotinic acid, Compound 61-5 can also be made through the ester hydrolysis of Compound 61 using standard LiOH hydrate ester hydrolysis conditions in MeOH and water with heating at 65° C.

Example 16: 5-Fluoro-4'-hydroxy-6'-methyl-[2,3'-bipyridine]-5'-carboxylic acid (63)

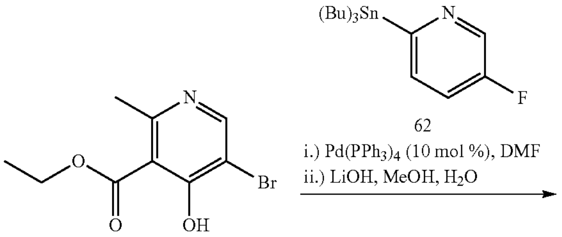

62

61

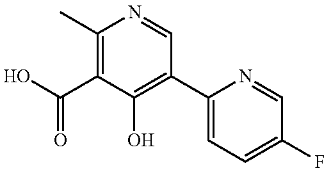

63

Compound 62 is commercially available or can be made by the method shown in Step 1 of Example 21. To a solution of Compound 61 (100 mg, 0.76 mmol) in DMF (5 mL) was added Compound 62 (356 mg, 0.92 mmol) and $Pd(PPh_3)_4$ (22 mg, 0.09 mmol). The solution was brought to 90° C. and the reaction was allowed to proceed overnight. The solution was then filtered through Celite and the filter cake was washed with DCM (25 mL). The resulting filtrate was then transferred to a separatory funnel and partitioned with aq 10% NaOH solution (25 mL). The phases were separated and the organic phase was concentrated in vacuo. The resulting residue was taken up in MeOH (5 ml) and water (1 ml) and LiOH monohydrate (200 mg, 4.87 mmol) was added in a single portion. The resulting solution was heated to 60° C. for 16 h. The reaction was cooled to room temperature and was acidified to pH 4 with aq 6 M HCl. The resulting mixture was concentrated to near dryness, and the precipitate was collected by vacuum filtration to yield Compound 63 as a white solid (40 mg, 21% yield). $^1H$ NMR (400 MHz, $CD_3OD$) δ 8.86 (s, 1H), 8.75 (dd, 1H), 8.56 (dd, 1H), 8.12 (td, 1H), 2.86 (s, 3H); MS for $C_{12}H_9FN_2O_3$: m/z 249.0 (MH+).

Example 17: 4'-Hydroxy-6'-methyl-[2,3'-bipyridine]-5'-carboxylic acid (65)

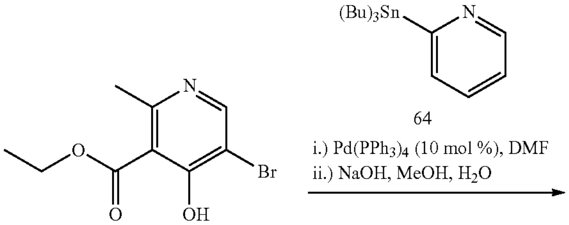

64

61

-continued

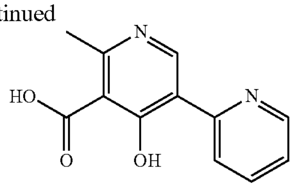

65

Compound 65 was synthesized using an analogous method to the synthesis of Compound 63 in Example 16, replacing Compound 62 with Compound 64. $^1H$ NMR (400 MHz, DMSO-$d_6$) δ 13.28 (s, 1H), 8.67 (d, 1H), 8.61 (s, 1H), 8.40 (d, 1H), 7.88 (td, 1H), 7.39 (dd, 1H), 2.79 (s, 3H); MS for $C_{12}H_{10}N_2O_3$: m/z 231.0 (MH+).

Example 18: Ethyl 5-bromo-1,2-dimethyl-4-oxo-1,4-dihydropyridine-3-carboxylate (66)

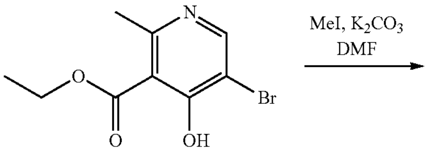

61

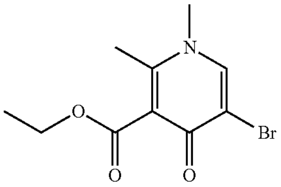

66

To a solution of Compound 61 (1.0 g, 3.84 mmol) and potassium carbonate (636 mg, 4.61 mmol) in DMF (15 ml) at 0° C. was added MeI (0.26 mL, 4.22 mmol) dropwise over a period of 5 min. The reaction was allowed to warm to room temperature over 1 h. The solution was then partitioned between water (40 ml) and 10% MeOH in DCM (40 mL). The organics were collected, dried over anhyd. $Na_2SO_4$, and concentrated under reduced pressure to yield a yellow oil which was triturated with EtOAc to yield Compound 66 as a yellow solid (260 mg, 24% yield). 1H NMR (400 MHz, $CDCl_3$) δ 7.71 (s, 1H), 4.48-4.20 (m, 2H), 3.58 (d, 3H), 2.44-2.19 (m, 3H), 1.48-1.23 (m, 3H); MS for $C_{10}H_{12}BrNO_3$: m/z 274.0 (MH+).

Example 19: 5-Fluoro-1',6'-dimethyl-4'-oxo-1',4'-dihydro-[2,3'-bipyridine]-5'-carboxylic acid (67)

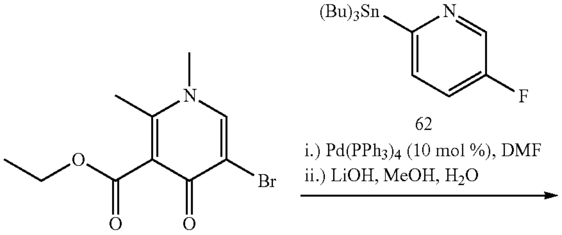

62

66

-continued

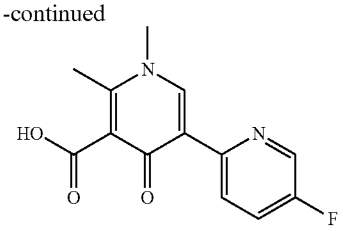

67

Compound 67 was synthesized using an analogous method to the synthesis of Compound 63 in Example 16, replacing Compound 61 with Compound 66. $^1$H NMR (400 MHz, $CDCl_3$) δ 8.65 (dd, 1H), 8.61 (s, 1H), 8.48 (d, 1H), 7.55-7.46 (m, 1H), 3.94 (s, 3H), 3.08 (s, 3H); MS for $C_{13}H_{11}FN_2O_3$: m/z 263.0 (MH+).

Example 20: N-[4-[(6,7-Dimethoxy-1,5-naphthyridin-4-yl)oxy]-3-fluorophenyl]-5-(5-fluoropyridin-2-yl)-4-hydroxy-2-methylpyridine-3-carboxamide (68)

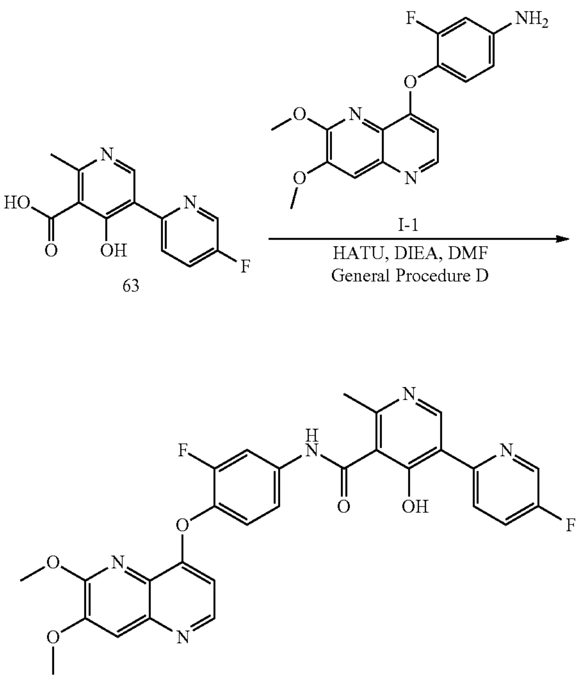

63 I-1 68

Compound 68 and the following compounds were made by General Procedure D, similar to the synthesis of Compound 41 from Compound 35 and Intermediate I-1 in Example 11. The temperatures of the reactions can vary from room temperature to 40° C. Reaction times can vary from 2-4 h. EtOAc can replace DCM as the extraction solvent.

N-[4-[(6,7-Dimethoxy-1,5-naphthyridin-4-yl)oxy]-3-fluorophenyl]-5-(5-fluoropyridin-2-yl)-4-hydroxy-2-methylpyridine-3-carboxamide (68): Compound 35 in Example 11 was replaced with Compound 63. $^1$H NMR (400 MHz, DMSO-$d_6$) δ 12.34 (s, 2H), 8.63-8.51 (m, 2H), 8.47 (d, 1H), 8.36 (s, 1H), 7.94 (dd, 1H), 7.71 (td, 1H), 7.59 (s, 1H), 7.42-7.33 (m, 1H), 7.27 (t, 1H), 6.74 (d, 1H), 3.91 (s, 6H), 2.53 (s, 3H); MS for $C_{28}H_{21}F_2N_5O_5$: m/z 546.2 (MH+).

N-[4-[(6,7-Dimethoxy-1,5-naphthyridin-4-yl)oxy]-3-fluorophenyl]-4-hydroxy-2-methyl-5-pyridin-2-ylpyridine-3-carboxamide (69): Compound 35 in Example 11 was replaced with Compound 65. $^1$H NMR (400 MHz, DMSO-$d_6$) δ 12.77 (s, 1H), 8.58-8.38 (m, 4H), 7.95 (dd, 1H), 7.75 (t, 1H), 7.59 (s, 1H), 7.37 (d, 1H), 7.32-7.19 (m, 2H), 6.73 (d, 1H), 3.91 (s, 6H), 2.55 (s, 3H); MS for $C_{28}H_{22}FN_5O_5$: m/z 528.2 (MH+).

N-[3-Fluoro-4-[(7-methoxy-1,5-naphthyridin-4-yl)oxy]phenyl]-4-hydroxy-2-methyl-5-pyridin-2-ylpyridine-3-carboxamide (70): Compound 35 in Example 11 was replaced with Compound 65 and Intermediate I-1 was replaced with Intermediate I-3. $^1$H NMR (400 MHz, DMSO-$d_6$) δ 12.39 (s, 2H), 8.76 (d, 1H), 8.71 (d, 1H), 8.63 (d, 1H), 8.56 (d, 1H), 8.48 (s, 1H), 8.04 (dd, 1H), 7.84 (t, 1H), 7.81 (d, 1H), 7.51 (dd, 1H), 7.42 (t, 1H), 7.34 (t, 1H), 6.76 (d, 1H), 4.01 (s, 3H), 2.61 (s, 3H); MS for $C_{27}H_{20}FN_5O_4$: m/z 498.2 (MH+).

N-[4-[(6,7-Dimethoxy-1,5-naphthyridin-4-yl)oxy]-3-fluorophenyl]-5-(5-fluoropyridin-2-yl)-1,2-dimethyl-4-oxopyridine-3-carboxamide (71): Compound 35 in Example 11 was replaced with Compound 67. $^1$H NMR (400 MHz, DMSO-$d_6$) δ 10.82 (s, 1H), 8.66 (dd, 1H), 8.61-8.51 (m, 2H), 8.46 (d, 1H), 7.90 (dd, 1H), 7.70 (td, 1H), 7.59 (s, 1H), 7.42 (d, 1H), 7.29 (t, 1H), 6.71 (d, 1H), 3.92 (s, 3H), 3.91 (s, 3H), 3.75 (s, 3H), 2.36 (s, 3H); MS for $C_{29}H_{23}F_2N_5O_5$: m/z 560.2 (MH+).

N-[4-[(6,7-Dimethoxy-1,5-naphthyridin-4-yl)oxy]phenyl]-5-(5-fluoropyridin-2-yl)-1,2-dimethyl-4-oxopyridine-3-carboxamide (72): Compound 35 in Example 11 was replaced with Compound 67 and Intermediate I-1 was replaced with Intermediate I-2. $^1$H NMR (400 MHz, DMSO-$d_6$) δ 10.70 (s, 1H), 8.74 (dd, 1H), 8.66-8.57 (m, 2H), 8.52 (d, 1H), 7.85-7.69 (m, 3H), 7.64 (s, 1H), 7.20 (d, 2H), 6.75 (d, 1H), 3.98 (s, 3H), 3.97 (s, 3H), 3.82 (s, 3H), 2.43 (s, 3H); MS for $C_{29}H_{24}FN_5O_5$: m/z 542.2 (MH+).

N-[3-Fluoro-4-[(7-methoxy-1,5-naphthyridin-4-yl)oxy]phenyl]-5-(5-fluoropyridin-2-yl)-1,2-dimethyl-4-oxopyridine-3-carboxamide (73): Compound 35 in Example 11 was replaced with Compound 67 and Intermediate I-1 was replaced with Intermediate I-3. $^1$H NMR (400 MHz, DMSO-$d_6$) δ 10.85 (s, 1H), 8.69-8.61 (m, 3H), 8.59-8.46 (m, 2H), 7.93 (dd, 1H), 7.78-7.63 (m, 2H), 7.46 (d, 1H), 7.35 (t, 1H), 6.69 (d, 1H), 3.94 (s, 3H), 3.75 (s, 3H), 2.36 (s, 3H); MS for $C_{28}H_{21}F_2N_5O_4$: m/z 530.0 (MH+).

Example 21: 5-Fluoro-4'-hydroxy-2'-methyl-[2,3'-bipyridine]-5'-carboxylic acid (78)

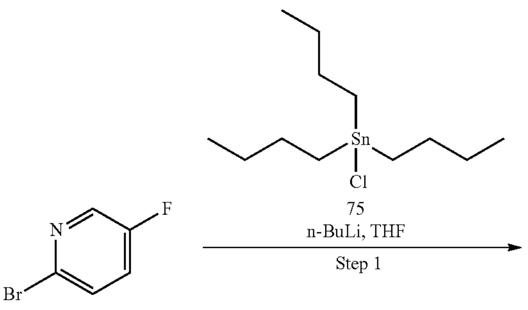

75 74

-continued

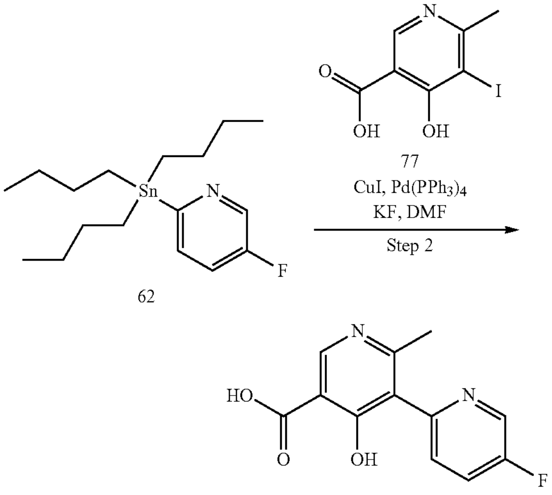

62

77

78

Step 1: 5-Fluoro-2-(tributylstannyl)pyridine (62): To a solution of Compound 74 (1.21 g, 6.88 mmol, 1 eq) in THF (15 mL) was added n-BuLi (2.5 M, 2.75 mL, 1 eq) and the mixture was stirred at −78° C. for 30 min under nitrogen. Compound 75 (12.35 g, 7.22 mmol, 1.94 mL, 1.05 eq) was added and the mixture was stirred at the same temperature for another 2 h. Aq saturated $NH_4Cl$ solution (150 mL) was added to the reaction solution and the resulting mixture was extracted with EtOAc (3×150 mL). The combined organic extracts were dried over anhyd. $Na_2SO_4$ and concentrated in vacuum to give crude Compound 62 as a colorless oil (3 g). MS for $C_{17}H_{30}FNSn$: m/z 387.0 (MH+).

Step 2: 5-Fluoro-4'-hydroxy-2'-methyl-[2,3'-bipyridine]-5'-carboxylic acid (78): A mixture of Compound 77 (200 mg, 0.72 mmol, 1 eq), Compound 62 (1.94 g, 5.02 mmol, 7 eq), $Pd(PPh_3)_4$(166 mg, 0.14 mmol, 0.2 eq), CuI (27.3 mg, 0.14 mmol, 0.2 eq) and KF (125 mg, 2.15 mmol, 3 eq) in DMF (20 ml) was degassed and purged with nitrogen 3 times and then the mixture was stirred at 120° C. for 16 h under nitrogen. The reaction mixture was concentrated under reduced pressure and the resulting residue was purified by column chromatography ($SiO_2$, DCM:MeOH=100/1 to 1/100) followed by further purification by HCl prep-HPLC (Column: Venusil ASB Phenyl 150*30 mm*5 um; mobile phase:[water (0.05% HCl)-ACN]; B %: 10%-40%, 9 min) to give Compound 78 as a yellow solid (50 mg, 12.50% yield). $^1H$ NMR (400 MHz, DMSO-$d_6$) δ 13.45 (br s, 1H), 8.90-8.38 (m, 3H), 7.49 (br s, 1H), 2.24 (s, 3H); MS for $C_{12}H_9FN_2O_3$: m/z 248.8 (MH+).

The following compounds were made in a manner similar to Compounds 62 and 78 in Example 21:

62-2

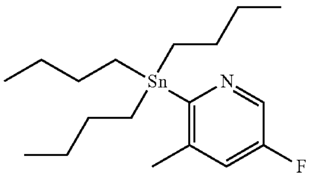

-continued 78-3

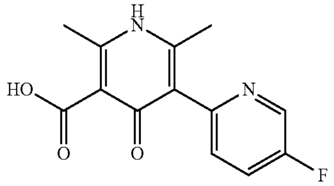

78-4

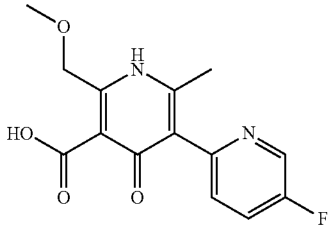

5-Fluoro-3-methyl-2-(tributylstannyl)pyridine (62-2): Compound 74 in Step 1 was replaced with 2-bromo-5-fluoro-3-methylpyridine. $^1H$ NMR (400 MHz, $CDCl_3$) δ 8.47 (d, 1H), 7.11 (dd, 1H), 2.41 (s, 3H), 1.64-1.48 (m, 6H), 1.34 (h, 6H), 1.24-1.06 (m, 6H), 0.93-0.85 (m, 9H)

5-Fluoro-2',6'-dimethyl-4'-oxo-1',4'-dihydro-[2,3'-bipyridine]-5'-carboxylic acid (78-3): Compound 77 in Step 2 was replaced with Compound 61-3. MS for $C_{13}H_{11}FN_2O_3$: m/z 263 (MH+).

5-Fluoro-6'-(methoxymethyl)-2'-methyl-4'-oxo-1',4'-dihydro-[2,3'-bipyridine]-5'-carboxylic acid (78-4): Compound 77 in Step 2 was replaced with Compound 61-4. $^1H$ NMR (400 MHz, DMSO-$d_6$) δ 12.05 (s, 1H), 8.60 (d, 1H), 7.76 (tdd, 1H), 7.48 (dd, 1H), 4.99 (s, 2H), 3.42 (s, 3H), 2.24 (s, 3H); MS for $C_{14}H_{13}FN_2O_4$: m/z 293.0 (MH+).

Example 22: 5-Fluoro-1',2'-dimethyl-4'-oxo-1',4'-dihydro-[2,3'-bipyridine]-5'-carboxylic acid (84)

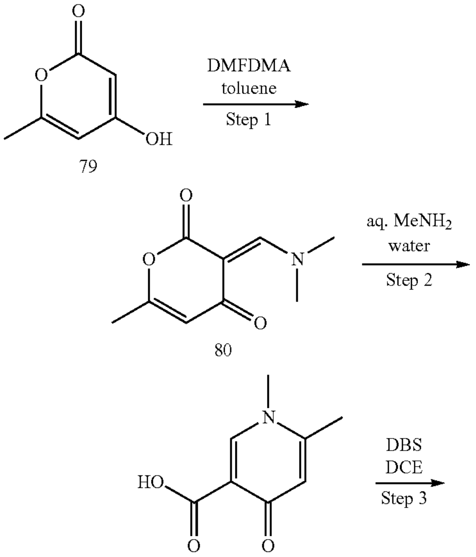

79

80

81

-continued

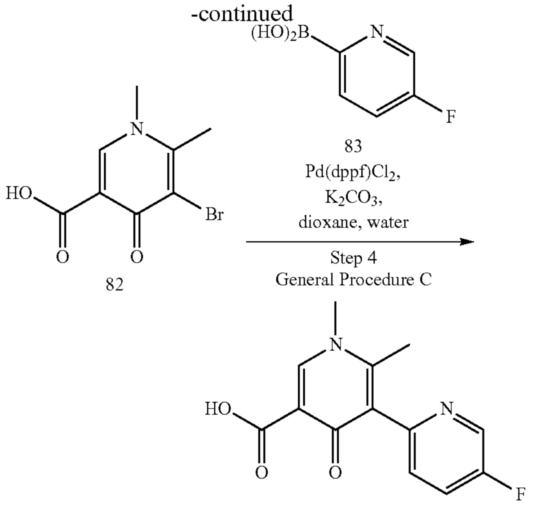

84

Step 1: (E)-3-((Dimethylamino)methylene)-6-methyl-2H-pyran-2,4(3H)-dione (80): To a white suspension of Compound 79 (15 g, 119 mmol, 1 eq) in toluene (40 mL) was added DMF-DMA (15 g, 127 mmol, 17 mL, 1.1 eq). The orange mixture was stirred at 15° C. for 2 h. The reaction mixture was concentrated under reduced pressure and co-evaporated with toluene (50 mL) 3 times and with DCM (50 mL) 2 times to give Compound 80 as a red-brown solid (21 g, 97% yield) which was used in subsequent reactions without further purification. $^1$H NMR (400 MHz, $CDCl_3$) δ 8.23 (s, 1H), 5.66 (s, 1H), 3.46 (s, 3H), 3.37 (s, 3H), 2.13 (s, 3H); MS for $C_9H_{11}NO_3$: m/z 181.8 (MH+).

Step 2: 1,6-Dimethyl-4-oxo-1,4-dihydropyridine-3-carboxylic acid (81): To a red-brown solution of Compound 80 (5 g, 27.6 mmol, 1 eq) in water (50 mL) was added $MeNH_2$ (15 mL). The red-brown solution was stirred at 100° C. for 1 h. The reaction solution was acidified with AcOH to pH 3 and concentrated under reduced pressure. The residue was triturated with DCM: EtOH (10:1) for 1 min. The mixture was filtered and the filter cake was washed with DCM (2×20 mL). The filtrate was concentrated under reduced pressure. Water (50 mL) was added to the resulting residue and the mixture extracted with 10:1 DCM:MeOH (3×50 mL). The combined organic extracts were concentrated under reduced pressure to give crude Compound 81 as a red-brown solid (2.5 g) which was used without further purification in subsequent reactions. 1H NMR (400 MHz, DMSO-$d_6$) δ 8.71 (s, 1H), 6.71 (s, 1H), 3.82 (s, 3H), 2.42 (s, 3H).

Step 3: 5-Bromo-1,6-dimethyl-4-oxo-1,4-dihydropyridine-3-carboxylic acid (82): To a mixture of Compound 81 (2 g, 12 mmol, 1 eq) in DCE (50 mL) was added NBS (3.19 g, 17.95 mmol, 1.5 eq). The red-brown solution was stirred at 20° C. for 4 h. The reaction mixture was diluted with water and extracted with DCM (3×50 mL). The combined organic extracts were dried over anhyd. $Na_2SO_4$ and concentrated to give crude Compound 82 with was used in subsequent reactions without further purification. $^1$H NMR (400 MHz, DMSO-$d_6$) δ 11.05 (br s, 1H), 8.79 (s, 1H), 3.94 (s, 3H), 2.66 (s, 3H).

Step 4: 5-Fluoro-1',2'-dimethyl-4'-oxo-1',4'-dihydro-[2,3'-bipyridine]-5'-carboxylic acid (84): Using General Procedure C, to a mixture of Compound 82 (0.2 g, 0.81 mmol, 1 eq) and Compound 83 (172 mg, 1.22 mmol, 1.5 eq) in dioxane (5 mL) and water (2 mL) was added $K_2CO_3$(337 mg, 2.44 mmol, 3 eq) and Pd(dppf)$Cl_2$ (178 mg, 0.24 mmol, 0.3 eq). The mixture was stirred at 105° C. for 15 h under nitrogen. Water (50 mL) and aq 1N NaOH (50 mL) was added to the reaction mixture to give a pH of 13. The resulting mixture was washed with DCM (2×80 mL). The aqueous layer was acidified with aq 2N HCl to pH 1-2 and extracted with 9:1 DCM:MeOH (5×50 mL). The combined organic extracts were dried over anhyd. $Na_2SO_4$ and concentrated under reduced pressure Compound 84 as a brown oil (150 mg, 70.37% yield) which was used directly without further purification in subsequent steps. MS for $C_{13}H_{11}FN_2O_3$: m/z 263.1 (MH+).

Example 23: N-[4-[(6,7-Dimethoxy-1,5-naphthyridin-4-yl)oxy]-3-fluorophenyl]-5-(5-fluoropyridin-2-yl)-4-hydroxy-6-methylpyridine-3-carboxamide (85)

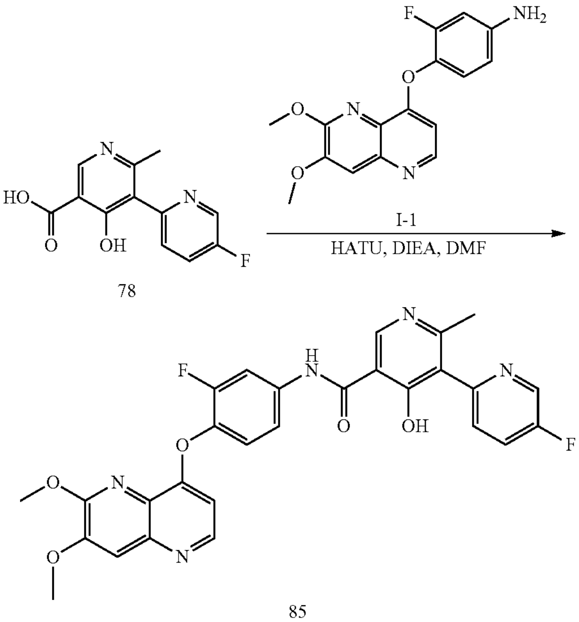

85

Compound 85 and the following compounds were made by General Procedure D, similar to the synthesis of Compound 41 in Example 11 from Compound 35 and Intermediate I-1. The temperatures of the reactions can vary from room temperature to 40° C. Reaction times can vary from 2-4 h. EtOAc can replace DCM as the extraction solvent.

N-[4-[(6,7-Dimethoxy-1,5-naphthyridin-4-yl)oxy]-3-fluorophenyl]-5-(5-fluoropyridin-2-yl)-4-hydroxy-6-methylpyridine-3-carboxamide (85): Compound 35 in Example 11 was replaced with Compound 78. $^1$H NMR (400 MHz, DMSO-$d_6$) δ 12.92 (s, 1H), 8.66 (s, 1H), 8.61 (s, 1H), 8.54 (d, 1H), 8.51 (d, 1H), 8.00 (dd, 1H), 7.64 (s, 1H), 7.48-7.37 (m, 2H), 7.37-7.25 (m, 1H), 6.82 (d, 1H), 3.95 (d, 6H), 2.19 (s, 3H); MS for $C_{28}H_{21}F_2N_5O_5$: m/z 546.1 (MH+).

N-[4-[(6,7-Dimethoxy-1,5-naphthyridin-4-yl)oxy]phenyl]-5-(5-fluoropyridin-2-yl)-1,6-dimethyl-4-oxopyridine-3-carboxamide (86): Compound 35 in Example 11 was replaced with Compound 84 and Intermediate I-1 was replaced with Intermediate I-2. $^1$H NMR (400 MHz, $CD_3OD$) δ 8.92-8.82 (m, 2H), 8.68 (br d, 1H), 8.21-8.12 (m, 1H), 7.89 (br d, 2H), 7.85-7.78 (m, 1H), 7.65-7.58 (m, 1H), 7.33 (br d, 2H), 7.12 (br d, 1H), 4.19 (s, 3H), 4.14 (s, 3H), 3.97 (s, 3H), 2.34 (s, 3H); MS for $C_{29}H_{24}FN_5O_5$: m/z 542.2 (MH+).

Example 24: N-[4-[(6,7-Dimethoxy-1,5-naphthyridin-4-yl)oxy]-3-fluorophenyl]-5-(furan-2-yl)-4-hydroxy-6-methylpyridine-3-carboxamide (89)

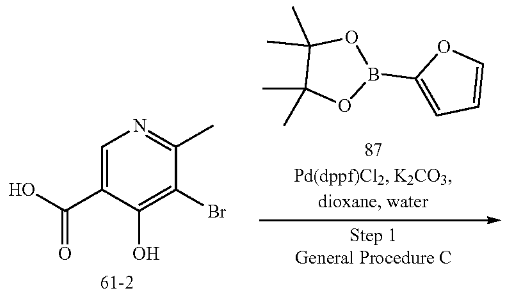

87
61-2

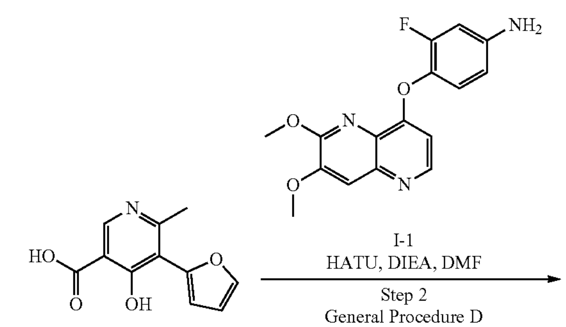

I-1
88

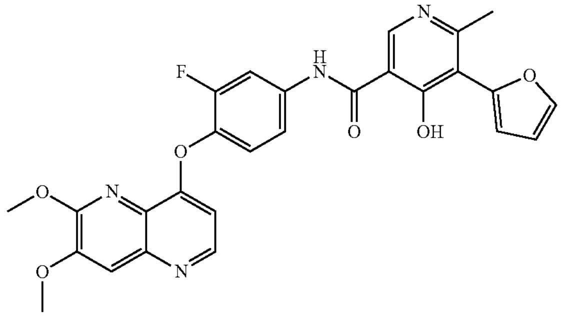
89

Step 1: 5-(Furan-2-yl)-4-hydroxy-6-methylnicotinic acid (88): Compound 88 was made following General Procedure C. Specifically in this case, a mixture of Compound 61-2 (717 mg, 3.1 mmol, 1 eq), Compound 87 (1.5 g, 7.7 mmol, 2.5 eq), Pd(dppf)$Cl_2$ (226 mg, 0.31 mmol, 0.1 eq) and $K_2CO_3$ (855 mg, 6.2 mmol, 2 eq) in water (2.5 ml) and dioxane (10 ml) was degassed and purged with nitrogen 3 times, and then the mixture was stirred at 110° C. for 12 h under an atmosphere of nitrogen. The reaction mixture was concentrated under reduced pressure. The resulting residue was dissolved in water (200 ml) and washed with EtOAc (200 ml) followed with DCM (200 mL). The aqueous phase was acidified with aq 2 N HCl to pH 2 and the resulting solid was filtered. The solid was then washed with water (2×50 mL) and dried under reduced pressure to give Compound 88 as a yellow solid (250 mg, 37% yield) which was used without further purification. MS for $C_{11}H_9NO_4$: m/z 219.9 (MH+).

Step 2: N-[4-[(6,7-Dimethoxy-1,5-naphthyridin-4-yl)oxy]-3-fluorophenyl]-5-(furan-2-yl)-4-hydroxy-6-methylpyridine-3-carboxamide (89): Compound 89 was made following General Procedure D. Specifically in this case, to a solution of Compound 88 (150 mg, 0.68 mmol, 1 eq) in DMF (2 ml) was added Intermediate I-1 (173 mg, 0.55 mmol, 0.8 eq), HATU (312 mg, 0.82 mmol, 1.2 eq) and DIEA (265 mg, 2.1 mmol, 3 eq). The mixture was stirred at 25° C. for 15 hr. The reaction mixture was diluted with water (50 ml) and extracted with EtOAc (2×50 mL). The combined organic extracts were washed with aq saturated NaCl (5×150 mL), dried over anhyd $Na_2SO_4$ and concentrated under reduced pressure. The resulting residue was purified by flash silica gel chromatography (0-2% MeOH in DCM) to give Compound 89 as a white solid (77.4 mg, 22% yield). 1H NMR (400 MHz, DMSO-$d_6$) δ 13.08 (s, 1H), 12.66 (br s, 1H), 8.54 (d, 1H), 8.49 (s, 1H), 8.02 (dd, 1H), 7.77 (d, 1H), 7.64 (s, 1H), 7.46-7.41 (m, 1H), 7.36-7.31 (m, 1H), 6.94 (d, 1H), 6.82 (d, 1H), 6.61 (dd, 1H), 3.95 (d, 6H), 2.45 (s, 3H); MS for $C_{27}H_{21}FN_4O_6$: m/z 517.1 (MH+).

The following compounds were made using General Procedure C followed by General Procedure D as exemplified by the synthesis of Compound 89 in Example 24:

N-[4-[(6,7-Dimethoxy-1,5-naphthyridin-4-yl)oxy]-3-fluoro-phenyl]-4-hydroxy-6-methyl-5-(2-thienyl)pyridine-3-carboxamide (90)): 1H NMR (400 MHz, DMSO-$d_6$) δ 13.10 (s, 1H), 8.57-8.51 (m, 2H), 8.02 (dd, 1H), 7.67-7.64 (m, 2H), 7.42 (br d, 1H), 7.35-7.29 (m, 1H), 7.16-7.11 (m, 2H), 6.82 (d, 1H), 3.95 (d, 6H), 2.37 (s, 3H); MS for $C_{27}H_{21}FN_4O_5S$: m/z 533.1 (MH+).

N-[4-[(6,7-Dimethoxy-1,5-naphthyridin-4-yl)oxy]-3-fluoro-phenyl]-4-hydroxy-6-methyl-5-(4-methyl-2-thienyl)pyridine-3-carboxamide (91): $^1H$ NMR (400 MHz, DMSO-$d_6$) δ 13.15 (s, 1H), 12.92 (br d, 1H), 8.81 (d, 1H), 8.49 (d, 1H), 8.13-8.06 (m, 1H), 7.83 (s, 1H), 7.54-7.47 (m, 2H), 7.22 (s, 1H), 7.17 (d, 1H), 6.93 (d, 1H), 4.05 (d, 6H), 2.39 (s, 3H), 2.26 (s, 3H); MS for $C_{28}H_{23}FN_4O_5S$: m/z 547.2 (MH+).

N-[4-[(6,7-Dimethoxy-1,5-naphthyridin-4-yl)oxy]-3-fluoro-phenyl]-4-hydroxy-6-methyl-5-(5-methyl-2-furyl)pyridine-3-carboxamide (92): $^1H$ NMR (400 MHz, DMSO-$d_6$) δ 13.14 (s, 1H), 12.72 (br d, 1H), 8.60 (d, 1H), 8.47 (d, 1H), 8.04 (dd, 1H), 7.67 (s, 1H), 7.46 (br d, 1H), 7.40-7.33 (m, 1H), 6.89 (d, 1H), 6.84 (d, 1H), 6.21 (d, 1H), 3.97 (d, 6H), 2.48 (s, 3H), 2.33 (s, 3H). MS for $C_{28}H_{23}FN_4O_6$: m/z 531.2 (MH+).

N-[4-[(6,7-Dimethoxy-1,5-naphthyridin-4-yl)oxy]-3-fluoro-phenyl]-4-hydroxy-6-methyl-5-(3-thienyl)pyridine-3-carboxamide (93): MS for $C_{27}H_{21}FN_4O_5S$: m/z 533.4 (MH+).

N-[4-[(6, 7-Dimethoxy-1, 5-naphthyridin-4-yl) oxy]-3-fluoro-phenyl]-4-hydroxy-6-methyl-5-(5-methyl-2-thienyl)pyridine-3-carboxamide (94): $^1H$ NMR (400 MHz, $CD_3OD$) δ 9.22 (s, 1H), 8.78 (d, 1H), 8.12-8.03 (m, 1H), 7.78 (s, 1H), 7.70 (br d, 1H), 7.52 (t, 1H), 7.26 (d, 1H), 7.02-6.99 (m, 1H), 7.00 (d, 1H), 6.90 (br s, 1H), 4.15 (d, 6H), 2.59 (s, 3H), 2.56 (s, 3H); MS for $C_{28}H_{23}FN_4O_5S$: m/z 547.2 (MH+).

N-[4-[(6,7-Dimethoxy-1,5-naphthyridin-4-yl)oxy]-3-fluoro-phenyl]-5-(3-furyl)-4-hydroxy-6-methyl-pyridine-3-carboxamide (95): $^1H$ NMR (400 MHz, DMSO-$d_6$) δ 13.24

(s, 1H), 12.58 (s, 1H), 8.54 (d, 1H), 8.49 (s, 1H), 8.02 (dd, 1H), 7.90 (d, 1H), 7.74 (t, 1H), 7.65 (s, 1H), 7.43-7.39 (m, 1H), 7.36-7.30 (m, 1H), 6.82 (d, 1H), 6.69 (d, 1H), 3.97 (s, 3H), 3.95 (s, 3H), 2.38 (s, 3H); MS for $C_{27}H_{21}FN_4O_6$: m/z 517.0 (MH+).

N-[3-Fluoro-4-[(7-methoxy-1,5-naphthyridin-4-yl)oxy]phenyl]-5-(2-furyl)-4-hydroxy-6-methyl-pyridine-3-carboxamide (96): $^1$H NMR (400 MHz, DMSO-$d_6$) δ 13.17 (s, 1H), 12.80-12.76 (m, 1H), 8.89-8.85 (m, 2H), 8.51 (d, 1H), 8.10 (dd, 1H), 7.85 (d, 1H), 7.80-7.77 (m, 1H), 7.56-7.46 (m, 2H), 7.00-6.93 (m, 2H), 6.62 (dd, 1H), 4.05 (s, 3H), 2.46 (s, 3H); MS for $C_{26}H_{19}FN_4O_5$: m/z 487.1 (MH+).

N-[3-Fluoro-4-[(7-methoxy-1,5-naphthyridin-4-yl)oxy]phenyl]-4-hydroxy-6-methyl-5-(5-methyl-2-furyl)pyridine-3-carboxamide (97): $^1$H NMR (400 MHz, DMSO-$d_6$) δ 13.20 (s, 1H), 12.78-12.73 (m, 1H), 8.91-8.85 (m, 2H), 8.48 (d, 1H), 8.11 (dd, 1H), 7.86 (d, 1H), 7.56-7.46 (m, 2H), 6.98 (d, 1H), 6.84 (d, 1H), 6.23-6.20 (m, 1H), 4.05-4.02 (m, 3H), 2.48 (br s, 3H), 2.33 (s, 3H). MS for $C_{27}H_{21}FN_4O_5$: m/z 501.1 (MH+).

N-[3-Fluoro-4-[(7-methoxy-1,5-naphthyridin-4-yl)oxy]phenyl]-4-hydroxy-6-methyl-5-(3-thienyl)pyridine-3-carboxamide (98): $^1$H NMR (400 MHz, DMSO-$d_6$) δ 13.28 (s, 1H), 12.69-12.64 (m, 1H), 8.88-8.81 (m, 2H), 8.52 (d, 1H), 8.08 (dd, 1H), 7.83 (d, 1H), 7.59 (dd, 1H), 7.53-7.43 (m, 3H), 7.15 (dd, 1H), 6.91 (br d, 1H), 4.03 (s, 3H), 2.28 (s, 3H); MS for $C_{26}H_{19}FN_4O_4S$: m/z 503.1 (MH+).

N-[3-Fluoro-4-[(7-methoxy-1,5-naphthyridin-4-yl)oxy]phenyl]-5-(3-furyl)-4-hydroxy-6-methyl-pyridine-3-carboxamide (99): $^1$H NMR (400 MHz, DMSO-$d_6$) δ 13.30 (s, 1H), 12.76 (d, 1H), 8.93-8.84 (m, 2H), 8.49 (d, 1H), 8.14-8.06 (m, 1H), 7.93-7.86 (m, 2H), 7.74 (t, 1H), 7.53-7.46 (m, 2H), 7.01 (d, 1H), 6.69 (d, 1H), 4.05 (s, 3H), 2.39 (s, 3H); MS for $C_{26}H_{19}FN_4O_5$: m/z 487.1 (MH+).

N-[3-Fluoro-4-[(7-methoxy-1,5-naphthyridin-4-yl)oxy]phenyl]-4-hydroxy-6-methyl-5-(2-thienyl)pyridine-3-carboxamide (100): MS for $C_{26}H_{19}FN_4O_4S$: m/z 503.1 (MH+).

N-[3-Fluoro-4-[(7-methoxy-1, 5-naphthyridin-4-yl) oxy]phenyl]-4-hydroxy-6-methyl-5-(5-methyl-2-thienyl) pyridine-3-carboxamide (101): $^1$H NMR (400 MHz, $CD_3OD$) δ 8.99-8.94 (m, 2H), 8.60 (s, 1H), 8.12 (br d, 1H), 7.81 (br s, 1H), 7.56-7.46 (m, 2H), 7.25 (br d, 1H), 6.88-6.82 (m, 2H), 4.17 (s, 3H), 2.53 (s, 3H), 2.43 (s, 3H); MS for $C_{27}H_{21}FN_4O_4S$: m/z 517.1 (MH+).

N-[3-Fluoro-4-[(7-methoxy-1, 5-naphthyridin-4-yl) oxy]phenyl]-4-hydroxy-6-methyl-5-(4-methyl-2-thienyl) pyridine-3-carboxamide (102): $^1$H NMR (400 MHz, DMSO-$d_6$) δ 13.16 (s, 1H), 12.90 (br d, 1H), 8.97-8.92 (m, 2H), 8.51 (d, 1H), 8.15-8.08 (m, 1H), 7.93 (d, 1H), 7.57-7.48 (m, 2H), 7.23 (s, 1H), 7.09 (d, 1H), 6.94 (d, 1H), 4.07 (s, 3H), 2.38 (s, 3H), 2.26 (s, 3H); MS for $C_{27}H_{21}FN_4O_4S$: m/z 517.1 (MH+).

N-[4-[(6, 7-Dimethoxy-1, 5-naphthyridin-4-yl) oxy]-3-fluoro-phenyl]-4-hydroxy-6-methyl-5-(3-methyl-2-thienyl) pyridine-3-carboxamide (103): MS for $C_{28}H_{23}FN_4O_5S$: m/z 547.2 (MH+).

N-[4-[(6,7-Dimethoxy-1,5-naphthyridin-4-yl)oxy]-3-fluoro-phenyl]-4-hydroxy-6-methyl-5-(2-methylpyrazol-3-yl)pyridine-3-carboxamide (104): MS for $C_{27}H_{23}FN_6O_5$: m/z 531.1 (MH+).

N-[4-[(6,7-Dimethoxy-1,5-naphthyridin-4-yl)oxy]-3-fluoro-phenyl]-4-hydroxy-6-methyl-5-[2-methyl-5-(trifluoromethyl)pyrazol-3-yl]pyridine-3-carboxamide (105): $^1$H NMR (400 MHz, DMSO-$d_6$) δ 13.12 (br d, 1H), 12.93 (s, 1H), 8.77 (d, 1H), 8.62 (d, 1H), 8.07 (dd, 1H), 7.77 (s, 1H), 7.56-7.43 (m, 2H), 7.11 (d, 1H), 6.78 (s, 1H), 4.04 (s, 6H), 3.72 (s, 3H), 2.25 (s, 3H); MS for $C_{25}H_{22}F_4N_6O_5$: m/z 599.1 (MH+).

N-[4-[(6,7-Dimethoxy-1,5-naphthyridin-4-yl)oxy]-3-fluoro-phenyl]-4-hydroxy-2,6-dimethyl-5-(3-thienyl)pyridine-3-carboxamide (106): MS for $C_{28}H_{23}FN_4O_5S$: m/z 547.1 (MH+).

N-[4-[(6,7-Dimethoxy-1,5-naphthyridin-4-yl)oxy]-3-fluoro-phenyl]-4-hydroxy-2,6-dimethyl-5-(2-thienyl)pyridine-3-carboxamide (107): $^1$H NMR (400 MHz, DMSO-$d_6$) δ 13.05-12.85 (m, 1H), 12.07-11.87 (m, 1H), 8.61-8.45 (m, 1H), 8.06-7.91 (m, 1H), 7.64 (br s, 2H), 7.42-7.26 (m, 2H), 7.18-7.06 (m, 2H), 6.86-6.67 (m, 1H), 3.96 (br s, 6H), 2.83-2.65 (s, 3H), 2.43-2.27 (s, 3H); MS for $C_{28}H_{23}FN_4O_5S$ m/z 547.1 (MH+).

N-[4-[(6,7-Dimethoxy-1,5-naphthyridin-4-yl)oxy]-3-fluoro-phenyl]-4-hydroxy-2, 6-dimethyl-5-(2-methylpyrazol-3-yl) pyridine-3-carboxamide (108): $^1$H NMR (400 MHz, DMSO-$d_6$) δ 13.06 (br s, 1H), 12.41-11.66 (m, 1H), 8.53 (d, 1H), 7.98 (dd, 1H), 7.64 (s, 1H), 7.45 (d, 1H), 7.41-7.37 (m, 1H), 7.33-7.28 (m, 1H), 6.78 (d, 1H), 6.19 (d, 1H), 3.96 (s, 3H), 3.95 (s, 3H), 3.60 (s, 3H), 2.73 (s, 3H), 2.17 (s, 3H); MS for $C_{28}H_{25}FN_6O_5$: m/z 545.2 (MH+).

N-[4-[(6,7-Dimethoxy-1,5-naphthyridin-4-yl)oxy]-3-fluoro-phenyl]-5-(2,5-dimethylpyrazol-3-yl)-4-hydroxy-2,6-dimethyl-pyridine-3-carboxamide (109): $^1$H NMR (DMSO-$d_6$ 400 MHz) δ 13.10 (s, 1H), 12.01 (s, 1H), 8.53 (d, 1H), 7.98 (dd, 1H), 7.64 (s, 1H), 7.40-7.35 (m, 1H), 7.33-7.28 (m, 1H), 6.78 (d, 1H), 5.95 (s, 1H), 3.96 (s, 3H), 3.95 (s, 3H), 3.50 (s, 3H), 2.73 (s, 3H), 2.17 (d, 6H); MS for $C_{29}H_{27}FN_6O_5$: m/z 559.3 (MH+).

N-[4-[(6,7-Dimethoxy-1,5-naphthyridin-4-yl)oxy]-3-fluoro-phenyl]-4-hydroxy-2,6-dimethyl-5-(5-methyl-2-furyl)pyridine-3-carboxamide (110): $^1$H NMR (400 MHz, DMSO-$d_6$) δ 12.98 (s, 1H), 11.92-11.80 (m, 1H), 8.54 (d, 1H), 7.99 (dd, 1H), 7.64 (s, 1H), 7.42-7.37 (m, 1H), 7.34-7.28 (m, 1H), 6.79 (d, 1H), 6.75 (d, 1H), 6.18 (d, 1H), 3.96 (d, 6H), 2.68 (s, 3H), 2.43 (s, 3H), 2.31 (s, 3H); MS for $C_{29}H_{25}FN_4O_6$: m/z 545.2 (MH+).

N-[4-[(6,7-Dimethoxy-1,5-naphthyridin-4-yl)oxy]-3-fluoro-phenyl]-4-hydroxy-2,6-dimethyl-5-(5-methyl-2-thienyl)pyridine-3-carboxamide (111): $^1$H NMR (400 MHz, DMSO-$d_6$) δ 13.09 (s, 1H), 12.08 (br s, 1H), 8.74 (d, 1H), 8.05 (br d, 1H), 7.75 (s, 1H), 7.49-7.37 (m, 2H), 7.07 (br d, 1H), 6.87 (d, 1H), 6.80 (d, 1H), 4.04 (d, 6H), 2.70 (s, 3H), 2.47 (s, 3H), 2.37 (s, 3H); MS for $C_{29}H_{25}FN_4O_5S$: m/z 561.2 (MH+).

N-[4-[(6,7-Dimethoxy-1,5-naphthyridin-4-yl)oxy]-3-fluoro-phenyl]-5-(3-furyl)-4-hydroxy-2,6-dimethyl-pyridine-3-carboxamide (112): $^1$H NMR (400 MHz, DMSO-$d_6$) δ 13.28 (s, 1H), 11.94-11.79 (m, 1H), 8.54 (d, 1H), 8.05-7.96 (m, 1H), 7.87 (d, 1H), 7.73 (t, 1H), 7.65 (s, 1H), 7.37 (br d, 1H), 7.35-7.27 (m, 1H), 6.80 (d, 1H), 6.66 (d, 1H), 3.97 (d, 6H), 2.72 (s, 3H), 2.36 (s, 3H); MS for $C_{28}H_{23}FN_4O_6$: m/z 531.1 (MH+).

Example 25: N-[4-[(6,7-Dimethoxy-1,5-naphthyridin-4-yl)oxy]-3-fluorophenyl]-4-hydroxy-2-(methoxymethyl)-6-methyl-5-thiophen-2-ylpyridine-3-carboxamide (115)

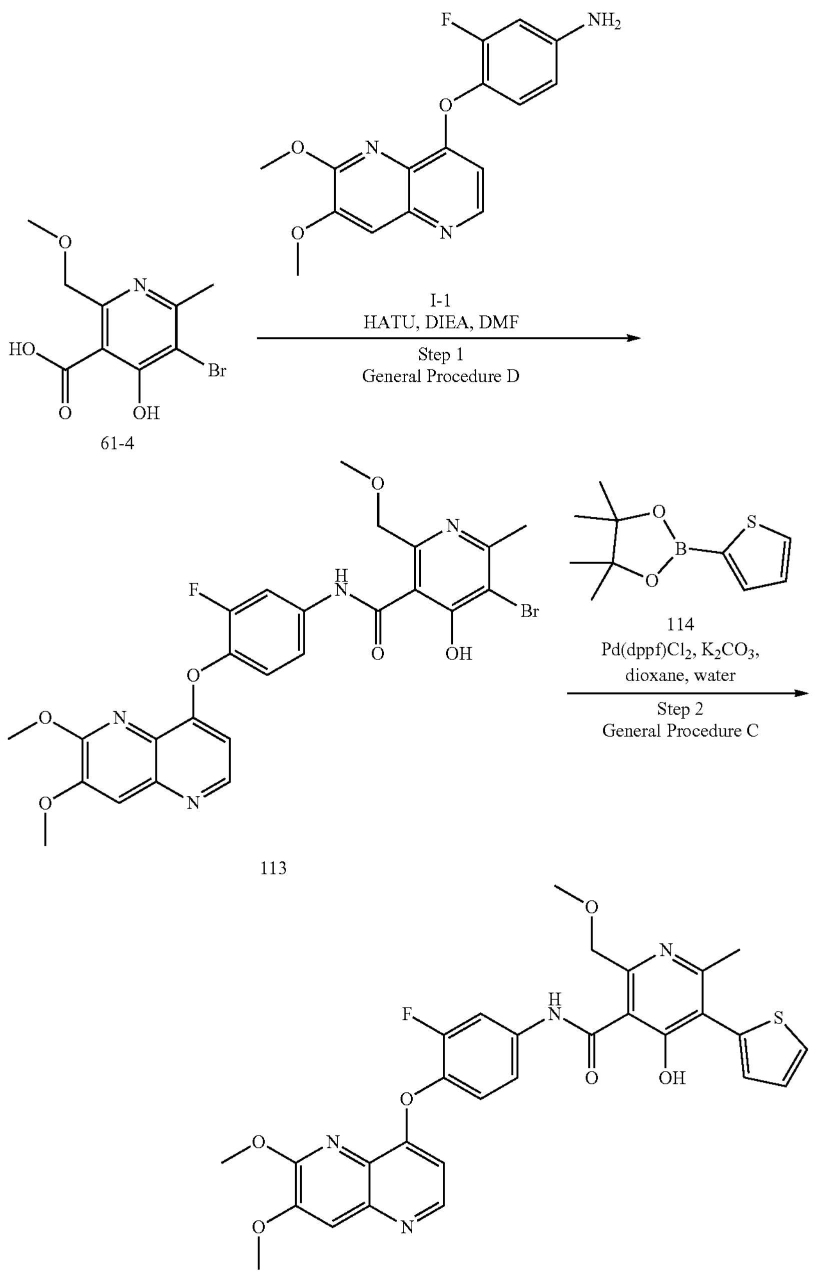

61-4

113

115

Step 1: 5-Bromo-N-(4-((6,7-dimethoxy-1,5-naphthyridin-4-yl)oxy)-3-fluorophenyl)-4-hydroxy-2-(methoxymethyl)-6-methylnicotinamide (113): Compound 113 was made following General Procedure D. Specifically in this case, a mixture of Intermediate I-1 (94.5 mg, 0.30 mmol), Compound 61-4 (124 mg, 0.45 mmol), HATU (230 mg, 0.61 mmol) in DMF (1.5 mL) was chilled to 0° C. in an ice bath and DIEA (0.15 mL, 0.86 mmol) was added dropwise. The resulting reaction mixture was stirred at room temperature overnight. The reaction mixture was diluted with DCM and was washed with aq saturated $K_2CO_3$ solution followed by water twice. The organic phase was then dried over anhyd $Na_2SO_4$ and concentrated under reduced pressure. The resulting residue was absorbed into silica gel and purified by flash chromatography (95% DCM:5% MeOH) to give Compound 113 as an off-white solid (140 mg, 81% yield). MS for $C_{25}H_{22}BrFN_4O_6$: m/z 573/575 (MH+).

Step 2: N-[4-[(6,7-Dimethoxy-1,5-naphthyridin-4-yl)oxy]-3-fluorophenyl]-4-hydroxy-2-(methoxymethyl)-6-methyl-5-thiophen-2-ylpyridine-3-carboxamide (115): Compound 115 was made following General Procedure C. Specifically in this case, a mixture of Compound 113 (37.6 mg, 0.066 mmol), Compound 114 (12.6 mg, 0.10 mmol) and $K_2CO_3$ (21.0 mg, 0.152 mmol) in 1,4-dioxane (0.69 mL) and water (0.2 mL) in a 5 mL microwave tube was degassed with nitrogen followed by addition of $Pd(PPh_3)_4$(3.6 mg, 0.0031 mmol). The resulting mixture was heated at 160 15° C. under microwave irradiation for 40 min. The mixture was then diluted with MeOH and filtered. The filtrate was concentrated, and the resulting residue was purified using flash chromatography (95% EtOAc:5% MeOH) to give Compound 115 (11.6 mg, 31% yield). $^1$H NMR (400 MHz, DMSO-$d_6$) δ 12.93 (s, 1H), 11.54 (s, 1H), 8.55 (d, 1H), 7.99 (dd, 1H), 7.77-7.57 (m, 2H), 7.47-7.35 (m, 1H), 7.32 (t, 1H), 7.19-7.06 (m, 2H), 6.81 (dd, 1H), 4.98 (s, 2H), 3.97 (d, 6H), 3.47 (s, 3H), 2.45 (s, 3H). MS for $C_{29}H_{25}FN_4O_6S$: m/z 577.0 (MH+).

The following compounds were made using General Procedure D followed by General Procedure C as exemplified by the syntheses of 115 in Example 25:

N-[4-[(6,7-Dimethoxy-1,5-naphthyridin-4-yl)oxy]-3-fluorophenyl]-4-hydroxy-2-(methoxymethyl)-6-methyl-5-thiophen-2-ylpyridine-3-carboxamide (116): MS for $C_{29}H_{25}FN_4O_7$: m/z 561.0 (MH+).

N-[4-[(6,7-Dimethoxy-1,5-naphthyridin-4-yl)oxy]-3-fluorophenyl]-4-hydroxy-2-(methoxymethyl)-6-methyl-5-(5-methylfuran-2-yl)pyridine-3-carboxamide (117): MS for $C_{30}H_{27}FN_4O_7$: m/z 575.0 (MH+).

N-[3-Fluoro-4-[(6-methoxy-1,5-naphthyridin-4-yl)oxy]phenyl]-5-(furan-2-yl)-4-hydroxy-6-methylpyridine-3-carboxamide (118): $^1$H NMR (400 MHz, DMSO-$d_6$) δ 13.11 (s, 1H), 12.69 (d, 1H), 8.63 (d, 1H), 8.51 (d, 1H), 8.30 (d, 1H), 8.05 (dd, 1H), 7.79 (d, 1H), 7.55-7.22 (m, 3H), 6.97 (dd, 2H), 6.62 (dd, 1H), 3.94 (s, 3H), 2.46 (s, 3H); MS for $C_{26}H_{19}FN_4O_5$: m/z 487.0 (MH+).

N-[4-[(6,7-Dimethoxy-1,5-naphthyridin-4-yl)oxy]-3-fluorophenyl]-5-(furan-2-yl)-4-hydroxy-2-methylpyridine-3-carboxamide (119): $^1$H NMR (400 MHz, DMSO-$d_6$) δ 12.43 (s, 1H), 12.32 (s, 1H), 8.48 (d, 1H), 8.06 (s, 1H), 7.94 (dd, 1H), 7.69-7.62 (m, 1H), 7.59 (s, 1H), 7.41-7.33 (m, 1H), 7.33-7.15 (m, 2H), 6.82-6.64 (m, 1H), 6.53 (dd, 1H), 3.91 (s, 6H), 2.55 (s, 3H); MS for $C_{27}H_{21}FN_4O_6$: m/z 517.1 (MH+).

N-[4-[(6,7-Dimethoxy-1,5-naphthyridin-4-yl)oxy]-3-fluorophenyl]-4-hydroxy-2-methyl-5-(5-methylfuran-2-yl)pyridine-3-carboxamide (120): $^1$H NMR (400 MHz, DMSO-$d_6$) δ 12.50 (s, 1H), 12.27 (s, 1H), 8.48 (d, 1H), 7.94 (dd, 2H), 7.59 (s, 1H), 7.41-7.33 (m, 1H), 7.27 (t, 1H), 7.15 (d, 1H), 6.74 (d, 1H), 6.13 (dd, 1H), 3.90 (s, 6H), 2.55 (s, 3H), 2.28 (s, 3H); MS for $C_{28}H_{23}FN_4O_6$: m/z 531.1 (MH+).

N-[4-[(6,7-Dimethoxy-1,5-naphthyridin-4-yl)oxy]-3-fluorophenyl]-5-(5-formylfuran-2-yl)-4-hydroxy-2-methylpyridine-3-carboxamide (121): $^1$H NMR (400 MHz, DMSO-$d_6$) δ 12.47 (s, 1H), 12.01 (s, 1H), 9.53 (s, 1H), 8.47 (d, 1H), 8.24 (s, 1H), 7.93 (dd, 1H), 7.66-7.50 (m, 2H), 7.47 (d, 1H), 7.38 (d, 1H), 7.29 (d, 1H), 6.73 (d, 1H), 3.91 (s, 6H), 2.50 (s, 3H); MS for $C_{28}H_{21}FN_4O_7$: m/z 545 (MH+).

N-[4-[(6,7-Dimethoxy-1,5-naphthyridin-4-yl)oxy]-3-fluorophenyl]-5-(furan-3-yl)-4-hydroxy-2-methylpyridine-3-carboxamide (122): $^1$H NMR (400 MHz, DMSO-$d_6$) δ 12.77 (s, 1H), 12.36 (d, 1H), 8.67-8.50 (m, 2H), 8.19 (d, 1H), 8.02 (dd, 1H), 7.73 (t, 1H), 7.66 (s, 1H), 7.49-7.39 (m, 1H), 7.35 (t, 1H), 7.11 (d, 1H), 6.81 (dd, 1H), 3.98 (s, 6H), 2.65 (s, 3H); MS for $C_{27}H_{21}FN_4O_6$: m/z 517.1 (MH+).

N-[4-[(6,7-Dimethoxy-1,5-naphthyridin-4-yl)oxy]-3-fluorophenyl]-4-hydroxy-2-methyl-5-thiophen-2-ylpyridine-3-carboxamide (123): $^1$H NMR (400 MHz, DMSO-$d_6$) δ 12.46 (s, 1H), 12.40 (s, 1H), 8.55 (d, 1H), 8.43 (s, 1H), 8.02 (dd, 1H), 7.75 (dd, 1H), 7.66 (s, 1H), 7.54 (dd, 1H), 7.47-7.31 (m, 2H), 7.13 (dd, 1H), 6.81 (dd, 1H), 3.98 (s, 6H), 2.63 (s, 3H); MS for $C_{27}H_{21}FN_4O_5S$: m/z 533.0 (MH+).

N-[4-[(6,7-Dimethoxy-1,5-naphthyridin-4-yl)oxy]-3-fluorophenyl]-4-hydroxy-2-methyl-5-(5-methylthiophen-2-yl)pyridine-3-carboxamide (124): $^1$H NMR (400 MHz, DMSO-$d_6$) δ 12.55 (s, 1H), 12.43 (s, 1H), 8.55 (d, 1H), 8.33 (s, 1H), 8.02 (dd, 1H), 7.66 (s, 1H), 7.53 (d, 1H), 7.44 (ddd, 1H), 7.35 (t, 1H), 6.99-6.70 (m, 2H), 3.97 (s, 6H), 2.63 (s, 3H), 2.48 (d, 3H); MS for $C_{25}H_{23}FN_4O_5S$: m/z 547 (MH+).

N-[4-[(6,7-Dimethoxy-1,5-naphthyridin-4-yl)oxy]-3-fluorophenyl]-4-hydroxy-2-methyl-5-(4-methylthiophen-2-yl)pyridine-3-carboxamide (125): $^1$H NMR (400 MHz, DMSO-$d_6$) δ 12.36 (d, 2H), 8.48 (d, 1H), 8.31 (s, 1H), 7.95 (dd, 1H), 7.59 (s, 1H), 7.50 (d, 1H), 7.38 (dd, 1H), 7.28 (t, 1H), 7.04 (d, 1H), 6.74 (d, 1H), 3.90 (s, 6H), 2.55 (s, 3H), 2.19 (s, 3H); MS for $C_{28}H_{23}FN_4O_5S$: m/z 547.1 (MH+).

N-[4-[(6,7-Dimethoxy-1,5-naphthyridin-4-yl)oxy]-3-fluorophenyl]-4-hydroxy-2-methyl-5-(3-methylthiophen-2-yl)pyridine-3-carboxamide (126): $^1$H NMR (400 MHz, DMSO-$d_6$) δ 12.61 (s, 1H), 12.34 (d, 1H), 8.54 (d, 1H), 8.01 (dd, 1H), 7.91 (d, 1H), 7.66 (s, 1H), 7.49 (d, 1H), 7.42 (d, 1H), 7.34 (t, 1H), 6.98 (d, 1H), 6.80 (d, 1H), 3.97 (s, 6H), 2.65 (s, 3H), 2.23 (s, 3H); MS for $C_{28}H_{23}FN_4O_5S$: m/z 547.1 (MH+).

N-[4-[(6,7-Dimethoxy-1,5-naphthyridin-4-yl)oxy]-3-fluorophenyl]-4-hydroxy-2-methyl-5-thiophen-3-ylpyridine-3-carboxamide (127): $^1$H NMR (400 MHz, DMSO-$d_6$) δ 12.67 (s, 1H), 12.24 (s, 1H), 8.47 (d, 1H), 8.27 (dd, 1H), 8.12 (s, 1H), 7.95 (dd, 1H), 7.63-7.55 (m, 2H), 7.51 (dd, 1H), 7.43-7.30 (m, 1H), 7.27 (t, 1H), 6.74 (d, 1H), 3.90 (s, 6H), 2.57 (s, 3H); MS for $C_{27}H_{21}FN_4O_5S$: m/z 533.0 (MH+).

N-[3-Fluoro-4-[(6-methoxy-1,5-naphthyridin-4-yl)oxy]phenyl]-4-hydroxy-6-methyl-5-thiophen-2-ylpyridine-3-carboxamide (128): MS (EI) for $C_{26}H_{19}FN_4O_4S$: m/z 503.1 (MH+).

5-(Furan-2-yl)-4-hydroxy-N-[4-[(7-methoxy-1,5-naphthyridin-4-yl)oxy]phenyl]-6-methylpyridine-3-carboxamide (129): $^1$H NMR (400 MHz, DMSO-$d_6$) δ 12.92 (s, 1H), 12.59 (s, 1H), 8.65 (dd, 2H), 8.44 (s, 1H), 7.85-7.73 (m, 2H), 7.72 (d, 2H), 7.26-7.08 (m, 2H), 6.88 (d, 1H), 6.68 (d, 1H), 6.55 (dd, 1H), 3.93 (s, 3H), 2.38 (s, 3H); MS for $C_{26}H_{20}N_4O_5$: m/z 469.2 (MH+).

Example 26: 4-Hydroxy-2-(methoxymethyl)-6-methylnicotinic acid (132)

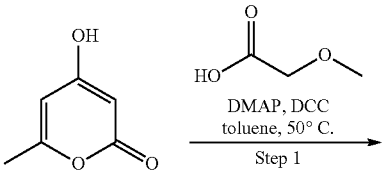

130

-continued

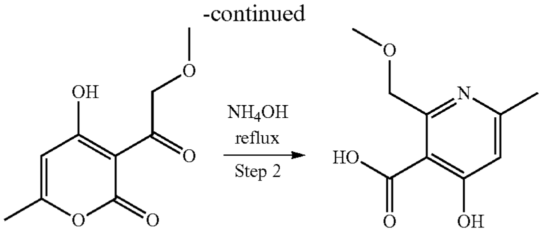

131 132

Step 1: 4-Hydroxy-3-(2-methoxyacetyl)-6-methyl-2H-pyran-2-one (131): To a solution of Compound 130 (10 g, 79 mmol, 1 eq) in toluene (100 ml) was added 2-methoxyacetic acid (7.1 g, 79 mmol, 1 eq), DCC (16.3 g, 79 mmol, 1 eq) and DMAP (9.6 g, 79 mmol, 1 eq). The resulting mixture was heated to 50° C. The resulting solid was filtered and then purified by flash silica gel column chromatography (0-100% EtOAc/hexanes) to give Compound 131. MS for $C_9H_{10}O_5$: m/z 199 (MH+).

Step 2: 4-Hydroxy-2-(methoxymethyl)-6-methylnicotinic acid (132): To a solution of Compound 131 (12.5 g, 63 mmol, 1 eq) in water (200 ml) was added ammonium hydroxide (40% in water, 60 mL). The resulting mixture was heated to reflux overnight. After allowing the reaction mixture to cool to room temperature, the solvent was partially removed under vacuum. The resulting mixture was cooled to 0° C. and acidified to pH 2 using aq 6 N HCl. The resulting solid was filtered and allowed to dry in the open air to give Compound 132. MS for $C_9H_{11}NO_4$: m/z 198 (MH+).

Example 27: N-[4-[(6,7-Dimethoxy-1,5-naphthyridin-4-yl)oxy]-3-fluorophenyl]-5-(furan-2-yl)-4-hydroxy-2,6-dimethylpyridine-3-carboxamide (135)

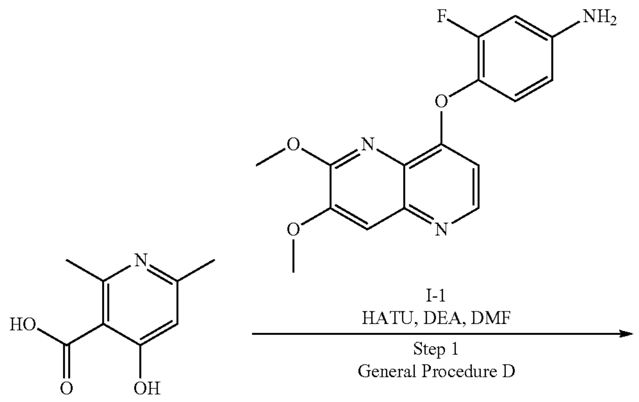

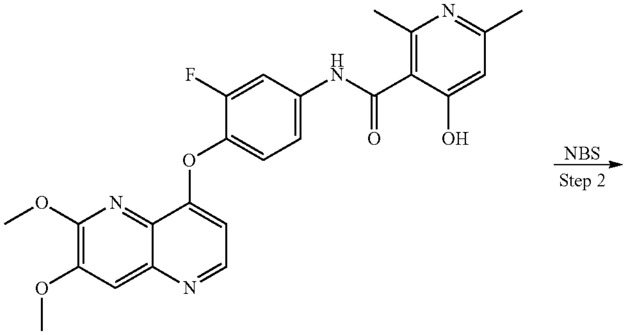

133

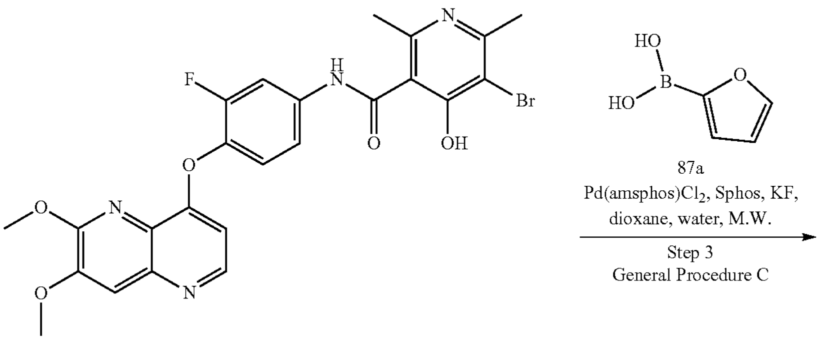

134

-continued

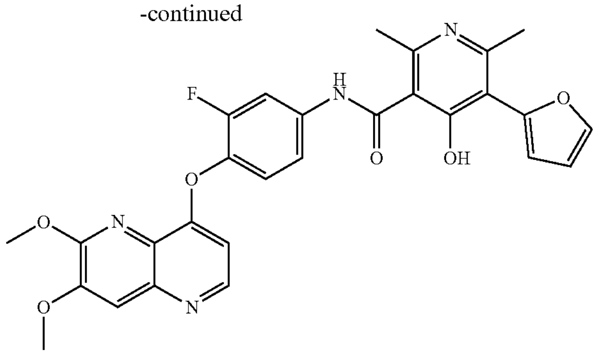

135

Step 1: N-(4-((6,7-Dimethoxy-1,5-naphthyridin-4-yl)oxy)-3-fluorophenyl)-4-hydroxy-2,6-dimethylnicotinamide (133): Compound 133 was synthesized using General Procedure D. Specifically in this case, to a mixture of 4-hydroxy-2,6-dimethyl-pyridine-3-carboxylic acid (150 mg, 0.9 mmol, 1 eq) and Intermediate I-1 (226 mg, 0.72 mmol, 0.8 eq) in DMF (1 ml) was added HATU (512 mg, 1.35 mmol, 1.5 eq) and DIEA (116 mg, 0.9 mmol, 1 eq). The mixture was stirred at 25° C. for 24 h. The reaction mixture was diluted with EtOAc (50 ml) and washed with water (10×30 mL). The combined organic layers were washed with aq saturated NaCl (10 mL), dried over anhyd $Na_2SO_4$ and concentrated under reduced pressure to give Compound 133 as a yellow solid (270 mg, 80% yield). MS for $C_4H_{21}FN_4O_5$: m/z 465.1 (MH+).

Step 2: 5-Bromo-N-(4-((6,7-dimethoxy-1,5-naphthyridin-4-yl)oxy)-3-fluorophenyl)-4-hydroxy-2,6-dimethylnicotinamide (134): Compound 134 was synthesized in a manner similar to Compound 61 in Example 15. Specifically, in this case, to a solution of Compound 133 (270 mg, 0.58 mmol, 1 eq) in DMF (5 ml) was added NBS (109 mg, 0.61 mmol, 1.05 eq). The mixture was stirred at 25° C. for 1 h. The reaction mixture was diluted with water (10 ml) and extracted with EtOAc (3×20 mL). The combined organic layers were washed with aq saturated NaCl (10 mL), dried over anhyd $Na_2SO_4$ and concentrated under reduced pressure to give Compound 134 as a yellow solid (304 mg, 96% yield). MS for $C_{24}H_{20}BrFN_4O_5$: m/z 544.7 (MH+).

Step 3: N-[4-[(6,7-Dimethoxy-1,5-naphthyridin-4-yl)oxy]-3-fluorophenyl]-5-(furan-2-yl)-4-hydroxy-2,6-dimethylpyridine-3-carboxamide (135): Compound 135 was synthesized using General Procedure C. Specifically in this case, Compound 134 (30.0 mg, 0.06 mmol, 1 eq), Compound 87a (18.5 mg, 0.17 mmol, 3 eq), Sphos (22.7 mg, 0.06 mmol, 1 eq), KF (9.6 mg, 0.17 mmol, 3 eq) and 4-ditert-butylphosphanyl-N,N-dimethyl-aniline dichloropalladium (3.9 mg, 0.006 mmol, 0.1 eq) were combined in a microwave tube in dioxane (1 ml) and water (1 mL). The sealed tube was heated under microwave irradiation at 120° C. for 35 min, cooled to room temperature, diluted with water (15 mL), and extracted with EtOAc (3×15 mL). The combined extracts were washed with aq saturated NaCl (10 mL), dried over anhyd $Na_2SO_4$ and concentrated under reduced pressure. The resulting residue was purified by prep HPLC to give Compound 135 as yellow solid (23.6 mg, 81% yield). $^1H$ NMR (400 MHz, DMSO-$d_6$) δ 12.99 (s, 1H), 12.20 (br s, 1H), 8.83 (d, 1H), 8.15-8.01 (m, 1H), 7.85 (s, 1H), 7.75 (s, 1H), 7.53-7.41 (m, 2H), 7.17 (d, 1H), 6.91-6.80 (m, 1H), 6.59 (dd, 1H), 4.07 (d, 6H), 2.69 (s, 3H), 2.43 (s, 3H); MS for $C_{28}H_{23}FN_4O_6$: m/z 530.9 (MH+).

The following compounds were made using the same three step procedure as exemplified by the synthesis of Compound 135 in Example 27:

N-[4-[(6,7-Dimethoxy-1,5-naphthyridin-4-yl)oxy]-3-fluorophenyl]-5-(2,5-dimethylpyrazol-3-yl)-4-hydroxy-6-methylpyridine-3-carboxamide (136): $^1H$ NMR (400 MHz, DMSO-$d_6$) δ 13.14 (br d, 1H), 13.09 (s, 1H), 8.84 (br d, 1H), 8.56 (br d, 1H), 8.09 (br d, 1H), 7.87 (s, 1H), 7.51 (br s, 2H), 7.20 (br d, 1H), 6.05 (s, 1H), 4.07 (br s, 3H), 4.06 (br s, 3H), 3.54 (s, 3H), 2.23 (br s, 3H), 2.19 (s, 3H); MS for $C_{28}H_{25}FN_6O_5$: m/z 545.2 (MH+).

N-[4-[(6,7-Dimethoxy-1,5-naphthyridin-4-yl)oxy]-3-fluorophenyl]-4-hydroxy-2,6-dimethyl-5-(4-methylthiophen-2-yl)pyridine-3-carboxamide (137): $^1H$ NMR (400 MHz, DMSO-$d_6$) δ 13.04 (s, 1H), 12.31 (br s, 1H), 8.87-8.77 (m, 1H), 8.08 (br d, 1H), 7.87 (s, 1H), 7.52-7.42 (m, 2H), 7.21-7.15 (m, 2H), 6.90 (d, 1H), 4.07 (d, 6H), 2.71 (s, 3H), 2.38 (s, 3H), 2.29-2.18 (m, 3H); MS for $C_{29}H_{25}FN_4O_5S$: m/z 560.9 (MH+).

N-[4-[(6,7-Dimethoxy-1,5-naphthyridin-4-yl)oxy]-3-fluorophenyl]-4-hydroxy-2,6-dimethyl-5-[2-methyl-5-(trifluoromethyl)pyrazol-3-yl]pyridine-3-carboxamide (138): $^1H$ NMR (400 MHz, DMSO-$d_6$) δ 12.92 (s, 1H), 12.60 (br s, 1H), 8.84 (d, 1H), 8.11-7.97 (m, 1H), 7.92-7.83 (m, 1H), 7.54-7.44 (m, 2H), 7.18 (d, 1H), 6.74 (s, 1H), 4.06 (d, 6H), 3.70 (s, 3H), 2.75 (s, 3H), 2.24 (s, 3H); MS for $C_{29}H_{24}F_4N_6O_5$: m/z 613.1 (MH+).

N-[4-[(6,7-Dimethoxy-1,5-naphthyridin-4-yl)oxy]-3-fluorophenyl]-4-hydroxy-2,6-dimethyl-5-(3-methylthiophen-2-yl)pyridine-3-carboxamide (139): $^1H$ NMR (400 MHz, DMSO-$d_6$) δ 13.27 (s, 1H), 12.25 (br s, 1H), 8.67 (d, 1H), 8.02 (dd, 1H), 7.73 (s, 1H), 7.51 (d, 1H), 7.46-7.30 (m, 2H), 7.01-6.93 (m, 2H), 4.00 (s, 6H), 2.75 (s, 3H), 2.15 (s, 3H), 1.96 (s, 3H); MS for $C_{29}H_{25}FN_4O_5S$: m/z 561.2 (MH+).

N-[4-[(6,7-Dimethoxy-1,5-naphthyridin-4-yl)oxy]-3-fluorophenyl]-4-hydroxy-6-methyl-5-(1,2-oxazol-4-yl)pyridine-3-carboxamide (140): $^1H$ NMR (400 MHz, DMSO-$d_6$) δ 9.28 (s, 1H), 9.16 (s, 1H), 8.99 (s, 1H), 8.84 (s, 1H), 8.81 (br s, 1H), 8.52 (s, 1H), 8.09 (brd, 1H), 7.70 (s, 1H), 7.51 (brs, 2H), 7.19 (brs, 1H), 4.05 (br s, 6H), 2.41 (br s, 3H); MS for $C_{26}H_{20}FN_5O_6$: m/z 518.0 (MH+).

N-[4-[(6,7-Dimethoxy-1,5-naphthyridin-4-yl)oxy]-3-fluorophenyl]-4-hydroxy-6-methyl-5-(1,3-thiazol-5-yl)pyridine-3-carboxamide (141): $^1H$ NMR (400 MHz, DMSO-$d_6$) δ 13.01-12.87 (m, 2H), 9.21 (s, 1H), 8.67 (br s, 1H), 8.56 (d, 1H), 8.06 (br d, 1H), 8.02 (s, 1H), 7.72 (br s, 1H), 7.51-7.45

(m, 1H), 7.44-7.37 (m, 1H), 6.99 (br s, 1H), 4.00 (br d, 6H), 2.46 (s, 3H); MS for $C_{26}H_{20}FN_5O_5S$: m/z 534.1 (MH+).

N-[4-[(6,7-Dimethoxy-1,5-naphthyridin-4-yl)oxy]-3-fluorophenyl]-4-hydroxy-6-methyl-5-(1,3-thiazol-4-yl)pyridine-3-carboxamide (142): MS for $C_{26}H_{20}FN_5O_5S$: m/z 534.1 (MH+).

N-[4-[(6,7-Dimethoxy-1,5-naphthyridin-4-yl)oxy]-3-fluorophenyl]-4-hydroxy-6-methyl-5-(1,3-thiazol-2-yl)pyridine-3-carboxamide (143): MS for $C_{26}H_{20}FN_5O_5S$: m/z 534.1 (MH+). Example 28: N-[4-[(6,7-Dimethoxy-1,5-naphthyridin-4-yl)oxy]-3-fluorophenyl]-5-(5-ethylfuran-2-yl)-4-hydroxy-2,6-dimethylpyridine-3-carboxamide (147)

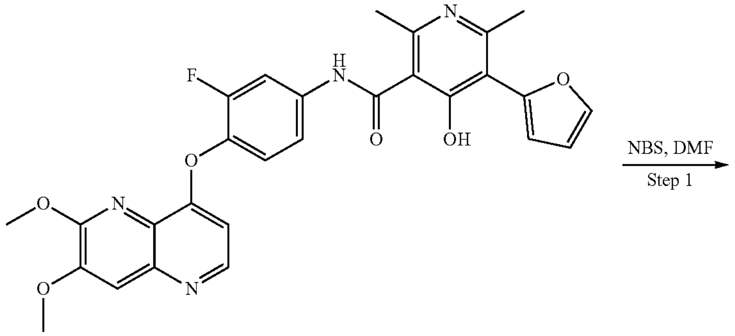

135

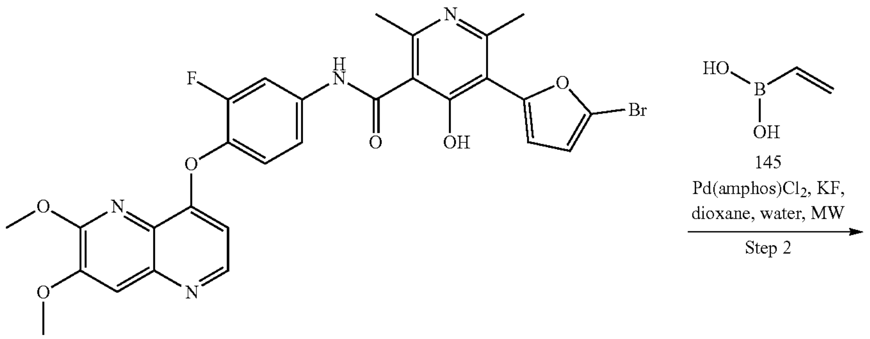

144

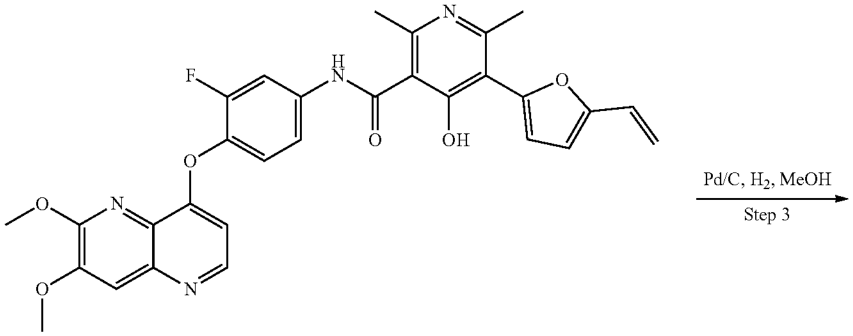

146

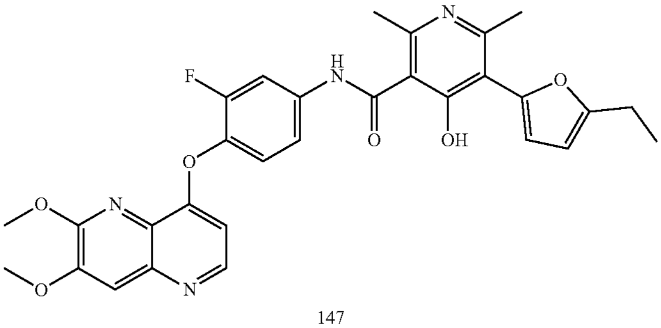

147

Step 1: 5-(5-Bromofuran-2-yl)-N-(4-((6,7-dimethoxy-1,5-naphthyridin-4-yl)oxy)-3-fluorophenyl)-4-hydroxy-2,6-dimethylnicotinamide (144): To a mixture of Compound 135 (0.12 g, 0.22 mmol, 1 eq) in DMF (3 mL) was added NBS (40.7 mg, 0.23 mmol, 1.1 eq). The mixture was stirred at 25° C. for 40 min, diluted with EtOAc (40 mL), and washed with water several times (40 mL each) followed by aq saturated NaCl (10 mL). The organic phase was dried over anhyd $Na_2SO_4$ and concentrated under reduced pressure to Compound 144 as a black solid (120 mg, 90% yield). MS for $C_{28}H_{22}BrFN_4O_6$: m/z 609/611 (MH+).

Step 2: N-(4-((6,7-Dimethoxy-1,5-naphthyridin-4-yl)oxy)-3-fluorophenyl)-4-hydroxy-2,6-dimethyl-5-(5-vinylfuran-2-yl)nicotinamide (146): Compound 144 (200 mg, 0.33 mmol, 1 eq), Compound 145 (283 mg, 3.9 mmol, 12 eq), KF (114 mg, 2.0 mmol, 6 eq) and 4-ditert-butylphosphanyl-N,N-dimethyl-aniline dichloropalladium (46.5 mg, 0.66 mmol, 0.2 eq) were combined in a microwave tube with dioxane (2 ml) and water (1 mL). The sealed tube was heated under microwave irradiation at 110° C. for 30 min, cooled to room temperature, diluted with water (20 mL), and extracted with EtOAc (30 mL×3). The combined extracts were washed with aq saturated NaCl (10 mL), dried over anhyd $Na_2SO_4$ and concentrated under reduced pressure to give Compound 146 as a black solid (150 mg, 82% yield). MS for $C_{30}H_{25}FN_4O_6$: m/z 557.3 (MH+).

Step 3: N-[4-[(6,7-Dimethoxy-1,5-naphthyridin-4-yl)oxy]-3-fluorophenyl]-5-(5-ethylfuran-2-yl)-4-hydroxy-2,6-dimethylpyridine-3-carboxamide (147): To a mixture of Compound 146 (150 mg, 0.27 mmol, 1 eq) in MeOH (40 ml) was added 10% Pd/C (30 mg) in one portion at 25° C. under an atmosphere of hydrogen (15 psi). The mixture was stirred at 25° C. for 60 min. The reaction mixture was filtered, and the filter cake washed with MeOH (60 mL). The filtrate was dried over anhyd $Na_2SO_4$ and concentrated under reduced pressure. The resulting residue was purified by prep-HPLC to give Compound 147 as a brown solid (27.6 mg, 18% yield). MS for $C_{30}H_{27}FN_4O_6$: m/z 559.2 (MH+).

The following compound was made using the same three step procedure as exemplified by the synthesis of Compound 147 in Example 28:

N-[4-[(6,7-Dimethoxy-1,5-naphthyridin-4-yl)oxy]-3-fluorophenyl]-4-hydroxy-2,6-dimethyl-5-(5-propan-2-yl-furan-2-yl)pyridine-3-carboxamide (148): MS for $C_{30}H_{27}FN_4O_6$: m/z 573.2 (MH+).

Example 29: N-[4-[(6,7-Dimethoxy-1,5-naphthyridin-4-yl)oxy]-3-fluorophenyl]-5-(5-ethenylfuran-2-yl)-4-hydroxy-6-methylpyridine-3-carboxamide (151)

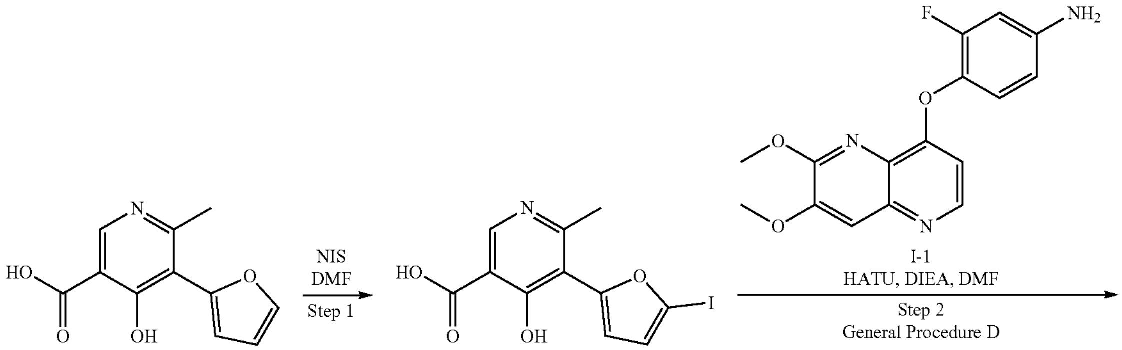

88 149

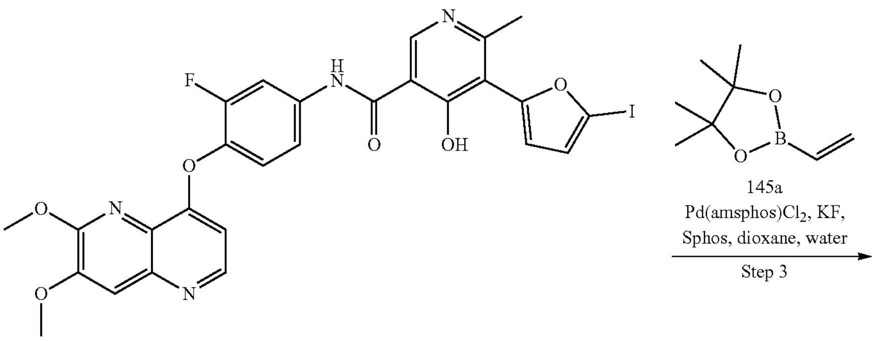

150

-continued

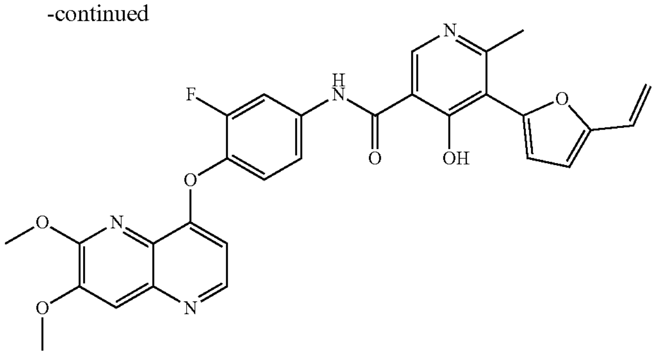

151

Step 1: 4-Hydroxy-5-(5-iodofuran-2-yl)-6-methylnicotinic acid (149): To a mixture of Compound 88 (1.15 g, 5.3 mmol, 1 eq) in DMF (10 mL) was added NIS (1.30 g, 5.8 mmol, 1.1 eq). The mixture was stirred at 25° C. for 15 h. The reaction mixture was diluted with water (30 ml) and extracted with EtOAc (30 mL×3). The combined extracts were washed with aq saturated NaCl (10 mL), dried over anhyd $Na_2SO_4$ and concentrated under reduced pressure to give Compound 149 as a yellow solid (1.2 g, 66% yield). MS for $C_{11}H_8INO_4$: m/z 345.9 (MH+).

Step 2: N-(4-((6,7-Dimethoxy-1,5-naphthyridin-4-yl)oxy)-3-fluorophenyl)-4-hydroxy-5-(5-iodofuran-2-yl)-6-methylnicotinamide (150): Compound 149 was synthesized in the manner of General Procedure D. Specifically in this case, to a mixture of Compound 149 (160 mg, 0.46 mmol, 1.1 eq) and intermediate I-1 (120 mg, 0.38 mmol, 0.9 eq) in DMF (2 ml.) was added HATU (321 mg, 0.84 mmol, 2 eq) and DIEA (163 mg, 1.26 mmol, 3 eq). The mixture was stirred at 25° C. for 15 h. The reaction mixture was diluted with water (40 ml.) and extracted with EtOAc (30 ml×5). The combined extracts were washed with aq saturated NaCl (20 mL), dried over anhyd $Na_2SO_4$ and concentrated under reduced pressure to give Compound 150 as a yellow solid (260 mg, 96.0% yield). MS for $C_{27}H_{20}FIN_4O_6$: m/z 643.0 (MH+).

Step 3: N-[4-[(6,7-Dimethoxy-1,5-naphthyridin-4-yl)oxy]-3-fluorophenyl]-5-(5-ethenylfuran-2-yl)-4-hydroxy-6-methylpyridine-3-carboxamide (151): Compound 150 (160 mg, 0.25 mmol, 1 eq), Compound 145a (230 mg, 1.5 mmol, 6 eq), 4-ditert-butylphosphanyl-N,N-dimethyl-aniline dichloropalladium (17.6 mg, 0.025 mmol, 0.1 eq), KF (14.5 mg, 0.25 mmol, 1 eq) and SPhos (102 mg, 0.25 mmol, 1 eq) were combined in a microwave tube with dioxane (1 ml.) and water (1 mL). The sealed tube was heated under microwave irradiation at 140° C. for 35 min, cooled to room temperature, diluted with water (10 ml.) and extracted with EtOAc (15 mL×3). The combined extracts were washed with aq saturated NaCl (10 mL), dried over anhyd $Na_2SO_4$ and 25 concentrated under reduced pressure. The resulting residue was purified prep HPLC to give Compound 151 as a yellow solid (65 mg, 48% yield). $^1H$ NMR (400 MHz, DMSO-$d_6$) δ 13.14 (s, 1H), 12.84 (br d, 1H), 8.76 (d, 1H), 8.49 (d, 1H), 8.10 (dd, 1H), 7.77-7.70 (m, 1H), 7.56-7.42 (m, 2H), 7.16-7.06 (m, 2H), 6.69-6.57 (m, 2H), 5.63 (d, 1H), 5.23 (d, 1H), 4.04 (s, 6H), 2.57 (s, 3H); MS for $C_{29}H_{23}FN_4O_6$: m/z 543.1 (MH+).

The following compound was made using the same three step procedure as exemplified by the synthesis of Compound 151 in Example 29:

N-[4-[(6,7-Dimethoxy-1,5-naphthyridin-4-yl)oxy]-3-fluorophenyl]-4-hydroxy-6-methyl-5-(5-prop-1-en-2-yl-furan-2-yl)pyridine-3-carboxamide (152): MS for $C_{30}H_{25}FN_4O_6$: m/z 557.2 (MH+).

Example 30: N-[4-[(6,7-Dimethoxy-1,5-naphthyridin-4-yl)oxy]-3-fluorophenyl]-5-(5-ethylfuran-2-yl)-4-hydroxy-6-methylpyridine-3-carboxamide (153)

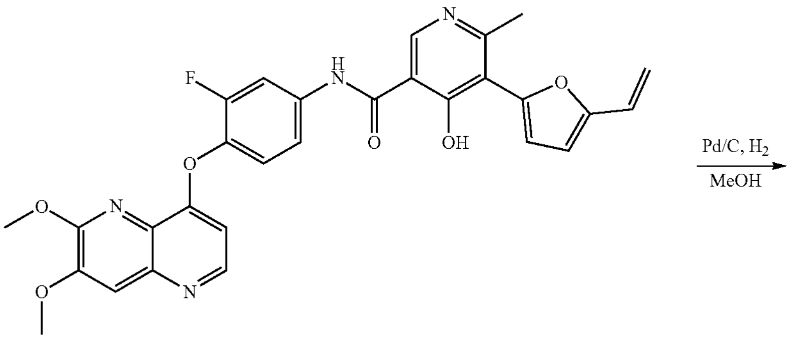

151

-continued

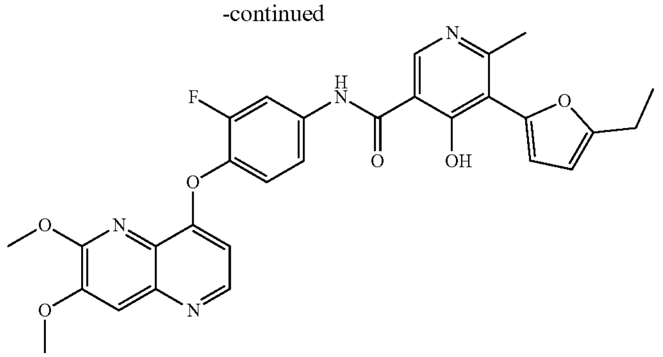

153

N-[4-[(6,7-Dimethoxy-1,5-naphthyridin-4-yl)oxy]-3-fluorophenyl]-5-(5-ethylfuran-2-yl)-4-hydroxy-6-methylpyridine-3-carboxamide (153): To a mixture of Compound 151 (72 mg, 0.13 mmol, 1 eq) in MeOH (10 mL) was added 10% Pd/C (20 mg) in one portion at 25° C. under an atmosphere of hydrogen. The mixture was stirred at 25° C. for 120 min under hydrogen (15 psi). The reaction mixture was filtered, and the filtrate concentrated under reduced pressure. The resulting residue was purified by silica gel column chromatography (DCM:MeOH=20:1) to give Compound 153 as a light-yellow solid (20 mg, 28% yield). MS for $C_{29}H_{25}FN_4O_6$: m/z 545.2 (MH+).

The following compound was made using the same procedure as exemplified by the synthesis of Compound 153 in Example 30:

N-[4-[(6,7-Dimethoxy-1,5-naphthyridin-4-yl)oxy]-3-fluorophenyl]-4-hydroxy-6-methyl-5-(5-propan-2-ylfuran-2-yl)pyridine-3-carboxamide (154): $^1$H NMR 400 MHz, DMSO-$d_6$) δ 13.23 (s, 1H), 13.02 (br d, 1H), 8.79 (d, 1H), 8.44 (d, 1H), 8.18-8.05 (m, 1H), 7.87 (s, 1H), 7.56-7.45 (m, 2H), 7.14 (d, 1H), 6.96 (d, 1H), 6.20 (d, 1H), 4.05 (d, 6H), 3.02-2.86 (m, 1H), 2.53 (s, 3H), 1.24 (d, 6H); MS for $C_{30}H_{27}FN_4O_6$: m/z 559.2 (MH+).

Example 31: N-[4-[(6,7-Dimethoxy-1,5-naphthyridin-4-yl)oxy]-3-fluorophenyl]-4-hydroxy-6-methyl-5-(5-prop-2-enylfuran-2-yl)pyridine-3-carboxamide (155)

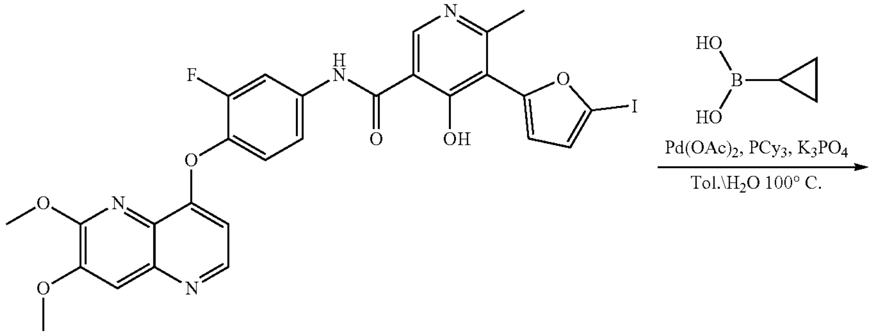

150

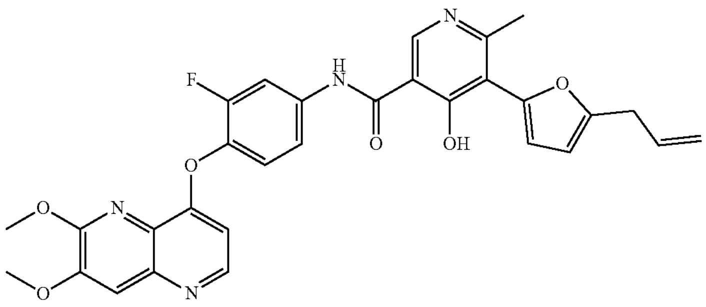

155

N-[4-[(6,7-Dimethoxy-1,5-naphthyridin-4-yl)oxy]-3-fluorophenyl]-4-hydroxy-6-methyl-5-(5-prop-2-enylfuran-2-yl)pyridine-3-carboxamide (155): To a mixture of Compound 150 (100 mg, 0.16 mmol, 1 eq), cyclopropylboronic acid (66.9 mg, 0.78 mmol, 5 eq) and $P(Cy)_3$ (8.73 mg, 0.031 mmol, 0.2 eq) in toluene (5 mL) and water (0.1 mL) was added $K_3PO_4$ (99.1 mg, 0.47 mmol, 3 eq) followed by $Pd(OAc)_2$ (3.49 mg, 0.016 mmol, 0.1 eq). The resulting mixture was flushed with nitrogen, and then stirred at 100° C. for 12 h under an atmosphere of nitrogen. The reaction mixture was then cooled to room temperature, diluted with water (20 ml) and extracted with DCM (20 mL×3). The combined extracts were washed with aq saturated NaCl (10 mL), dried over anhyd $Na_2SO_4$ and concentrated under reduced pressure. The resulting residue was purified by flash silica gel chromatography (0-5% of MeOH in DCM) followed additional purification by prep HPLC to give Compound 155 as a yellow solid (8.2 mg, 9.5% yield). $^1$H NMR (400 MHz, DMSO-$d_6$) δ 12.96 (s, 1H), 8.72 (s, 1H), 8.54 (d, 1H), 8.00 (br dd, 1H), 7.78 (s, 1H), 7.64 (s, 1H), 7.43 (br d, 1H), 7.38-7.29 (m, 1H), 6.83 (d, 1H), 6.68-6.58 (m, 2H), 6.19-6.02 (m, 1H), 5.32 (br d, 1H), 5.07 (br d, 1H), 4.95 (br s, 2H), 3.96 (s, 3H), 3.93 (s, 3H), 2.34 (s, 3H); MS for $C_{30}H_{25}FN_4O_6$: m/z 557.3 (MH+).

Example 31A: 5-(5-Cyclopropylfuran-2-yl)-N-[4-[(6,7-dimethoxy-1,5-naphthyridin-4-yl)oxy]-3-fluorophenyl]-4-hydroxy-6-methylpyridine-3-carboxamide (155A)

5-(5-Cyclopropylfuran-2-yl)-N-[4-[(6,7-dimethoxy-1,5-naphthyridin-4-yl)oxy]-3-fluorophenyl]-4-hydroxy-6-methylpyridine-3-carboxamide hydrochloride (155A): Compound 150 (50 mg, 0.078 mmol, 1 eq), cyclopropylboronic acid (33 mg, 0.39 mmol, 5 eq), $K_2CO_3$ (54 mg, 0.39 mmol, 5 eq) and $Pd(dppf)Cl_2$ (5.7 mg, 0.0078 mmol, 0.1 eq) were combined in a microwave tube in dioxane (0.5 ml) and water (0.5 mL). The sealed tube was heated at 100° C. for 30 min under microwave irradiation. The reaction mixture was diluted with water (10 ml) and extracted with EtOAc (3×15 mL). The combined organic layers were washed with aq saturated NaCl (10 mL), dried over with anhyd. $Na_2SO_4$ and concentrated under reduced pressure. The resulting residue was purified by prep-HPLC to give Compound 155A as a yellow solid (2.9 mg, 6% yield). $^1$H NMR (400 MHz, DMSO-$d_6$) δ 13.21 (s, 1H), 12.94 (br d, 1H), 8.75 (d, 1H), 8.45 (d, 1H), 8.06-8.17 (m, 1H), 7.81 (s, 1H), 7.41-7.55 (m, 2H), 7.08 (d, 1H), 6.94 (d, 1H), 6.23 (d, 1H), 4.04 (s, 6H), 2.49-2.50 (m, 3H), 1.93-2.07 (m, 1H), 0.89-0.99 (m, 2H), 0.72-0.84 (m, 2H); MS for $C_{30}H_{25}FN_4O_6$: m/z 557.1 (MH+).

The following compound was made in the same manner as Compound 155A in Example 31A:

5-(5-Cyclopropylfuran-2-yl)-N-[4-[(6,7-dimethoxy-1,5-naphthyridin-4-yl)oxy]-3-fluorophenyl]-4-hydroxy-2,6-dimethylpyridine-3-carboxamide (155B): Compound 150 was replaced with Compound 144. MS for $C_{31}H_{27}FN_4O_6$: m/z 571.2 (MH+).

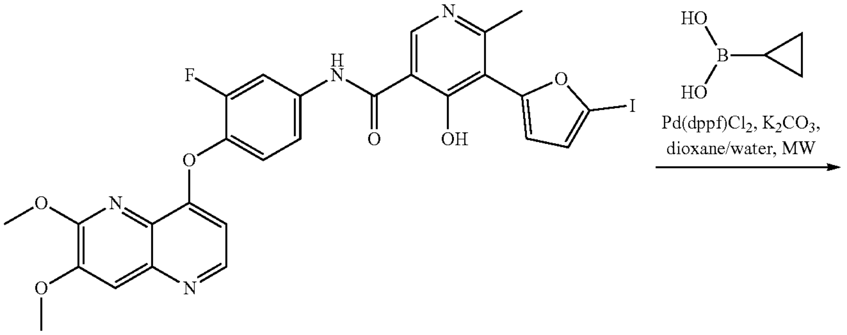

150

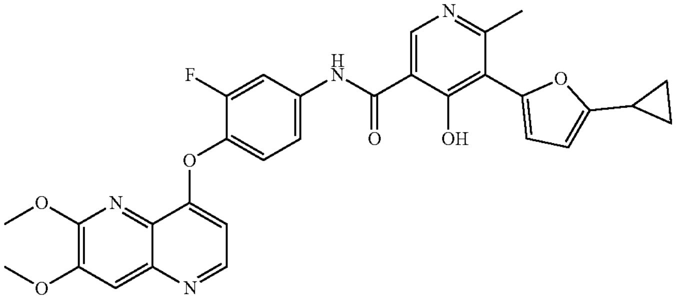

155A

Example 32: N-[4-[(6,7-Dimethoxy-1,5-naphthyridin-4-yl)oxy]-3-fluorophenyl]-5-(furan-2-yl)-1,2,6-trimethyl-4-oxopyridine-3-carboxamide (160)

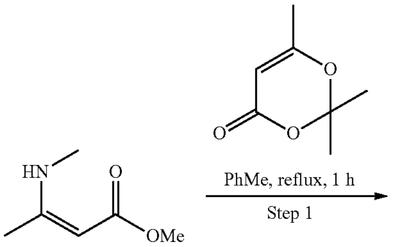

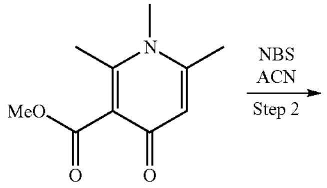

156

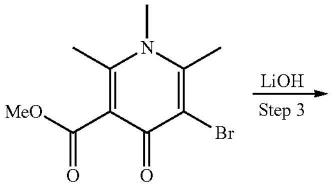

157

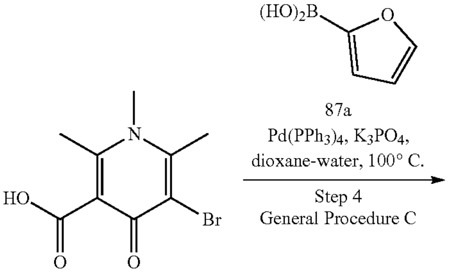

158

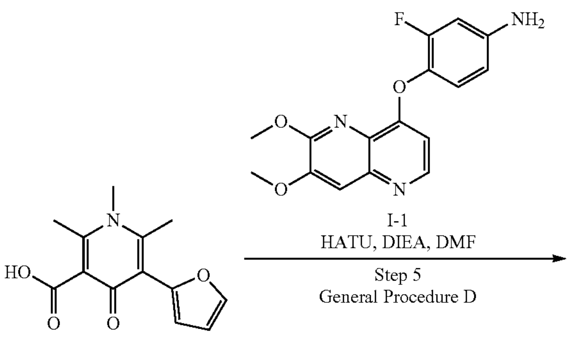

159

-continued

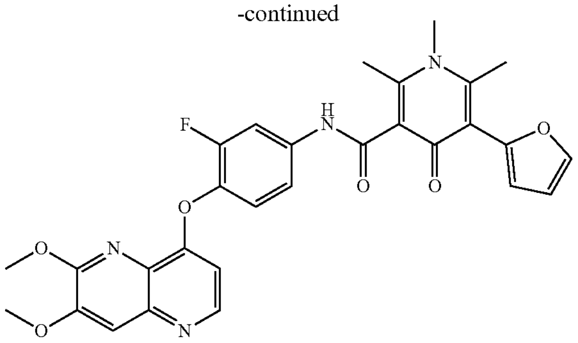

160

Step 1: Methyl 1,2,6-trimethyl-4-oxo-1,4-dihydropyridine-3-carboxylate (156): Methyl 3-(methylamino)but-2-enoate (1.7 g, 13 mmol), 2,2,6-trimethyl-4H-1,3-dioxin-4-one (4 g, 28 mmol) and toluene (20 mL) were combined in a round bottom flask equipped with a with a Dean-Stark trap. The resulting mixture was stirred at 130° C. until reflux ceased. The mixture was allowed to cool to room temperature, followed by the addition of acetone (5 mL). The resulting suspension was filtered, washed with cold acetone and dried to give crude Compound 156 (2.11 g, 82%). MS for $C_{10}H_{13}NO_3$: m/z 196 (MH+).

Step 2: Methyl 5-bromo-1,2,6-trimethyl-4-oxo-1,4-dihydropyridine-3-carboxylate (157): Compound 157 was synthesized from Compound 156 using the bromination procedure exemplified by the synthesis of Compound 61 in Example 15. MS for $C_{10}H_{12}BrNO_3$: m/z 274/276 (MH+).

Step 3: 5-Bromo-1,2,6-trimethyl-4-oxo-1,4-dihydropyridine-3-carboxylic acid (158): Compound 158 was synthesized from Compound 157 using standard lithium hydroxide ester hydrolysis conditions much like those used to convert Compound 34 to Compound 35 in Step 3 of Example 8. MS for $C_9H_{10}BrNO_3$: m/z 260/262 (MH+).

Step 4: 5-(Furan-2-yl)-1,2,6-trimethyl-4-oxo-1,4-dihydropyridine-3-carboxylic acid (159): Compound 159 was synthesized from Compound 158 and Compound 87a using General Procedure C. MS for $C_{13}H_{13}NO_4$: m/z 248 (MH+). Step 5: N-[4-[(6,7-dimethoxy-1,5-naphthyridin-4-yl)oxy]-3-fluorophenyl]-5-(furan-2-yl)-1,2,6-trimethyl-4-oxopyridine-3-carboxamide (160): Compound 160 was made from Compound 159 and Intermediate I-1 using General Procedure D. $^1H$ NMR (400 MHz, DMSO-$d_6$) δ 10.96 (s, 1H), 8.45 (d, 1H), 7.88 (dd, 1H), 7.65 (d, 1H), 7.58 (s, 1H), 7.43-7.36 (m, 1H), 7.28 (t, 1H), 6.70 (d, 1H), 6.55-6.43 (m, 2H), 3.91 (d, 6H), 3.56 (s, 3H), 2.41 (s, 3H), 2.27 (s, 3H): MS for $C_{29}H_{25}FN_4O_6$: m/z 545 (MH+).

The following compounds were made using the same procedure as exemplified by the synthesis of Compound 160 in Example 32:

5-(Furan-2-yl)-N-[4-[(7-methoxy-1,5-naphthyridin-4-yl)oxy]phenyl]-1,2,6-trimethyl-4-oxopyridine-3-carboxamide (161): In Step 5 of Example 32, Compound I-1 was replaced with Compound I-4. $^1H$ NMR (400 MHz, DMSO-$d_6$) δ 10.85 (s, 1H), 8.73 (d, 1H), 8.68 (d, 1H), 7.86-7.76 (m, 3H), 7.73 (d, 1H), 7.27-7.20 (m, 2H), 6.72 (d, 1H), 6.60-6.55 (m, 1H), 6.52 (d, 1H), 4.01 (s, 3H), 1693.63 (s, 3H), 2.49 (s, 3H), 2.34 (s, 3H); MS for $C_{28}H_{24}N_4O_5$: m/z 497 (MH+).

N-[3-Fluoro-4-[(7-methoxy-1,5-naphthyridin-4-yl)oxy]phenyl]-5-(furan-2-yl)-1,2,6-trimethyl-4-oxopyridine-3-carboxamide (162): In Step 5 of Example 32, Compound I-1 was replaced with Compound I-3. $^1H$ NMR (400 MHz, DMSO-$d_6$) δ 10.99 (s, 1H), 8.68 (d, 1H), 8.62 (d, 1H), 7.91

(dd, 1H), 7.73 (d, 1H), 7.65 (dd, 1H), 7.44 (dd, 1H), 7.34 (t, 1H), 6.68 (d, 1H), 6.53-6.43 (m, 2H), 3.94 (s, 3H), 3.56 (s, 3H), 2.42 (s, 3H), 2.27 (s, 3H); MS for $C_{28}H_{23}FN_4O_5$: m/z 515 (MH+).

N-[4-[(6,7-Dimethoxy-1,5-naphthyridin-4-yl)oxy]-2,5-difluorophenyl]-5-(furan-2-yl)-1,2,6-trimethyl-4-oxopyridine-3-carboxamide (163): In Step 5 of Example 32, Compound I-1 was replaced with Compound I-8. $^1H$ NMR (400 MHz, DMSO-$d_6$) δ 12.90 (s, 1H), 8.57 (d, 1H), 8.41 (dd, 1H), 7.76 (d, 1H), 7.67 (s, 1H), 7.52 (dd, 1H), 6.93 (d, 1H), 6.62-6.56 (m, 1H), 6.53 (d, 1H), 3.95 (d, 6H), 3.69 (s, 3H), 2.80 (s, 3H), 2.35 (s, 3H); MS for $C_{29}H_{24}FN_4O_6$: m/z 563 (MH+).

N-[4-[(6,7-Dimethoxy-1,5-naphthyridin-4-yl)oxy]phenyl]-5-(furan-2-yl)-1,2,6-trimethyl-4-oxopyridine-3-carboxamide (164): In Step 5 of Example 32, Compound I-1 was replaced with Compound 1-2. $^1H$ NMR (400 MHz, DMSO-$d_6$) δ 10.84 (s, 1H), 8.52 (d, 1H), 7.82-7.75 (m, 2H), 7.72 (dd, 1H), 7.64 (s, 1H), 7.22-7.15 (m, 2H), 6.75 (d, 1H), 6.57 (dd, 1H), 6.52 (dd, 1H), 3.97 (d, 6H), 3.63 (s, 3H), 2.51 (s, 3H), 2.34 (s, 3H); MS for $C_{29}H_{26}N_4O_6$: m/z 527 (MH+).

N-[4-[(7-Methoxy-1,5-naphthyridin-4-yl)oxy]phenyl]-1,2,6-trimethyl-4-oxo-5-thiophen-2-ylpyridine-3-carboxamide (165): In Step 4 of Example 32, Compound 87a was replaced with thiophen-2-ylboronic acid and in Step 5, Compound I-1 was replaced with Compound I-4. $^1H$ NMR (400 MHz, DMSO-$d_6$) δ 10.89 (s, 1H), 8.73 (d, 1H), 8.68 (d, 1H), 7.86-7.76 (m, 3H), 7.61 (d, 1H), 7.23 (d, 2H), 7.11 (dd, 1H), 6.93 (d, 1H), 6.72 (d, 1H), 4.00 (s, 3H), 3.64 (s, 3H), 2.51 (s, 3H), 2.39 (s, 3H); MS for $C_{28}H_{24}N_4O_4S$: m/z 513 (MH+).

N-[3-Fluoro-4-[(7-methoxy-1,5-naphthyridin-4-yl)oxy]phenyl]-1,2,6-trimethyl-4-oxo-5-thiophen-2-ylpyridine-3-carboxamide (166): In Step 4 of Example 32, Compound 87a was replaced with thiophen-2-ylboronic acid and in Step 5, Compound I-1 was replaced with Compound I-3. $^1H$ NMR (400 MHz, DMSO-$d_6$) δ 11.10 (s, 1H), 8.75 (d, 1H), 8.70 (d, 1H), 7.98 (dd, 1H), 7.80 (d, 1H), 7.64-7.58 (m, 1H), 7.51 (d, 1H), 7.41 (t, 1H), 7.12 (dd, 1H), 6.94 (dd, 1H), 6.75 (d, 1H), 4.01 (s, 3H), 3.65 (s, 3H), 2.51 (s, 3H), 2.39 (s, 3H); MS for $C_{28}H_{23}FN_4O_4S$: m/z 531 (MH+).

N-[4-[(6,7-Dimethoxy-1,5-naphthyridin-4-yl)oxy]phenyl]-1,2,6-trimethyl-4-oxo-5-thiophen-2-ylpyridine-3-carboxamide (167): In Step 4 of Example 32, Compound 87a was replaced with thiophen-2-ylboronic acid and in Step 5, Compound I-1 was replaced with Compound I-2. $^1H$ NMR (400 MHz, DMSO-$d_6$) δ 10.80 (s, 1H), 8.44 (d, 1H), 7.75-7.69 (m, 2H), 7.59-7.50 (m, 2H), 7.15-7.08 (m, 2H), 7.04 (dd, 1H), 6.85 (dd, 1H), 6.67 (d, 1H), 3.90 (d, 6H), 3.57 (s, 3H), 2.51 (s, 3H), 2.31 (s, 3H); MS for $C_{29}H_{26}N_4O_5S$: m/z 543 (MH+).

N-[4-[(6,7-Dimethoxy-1,5-naphthyridin-4-yl)oxy]-3-fluorophenyl]-1,2,6-trimethyl-4-oxo-5-thiophen-2-ylpyridine-3-carboxamide (168): In Step 4 of Example 32, Compound 87a was replaced with thiophen-2-ylboronic acid. $^1H$ NMR (400 MHz, DMSO-$d_6$) δ 11.08 (s, 1H), 8.53 (d, 1H), 7.95 (dd, 1H), 7.68-7.58 (m, 2H), 7.47 (d, 1H), 7.35 (t, 1H), 7.11 (dd, 1H), 6.93 (dd, 1H), 6.78 (d, 1H), 3.98 (d, 6H), 3.64 (s, 3H), 2.39 (s, 3H), 2.08 (d, 3H); MS for $C_{29}H_{25}FN_4O_5S$: m/z 561 (MH+).

Example 33: 4-Ethoxy-5'-fluoro-2-oxo-2H-[1,2'-bipyridine]-3-carboxylic acid (174)

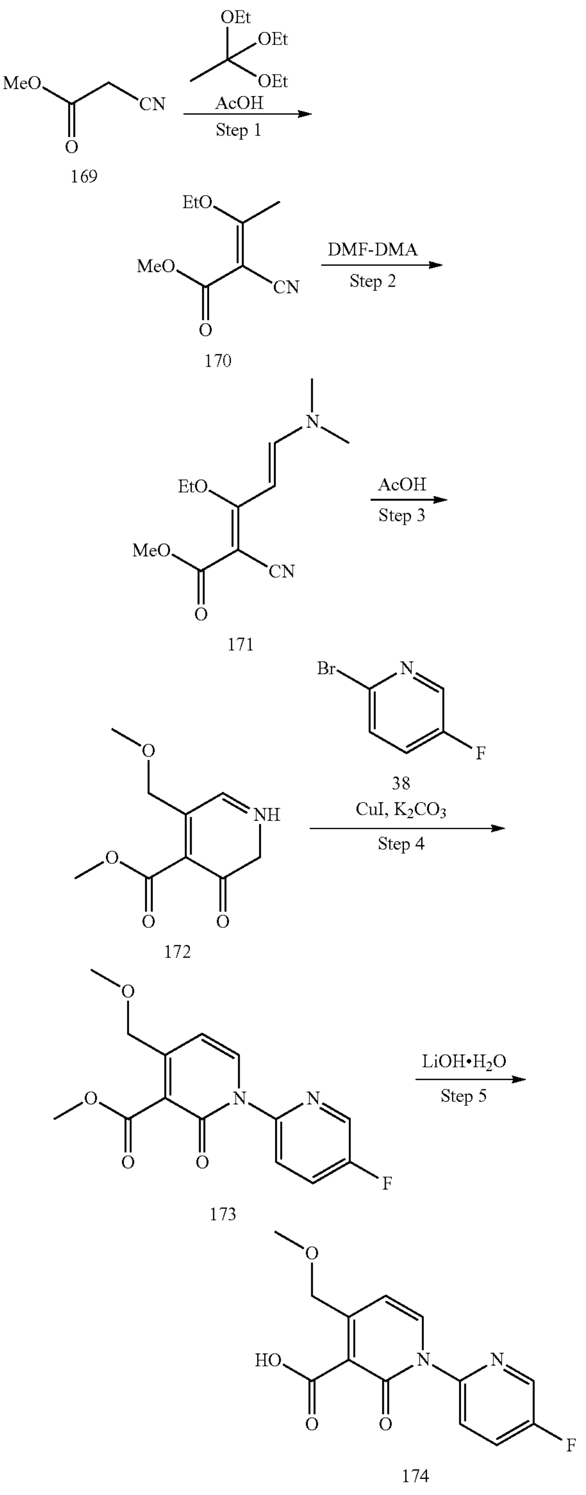

Step 1: Methyl (Z)-2-cyano-3-ethoxybut-2-enoate (170): To a solution of Compound 169 (10 g, 101 mmol, 1 eq) in triethyl orthoacetate (30 g, 185 mmol, 1.8 eq) was added AcOH (3.03 g, 50.5 mmol, 0.5 eq). The mixture was stirred at 120° C. for 12 h. The reaction mixture was concentrated under reduced pressure to give crude Compound 170 as a brown oil (17 g) which was used without further purification. MS for $C_8H_{11}NO_3$: m/z 169.8 (MH+).

Step 2: Methyl (2Z,4E)-2-cyano-5-(dimethylamino)-3-ethoxypenta-2,4-dienoate (171): A solution of crude Compound 170 (17 g, 100 mmol, 1 eq) in DMF-DMA (15.6 g, 131 mmol, 1.3 eq) was stirred at 70° C. for 12 h. The reaction mixture was concentrated under reduced pressure to give crude Compound 171 as a brown solid (20 g, 89% yield) which was used without further purification. MS for $C_{11}H_{16}N_2O_3$: m/z 224.8 (MH+).

Step 3: Methyl 4-(methoxymethyl)-2-oxo-1,2-dihydropyridine-3-carboxylate (172): A solution of Compound 171 (20 g, 89 mmol, 1 eq) in AcOH (50 ml) was stirred at 130° C. for 12 h. The reaction mixture was concentrated under reduced pressure and the pH was adjusted to 8 with aq 20% NaOH. The resulting mixture was extracted with EtOAc (3×50 ml) and DCM (5×50 mL). The combined organic extracts were washed with aq saturated NaCl (50 mL), dried over anhyd. $Na_2SO_4$ and concentrated under reduced pressure to give crude Compound 172 as a red solid (5 g, 28% yield). MS for $C_9H_{11}NO_4$: m/z 197.9 (MH+).

Step 4: Methyl 4-ethoxy-5'-fluoro-2-oxo-2H-[1,2'-bipyridine]-3-carboxylate (173): Compound 173 was synthesized from Compound 172 and Compound 38 in a similar manner to the method used to synthesize Compound 39 from Compound 37 and Compound 38 in step 1 of Example 10. MS for $C_{14}H_{13}FN_2O_4$: m/z 293 (MH+).

Step 5: 4-Ethoxy-5'-fluoro-2-oxo-2H-[1,2'-bipyridine]-3-carboxylic acid (174): Compound 174 was made from Compound 173 using the same method that was used to convert Compound 39 to Compound 40 in Step 2 of Example 10. MS for $C_{13}H_{11}FN_2O_4$: m/z 279 (MH+).

Example 34: 5-(5-Fluoropyridin-2-yl)-4-methoxy-6-methylpyridazine-3-carboxylic acid (179)

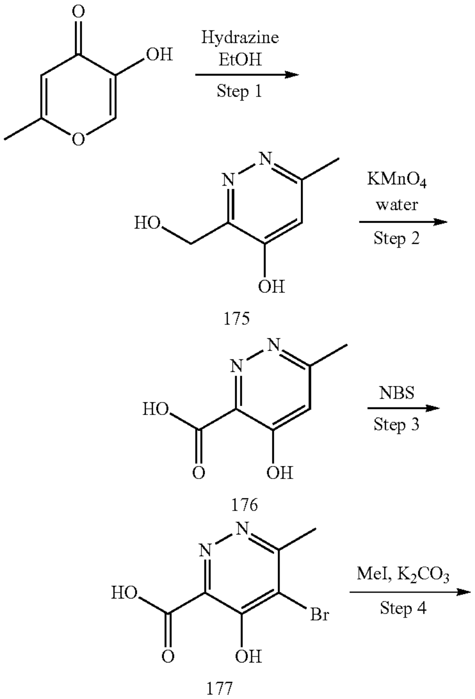

177

-continued

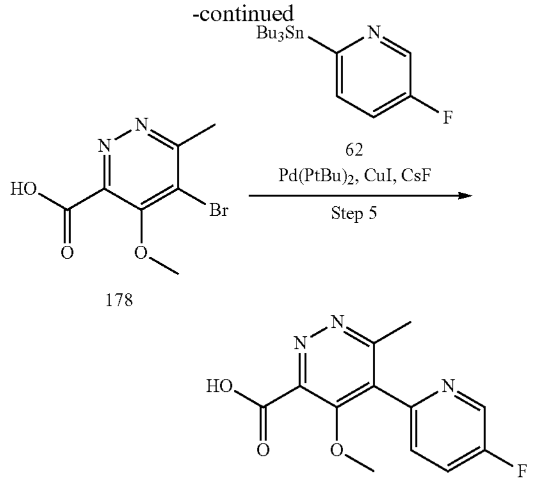

179

Step 1: 3-(Hydroxymethyl)-6-methylpyridazin-4-ol (175): To a solution of 5-hydroxy-2-methyl-4H-pyran-4-one (2.5 g, 19.8 mmol) in EtOH (80 mL) was added hydrazine (4 mL, 60% in water). The resulting mixture was heated to reflux for 90 min. The reaction mixture was allowed to cool to room temperature. The resulting precipitate was filtered and allowed to dry in the open air to afford Compound 175 as a white powder (1.4 g, 51% yield). MS for $C_6H_8N_2O_2$: m/z 141 (MH+).

Step 2: 4-Hydroxy-6-methylpyridazine-3-carboxylic acid (176): To a solution of Compound 175 (1.4 g, 10 mmol) in water (56 mL) at 75° C. was added $KMnO_4$(17.2 mmol, 1.8 eq) in water (84 ml) dropwise over 20 min. The mixture was allowed to cool to room temperature and filtered through a Celite pad. The solvent was partially removed, and the resulting mixture was acidified using 6 M HCl to pH 2. The solution was chilled to 0° C. along with scraping the side of the flask to facilitate precipitation. The resulting solid was filtered and allowed to dry in the open air to afford Compound 176 as a white powder (912 mg, 59% yield). MS for $C_6H_6N_2O_3$: m/z 155 (MH+).

Step 3: 5-Bromo-4-hydroxy-6-methylpyridazine-3-carboxylic acid (177): Compound 177 was synthesized from Compound 176 using a similar method to that used to convert Compound 60 to Compound 61 in Example 15. MS for $C_6H_5BrN_2O_3$: m/z 233 (MH+).

Step 4: 5-Bromo-4-methoxy-6-methylpyridazine-3-carboxylic acid (178): To a 40 mL vial equipped with a magnetic stir bar and a pressure relief septum was added Compound 177 (1.31 g, 5.6 mmol, 1.0 eq) in DMF (10 mL) and water (10 mL). Cesium carbonate (4.0 g, 12 mmol, 2.2 eq) was added portionwise at room temperature, followed by iodomethane (2 mL, 32.1 mmol, 5.7 eq). The reaction was then heated to 60° C. for 3 h. Aq 10% NaOH (10 mL) was then added, and the reaction heated to 60° C. for 2 h. The reaction was then acidified to pH=4 with aq 6 M HCl, and the resulting precipitate was collected by vacuum filtration to yield a mixture of Compound 178 and 5-bromo-1,6-dimethyl-4-oxo-pyridazine-3-carboxylic acid, which was carried forward without further purification.

Step 5: 5-(5-Fluoropyridin-2-yl)-4-methoxy-6-methylpyridazine-3-carboxylic acid (179): To a 20-mL vial equipped with a magnetic stir bar and a pressure relief septum was added the crude mixture from Step 4 (300 mg, 1.2 mmol), Compound 62 (1.50 g, 3.9 mmol, 3.2 eq), and cesium fluoride (500 mg, 3.29 mmol, 2.7 eq) in DMF (5 mL). Copper iodide (30 mg, 0.16 mmol, 0.13 eq) and palladium tri-tert-butylphosphane (80 mg, 0.16 mmol, 0.13 eq) were then added, and the reaction vial was purged with $N_2$ and sealed. The resulting solution was heated to 85° C. overnight. The resulting mixture was concentrated, adsorbed onto Celite and purified by silica gel column chromatography (0 to 10% MeOH in DCM), followed by further purification by prep HPLC to give Compound 179 as an off-white, foamy solid (25 mg, 7.8% yield over two steps). $^1$H NMR (400 MHz, $CDCl_3$) δ 8.60 (d, 1H), 7.68 (dd, 1H), 7.59 (td, 1H), 4.23 (s, 3H), 2.52 (s, 3H).

Example 35: 5'-Fluoro-4,6-dimethyl-2-oxo-2H-[1,2'-bipyridine]-3-carboxylic acid (182)

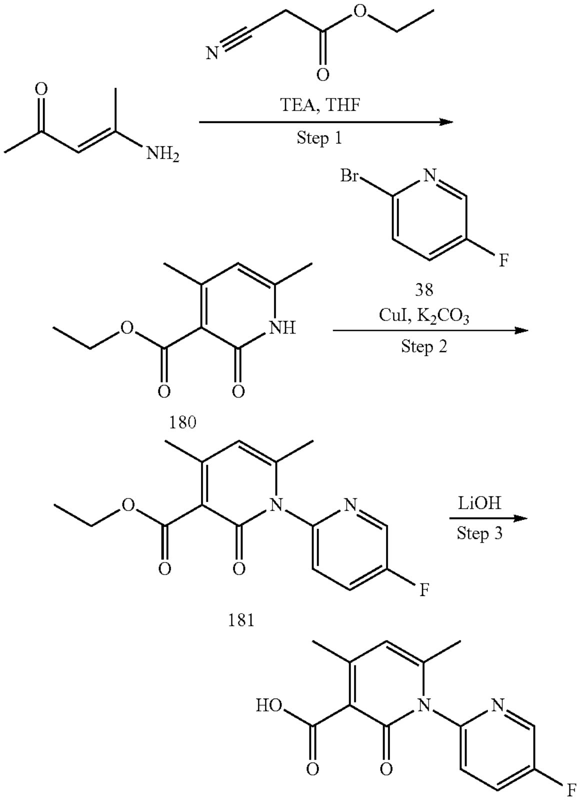

180

181

182

Step 1: Ethyl 4,6-dimethyl-2-oxo-1,2-dihydropyridine-3-carboxylate (180): A mixture of ethyl 2-cyanoacetate (1.71 g, 15.1 mmol) and TEA (1.53 g, 15.1 mmol) in THF (15 mL) at 25° C. was added dropwise to a solution of 4-aminopent-3-en-2-one (1.5 g, 15.1 mmol) in THF (15 mL). The mixture was stirred at 65° C. for 36 h. After cooling to room temperature, water (50 mL) and DCM (50 mL) were added. The phases were separated, and the aqueous phase further extracted with DCM (3×20 mL). The combined organic extracts were concentrated under reduced pressure and the residue was purified by column chromatography to give Compound 180 as a yellow solid (900 mg, 30.5%). 1H NMR (400 MHz, $CDCl_3$) δ 12.57 (br s, 1H), 5.94 (s, 1H), 4.39 (q, 2H), 2.31 (s, 3H), 2.24 (s, 3H), 1.38 (t, 3H).

Step 2: Ethyl 5'-fluoro-4,6-dimethyl-2-oxo-2H-[1,2'-bipyridine]-3-carboxylate (181): Compound 181 was made from Compound 180 in a similar manner to the way Compound 39 was made from Compound 37 in Step 1 of Example 10. $^1$H NMR: (400 MHz, $CDCl_3$) δ 8.48 (d, 1H), 7.65-7.55 (m, 1H), 7.38 (dd, 1H), 6.01 (s, 1H), 4.36 (q, 2H), 2.27 (s, 3H), 1.99 (s, 3H), 1.36 (t, 3H); MS for $C_{15}H_{15}FN_2O_3$: m/z 291.1 (MH+).

Step 3: 5'-Fluoro-4,6-dimethyl-2-oxo-2H-[1,2'-bipyridine]-3-carboxylic acid (182): Compound 182 was made from Compound 181 in a similar manner to the way Compound 40 was made from Compound 39 in Step 2 of Example 10. MS for $C_{13}H_{11}FN_2O_3$: m/z 262.1 (MH+).

Example 36: 4-(5-Fluoropyridin-2-yl)-5-methyl-3-oxo-3,4-dihydropyrazine-2-carboxylic Acid (189)

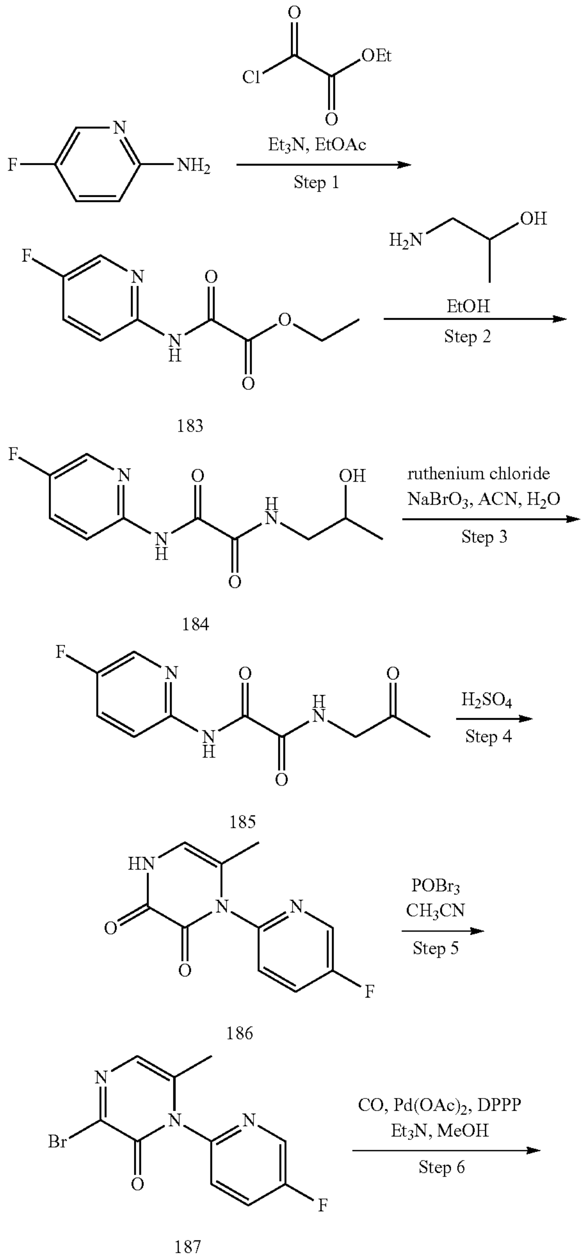

183

184

185

186

187

-continued

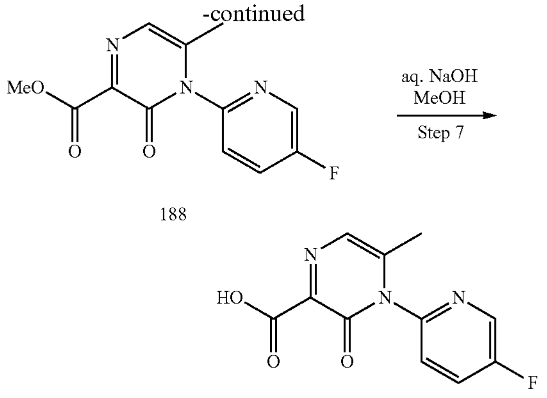

188

189

Step 1: Ethyl 2-((5-fluoropyridin-2-yl)amino)-2-oxoacetate (183): To a solution of 5-fluoropyridin-2-amine (3 g, 27 mmol) and $Et_3N$ (4.06 g, 40 mmol) in EtOAc (40 mL) was added ethyl 2-chloro-2-oxo-acetate (4.38 g, 32 mmol) at 0° C. The yellow suspension was stirred at room temperature for 15 h. The reaction mixture was quenched with water (100 mL) and extracted with EtOAc (3×50 mL). The combined organic extracts were dried over anhyd. $Na_2SO_4$ and concentrated under reduced pressure. The residue was purified by flash silica gel chromatography to give Compound 183 as a white solid (2.2 g, 39% yield). $^1H$ NMR: (400 MHz, $CDCl_3$) δ 9.41 (br s, 1H), 8.32-8.25 (m, 1H), 8.22 (d, 1H), 7.55-7.47 (m, 1H), 4.45 (q, 2H), 1.45 (t, 3H); MS for $C_9H_9FN_2O_3$: m/z 213 (MH+).

Step 2: N1-(5-Fluoropyridin-2-yl)-$N_2$-(2-hydroxypropyl) oxalamide (184): To a mixture of Compound 183 (0.6 g, 2.8 mmol) in EtOH (10 mL) was added 1-aminopropan-2-ol (234 mg, 3.1 mmol). The mixture was stirred at 80° C. for 1 h. The reaction mixture was concentrated under reduced pressure. To the resulting residue was added with EtOH (5 mL) and petroleum ether (100 mL). The mixture was stirred for 0.5 h and filtered. The filter cake was washed with petroleum ether (2×15 mL) and dried to give Compound 184 as a white solid (660 mg, 97% yield) which was used without further purification. $^1H$ NMR: (400 MHz, $CDCl_3$) δ 9.79 (br s, 1H), 8.27-8.21 (m, 2H), 7.97-7.80 (m, 1H), 7.54-7.44 (m, 1H), 4.10-3.97 (m, 1H), 3.63-3.53 (m, 1H), 3.33-3.23 (m 1H), 2.11 (br s, 1H), 1.27 (d, 3H); MS for $C_{10}H_{12}FN_3O_3$: m/z 242 (MH+).

Step 3: N1-(5-Fluoropyridin-2-yl)-$N_2$-(2-oxopropyl)oxalamide (185): To a mixture of Compound 184 (660 mg, 2.7 mmol) in ACN (10 ml) was added a solution of $RuCl_3$ (8.5 mg, 0.041 mmol) in water (1 mL) followed by a solution of sodium bromate (454 mg, 3.0 mmol) in water (2 mL). The resulting mixture was stirred at room temperature for 1 h. The reaction mixture was concentrated under reduced pressure. To the residue was added water (80 mL) and the resulting mixture stirred for 0.5 h. The resulting solid was filtered, and the filter cake was washed with water (2×20 mL) and dried under vacuum to give Compound 185 as an off-white solid (0.55 g, 84% yield) which was used without further purification.

Step 4: 1-(5-Fluoropyridin-2-yl)-6-methyl-1,4-dihydropyrazine-2,3-dione (186): To $H_2SO_4$ (3 mL) was added Compound 185 (0.3 g, 1.25 mmol) at 55° C. The resulting solution was stirred at 55° C. for 2 h. The reaction was slowly added to ice-water. The mixture was neutralized with aq 3 N LiOH to pH=6 and concentrated under reduced pressure. To the residue was added 10:1 DCM:MeOH (100 mL) and the resulting mixture stirred for 5 h. The mixture was filtered, and the filter cake was washed with DCM (50 mL). The filtrate was concentrated under reduced pressure. The resulting residue was purified by flash silica gel chromatography to give Compound 186 as a yellow solid (250 mg, 90% yield) as yellow solid. MS for $C_{10}H_8FN_3O_2$: m/z 221.9 (MH+).

Step 5: 3-Bromo-1-(5-fluoropyridin-2-yl)-6-methylpyrazin-2(1H)-one (187): To a mixture of Compound 186 (250 mg, 1.13 mmol) in ACN (3 mL) was added $POBr_3$ (356 mg, 1.2 mmol). The resulting suspension was stirred at 65° C. for 6 h. The reaction mixture was added to aq saturated $NaHCO_3$ (100 mL). The resulting mixture was stirred for 10 min and then extracted with EtOAc (3×50 mL). The combined organic extracts were dried over anhyd. $Na_2SO_4$ and concentrated under reduced pressure. The resulting residue was purified by flash silica gel chromatography to give Compound 187 as a white solid (150 mg, 47% yield). MS for $C_{10}H_7BrFN_3O$: m/z 285.9 (MH+).

Step 6: Methyl 4-(5-fluoropyridin-2-yl)-5-methyl-3-oxo-3,4-dihydropyrazine-2-carboxylate (188): To a mixture of Compound 187 (150 mg, 0.53 mmol) in MeOH (10 mL) was added DPPP (43.6 mg, 0.106 mmol), $Et_3N$ (107 mg, 1.1 mmol) and $Pd(OAc)_2$ (11.9 mg, 0.053 mmol). The mixture was stirred at 70° C. for 30 h under CO (50 PSI). The reaction mixture was concentrated under reduced pressure. The resulting residue was purified by flash chromatography over silica gel to give Compound 188 as a yellow solid (110 mg, 79% yield). MS for $C_{12}H_{10}FN_3O_3$: m/z 264 (MH+).

Step 7: 4-(5-Fluoropyridin-2-yl)-5-methyl-3-oxo-3,4-dihydropyrazine-2-carboxylic acid (189): To a solution of Compound 188 (110 mg, 0.42 mmol, 1 eq) in MeOH (2 mL) was added water (0.5 mL) and NaOH (50 mg, 1.25 mmol). The mixture was stirred at room temperature for 1 h. The reaction mixture was diluted with water (10 mL) and then concentrated under reduced pressure to remove MeOH. The resulting aqueous mixture was acidified with aq 1 N HCl to pH=2-3 and then extracted with EtOAc (3×30 mL) and DCM (3×30 mL). The combined organic extracts were dried over anhyd. $Na_2SO_4$ and concentrated under reduced pressure to Compound 189 as a yellow solid (100 mg, 96% yield) which was used without further purification.

Example 37: 4-(5-Fluoropyridin-2-yl)-3-oxo-3,4-dihydropyrazine-2-carboxylic acid (194)

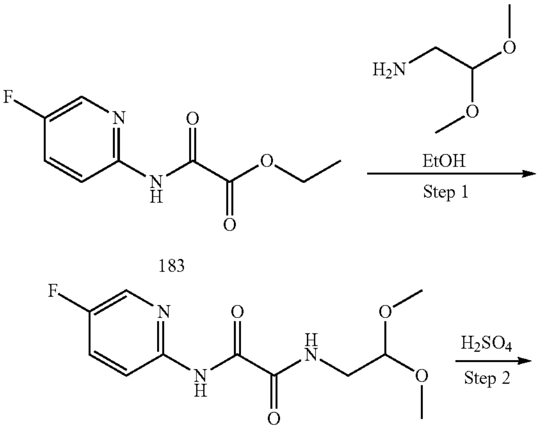

183

190

-continued

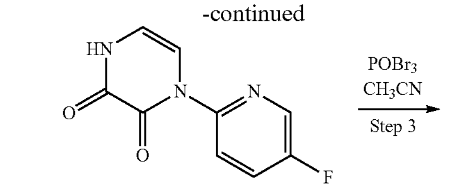

191

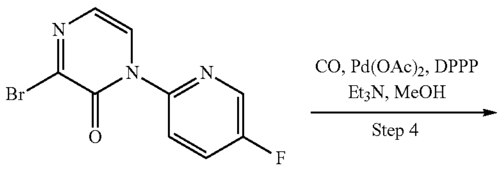

192

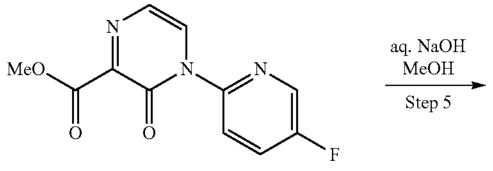

193

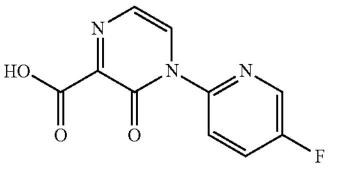

194

Step 1: N1-(2,2-Dimethoxyethyl)-N2-(5-fluoropyridin-2-yl)oxalamide (190): Compound 190 was synthesized from Compound 183 in a similar way to the method used to synthesize Compound 184 from Compound 183 in Step 2 of Example 36, replacing 1-amino-2-propanol with 2,2-dimethoxyethanamine. MS for $C_{11}H_{14}FN_3O_4$: m/z 271.8 (MH+).

Step 2: 1-(5-Fluoropyridin-2-yl)-1,4-dihydropyrazine-2,3-dione (191): Compound 191 was synthesized from Compound 190 in a similar way to the method used to synthesize Compound 186 from Compound 185 in Step 4 of Example 36 MS for $C_9H_6FN_3O_2$: m/z 207.9 (MH+).

Step 3: 3-Bromo-1-(5-fluoropyridin-2-yl)pyrazin-2(1H)-one (192): Compound 192 was synthesized from Compound 191 in a similar way to the method used to synthesize Compound 187 15 from Compound 186 in Step 5 of Example 36. $^1$H NMR: (400 MHz, DMSO-$d_6$) δ 8.66 (d, 1H), 8.07-8.00 (m, 1H), 7.99-7.95 (m, 1H), 7.94 (d, 1H), 7.30 (d, 1H); MS for $C_9H_5BrFN_3O$: m/z 271.8 (MH+).

Step 4: Methyl 4-(5-fluoropyridin-2-yl)-3-oxo-3,4-dihydropyrazine-2-carboxylate (193): Compound 193 was synthesized from Compound 192 in a similar way to the method used to synthesize Compound 188 from Compound 187 in Step 6 of Example 36. MS for $C_{11}H_8FN_3O_3$: m/z 249.9 (MH+).

Step 5: 4-(5-Fluoropyridin-2-yl)-3-oxo-3,4-dihydropyrazine-2-carboxylic acid (194): Compound 194 was synthesized from Compound 193 in a similar way to the method used to synthesize Compound 189 from Compound 188 in Step 7 of Example 36. MS for $C_{10}H_6FN_3O_3$: m/z 235.9 (MH+).

Example 38: N-[4-[(6,7-Dimethoxy-1,5-naphthyridin-4-yl)oxy]-3-fluorophenyl]-4-hydroxy-2-(methoxymethyl)-6-methyl-5-pyridin-2-ylpyridine-3-carboxamide (195)

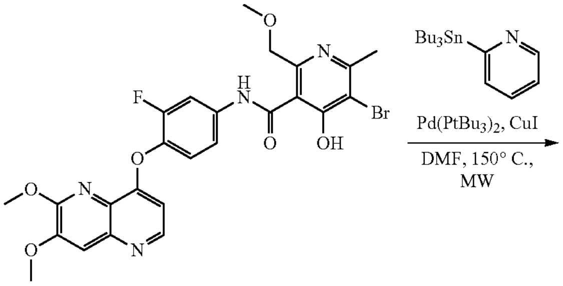

113

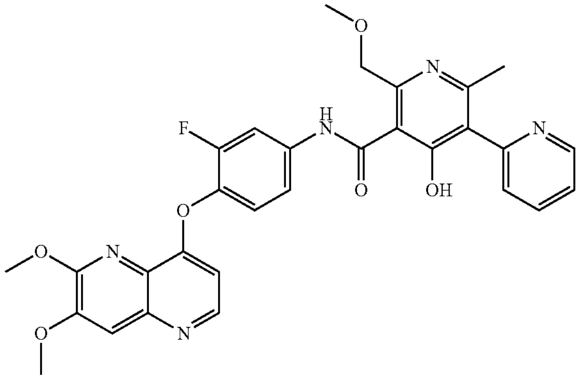

195

N-[4-[(6,7-Dimethoxy-1,5-naphthyridin-4-yl)oxy]-3-fluorophenyl]-4-hydroxy-2-(methoxymethyl)-6-methyl-5-pyridin-2-ylpyridine-3-carboxamide (195): To a 2 ml. microwave vial equipped with a magnetic stir bar was added Compound 113 (100 mg, 0.17 mmol, 1 eq), tributyl(2-pyridyl)stannane (150 mg, 0.41 mmol, 2.34 eq) and DMF (1.5 mL). The solution was degassed with Argon for 30 min, followed by the addition of $Pd(PtBu_3)_2$(20 mg, 0.04 mmol, 0.22 eq) and copper iodide (8 mg, 0.04 mmol, 0.24 eq). The reaction vial was sealed, and the resulting 10 heterogeneous mixture was heated to 150° C. for two h. The reaction mixture was filtered over Celite, concentrated, and purified by prep HPLC to yield a white solid (17.3 mg, 17% yield). $^1$H NMR (400 MHz, DMSO-$d_6$) δ 13.23 (s, 1H), 11.49 (s, 1H), 8.65 (d, 1H), 8.54 (dd, 1H), 8.02-7.93 (m, 1H), 7.86 (t, 1H), 7.65 (s, 1H), 7.44 (d, 1H), 7.40-7.25 (m, 3H), 6.81 (d, 1H), 5.05 (s, 2H), 3.97 (s, 3H), 3.95 (s, 3H), 3.50 (s, 3H), 2.24 (s, 3H); MS for $C_{30}H_{2\text{-}6}FN_5O_6$: m/z 572.2 (MH+).

The following compounds were made in the same manner as Compound 195 in Example 38:

N-[4-[(6,7-Dimethoxy-1,5-naphthyridin-4-yl)oxy]-3-fluorophenyl]-4-hydroxy-2-(methoxymethyl)-6-methyl-5-(3-methylpyridin-2-yl)pyridine-3-carboxamide (196): $^1$H NMR (400 MHz, $CD_3OD$) δ 8.53-8.45 (m, 2H), 7.95 (dd, 1H), 7.87-7.80 (m, 1H), 7.52 (s, 1H), 7.43 (dd, 1H), 7.32 (ddd, 1H), 7.25 (t, 1H), 6.82 (dd, 1H), 5.20 (d, 2H), 4.05 (s, 3H), 4.03 (s, 3H), 3.65 (s, 3H), 2.24 (s, 3H), 2.18 (s, 3H); MS for $C_{31}H_{28}FN_5O_6$: m/z 586.1 (MH+).

N-[4-[(6,7-Dimethoxy-1,5-naphthyridin-4-yl)oxy]-3-fluorophenyl]-4-hydroxy-2-(methoxymethyl)-6-methyl-5-(6-methylpyridin-2-yl)pyridine-3-carboxamide (197): $^1$H NMR (400 MHz, DMSO-$d_6$) δ 8.47 (d, 1H), 8.34 (s, 1H), 7.92 (dd, 1H), 7.64 (t, 1H), 7.58 (s, 1H), 7.32-7.17 (m, 2H), 7.11 (dd, 2H), 6.72 (d, 1H), 6.63 (s, 1H), 4.94 (s, 2H), 3.90 (s, 3H), 3.88 (s, 3H), 3.39 (s, 3H), 2.42 (s, 3H), 2.10 (s, 3H); MS for $C_{31}H_{28}FN_5O_6$: m/z 586.1 (MH+).

N-[4-[(6,7-Dimethoxy-1,5-naphthyridin-4-yl)oxy]-3-fluorophenyl]-4-hydroxy-2-(methoxymethyl)-6-methyl-5-(2-methylpyridin-4-yl)pyridine-3-carboxamide (198): $^1$H NMR (400 MHz, DMSO-$d_6$) δ 13.09 (s, 1H), 11.48 (s, 1H), 8.47 (d, 1H), 8.42 (d, 1H), 7.90 (dd, 1H), 7.58 (s, 1H), 7.34-7.27 (m, 1H), 7.23 (t, 1H), 7.08 (d, 1H), 7.01 (dd, 1H), 6.73 (d, 1H), 4.96 (s, 2H), 3.90 (s, 3H), 3.87 (s, 3H), 3.42 (s, 3H), 2.43 (s, 3H), 2.17 (s, 3H); MS for $C_{31}H_{28}FN_5O_6$: m/z 586.1 (MH+).

Example 39: N-[4-[(6,7-Dimethoxy-1,5-naphthyridin-4-yl)oxy]-3-fluorophenyl]-5-(5-fluoro-3-methylpyridin-2-yl)-4-hydroxy-2-methylpyridine-3-carboxamide (200)

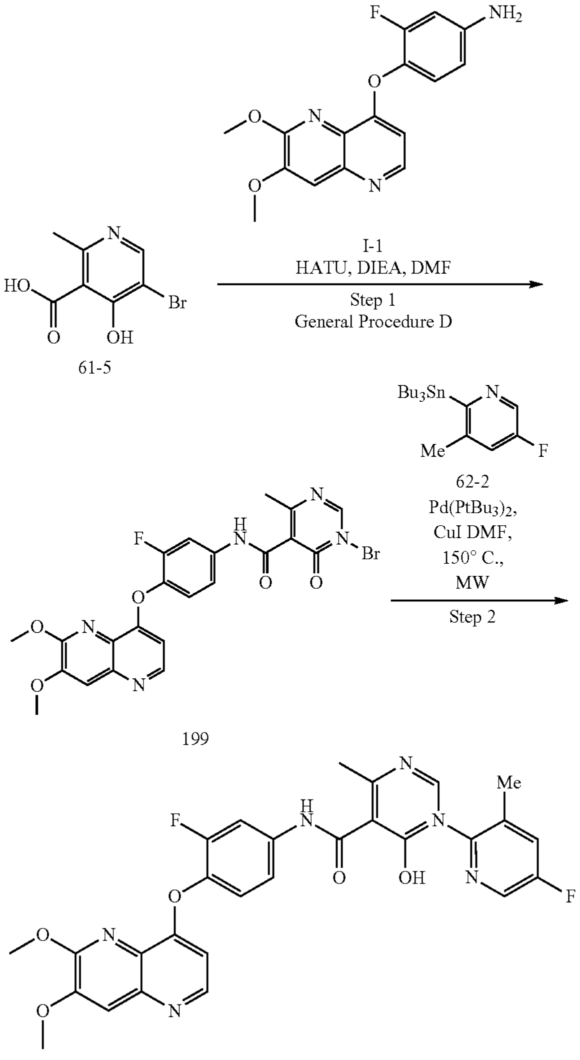

I-1

61-5

62-2

199

200

Step 1: 5-Bromo-N-(4-((6,7-dimethoxy-1,5-naphthyridin-4-yl)oxy)-3-fluorophenyl)-4-hydroxy-2-methylnicotinamide (199): Compound 199 was synthesized from Compound 61-5 and Intermediate I-1 using General Procedure D. $^1$H NMR (400 MHz, DMSO- $d_6$) δ 14.80 (s, 1H), 8.46 (d, 1H), 7.97 (d, 1H), 7.89 (s, 1H), 7.58 (s, 1H), 7.22 (d, 2H), 6.71 (d, 1H), 3.92 (s, 3H), 3.90 (s, 3H), 2.52 (s, 3H); MS for $C_{23}H_{18}BrFN_4O_5$: m/z 531.0 (MH+).

Step 2: N-[4-[(6,7-Dimethoxy-1,5-naphthyridin-4-yl)oxy]-3-fluorophenyl]-5-(5-fluoro-3-methylpyridin-2-yl)-4-hydroxy-2-methylpyridine-3-carboxamide (200): Compound 200 was made from Compound 199 and Compound 62-2 in the same manner that Compound 195 was made from Compound 113 and tributyl(2-pyridyl)stannane in Example 38. $^1$H NMR (400 MHz, DMSO-$d_6$) δ 13.35 (s, 1H), 8.46 (d, 1H), 8.35 (d, 1H), 7.94 (dd, 1H), 7.77 (s, 1H), 7.58 (q, 2H), 7.34-7.27 (m, 1H), 7.23 (t, 1H), 6.72 (dd, 1H), 3.90 (s, 6H), 2.64 (s, 3H), 2.16 (s, 3H); MS for $C_{29}H_{23}F_2N_5O_5$: m/z 560.2 (MH+).

Example 40: 2'-(2-(2-Ethoxyethoxy)ethoxy)-6-methyl-2-oxo-2H-[1,4'-bipyridine]-3-carboxylic acid (201)

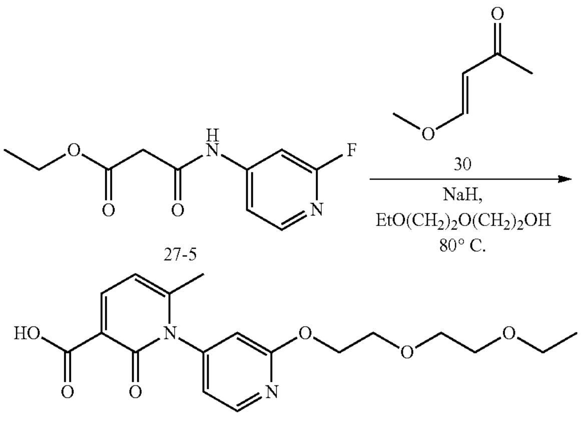

27-5

201

2'-(2-(2-Ethoxyethoxy)ethoxy)-6-methyl-2-oxo-2H-[1,4'-bipyridine]-3-carboxylic acid (201): Compound 201 was synthesized from Compound 27-5 using a method similar to that of Example 6. $^1$H NMR (400 MHz, DMSO-$d_6$) δ 13.99 (s, 1H), 8.50-8.32 (m, 2H), 7.15 (dd, 1H), 7.09 (dd, 1H), 6.81 (dd, 1H), 4.53-4.35 (m, 2H), 3.77 (t, 2H), 3.61-3.55 (m, 2H), 3.52-3.46 (m, 2H), 3.43 (q, 2H), 2.17-2.11 (m, 3H), 1.09 (t, 3H).

Example 41: 2'-Isopropoxy-6-methyl-2-oxo-2H-[1,4'-bipyridine]-3-carboxylic acid (202)

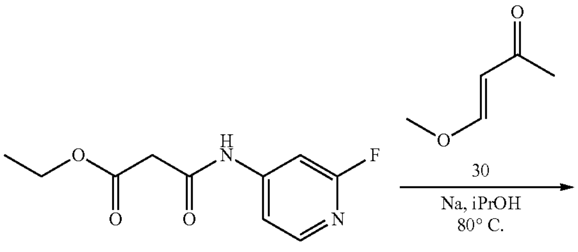

27-5

-continued

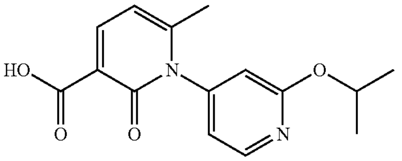

+

202

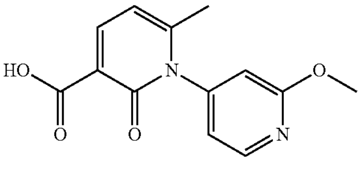

31-8

2'-Isopropoxy-6-methyl-2-oxo-2H-[1,4'-bipyridine]-3-carboxylic acid (202) and 2'-Methoxy-6-methyl-2-oxo-2H-[1,4'-bipyridine]-3-carboxylic acid (31-8): To a 100 mL round bottom flask equipped with a magnetic stir bar and a pressure relief septum was added isopropanol (10 mL), and the flask was cooled to 0° C. Sodium (200 mg, 8.7 mmol) was added in small portions until completely dissolved with vigorous stirring. Compound 27-5 (520 mg, 2.3 mmol, 1.0 eq) was added in a single portion, followed by Compound 30 (300 mg, 3.0 mmol, 1.3 eq). The resulting mixture was then heated to 80° C. for 3 h. After cooling to room temperature, the reaction mixture was acidified to pH=3 with aq 6 M HCl. The resulting suspension was filtered to yield a yellow solid, which was collected by vacuum filtration and purified by chromatography over silica gel to give Compound 202 and Compound 31-8 (72% yield total). Compound 202: $^1$H NMR (400 MHz, $CDCl_3$) δ 13.67 (s, 1H), 8.54 (dd, 1H), 8.42 (dt, 1H), 6.77 (dt, 1H), 6.68-6.40 (m, 2H), 5.43-5.28 (m, 1H), 2.23 (d, 3H), 1.42 (ddd, 6H); MS for $C_{15}H_{16}N_2O_4$: m/z 289.0 (MH+). Compound 31-8: $^1$H NMR (400 MHz, $CDCl_3$) δ 13.67 (s, 1H), 8.54 (d, 1H), 8.45 (dd, 1H), 6.80 (dd, 1H), 6.68 (dd, 1H), 6.57 (dd, 1H), 4.05 (s, 3H), 2.22 (s, 3H).

Example 42: 2-Oxo-2H-[1,4'-bipyridine]-3-carboxylic acid (204)

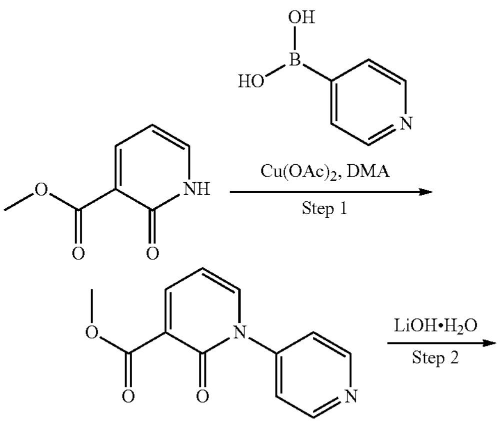

203

-continued

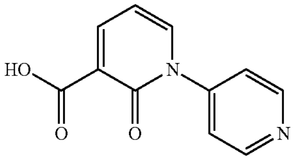

204

Step 1: Methyl 2-oxo-2H-[1,4'-bipyridine]-3-carboxylate (203): A mixture of methyl 2-oxo-1H-pyridine-3-carboxylate (1.00 g, 6.53 mmol), 4-pyridylboronic acid (2.41 g, 19.6 mmol) and $Cu(OAc)_2$ (3.56 g, 19.6 mmol) in DMA (10 ml) was stirred at 90° C. under an atmosphere of $O_2$ for 0.5 h, and then cooled to room temperature. Ammonium hydroxide (50 ml) was added and the resulting mixture was extracted with EtOAc (3×20 mL). The combined organic extracts were washed with water (20 mL), aq saturated NaCl (3×20 mL) and dried over anhyd. $Na_2SO_4$ and concentrated under reduced pressure. The resulting residue was purified by column chromatography to Compound 203 as a white solid (150 mg, 9.9% yield). $^1$H NMR (400 MHz, DMSO-$d_6$) δ 8.77-8.74 (m, 2H), 8.15 (dd, 1H), 8.00 (dd, 1H), 7.57-7.54 (m, 2H), 6.48 (t, 1H), 3.76 (s, 3H); MS for $C_{12}H_{10}N_2O_3$: m/z 231 (MH+).

Step 2: 2-Oxo-2H-[1,4'-bipyridine]-3-carboxylic acid (204): Compound 204 was synthesized from Compound 203 in the same manner Compound 40 was made from Compound 39 in Step 2 of Example 10. $^1$H NMR (400 MHz, DMSO-$d_6$) δ 13.94 (br s, 1H), 8.84-8.79 (m, 2H), 8.49 (dd, 1H), 8.23 (dd, 1H), 7.68-7.64 (m, 2H), 6.82 (t, 1H); MS for $C_{11}H_8N_2O_3$: m/z 216.8 (MH+).

The following compound was made in the same manner as Compound 204 in Example 42:

205

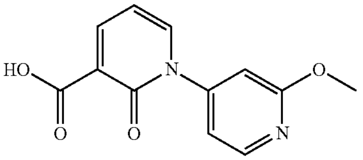

2'-Methoxy-2-oxo-2H-[1,4'-bipyridine]-3-carboxylic acid (205): In Step 1, the 4-pyridylboronic acid was replaced with (2-methoxypyridin-4-yl)boronic acid. MS for $C_{12}H_{10}N_2O_4$: m/z 246.9 (MH+).

Example 43: 3-Carboxy-6-methyl-2-oxo-2H-[1,4'-bipyridine]1'-oxide (206)

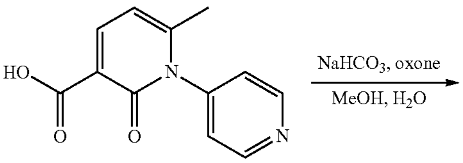

31-3

-continued

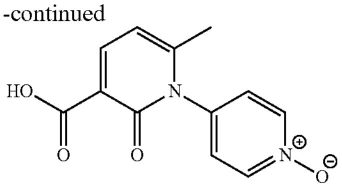

206

3-Carboxy-6-methyl-2-oxo-2H-[1,4'-bipyridine]1'-oxide (206): A mixture of Compound 31-3 (200 mg, 0.87 mmol) in MeOH (3 mL), $NaHCO_3$ (146 mg, 1.74 mmol), oxone (401 mg, 0.65 mmol) and water (3 mL) was stirred at 25° C. for 12 h. Aq $Na_2SO_3$ was added until starch potassium iodide paper tested negative. The mixture was concentrated and the pH adjusted to 1 with aq 2 M HCl. The mixture was extracted with 5:1 DCM:MeOH (2×15 mL). The combined organic extracts were dried over anhyd. $Na_2SO_4$ and concentrated under vacuum. The resulting residue was purified by prep-TLC to give Compound 206 as a white solid (94 mg, 44% yield). $^1H$ NMR: (400 MHz, DMSO-$d_6$) δ 13.98 (s, 1H), 8.54-8.44 (m, 3H), 7.70-7.63 (m, 2H), 6.86 (d, 1H), 2.24 (s, 3H); MS for $C_{12}H_{10}N_2O_4$: m/z 247 (MH+).

The following compound was made in the same manner as Compound 206 in Example 43:

207

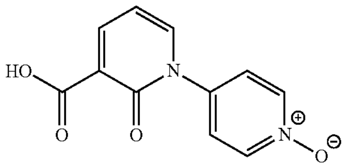

3-Carboxy-2-oxo-2H-[1,4'-bipyridine]1'-oxide (207): Compound 31-3 was replaced with Compound 204. $^1H$ NMR (400 MHz, DMSO-$d_6$) δ 13.91 (br s, 1H), 8.47 (dd, 1H), 8.44-8.37 (m, 2H), 8.22 (dd, 1H), 7.68 (d, 2H), 6.80 (t, 1H); MS for $C_{11}H_8N_2O_4$: m/z 232.9 (MH+).

Example 44: 2'-Hydroxy-6-methyl-2-oxo-2H-[1,4'-bipyridine]-3-carboxylic acid (208)

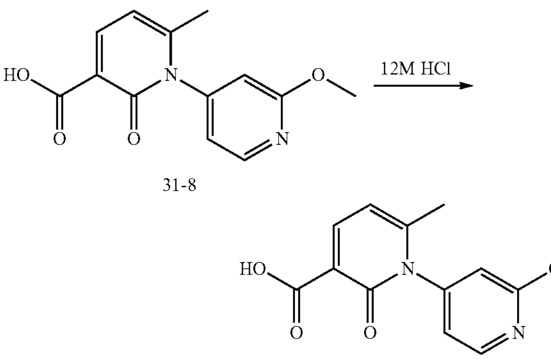

31-8

208

2'-Hydroxy-6-methyl-2-oxo-2H-[1,4'-bipyridine]-3-carboxylic acid (208): A mixture of Compound 31-8 (50 mg, 0.19 mmol) and HCl (12 M, 2.33 mL) was stirred at 110° C. for 4 h. The mixture was concentrated under vacuum to give Compound 208 as a yellow solid (47 mg, 99% yield). $^1H$ NMR: (400 MHz, DMSO-$d_6$) δ 7.88 (d, 1H), 7.69 (d, 1H), 6.20 (d, 1H), 5.77-5.71 (m, 1H), 5.71-5.63 (m, 1H), 2.06 (s, 3H); MS for $C_{12}H_{10}N_2O_4$: m/z 246.9 (MH+).

The following compound was made in the same manner as Compound 208 in Example 44:

209

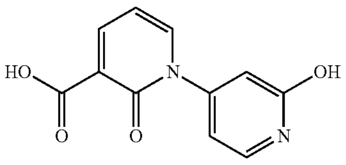

2'-Hydroxy-2-oxo-2H-[1,4'-bipyridine]-3-carboxylic acid (209): Compound 31-8 was replaced with Compound 205. $^1H$ NMR (400 MHz, DMSO-$d_6$) δ 8.45 (br, d, 1H), 8.17 (br, d, 1H), 7.57 (br, d, 1H), 6.77 (br, t, 1H), 6.55 (s, 1H), 6.40 (br, d, 1H); MS for $C_{11}H_8N_2O_4$: m/z 232.9 (MH+).

Example 45: 2'-Fluoro-6-methyl-2-oxo-2H-[1,4'-bipyridine]-3-carboxylic acid (211)

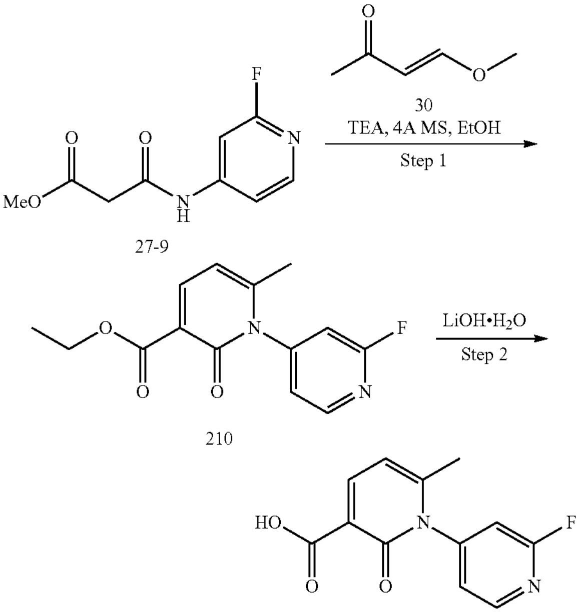

30

27-9

210

211

Step 1: Ethyl 2'-fluoro-6-methyl-2-oxo-2H-[1,4'-bipyridine]-3-carboxylate (210): To a 20 solution of Compound 30 (354 mg, 3.5 mmol) and Compound 27-9 (500 mg, 2.4 mmol) in EtOH (5 ml) was added TEA (954 mg, 9.4 mmol) and 4A molecular sieves (50 mg, 2.4 mmol) under $N_2$. The resulting mixture was stirred at 90° C. for 36 h. The mixture was filtered, and the filtrate was concentrated under vacuum. The resulting residue was purified by column chromatography to give Compound 210 as a yellow solid (200 mg, 31% yield). $^1H$ NMR: (400 MHz, DMSO-$d_6$) δ 8.46 (d, 1H), 8.10 (d, 1H), 7.45 (d, 1H), 7.43 (s, 1H), 6.43 (d, 1H), 4.20 (q, 2H), 2.02 (s, 3H), 1.25-1.22 (m, 3H); MS for $C_{14}H_{13}FN_2O_3$: m/z 276.9 (MH+).

Step 2: 2'-Fluoro-6-methyl-2-oxo-2H-[1,4'-bipyridine]-3-carboxylic acid (211): Compound 211 was synthesized from Compound 210 in the same manner Compound 40 was made from Compound 39 in Step 2 of Example 10. $^{1}$H NMR: (400 MHz, DMSO-$d_6$) δ 13.77 (br s, 1H), 8.53 (d, 1H), 8.43 (d, 1H), 7.59 (d, 1H), 7.55 (s, 1H), 6.81 (d, 1H), 2.14 (s, 3H); MS for $C_{12}H_9FN_2O_3$: m/z 249 (MH+).

Example 46: N-[4-[(6,7-Dimethoxy-1,5-naphthyridin-4-yl)oxy]-3-fluorophenyl]-1-(5-ethoxypyridin-2-yl)-6-methyl-2-oxopyridine-3-carboxamide (212)

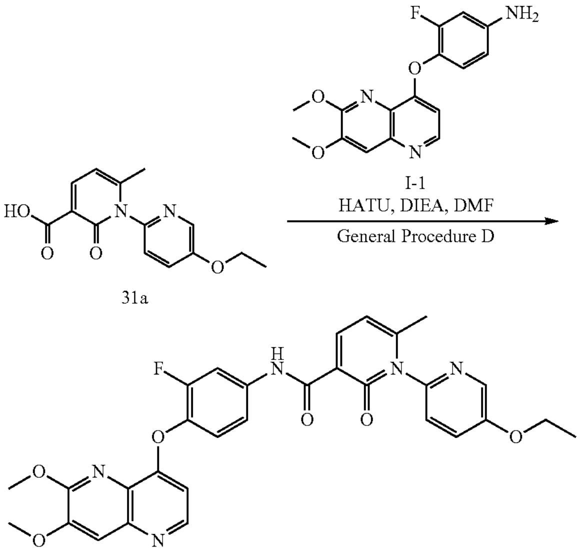

212

N-[4-[(6,7-Dimethoxy-1,5-naphthyridin-4-yl)oxy]-3-fluorophenyl]-1-(5-ethoxypyridin-2-yl)-6-methyl-2-oxopyridine-3-carboxamide (212): Compound 212 was synthesized from Compound 31a and Intermediate I-1 using General Procedure D. $^{1}$H NMR (400 MHz, DMSO-$d_6$) δ 11.97 (s, 1H), 8.63-8.41 (m, 2H), 8.35 (d, 1H), 8.00 (dt, 1H), 7.76-7.61 (m, 2H), 7.57 (dd, 1H), 7.44 (d, 1H), 7.35-7.21 (m, 1H), 6.82 (d, 1H), 6.70 (d, 1H), 4.33-4.13 (q, 2H), 3.97 (s, 3H), 3.93 (s, 3H), 2.06 (s, 3H), 1.40 (t, 3H); MS for $C_{30}H_{26}FN_5O_6$: m/z 572 (MH+).

The following compounds were also made using General Procedure D in the same fashion that Compound 212 was made from Compound 31a and Intermediate I-1 in Example 46:

1-(5-Ethoxypyridin-2-yl)-N-[3-fluoro-4-[(7-methoxy-1,5-naphthyridin-4-yl)oxy]phenyl]-6-methyl-2-oxopyridine-3-carboxamide (213): Intermediate I-1 was replaced with Intermediate I-3. $^{1}$H NMR (400 MHz, DMSO-$d_6$) δ 12.01 (s, 1H), 8.80-8.63 (m, 2H), 8.52 (dd, 1H), 8.35 (d, 1H), 8.04 (dt, 1H), 7.80 (dd, 1H), 7.68 (dd, 1H), 7.58 (dd, 1H), 7.50 (d, 1H), 7.43-7.31 (m, 1H), 6.72 (dd, 2H), 4.22 (q, 3H), 4.00 (s, 3H), 2.06 (s, 3H), 1.40 (t, 3H); MS for $C_{29}H_{24}FN_5O_5$: m/z 542 (MH+).

N-[4-[(6,7-Dimethoxy-1,5-naphthyridin-4-yl)oxy]-3-fluorophenyl]-5-(5-fluoropyridin-2-yl)-4-hydroxy-2-(methoxymethyl)-6-methylpyridine-3-carboxamid (214): Compound 31a was replaced with Compound 78-4. $^{1}$H NMR (400 MHz, DMSO-$d_6$) δ 13.28 (s, 1H), 8.57 (d, 1H), 8.47 (d, 1H), 7.91 (dd, 1H), 7.72 (td, 1H), 7.58 (s, 1H), 7.46

(dd, J=8.8, 4.6 Hz, 1H), 7.35-7.27 (m, 1H), 7.22 (t, 1H), 6.73 (d, 1H), 4.95 (s, 2H), 3.90 (s, 3H), 3.88 (s, 3H), 3.41 (s, 3H), 2.16 (s, 3H); MS for $C_{30}H_{25}F_2N_5O_6$: m/z 590.2 (MH+).

N-[4-[(6,7-Dimethoxy-1,5-naphthyridin-4-yl)oxy]-3-fluorophenyl]-5-(5-fluoropyridin-2-yl)-4-methoxy-6-methylpyridazine-3-carboxamide (215): Compound 31a was replaced with Compound 180. $^{1}$H NMR (400 MHz, DMSO-$d_6$) δ 12.49 (s, 1H), 8.65 (d, 1H), 8.48 (d, 2H), 7.92 (dd, 1H), 7.81 (td, 1H), 7.57 (d, 1H), 7.55-7.49 (m, 1H), 7.41 (d, 1H), 7.28 (t, 1H), 6.77 (d, 1H), 4.05 (s, 3H), 3.90 (s, 3H), 3.87 (s, 3H), 2.28 (s, 3H); MS for $C_{28}H_{22}F_2N_6O_5$: m/z 561.1 (MH+).

N-[4-[(6,7-Dimethoxy-1,5-naphthyridin-4-yl)oxy]phenyl]-5-(5-fluoropyridin-2-yl)-4-hydroxy-2,6-dimethylpyridine-3-carboxamide (216): Compound 31a was replaced with Compound 78-3 and Intermediate I-1 was replaced with Intermediate I-2. $^{1}$H NMR (400 MHz, DMSO-d6) δ 12.92 (s, 1H), 11.92 (s, 1H), 8.63 (s, 1H), 8.53 (d, 1H), 7.81-7.71 (m, 3H), 7.63 (s, 1H), 7.57-7.52 (m, 1H), 7.15 (d, 2H), 6.77 (d, 1H), 3.96 (d, 6H), 2.74 (s, 3H), 2.17 (s, 3H); MS for $C_{29}H_{24}FN_5O_5$: m/z 542 (MH+).

N-[3-Fluoro-4-[(7-methoxy-1,5-naphthyridin-4-yl)oxy]phenyl]-5-(5-fluoropyridin-2-yl)-4-hydroxy-2,6-dimethylpyridine-3-carboxamide (217): Compound 31a was replaced with Compound 78-3 and Intermediate I-1 was replaced with Intermediate I-3. $^{1}$H NMR (400 MHz, DMSO-$d_6$) δ 13.21 (s, 1H), 12.07 (s, 1H), 8.72 (dd, 2H), 8.63 (s, 1H), 8.03 (d, 1H), 7.79 (s, 2H), 7.53 (s, 1H), 7.42-7.34 (m, 2H), 6.73 (d, 1H), 4.00 (s, 3H), 2.74 (s, 3H), 2.16 (s, 3H); MS for $C_{25}H_{21}F_2N_5O_4$: m/z 530.2 (MH+).

N-[4-[(6,7-Dimethoxy-1,5-naphthyridin-4-yl)oxy]-3-fluorophenyl]-5-(5-fluoropyridin-2-yl)-4-hydroxy-2,6-dimethylpyridine-3-carboxamide (218): Compound 31a was replaced with Compound 78-4. $^{1}$H NMR (400 MHz, DMSO-$d_6$) δ 13.08 (s, 1H), 8.57 (d, 1H), 8.47 (d, 1H), 8.15 (s, 1H), 7.91 (d, 1H), 7.72 (td, 1H), 7.58 (s, 1H), 7.46 (dd, 1H), 7.30 (d, 1H), 7.22 (t, 1H), 6.72 (d, 1H), 3.89 (d, 6H), 2.67 (s, 3H), 2.10 (s, 3H); MS for $C_{29}H_{23}F_2N_5O_5$: m/z 560 (MH+).

N-[4-[(6,7-Dimethoxy-1,5-naphthyridin-4-yl)oxy]-3-fluorophenyl]-4-(5-fluoropyridin-2-yl)-5-methyl-3-oxopyrazine-2-carboxamide (219): Compound 31a was replaced with Compound 189. $^{1}$H NMR (400 MHz, $CDCl_3$) δ 11.60 (s, 1H), 8.61 (d, 1H), 8.53 (d, 1H), 7.95 (dd, 1H), 7.84 (s, 1H), 7.82-7.72 (m, 1H), 7.52 (s, 1H), 7.49-7.44 (m, 1H), 7.37 (d, 1H), 7.17 (t, 1H), 6.77 (d, 1H), 4.10 (s, 3H), 4.03 (s, 3H), 2.17 (s, 3H); MS for $C_{27}H_{20}F_2N_6O_5$: 547.1 (MH+).

N-[4-[(6,7-Dimethoxy-1,5-naphthyridin-4-yl)oxy]-3-fluorophenyl]-1-(3-fluoropyridin-4-yl)-6-methyl-2-oxopyridine-3-carboxamide (220): Compound 31a was replaced with Compound 31-2. $^{1}$H NMR (400 MHz, DMSO-$d_6$) δ 11.60 (s, 1H), 8.88 (s, 1H), 8.66 (d, 1H), 8.53-8.42 (m, 2H), 7.93 (dd, 1H), 7.75 (t, 1H), 7.58 (s, 1H), 7.41 (dd, 1H), 7.24 (t, 1H), 6.84-6.65 (m, 2H), 3.89 (s, 3H), 3.85 (s, 3H), 2.10 (s, 3H); MS for $C_{28}H_{21}F_2N_5O_5$: m/z 546.2 (MH+).

N-[4-[(6,7-Dimethoxy-1,5-naphthyridin-4-yl)oxy]-3-fluorophenyl]-6-methyl-2-oxo-1-pyridin-4-ylpyridine-3-carboxamid (221): Compound 31a was replaced with Compound 31-3. $^{1}$H NMR (400 MHz, DMSO-$d_6$) δ 11.82 (s, 1H), 8.78 (d, 2H), 8.46 (dd, 2H), 7.99-7.86 (m, 1H), 7.58 (s, 1H), 7.51 (d, 2H), 7.39 (d, 1H), 7.23 (t, 1H), 6.75 (d, 1H), 6.69 (d, 1H), 3.89 (s, 3H), 3.85 (s, 3H), 2.02 (s, 3H); MS for $C_{28}H_{22}FN_5O_5$: m/z 528.2 (MH+).

N-[4-[(6,7-Dimethoxy-1,5-naphthyridin-4-yl)oxy]-3-fluorophenyl]-6-methyl-2-oxo-1-pyridin-3-ylpyridine-3-carboxamide (222): Compound 31a was replaced with Compound 65.

$^1$H NMR (400 MHz, DMSO-$d_6$) δ 11.86 (s, 1H), 8.69-8.62 (m, 1H), 8.59 (d, 1H), 8.53-8.40 (m, 2H), 7.97-7.83 (m, 2H), 7.67-7.53 (m, 2H), 7.39 (d, 1H), 7.23 (t, 1H), 6.75 (d, 1H), 6.69 (d, 1H), 3.89 (d, 3H), 3.85 (d, 3H), 2.02 (s, 3H); MS for $C_{28}H_{22}FN_5O_5$: m/z 528.1 (MH+).

N-[3-Fluoro-4-[(6-methoxy-1,7-naphthyridin-4-yl)oxy]phenyl]-4-hydroxy-2-methyl-5-pyridin-2-ylpyridine-3-carboxamide (223): Compound 31a was replaced with Compound 65 and Intermediate I-1 was replaced with Compound 24. $^1$H NMR (400 MHz, DMSO-$d_6$) δ 12.41 (s, 2H), 9.19 (d, 1H), 8.67-8.61 (m, 2H), 8.56 (dt, 1H), 8.50 (s, 1H), 8.07 (dd, 1H), 7.85 (td, 1H), 7.56-7.45 (m, 2H), 7.44 (d, 1H), 7.34 (ddd, 1H), 6.78 (dd, 1H), 4.03 (s, 3H), 2.61 (s, 3H); MS for $C_{27}H_2OFN_5O_4$: m/z 498.0 (MH+).

N-[4-[(6,7-Dimethoxy-1,5-naphthyridin-4-yl)oxy]-3-fluorophenyl]-1-[2-[2-(2-ethoxyethoxy)ethoxy]pyridin-4-yl]-6-methyl-2-oxopyridine-3-carboxamide (224): Compound 31a was replaced with Compound 201. $^1$H NMR (400 MHz, DMSO- $d_6$) δ 11.87 (s, 1H), 8.48 (d, 1H), 8.43 (d, 1H), 8.32 (d, 1H), 7.94 (dd, 1H), 7.58 (s, 1H), 7.39 (ddd, 1H), 7.24 (t, 1H), 7.06 (dd, 1H), 7.00 (d, 1H), 6.75 (d, 1H), 6.67 (d, 1H), 4.39 (qt, 2H), 3.89 (s, 3H), 3.86 (s, 3H), 3.71 (t, 2H), 3.51 (dd, 2H), 3.42 (dd, 2H), 3.36 (q, 2H), 2.07 (s, 3H), 1.02 (t, 3H); MS for $C_{34}H_{34}FN_5O_8$: m/z 660.2 (MH+).

N-[4-[(6,7-Dimethoxy-1,5-naphthyridin-4-yl)oxy]-3-fluorophenyl]-6-methyl-2-oxo-1-(2-propan-2-yloxypyridin-4-yl)pyridine-3-carboxamide (225): Compound 31a was replaced with Compound 202. $^1$H NMR (400 MHz, DMSO-$d_6$) δ 11.86 (s, 1H), 8.48 (d, 1H), 8.43 (d, 1H), 8.31 (d, 1H), 7.94 (dd, 1H), 7.58 (s, 1H), 7.40 (dd, 1H), 7.24 (t, 1H), 7.01 (dd, 1H), 6.89 (d, 1H), 6.75 (d, 1H), 6.66 (d, 1H), 5.28-5.11 (m, 1H), 3.89 (s, 3H), 3.86 (s, 3H), 2.07 (s, 3H), 1.27 (t, 6H); MS for $C_{31}H_{28}FN_5O_6$: m/z 586.2 (MH+).

N-[4-[(6,7-Dimethoxy-1,5-naphthyridin-4-yl)oxy]-3-fluorophenyl]-1-(2-methoxypyridin-4-yl)-6-methyl-2-oxopyridine-3-carboxamide (226): Compound 31a was replaced with Compound 31-8. $^1$H NMR (400 MHz, DMSO- $d_6$) δ 11.86 (s, 1H), 8.48 (d, 1H), 8.43 (d, 1H), 8.34 (d, 1H), 7.94 (dd, 1H), 7.58 (s, 1H), 7.39 (dt, 1H), 7.24 (t, 1H), 7.06 (dd, 1H), 7.00 (d, 1H), 6.75 (d, 1H), 6.66 (d, 1H), 3.89 (s, 3H), 3.87 (s, 3H), 3.86 (s, 3H), 2.06 (s, 3H); MS for $C_{29}H_{24}FN_5O_6$: m/z 558.1 (MH+).

N-[4-[(6,7-Dimethoxy-1,5-naphthyridin-4-yl)oxy]-3-fluorophenyl]-1-(5-fluoro-6-methylpyridin-2-yl)-6-methyl-2-oxopyridine-3-carboxamide hydrochloride (227): Compound 31a was replaced with Compound 31-6. $^1$H NMR: (400 MHz, DMSO-$d_6$) δ 11.89 (s, 1H), 8.49-8.56 (m, 2H), 7.95-8.03 (m, 2H), 7.64 (s, 1H), 7.58 (m, 1H), 7.44 (br d, 1H), 7.27-7.33 (m, 1H), 6.82 (d, 1H), 6.71 (d, 1H), 3.94 (d, 6H), 3.43 (br s, 3H), 2.07 (s, 3H); MS for $C_{29}H_{23}F_2N_5O_5$: m/z 560.1 (MH+).

N-[4-[(6,7-Dimethoxy-1,5-naphthyridin-4-yl)oxy]-3-fluorophenyl]-4-hydroxy-2-methyl-5-pyridin-3-ylpyridine-3-carboxamide (228): Compound 31a was replaced with Compound 31-4. $^1$H NMR: (400 MHz, DMSO-$d_6$) δ 11.86 (s, 1H), 8.69-8.62 (m, 1H), 8.59 (d, 1H), 8.53-8.40 (m, 2H), 7.97-7.83 (m, 2H), 7.67-7.53 (m, 2H), 7.39 (d, 1H), 7.23 (t, 1H), 6.75 (d, 1H), 6.69 (d, 1H), 3.89 (d, 3H), 3.85 (d, 3H), 2.02 (s, 3H); MS for $C_{28}H_{22}FN_5O_5$: m/z 528.1 (MH+).

N-[4-[(6,7-Dimethoxy-1,5-naphthyridin-4-yl)oxy]-3-fluorophenyl]-2-oxo-1-pyridin-4-ylpyridine-3-carboxamide (229): Compound 31a was replaced with Compound 204. $^1$H NMR (400 MHz, DMSO-$d_6$) δ 11.92 (s, 1H), 8.83-8.80 (m, 2H), 8.60 (dd, 1H), 8.55 (d, 1H), 8.17 (dd, 1H), 8.01 (dd, 1H), 7.68-7.65 (m, 2H), 7.65 (s, 1H), 7.47 (dd, 1H), 7.32 (t, 1H), 6.84 (d, 1H), 6.78 (t, 1H), 3.96 (s, 3H), 3.92 (s, 3H); MS for $C_{27}H_{02}FN_5O_5$: m/z 514.1 (MH+).

N-[4-[(6,7-Dimethoxy-1,5-naphthyridin-4-yl)oxy]-3-fluorophenyl]-6-methyl-1-(2-methylpyridin-4-yl)-2-oxopyridine-3-carboxamide (230): Compound 31a was replaced with Compound 31-7. $^1$H NMR (400 MHz, DMSO-$d_6$) δ 11.91 (s, 1H), 8.69 (d, 1H), 8.54 (d, 1H), 8.51 (d, 1H), 8.00 (dd, 1H), 7.64 (s, 1H), 7.45 (br d, 1H), 7.41 (s, 1H), 7.35 (dd, 1H), 7.30 (t, 1H), 6.82 (d, 1H), 6.74 (d, 1H), 3.96 (s, 3H), 3.92 (s, 3H), 2.57 (s, 3H), 2.10 (s, 3H); MS for $C_{29}H_{24}FN_5O_5$: m/z 542.1 (MH+).

N-[4-[(6,7-Dimethoxy-1,5-naphthyridin-4-yl)oxy]-3-fluorophenyl]-6-methyl-1-(1-oxidopyridin-1-ium-4-yl)-2-oxopyridine-3-carboxamide (231): Compound 31a was replaced with Compound 206. $^1$H NMR: (400 MHz, $CD_3OD$) δ 8.78-8.69 (m, 3H), 8.63 (d, 1H), 8.13-8.06 (m, 1H), 7.82 (d, 2H), 7.64 (s, 1H), 7.51-7.42 (m, 2H), 7.23 (dd, 1H), 6.76 (d, 1H), 4.18 (d, 6H), 2.28 (s, 3H); MS for $C_{28}H_{22}FN_5O_6$: m/z 544 (MH+).

N-[4-[(6,7-Dimethoxy-1,5-naphthyridin-4-yl)oxy]-3-fluorophenyl]-1-(2-hydroxypyridin-4-yl)-6-methyl-2-oxopyridine-3-carboxamide (232): Compound 31a was replaced with Compound 208. $^1$H NMR: (400 MHz, $CDCl_3$) δ 11.62 (s, 1H), 8.57 (d, 1H), 8.45 (d, 1H), 7.84 (s, 1H), 7.51 (d, 1H), 7.44 (s, 1H), 7.25 (s, 1H), 7.09 (s, 1H), 6.67 (d, 1H), 6.50-6.44 (m, 2H), 6.14 (dd, 1H), 4.03 (s, 3H), 3.95 (s, 3H), 2.24 (s, 3H); MS for $C_{28}H_{22}FN_5O_6$: m/z 544.1 (MH+).

N-[4-[(6,7-Dimethoxy-1,5-naphthyridin-4-yl)oxy]-3-fluorophenyl]-1-(2-fluoropyridin-4-yl)-6-methyl-2-oxopyridine-3-carboxamide (233): Compound 31a was replaced with Compound 211. $^1$H NMR: (400 MHz, DMSO-$d_6$) δ 11.81 (s, 1H), 8.55-8.51 (m, 3H), 8.00 (dd, 1H), 7.64 (s, 1H), 7.59 (br d, 1H), 7.56 (s, 1H), 7.46 (br d, 1H), 7.30 (t, 1H), 6.82 (d, 1H), 6.76 (d, 1H), 3.96 (s, 3H), 3.92 (s, 3H), 2.13 (s, 3H); MS for $C_{28}H_{21}F_2N_5O_5$: m/z 546.2 (MH+).

N-[4-[(6,7-Dimethoxy-1,5-naphthyridin-4-yl)oxy]-3-fluorophenyl]-6-methyl-2-oxo-1-pyridazin-3-ylpyridine-3-carboxamide (234): Compound 31a was replaced with Compound 31-10. $^1$H NMR: (400 MHz, $CDCl_3$) δ 11.61 (s, 1H), 9.41 (br d, 1H), 8.70 (d, 1H), 8.52 (d, 1H), 7.91 (br d, 1H), 7.83 (m, 1H), 7.69 (br d, 1H), 7.53 (s, 1H), 7.31 (br d, 1H), 7.16 (br m, 1H), 6.74 (d, 1H), 6.58 (br d, 1H), 4.11 (s, 3H), 4.03 (s, 3H), 2.17 (s, 3H); MS for $C_{27}H_{21}FN_6O_8$: m/z 529.1 (MH+).

5-Acetyl-N-[4-[(6,7-dimethoxy-1,5-naphthyridin-4-yl)oxy]-3-fluorophenyl]-1-(furan-3-yl)-6-methyl-2-oxopyridine-3-carboxamide (235): Compound 31a was replaced with Compound 6b-3. $^1$H NMR (400 MHz, DMSO-$d_6$) δ 11.61 (s, 1H), 8.83 (s, 1H), 8.49 (d, 1H), 7.96 (m, 2H), 7.86 (t, 1H), 7.58 (s, 1H), 7.48-7.41 (m, 1H), 7.27 (t, 1H), 6.78 (d, 1H), 6.64 (d, 1H), 3.88 (d, 6H), 2.55 (s, 3H), 2.42 (d, 3H): MS for $C_{29}H_{23}FN_4O_7$: m/z 559 (MH+). [0459]5-Acetyl-N-[4-[(6,7-dimethoxy-1,5-naphthyridin-4-yl)oxy]-3-fluorophenyl]-1-(furan-2-yl)-6-methyl-2-oxopyridine-3-carboxamide (236): Compound 31a was replaced with Compound 6b-4. $^1$H NMR (400 MHz, DMSO-$d_6$) δ 11.31 (s, 1H), 8.83 (s, 1H), 8.49 (d, 1H), 7.95 (dd, 1H), 7.81 (dd, 1H), 7.58 (s, 1H), 7.46 (dd, 1H), 7.27 (t, 1H), 6.78 (d, 1H), 6.71-6.62 (m, 2H), 3.88 (d, 6H), 2.54 (s, 3H), 2.30 (s, 3H): MS for $C_{29}H_{23}FN_4O_7$: m/z 559 (MH+).

5-Acetyl-N-[4-[(6,7-dimethoxy-1,5-naphthyridin-4-yl)oxy]phenyl]-1-(furan-2-yl)-6-methyl-2-oxopyridine-3-carboxamide (237): Intermediate I-1 was replaced with Intermediate I-2 30 and Compound 31a was replaced with Compound 6b-4. $^1$H NMR (400 MHz, DMSO-$d_6$) δ 11.38 (s, 1H), 8.99 (s, 1H), 8.64 (d, 1H), 7.97 (d, 1H), 7.94-7.86 (m, 2H), 7.73 (s, 1H), 7.33-7.25 (m, 2H), 6.92 (d, 1H), 6.87-6.78 (m, 2H), 4.03 (d, 6H), 2.70 (s, 3H), 2.45 (s, 3H): MS for $C_{29}H_{24}N_4O_7$: m/z 541 (MH+).

5-Acetyl-N-[3-fluoro-4-[(7-methoxy-1,5-naphthyridin-4-yl)oxy]phenyl]-1-(furan-2-yl)-6-methyl-2-oxopyridine-3-carboxamide (238): Intermediate I-1 was replaced with Intermediate I-3 and Compound 31a was replaced with Compound 6b-4. $^1$H NMR (400 MHz, DMSO-$d_6$) δ 11.35 (s, 1H), 8.84 (s, 1H), 8.71-8.61 (m, 2H), 7.99 (dd, 1H), 7.82 (t, 1H), 7.73 (d, 1H), 7.56-7.48 (m, 1H), 7.36 (t, 1H), 6.72-6.63 (m, 3H), 3.94 (s, 3H), 2.55 (s, 3H), 2.30 (s, 3H): MS for $C_{28}H_{21}FN_4O_6$: m/z 529 (MH+).

5-Acetyl-N-[4-[(6,7-dimethoxy-1,5-naphthyridin-4-yl)oxy]phenyl]-1-(furan-3-yl)-6-methyl-2-oxopyridine-3-carboxamide (239): Intermediate I-1 was replaced with Intermediate I-2 and Compound 31a was replaced with Compound 6b-3. $^1$H NMR (400 MHz, DMSO-$d_6$) 11.17 (s, 1H), 8.83 (s, 1H), 8.61 (d, 1H), 8.10 (d, 1H), 7.62 (s, 1H), 7.52 (t, 1H), 7.38 (d, 2H), 7.25 (d, 2H), 7.03 (d, 1H), 6.64 (d, 1H), 3.91 (s, 3H), 3.79 (s, 3H), 2.55 (s, 3H), 2.29 (s, 3H): MS for $C_{29}H_{24}N_4O_7$: m/z 541 (MH+).

5-Acetyl-N-[3-fluoro-4-[(7-methoxy-1,5-naphthyridin-4-yl)oxy]phenyl]-1-(furan-3-yl)-6-methyl-2-oxopyridine-3-carboxamide (240): Intermediate I-1 was replaced with Intermediate I-3 and Compound 31a was replaced with Compound 6b-3. $^1$H NMR (400 MHz, DMSO-$d_6$) δ 11.66 (s, 1H), 8.85 (s, 1H), 8.68 (d, 1H), 8.65 (d, 1H), 8.01 (dd, 1H), 7.96 (dd, 1H), 7.87 (t, 1H), 7.74 (d, 1H), 7.51 (d, 1H), 7.36 (t, 1H), 6.71-6.67 (m, 1H), 6.66 (dd, 1H), 3.94 (s, 3H), 2.55 (s, 3H), 2.41 (s, 3H): MS for $C_{29}H_{24}N_4O_7$: m/z 529 (MH+).

5-acetyl-N-[4-[(6,7-dimethoxy-1,5-naphthyridin-4-yl)oxy]-3-fluorophenyl]-6-methyl-2-oxo-1-thiophen-3-ylpyridine-3-carboxamide (241): Compound 31a was replaced with Compound 6b-5. MS for $C_{29}H_{23}FN_4O_6S$: m/z 575 (MH+).

5-acetyl-N-[4-[(6,7-dimethoxy-1,5-naphthyridin-4-yl)oxy]phenyl]-6-methyl-2-oxo-1-thiophen-3-ylpyridine-3-carboxamide (242): Intermediate I-1 was replaced with Intermediate I-2 and Compound 31a was replaced with Compound 6b-5. MS for $C_{29}H_{24}N_4O_6S$: m/z 557 (MH+).

Example 47: N-[4-[(6,7-dimethoxy-1,5-naphthyridin-4-yl)oxy]-3-fluorophenyl]-4-ethoxy-1-(5-fluoropyridin-2-yl)-2-oxopyridine-3-carboxamide (243)

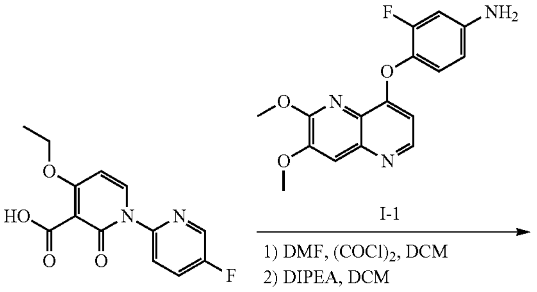

174

-continued

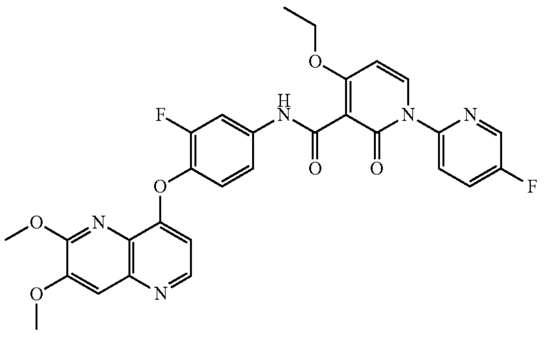

243

DMF (0.01 mL, 0.13 mmol, 0.48 eq) was added to a stirring suspension of oxalyl dichloride (0.06 mL, 0.7 mmol, 3 eq) and Compound 174 (75 mg, 0.27 mmol, 1 eq) in DCM (2 mL) at 0° C. The ice bath was removed, and the solution was stirred for another 30 minutes, then concentrated to dryness. Intermediate I-1 (85 mg, 0.27 mmol, 1 eq) was added and the resulting mixture was suspended in DCM (2 ml) and cooled to 0° C. DIEA (0.4 mL, 2 mmol, 9 eq) was added and the resulting mixture stirred overnight while the mixture was allowed to warm to room temperature. The reaction mixture was concentrated, and the resulting residue was purified by prep HPLC (0.1% formic acid in water and acetonitrile) to give Compound 243 as a white solid (36 mg, 23.2%). $^1$H NMR (400 MHz, DMSO-$d_6$) δ 10.53 (s, 1H), 8.63 (d, 1H), 8.53 (d, 1H), 8.05 (d, 1H), 7.98 (m, 1H), 7.91 (m, 1H), 7.85 (m, 1H), 7.65 (s, 1H), 7.46 (m, 1H), 7.34 (t, 1H), 6.79 (d, 1H), 6.60 (d, 1H), 4.29 (q, 2H), 3.98 (s, 6H), 1.32 (t, 3H); MS for $C_{29}H_{23}F_2N_5O_6$: m/z 576 (MH+).

The following compound was made using the same method used to make Compound 243 from Compound 174 in Example 47:

N-[4-[(6,7-Dimethoxy-1,5-naphthyridin-4-yl)oxy]phenyl]-4-ethoxy-1-(5-fluoropyridin-2-yl)-2-oxopyridine-3-carboxamide (244): Intermediate I-1 was replaced with Intermediate I-2. $^1$H NMR (400 MHz, DMSO-$d_6$) δ 10.33 (s, 1H), 8.63 (d, 1H), 8.51 (d, 1H), 8.02 (d, 1H), 7.96 (m, 1H), 7.85 (m, 1H), 7.78 (m, 2H), 7.63 (s, 1H), 7.18 (m, 2H), 6.74 (d, 1H), 6.59 (d, 1H), 4.28 (q, 2H), 3.97 (s, 6H), 1.31 (t, 3H); MS for $C_{29}H_2FN_5O_6$: m/z 558 (MH+).

N-[4-[(6,7-Dimethoxy-1,5-naphthyridin-4-yl)oxy]phenyl]-1-(5-fluoropyridin-2-yl)-4,6-dimethyl-2-oxopyridine-3-carboxamide (245): Compound 174 was replaced with Compound 182 and Intermediate I-1 was replaced with Intermediate I-2. $^1$H NMR (400 MHz, $CD_3OD$) δ 8.68 (d, 1H), 8.61 (d, 1H), 7.95-7.90 (m, 1H), 7.90-7.86 (m, 2H), 7.63-7.56 (m, 2H), 7.35-7.28 (m, 2H), 7.11 (d, 1H), 6.46 (s, 1H), 4.20 (s, 3H), 4.15 (s, 3H), 2.54 (s, 3H), 2.08 (s, 3H); MS for $C_{29}H_2FN_5O_5$: m/z 542.2 (MH+).

Example 48: N-[4-[(6,7Dimethoxy-1,5-naphthyridin-4-yl)oxy]-3-fluorophenyl]-4-(5-fluoropyridin-2-yl)-3-oxopyrazine-2-carboxamide (246)

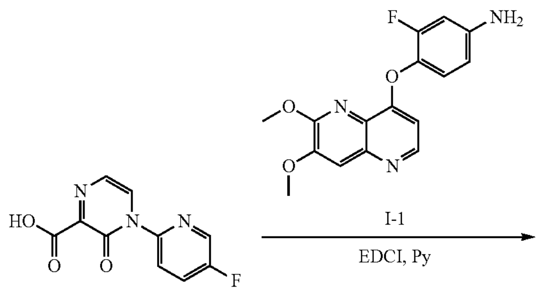

194

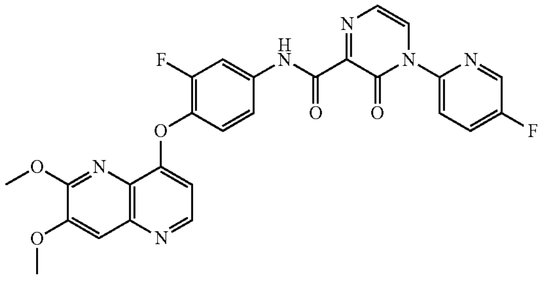

246

EDCI (96.0 mg, 0.50 mmol) was added to a solution of Compound 194 (40 mg, 170 μmol) and Intermediate I-1 (56 mg, 178 μmol) in pyridine (1 mL). The mixture was stirred at 20-30° C. for 4 h. The mixture was concentrated under vacuum and the resulting residue was purified by column chromatography on silica gel to give Compound 246 as a yellow solid (61 mg, 67% yield). $^1$H NMR: (400 MHz, DMSO-$d_6$) δ 11.12 (s, 1H), 8.72 (d, 1H), 8.55 (d, 1H), 8.13 (d, 1H), 8.10-8.00 (m, 2H), 7.94 (dd, 1H), 7.69-7.61 (m, 2H), 7.51 (br d, 1H), 7.42-7.31 (m, 1H), 6.84 (d, 1H), 3.97 (s, 3H), 3.95 (s, 3H); MS for $C_{26}H_{18}F_2N_6O_5$: m/z 533.1 (MH+).

Example 49: N-[4-[(6,7-Dimethoxy-1,5-naphthyridin-4-yl)oxy]-3-fluorophenyl]-1-(1-oxidopyridin-1-ium-4-yl)-2-oxopyridine-3-carboxamide hydrochloride (247)

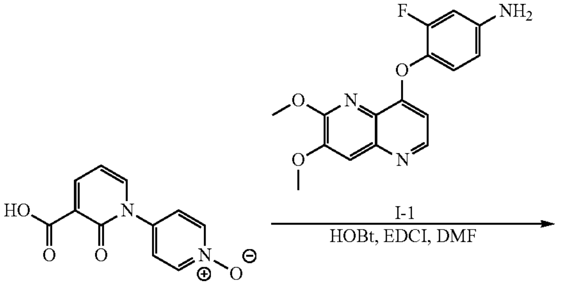

207

-continued

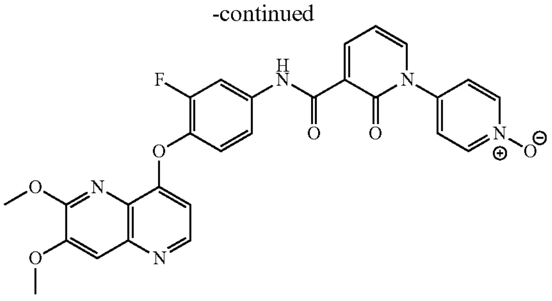

247

To a solution of Compound 207 (50 mg, 0.215 mmol) and Intermediate I-1 (56.6 mg, 0.18 mmol) in DMF (0.5 ml) was added HOBt (36.4 mg, 0.27 mmol) and EDCI (51.6 mg, 0.27 mmol). The resulting solution was stirred at 25° C. for 20 h. The mixture was filtered, and the filtrate was purified by prep-HPLC to give Compound 247 as a brown solid (16.2 mg, 16% yield). $^1$H NMR: (400 MHz, DMSO-$d_6$) δ 11.97 (s, 1H), 8.83 (d, 1H), 8.58 (dd, 1H), 8.45 (d, 2H), 8.17 (dd, 1H), 8.11 (dd, 1H), 7.86 (s, 1H), 7.71 (d, 2H), 7.61-7.55 (m, 1H), 7.55-7.49 (m, 1H), 7.20 (d, 1H), 6.78 (t, 1H), 4.05 (s, 6H); MS for $C_{27}H_{20}FN_5O_6$: m/z 530.2 (MH+).

The following compound was made using the same method used to make Compound 247 from Compound 207 in Example 49:

N-[4-[(6,7-Dimethoxy-1,5-naphthyridin-4-yl)oxy]-3-fluorophenyl]-1-(2-hydroxypyridin-4-yl)-2-oxopyridine-3-carboxamide hydrochloride (248): Compound 207 was replaced with Compound 209. $^1$H NMR (400 MHz, DMSO-$d_6$) δ 12.01 (s, 1H), 8.83 (d, 1H), 8.56 (dd, 1H), 8.15-8.08 (m, 2H), 7.85 (s, 1H), 7.58 (d, 2H), 7.54-7.49 (m, 1H), 7.19 (d, 1H), 6.74 (t, 1H), 6.56 (d, 1H), 6.42 (dd, 1H), 4.05 (s, 6H); MS for $C_{27}H_{20}FN_5O_6$: m/z 530.1 (MH+).

Example 50: 5-Bromo-N-(3-fluoro-4-((6-methoxy-7-(2-methoxyethoxy)-1,5-naphthyridin-4-yl)oxy)phenyl)-1,2,6-trimethyl-4-oxo-1,4-dihydropyridine-3-carboxamide (249)

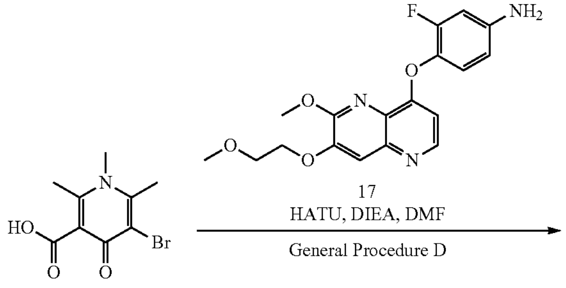

158

-continued

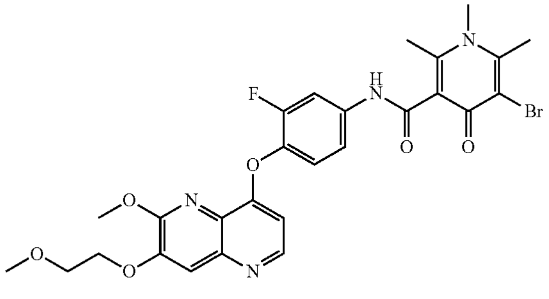

249

Compound 249 was made using General Procedure D. $^1$H NMR (400 MHz, DMSO-$d_6$) δ 10.79 (s, 1H), 8.53 (d, 1H), 7.95 (dd, 1H), 7.68 (s, 1H), 7.60-7.43 (m, 1H), 7.37 (t, 1H), 6.78 (dd, 1H), 4.38-4.25 (m, 2H), 4.00 (s, 3H), 3.86-3.74 (m, 2H), 3.67 (s, 3H), 2.70 (s, 3H), 2.42 (s, 3H); MS for $C_{27}H_{26}BrFN_4O_6$: m/z 601 (MH+).

The following compounds were made using the same method used to make Compound 249 from Compound 158 in Example 50:

250

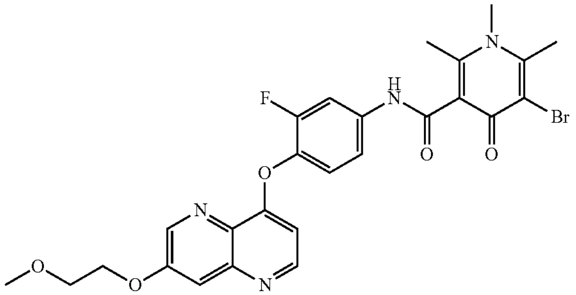

251

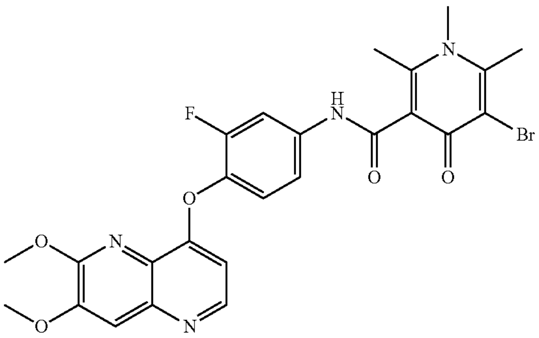

-continued

252

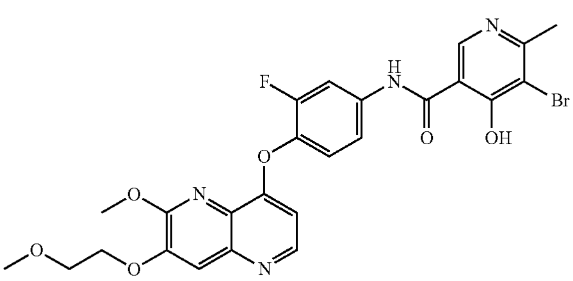

253

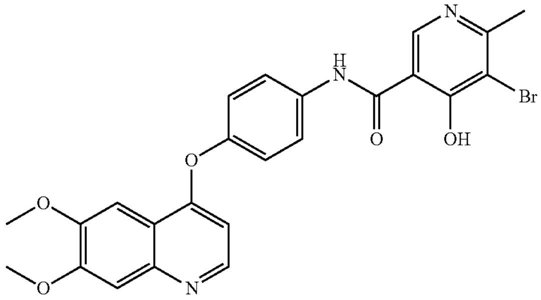

5-Bromo-N-(3-fluoro-4-((7-(2-methoxyethoxy)-1,5-naphthyridin-4-yl)oxy)phenyl)-1,2,6-trimethyl-4-oxo-1,4-dihydropyridine-3-carboxamide (250): $^1$H NMR (400 MHz, DMSO-$d_6$) δ 10.74 (s, 1H), 8.69 (d, 1H), 8.62 (d, 1H), 7.90 (dd, 1H), 7.76 (d, 1H), 7.44 (ddd, 1H), 7.36 (t, 1H), 6.68 (dd, 1H), 4.36-4.23 (m, 2H), 3.76-3.63 (m, 2H), 3.59 (s, 3H), 3.28 (s, 3H), 2.62 (s, 3H), 2.35 (s, 3H); MS for $C_{26}H_{24}BrFN_4O_5$: m/z 573 (MH+).

5-Bromo-N-(4-((6,7-dimethoxy-1,5-naphthyridin-4-yl)oxy)-3-fluorophenyl)-1,2,6-trimethyl-4-oxo-1,4-dihydropyridine-3-carboxamide (251): $^1$H NMR (400 MHz, DMSO-$d_6$) δ 10.82 (s, 1H), 8.64 (dd, 1H), 7.98 (dd, 1H), 7.68 (s, 1H), 7.51 (dd, 1H), 7.42 (t, 1H), 6.93 (d, 1H), 4.02 (d, 6H), 3.67 (s, 3H), 2.70 (s, 3H), 2.43 (s, 3H); MS for $C_{25}H_{22}BrFN_4O_5$: m/z 559 (MH+).

5-Bromo-N-(3-fluoro-4-((6-methoxy-7-(2-methoxyethoxy)-1,5-naphthyridin-4-yl)oxy)phenyl)-4-hydroxy-6-methylnicotinamide (252): $^1$H NMR (400 MHz, DMSO-$d_6$) δ 13.02 (d, 1H), 12.83 (s, 1H), 8.62 (d, 1H), 8.54 (d, 1H), 8.05 (dd, 1H), 7.70 (s, 1H), 7.50 (dd, 1H), 7.41 (t, 1H), 6.93 (d, 1H), 4.35 (t, 2H), 3.99 (s, 3H), 3.77 (t, 2H), 3.35 (s, 3H), 2.4 (s, 3H).

5-Bromo-N-(4-((6,7-dimethoxyquinolin-4-yl)oxy)phenyl)-4-hydroxy-6-methylnicotinamide (253): $^1$H NMR (400 MHz, DMSO-$d_6$) δ 13.79 (s, 1H), 8.49 (d, 2H), 8.13-8.03 (m, 1H), 7.55 (s, 1H), 7.47-7.32 (m, 4H), 6.50 (dd, 1H), 3.96 (s, 6H), 2.44 (s, 3H).

Example 51: N-[3-Fluoro-4-[[6-methoxy-7-(2-methoxyethoxy)-1,5-naphthyridin-4-yl]oxy]phenyl]-5-(furan-2-yl)-1,2,6-trimethyl-4-oxopyridine-3-carboxamide (254)

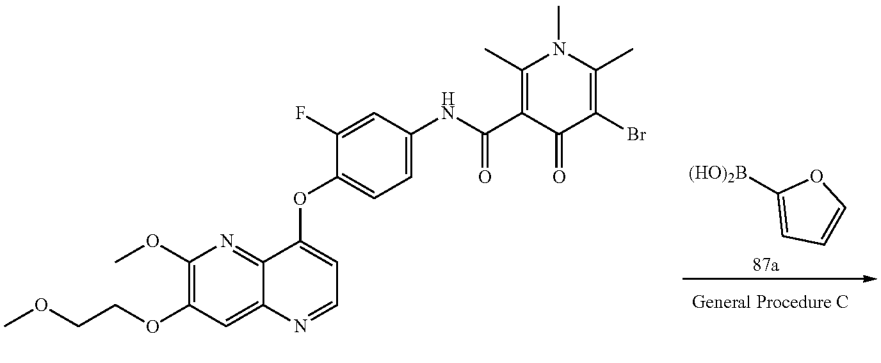

249

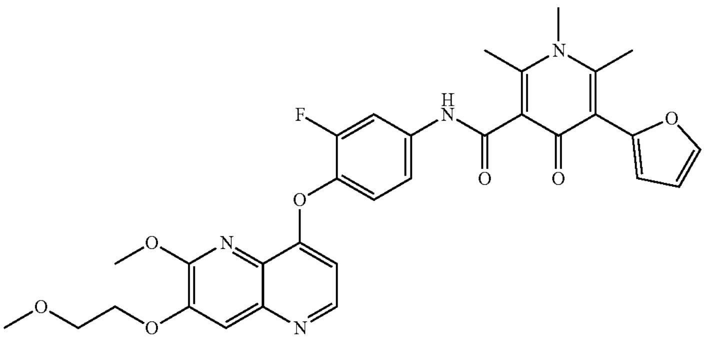

254

Compound 254 was made using General Procedure C. $^1$H NMR (400 MHz, DMSO-$d_6$) δ 10.98 (s, 1H), 8.45 (d, 1H), 7.88 (dd, 1H), 7.65 (dd, 1H), 7.61 (s, 1H), 7.40 (ddd, 1H), 7.28 (t, 1H), 6.70 (dd, 1H), 6.53-6.40 (m, 2H), 4.35-4.18 (m, 2H), 3.92 (s, 3H), 3.75-3.64 (m, 2H), 3.56 (s, 3H), 3.27 (s, 3H), 2.44 (s, 3H), 2.27 (s, 3H); MS for $C_{31}H_{29}FN_4O_7$: m/z 589 (MH+).

The following compounds were made using the same method used to make Compound 254 from Compound 249 in Example 51:

N-[4-[(6,7-Dimethoxy-1,5-naphthyridin-4-yl)oxy]phenyl]-5-(furan-2-yl)-4-hydroxy-6-methylpyridine-3-carboxamide (255): $^1$H NMR (400 MHz, DMSO-$d_6$) δ 12.87 (s, 1H), 12.57 (s, 1H), 8.47 (d, 1H), 8.43 (s, 1H), 7.74 (d, 1H), 7.72 (d, 2H), 7.58 (s, 1H), 7.14 (d, 1H), 7.12 (d, 1H), 6.88 (d, 1H), 6.74 (d, 1H), 6.55 (dd, 1H), 3.90 (s, 3H), 3.87 (s, 3H), 2.39 (s, 3H); MS for $C_{27}H_{22}N_4O_6$: m/z 499.15 (MH+).

N-[4-[(6,7-Dimethoxy-1,5-naphthyridin-4-yl)oxy]phenyl]-4-hydroxy-6-methyl-5-thiophen-2-ylpyridine-3-carboxamide (256): $^1$H NMR (400 MHz, DMSO-$d_6$) δ 12.83 (s, 1H), 12.61 (s, 1H), 8.47 (d, 1H), 8.45 (s, 1H), 7.73 (s, 1H), 7.71 (s, 1H), 7.59 (dd, 1H), 7.57 (s, 1H), 7.13 (s, 1H), 7.11 (s, 1H), 7.10-7.02 (m, 2H), 6.74 (s, 1H), 3.90 (s, 3H), 3.87 (s, 3H), 2.31 (s, 3H); MS for $C_{27}H_{22}N_4O_5S$: m/z 515.15 (MH+).

4-Hydroxy-N-[4-[(7-methoxy-1,5-naphthyridin-4-yl)oxy]phenyl]-6-methyl-5-thiophen-2-ylpyridine-3-carboxamide (257): $^1$H NMR (400 MHz, DMSO-$d_6$) δ 12.86 (s, 1H), 12.62 (s, 1H), 8.65 (dd, 2H), 8.46 (s, 1H), 7.84-7.66 (m, 3H), 7.60 (dd, 1H), 7.27-7.13 (m, 2H), 7.13-7.00 (m, 2H), 6.67 (d, 1H), 3.93 (s, 3H), 2.31 (s, 3H); MS for $C_{26}H_{20}N_4O_4S$: m/z 485.15 (MH+).

N-[4-(6,7-Dimethoxyquinolin-4-yl)oxyphenyl]-5-(furan-2-yl)-4-hydroxy-6-methylpyridine-3-carboxamide (258): $^1$H NMR (400 MHz, DMSO-$d_6$) δ 12.91 (s, 1H), 12.58 (s, 1H), 8.50-8.29 (m, 2H), 7.78 (d, 2H), 7.72 (dd, 1H), 7.45 (s, 1H), 7.33 (s, 1H), 7.20 (d, 2H), 6.88 (dd, 1H), 6.55 (dd, 1H), 6.43 (d, 1H), 3.88 (d, 6H), 2.39 (s, 3H); MS $C_{28}H_{23}N_3O_6$: m/z 498.0 (MH+).

N-[4-(6,7-Dimethoxyquinolin-4-yl)oxy-3-fluorophenyl]-5-(furan-2-yl)-4-hydroxy-6-methylpyridine-3-carboxamide (259). $^1$H NMR (400 MHz, DMSO-$d_6$) δ 13.14 (s, 1H), 12.64 (s, 1H), 8.45 (s, 1H), 8.42 (d, 1H), 8.08 (s, 1H), 8.00 (dd, 1H), 7.71 (dd, 1H), 7.47 (s, 1H), 7.45-7.36 (m, 1H), 7.35 (s, 1H), 6.87 (dd, 1H), 6.55 (dd, 1H), 6.43 (dd, 1H), 3.89 (s, 6H), 2.38 (s, 4H); MS for $C_{28}H_{22}FN_3O_6$: m/z 516.2 (MH+).

N-[3-Fluoro-4-[[6-methoxy-7-(2-methoxyethoxy)-1,5-naphthyridin-4-yl]oxy]phenyl]-5-(furan-2-yl)-4-hydroxy-6-methylpyridine-3-carboxamide (260): $^1$H NMR (400 MHz, DMSO-$d_6$) δ 13.06 (s, 1H), 12.62 (s, 1H), 8.47 (d, 1H), 8.44 (s, 1H), 7.96 (dd, 1H), 7.71 (dd, 1H), 7.61 (s, 1H), 7.37 (ddd, 1H), 7.27 (t, 1H), 6.87 (dd, 1H), 6.76 (dd, 1H), 6.54 (dd, 1H), 4.28-4.20 (m, 2H), 3.89 (s, 3H), 3.73-3.65 (m, 2H), 3.27 (s, 3H), 2.38 (s, 3H); MS for $C_{29}H_{25}FN_4O_7$: m/z 561.0 (MH+).

5-(1-Benzofuran-2-yl)-N-[4-[(6,7-dimethoxy-1,5-naphthyridin-4-yl)oxy]-3-fluorophenyl]-1,2,6-trimethyl-4-oxopyridine-3-carboxamide (261): $^1$H NMR (400 MHz, DMSO-$d_6$) δ 10.94 (s, 1H), 8.45 (d, 1H), 7.88 (dd, 1H), 7.69-7.56 (m, 2H), 7.56-7.45 (m, 1H), 7.45-7.36 (m, 1H), 7.36-7.16 (m, 3H), 6.90 (d, 1H), 6.71 (dd, 1H), 3.90 (d, 6H), 3.60 (s, 3H), 2.44 (s, 3H), 2.35 (s, 3H); MS for $C_{33}H_{27}FN_4O_6$: m/z 595.2 (MH+).

5-(1-Benzofuran-3-yl)-N-[4-[(6,7-dimethoxy-1,5-naphthyridin-4-yl)oxy]-3-fluorophenyl]-1,2,6-trimethyl-4-oxopyridine-3-carboxamide (262): $^1$H NMR (400 MHz, DMSO-$d_6$) δ 11.22 (s, 1H), 8.45 (d, 1H), 7.92-7.78 (m, 2H), 7.57 (d, 2H), 7.38 (ddd, 1H), 7.35-7.23 (m, 3H), 7.18 (td, 1H), 6.70 (dd, 1H), 3.90 (d, 6H), 3.61 (s, 3H), 2.51 (s, 3H), 2.27 (s, 3H); MS for $C_{33}H_{27}FN_4O_6$: m/z 595.2 (MH+).

5-(1-Benzofuran-2-yl)-N-[3-fluoro-4-[[6-methoxy-7-(2-methoxyethoxy)-1,5-naphthyridin-4-yl]oxy]phenyl]-1,2,6-trimethyl-4-oxopyridine-3-carboxamide (263): 1H NMR (400 MHz, DMSO-$d_6$) δ 10.94 (s, 1H), 8.45 (d, 1H), 7.88 (dd, 1H), 7.66-7.58 (m, 2H), 7.55-7.46 (m, 1H), 7.46-7.37 (m, 1H), 7.35-7.10 (m, 3H), 6.90 (d, 1H), 6.71 (dd, 1H), 4.34-4.13 (m, 2H), 3.91 (s, 3H), 3.81-3.64 (m, 2H), 3.60 (s, 3H), 3.27 (s, 3H), 2.44 (s, 3H), 2.35 (s, 3H); MS for $C_{35}H_{31}FN_4O_7$: m/z 639.2 (MH+).

5-(1-Benzofuran-3-yl)-N-[3-fluoro-4-[[6-methoxy-7-(2-methoxyethoxy)-1,5-naphthyridin-4-yl]oxy]phenyl]-1,2,6-trimethyl-4-oxopyridine-3-carboxamide (264): $^1$H NMR (400 MHz, DMSO-$d_6$) δ 11.22 (s, 1H), 8.44 (d, 1H), 7.95-7.79 (m, 2H), 7.65-7.53 (m, 2H), 7.38 (ddd, 1H), 7.32-7.12 (m, 4H), 6.69 (dd, 1H), 4.30-4.17 (m, 2H), 3.91 (s, 3H), 3.76-3.66 (m, 2H), 3.61 (s, 3H), 3.27 (s, 3H), 2.51 (s, 3H), 2.27 (s, 3H); MS for $C_{35}H_{31}FN_4O_7$: m/z 639.25 (MH+).

5-(1-Benzofuran-3-yl)-N-[3-fluoro-4-[[7-(2-methoxyethoxy)-1,5-naphthyridin-4-yl]oxy]phenyl]-1,2,6-trimethyl-4-oxopyridine-3-carboxamide (265): $^1$H NMR (400 MHz, DMSO-$d_6$) δ 11.25 (s, 1H), 8.70 (d, 1H), 8.63 (d, 1H), 7.98-7.80 (m, 2H), 7.75 (d, 1H), 7.57 (dd, 1H), 7.46-7.38 (m, 1H), 7.38-7.24 (m, 3H), 7.18 (td, 1H), 6.69 (dd, 1H), 4.41-4.26 (m, 2H), 3.77-3.67 (m, 2H), 3.62 (s, 3H), 3.28 (s, 3H), 2.51 (s, 3H), 2.28 (s, 3H); MS for $C_{34}H_{29}FN_4O_6$: m/z 609.2 (MH+).

N-[3-Fluoro-4-[[7-(2-methoxyethoxy)-1,5-naphthyridin-4-yl]oxy]phenyl]-5-(furan-2-yl)-1,2,6-trimethyl-4-oxopyridine-3-carboxamide (266): $^1$H NMR (400 MHz, DMSO-$d_6$) δ 11.00 (s, 1H), 8.69 (d, 1H), 8.62 (d, 1H), 7.91 (dd, 1H), 7.75 (d, 1H), 7.65 (dd, 1H), 7.42 (dd, 1H), 7.34 (t, 1H), 6.68 (dd, 1H), 6.53-6.41 (m, 2H), 4.38-4.19 (m, 2H), 3.80-3.65 (m, 2H), 3.56 (s, 3H), 3.29 (s, 3H), 2.44 (s, 3H), 2.27 (s, 3H); MS for $C_{30}H_{27}FN_4O_6$: m/z 559.15 (MH+).

Example 52: N-[4-[(6,7-Dimethoxy-1,5-naphthyridin-4-yl)oxy]-3-fluorophenyl]-6-(furan-2-yl)-5-methylpyrazine-2-carboxamide (269)

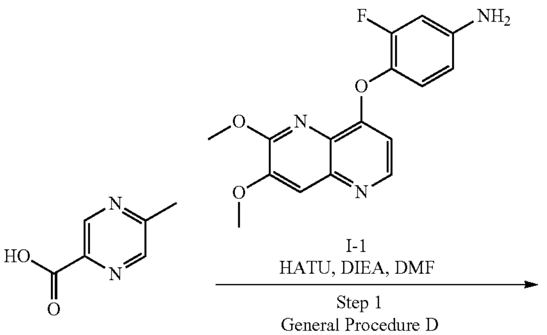

-continued

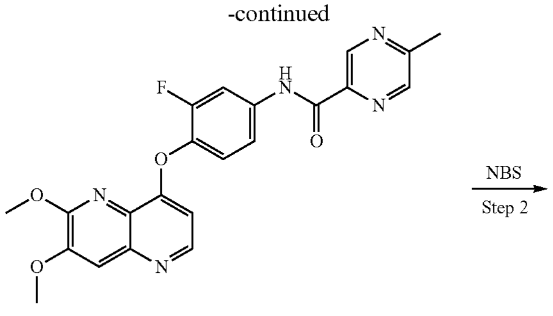

267

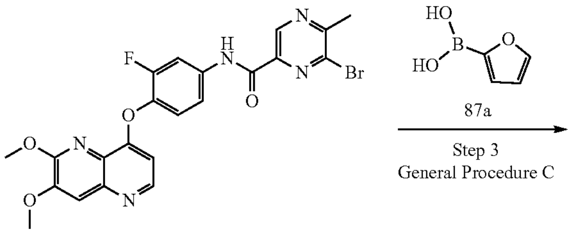

268

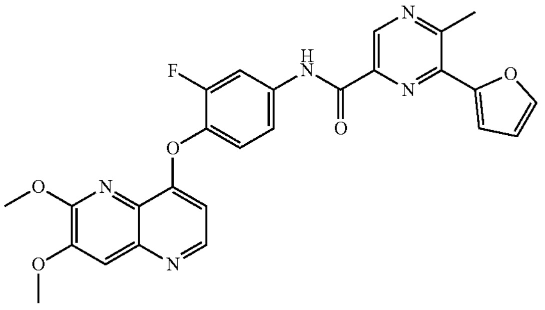

269

Step 1: N-(4-((6,7-Dimethoxy-1,5-naphthyridin-4-yl)oxy)-3-fluorophenyl)-5-methylpyrazine-2-carboxamide (267): Compound 267 was synthesized using General Procedure D. $^1$H NMR (400 MHz, DMSO-$d_6$) δ 11.02 (s, 1H), 9.20 (d, 1H), 8.73 (d, 1H), 8.56 (d, 1H), 8.12 (dd, 1H), 7.85 (dt, 1H), 7.66 (s, 1H), 7.39 (t, 1H), 6.82 (d, 1H), 3.96 (d, 6H), 2.65 (s, 3H); MS $C_{22}H_{18}FN_5O_4$: m/z 436.1 (MH+).

Step 2: 6-Bromo-N-(4-((6,7-dimethoxy-1,5-naphthyridin-4-yl)oxy)-3-fluorophenyl)-5-methylpyrazine-2-carboxamide (268): Compound 268 was synthesized in a manner similar to Compound 36 in Example 9. In this particular case the reaction was heated at 60° C. overnight. 1H NMR (400 MHz, DMSO-$d_6$) δ 10.44 (s, 1H), 9.23 (d, 1H), 8.75 (s, 1H), 8.62 (d, 1H), 8.34 (d, 1H), 7.85 (d, 1H), 7.68 (s, 1H), 7.04 (d, 1H), 3.97 (s, 3H), 3.88 (s, 3H), 2.66 (s, 3H); MS for $C_{22}H_{17}BrFN_5O_4$: m/z 516.0 (MH+).

Step 3: N-[4-[(6,7-Dimethoxy-1,5-naphthyridin-4-yl)oxy]-3-fluorophenyl]-6-(furan-2-yl)-5-methylpyrazine-2-carboxamide (269): Compound 135 was synthesized using General Procedure C. $^1$H NMR (400 MHz, DMSO-$d_6$) δ 11.06 (s, 1H), 9.15 (d, 1H), 8.69 (d, 1H), 8.53 (d, 1H), 8.29 (d, 1H), 7.82 (dd, 1H), 7.66 (d, 1H), 7.60 (s, 1H), 7.02-6.86 (m, 2H), 6.60 (dd, 1H), 3.90 (s, 3H), 3.85 (s, 3H), 2.59 (s, 3H); MS for $C_{26}H_{20}FN_5O_5$: m/z 502.1 (MH+).

Example 53: 1-(2,2-Difluoroethyl)-N-[4-[(6,7-dimethoxy-1,5-naphthyridin-4-yl)oxy]-3-fluorophenyl]-5-(furan-2-yl)-2-methyl-4-oxopyridine-3-carboxamide (275)

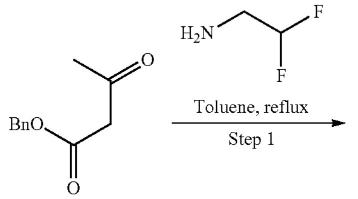

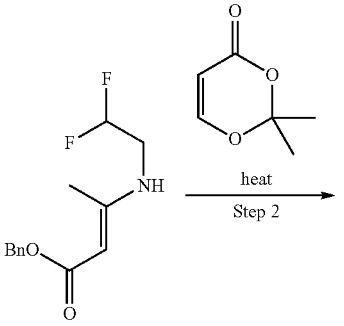

270

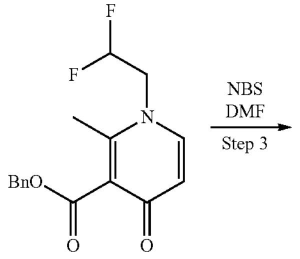

271

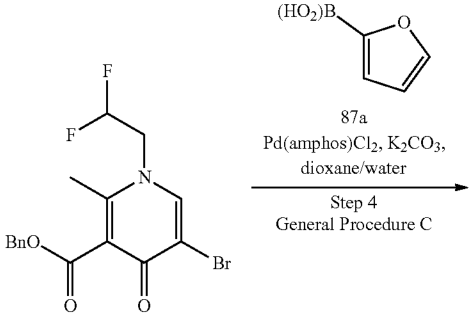

272

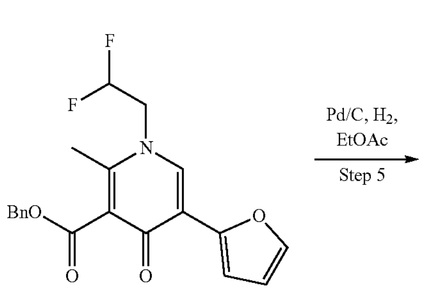

273

-continued

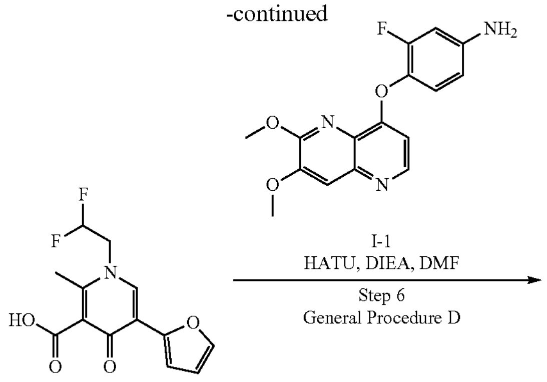

274

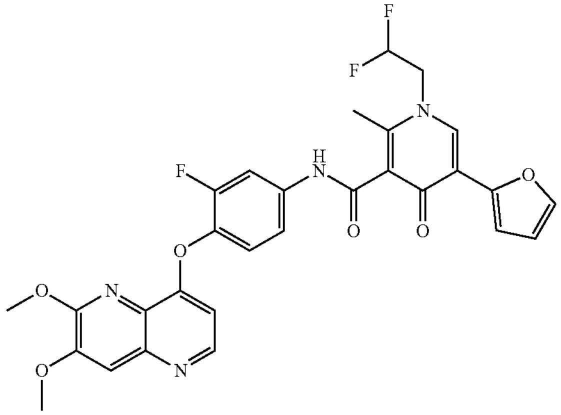

275

Step 1: Benzyl (E)-3-((2,2-difluoroethyl)amino)but-2-enoate (270): To a 100 ml. round bottom flask equipped with a magnetic stir bar, a Dean Stark trap, and a pressure relief septum was added benzyl 3-oxobutanoate (6 g, 31.2 mmol, 1.0 eq), 2,2-difluoroethanamine (2.5 g, 31 mmol, 1.0 eq), and toluene (20 mL). The solution was heated to reflux for 3 hours, until no precipitation of water was observed. The solution was then concentrated under reduced pressure to yield 270 as a yellow oil (7.8 g), which was used without further purification. $^1$H NMR (400 MHz, DMSO-$d_6$) δ 8.63 (t, 1H), 7.42-7.27 (m, 5H), 6.15 (tt, 1H), 5.04 (s, 2H), 4.56 (s, 1H), 3.69 (tdd, 2H), 1.94 (s, 3H).

Step 2: Benzyl 1-(2,2-difluoroethyl)-2-methyl-4-oxo-1,4-dihydropyridine-3-carboxylate (271): Compound 271 can be synthesized from Compound 270 and 2,2-dimethyl-4H-1,3-dioxin-4-one in a manner similar to the way Compound 156 was made from methyl 3-(methylamino)but-2-enoate and 2,2,6-trimethyl-4H-1,3-dioxin-4-one in the first step of Example 32. 1H NMR (400 MHz, DMSO-d6) δ 7.48-7.42 (m, 2H), 7.42-7.29 (m, 3H), 6.47 (tt, 1H), 6.15 (s, 1H), 5.26 (s, 2H), 4.51 (td, 2H), 2.35 (s, 3H), 2.26 (s, 3H); MS for $C_{17}H_{18}F_2NO_3$: m/z 322.1 (MH+).

Step 3: Benzyl 5-bromo-1-(2,2-difluoroethyl)-2-methyl-4-oxo-1,4-dihydropyridine-3-carboxylate (272): Compound 272 can be synthesized from Compound 271 by established conditions using NBS such as those exemplified by the synthesis of Compound 36 in Example 9.

Step 4: Benzyl 1-(2,2-difluoroethyl)-5-(furan-2-yl)-2-methyl-4-oxo-1,4-dihydropyridine-3-carboxylate (273): Compound 273 can be synthesized from Compound 272 using General Procedure C.

Step 5: 1-(2,2-Difluoroethyl)-5-(furan-2-yl)-2-methyl-4-oxo-1,4-dihydropyridine-3-carboxylic acid (274): Compound 274 can be synthesized from Compound 273 using standard hydrogenation conditions.

Step 6: 1-(2,2-Difluoroethyl)-N-[4-[(6,7-dimethoxy-1,5-naphthyridin-4-yl)oxy]-3-fluorophenyl]-5-(furan-2-yl)-2-methyl-4-oxopyridine-3-carboxamide (275): Compound 275 can be synthesized from Compound 274 using General Procedure D. MS for $C_{29}H_{23}F_3N_4O_6$: m/z 581.2 (MH+).

Example 54: Methyl 7-bromo-8-oxo-1,3,4,8-tetrahydropyrido[2,1-c][1,4]oxazine-9-carboxylate (282)

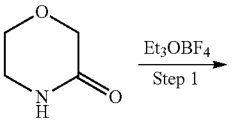

276

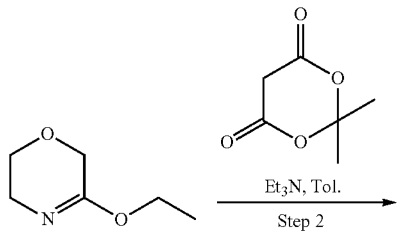

277

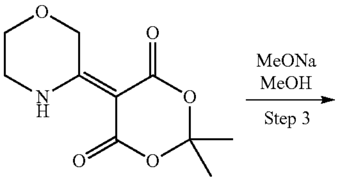

278

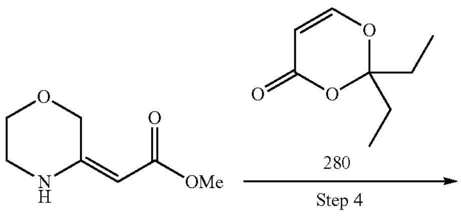

279

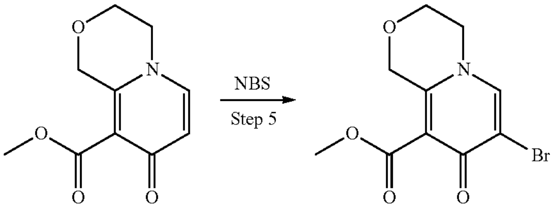

281

282

Step 1: 5-Ethoxy-3,6-dihydro-2H-1,4-oxazine (277): To a solution of Compound 276 (5 g, 49.4 mmol, 1 eq) in DCM (80 mL) was added $Et_3OBF_4$ (10.3 g, 54.4 mmol, 1.1 eq) at 20° C. and the resulting reaction mixture was stirred at 20° C. for 12 h. The reaction mixture was quenched by the addition of aq saturated $Na_2CO_3$ to pH=8. The organic layer was separated, dried over anhyd $Na_2SO_4$ and concentrated in vacuo to give crude Compound 277 as a yellow oil in DCM (6.3 g) which was used without further purification. $^1H$ NMR (400 MHz, $CDCl_3$) δ 4.09 (m, 2H), 4.03 (s, 2H), 3.62-3.68 (m, 2H), 3.49-3.55 (m, 2H), 1.26 (m, 3H).

Step 2: 2,2-Dimethyl-5-(morpholin-3-ylidene)-1,3-dioxane-4,6-dione (278): A solution of Compound 277 (5 g, 39 mmol, 1 eq), 2,2-dimethyl-1,3-dioxane-4,6-dione (5.6 g, 39 mmol, 1 eq) and $Et_3N$ (1.08 mL, 7.74 mmol, 0.2 eq) in toluene (50 mL) was stirred at 105° C. for 3 h. The mixture was cooled to room temperature and the solvent evaporated in vacuo. The resulting residue was purified by flash silica gel chromatography (0-50% EtOAc/petroleum ether) to give Compound 278 as a yellow solid (1.4 g, 16% yield). $^1H$ NMR (400 MHz, $CDCl_3$) δ 11.48 (br s, 1H), 5.05 (s, 2H), 3.94 (m, 2H), 3.55-3.63 (m, 2H), 1.68 (s, 6H); MS for $C_{10}H_{13}NO_5$: m/z 169.8 (MH+).

Step 3: Methyl (E)-2-(morpholin-3-ylidene)acetate (279): A solution of Compound 278 (1.3 g, 5.7 mmol, 1 eq) and NaOMe (371 mg, 6.9 mmol, 1.2 eq) in MeOH (30 mL) was stirred at 80° C. for 12 h. The mixture was cooled to room temperature and then concentrated in vacuo. The resulting residue was dissolved in aq saturated $NH_4Cl$ (100 mL) and extracted with EtOAc (3×50 mL). The combined organic extracts were dried over anhyd $Na_2SO_4$ and concentrated in vacuo to give Compound 279 as a yellow solid (617 mg, 69% yield) which was used without further purification. 1H NMR (400 MHz, $CDCl_3$) δ 8.56 (br s, 1H), 4.34 (s, 1H), 4.28 (s, 2H), 3.88-3.94 (m, 2H), 3.64 (s, 3H), 3.36 (m, 2H); MS for $C_7H_{11}NO_3$: m/z 157.9 (MH+).

Step 4: 5 Methyl 8-oxo-1,3,4,8-tetrahydropyrido[2,1-c][1,4]oxazine-9-carboxylate (281): A mixture of Compound 279 (300 mg, 1.9 mmol, 1 eq) and Compound 280 (596 mg. 3.8 mmol, 2 eq) was stirred at 130° C. for 1 0.5 h with Dean-Stark trap removal of water. The reaction mixture was concentrated under vacuum. The resulting residue was purified by flash silica gel chromatography (0~10% MeOH in DCM) to give Compound 281 as a yellow solid (220 mg, 55% yield). $^1H$ NMR (400 MHz, $CDCl_3$) δ 7.17 (d, 1H), 6.48 (d, 1H), 4.83 (s, 2H), 4.08-4.05 (t, 2H), 3.95-3.92 (t, 2H), 3.90 (s, 3H); MS for $C_{10}H_{11}NO_4$: m/z 209.9 (MH+).

Methyl 7-bromo-8-oxo-1,3,4,8-tetrahydropyrido[2,1-c][1,4]oxazine-9-carboxylate (282): To a solution of Compound 281 (210 mg, 1.00 mmol, 1 eq) in DMF (2 mL) was added NBS (214 mg, 1.20 mmol, 1.2 eq) and the resulting mixture was stirred at 25° C. for 2 h. The resulting mixture was diluted with aq saturated $NaHCO_3$ (50 mL) and extracted with DCM (3×50 mL). The combined DCM extracts were washed with aq saturated NaCl (20 mL), dried over anhyd $Na_2SO_4$ and concentrated to give Compound 282 as a yellow solid (260 mg, 90% yield). MS for $C_{10}H_{10}BrNO_4$: m/z 289.7 (MH+).

Example 55: Methyl 7-bromo-6-methyl-8-oxo-1,3,4,8-tetrahydropyrido[2,1-c][1,4]oxazine-9-carboxylate (284)

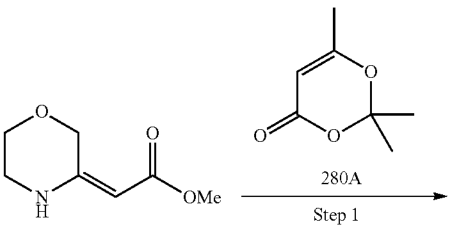

279

-continued

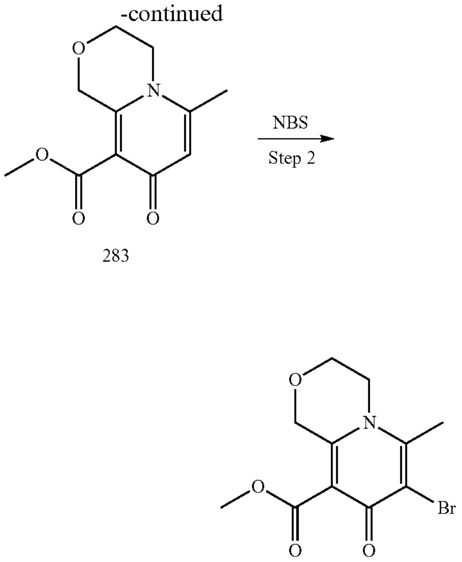

283

284

Step 1: Methyl 6-methyl-8-oxo-1,3,4,8-tetrahydropyrido[2,1-c][1,4]oxazine-9-carboxylate (283): A mixture of Compound 279 (500 mg, 3.2 mmol, 1 eq) and Compound 280A (1.08 g, 7.6 mmol, 2.4 eq) was stirred at 130° C. for 1 h with a Dean-Stark trap. The reaction mixture was concentrated under vacuum. The resulting residue was purified by column chromatography to give Compound 283 as a brown solid (330 mg, 41% yield). MS for $C_{11}H_{13}NO_4$: m/z 224.1 (MH+).

Step 2: Methyl 7-bromo-6-methyl-8-oxo-1,3,4,8-tetrahydropyrido[2,1-c][1,4]oxazine-9-carboxylate (284): NBS (300 mg, 1.7 mmol, 1.25 eq) was added to a solution of Compound 283 (300 mg, 1.34 mmol, 1 eq) in DCM (10 mL). The mixture was stirred at 25-30° C. for 12 h. The mixture was concentrated, and the resulting residue was purified by column chromatography to give Compound 284 as a yellow solid (373 mg, 90% yield). MS for $C_{11}H_{12}BrNO_4$: m/z 304.0 (MH+).

Example 56: 7-(Furan-2-yl)-8-oxo-1,3,4,8-tetrahydropyrido[2,1-c][1,4]oxazine-9-carboxylic acid (286)

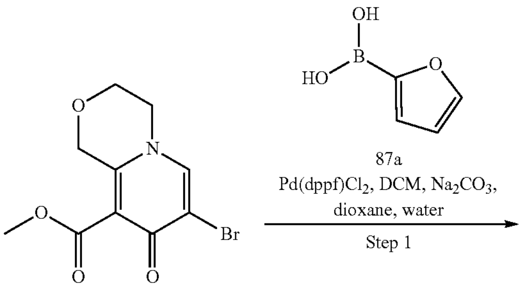

87a

282

-continued

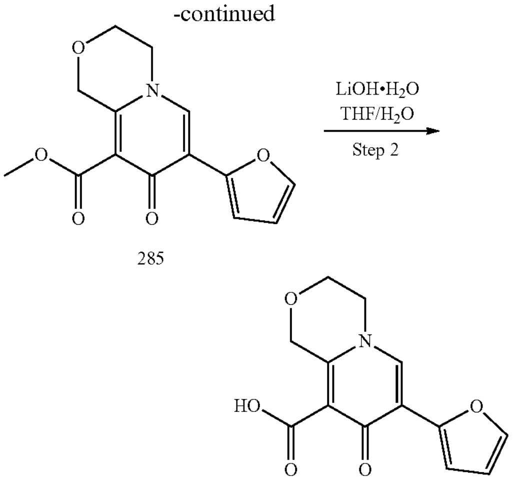

285

286

Step 1: Methyl 7-(furan-2-yl)-8-oxo-1,3,4,8-tetrahydropyrido[2,1-c][1,4]oxazine-9-carboxylate (285): To a solution of Compound 282 (50 mg, 0.17 mmol, 1 eq) and Compound 87a (58 mg, 0.52 mmol, 3 eq) in dioxane (3 ml) and water (0.3 ml) was added Pd(dppf)$Cl_2$·$CH_2C_{12}$ (14.2 mg, 0.017 mmol, 0.1 eq) and $Na_2CO_3$ (55 mg, 0.52 mmol, 3 eq). The mixture was stirred at 100° C. for 12 h. The reaction mixture was concentrated under reduced pressure and the resulting residue was purified by flash chromatography over silica gel to give Compound 285 as a yellow solid (32 mg, 67% yield). MS for $C_{14}H_{13}NO_5$: m/z 276.0 (MH+).

Step 2: 7-(Furan-2-yl)-8-oxo-1,3,4,8-tetrahydropyrido[2,1-c][1,4]oxazine-9-carboxylic acid (286): To a solution of Compound 285 (32 mg, 0.12 mmol, 1 eq) in THF (1 ml) and water (1 ml) was added LiOH—$H_2O$ (14.6 mg, 0.35 mmol, 3 eq). The mixture was stirred at 25° C. for 2 h. The reaction mixture was concentrated under reduced pressure to remove THF. The resulting residue was diluted with water (5 ml) and extracted with EtOAc (30 mL). The organic layer was washed with aq saturated NaCl (10 mL), dried over anhyd. $Na_2SO_4$ and concentrated under reduced pressure to give Compound 286 as a yellow solid (16 mg, 53% yield). MS for $C_{13}H_{11}NO_5$: m/z 262.1 (MH+).

The following compounds were made using the same method used to make Compound 286 in two steps from Compound 282 and Compound 87a in Example 56:

287

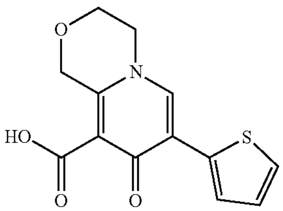

288

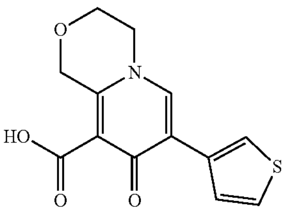

-continued

289

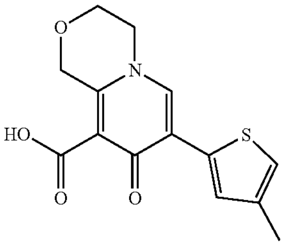

290

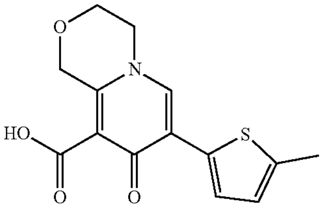

291

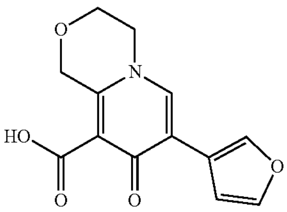

292

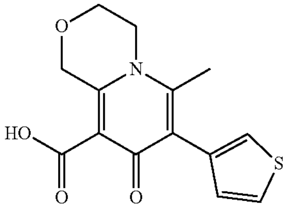

293

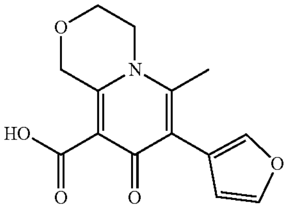

294

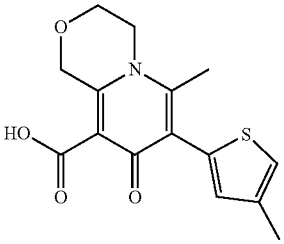

295

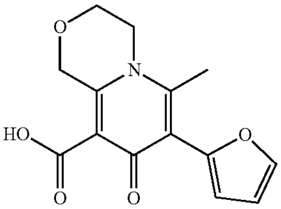

-continued

296

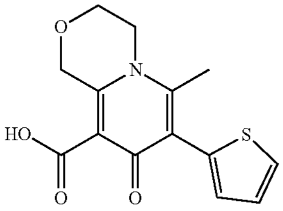

8-oxo-7-(Thiophen-2-yl)-1,3,4,8-tetrahydropyrido[2,1-c][1,4]oxazine-9-carboxylic acid (287): MS for $C_{13}H_{11}NO_4S$: m/z 278.0 (MH+).

8-oxo-7-(Thiophen-3-yl)-1,3,4,8-tetrahydropyrido[2,1-c][1,4]oxazine-9-carboxylic acid (288): MS for $C_{13}H_{11}NO_4S$: m/z 277.8 (MH+).

7-(4-Methylthiophen-2-yl)-8-oxo-1,3,4,8-tetrahydropyrido[2,1-c][1,4]oxazine-9-carboxylic acid (289): MS for $C_{14}H_{13}NO_4S$: m/z 291.8 (MH+).

7-(5-Methylthiophen-2-yl)-8-oxo-1,3,4,8-tetrahydropyrido[2,1-c][1,4]oxazine-9-carboxylic acid (290): MS for $C_{14}H_{13}NO_4S$: m/z 291.9 (MH+).

7-(Furan-3-yl)-8-oxo-1,3,4,8-tetrahydropyrido[2,1-c][1,4]oxazine-9-carboxylic acid (291): MS for $C_{13}H_{11}NO_5$: m/z 262.1 (MH+).

6-Methyl-8-oxo-7-(thiophen-3-yl)-1,3,4,8-tetrahydropyrido[2,1-c][1,4]oxazine-9-carboxylic acid (292): MS for $C_{14}H_{13}NO_4S$: m/z 292.0 (MH+).

7-(Furan-3-yl)-6-methyl-8-oxo-1,3,4,8-tetrahydropyrido[2,1-c][1,4]oxazine-9-carboxylic acid (293).

6-Methyl-7-(4-methylthiophen-2-yl)-8-oxo-1,3,4,8-tetrahydropyrido[2,1-c][1,4]oxazine-9-carboxylic acid (294).

7-(Furan-2-yl)-6-methyl-8-oxo-1,3,4,8-tetrahydropyrido[2,1-c][1,4]oxazine-9-carboxylic acid (295).

6-Methyl-8-oxo-7-(thiophen-2-yl)-1,3,4,8-tetrahydropyrido[2,1-c][1,4]oxazine-9-carboxylic acid (296).

Example 57: N-[4-[(6,7-Dimethoxy-1,5-naphthyridin-4-yl)oxy]-3-fluorophenyl]-7-(furan-2-yl)-8-oxo-3,4-dihydro-1H-pyrido[2,1-c][1,4]oxazine-9-carboxamide (297)

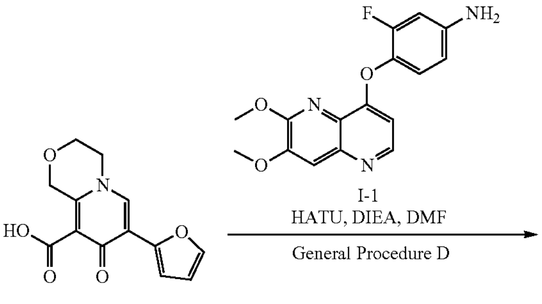

286

-continued

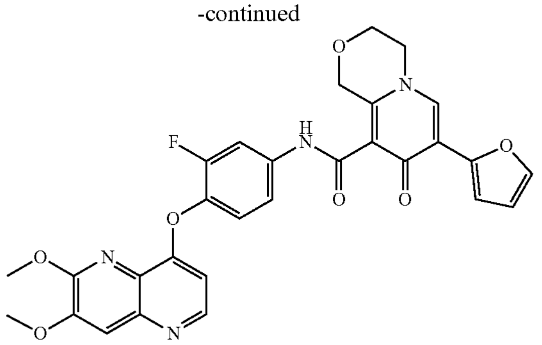

297

N-[4-[(6,7-Dimethoxy-1,5-naphthyridin-4-yl)oxy]-3-fluorophenyl]-7-(furan-2-yl)-8-oxo-3,4-dihydro-1H-pyrido[2,1-c][1,4]oxazine-9-carboxamide (297). Compound 297 was made using General Procedure D. $^1$H NMR (400 MHz, DMSO-$d_6$) δ 12.92 (s, 1H), 8.54 (d, 1H), 8.30 (s, 1H), 7.98 (d, 1H), 7.79 (s, 1H), 7.66 (s, 1H), 7.43 (m, 2H), 7.34 (t, 1H), 6.81 (d, 1H), 6.64 (d, 1H), 5.20 (s, 2H), 4.30 (t, 2H), 4.07 (t, 2H), 3.97 (s, 3H), 3.96 (s, 3H), MS for $C_{29}H_{23}FN_4O_7$: m/z 559.1 (MH+).

The following compounds were made using the same method used to make Compound 297 from Compound 286 and Intermediate I-1 using General Procedure D as in Example 57:

N-[4-[(6,7-Dimethoxy-1,5-naphthyridin-4-yl)oxy]phenyl]-7-(furan-2-yl)-8-oxo-3,4-dihydro-1H-pyrido[2,1-c][1,4]oxazine-9-carboxamide (298): Intermediate I-1 was replaced with Intermediate I-2. $^1$H NMR (400 MHz, DMSO-$d_6$) δ 12.76 (s, 1H), 8.54 (d, 1H), 8.29 (s, 1H), 7.78 (dd, 3H), 7.64 (s, 1H), 7.41 (d, 1H), 7.19 (dd, 2H), 6.79 (d, 1H), 6.64 (s, 1H), 5.21 (s, 2H), 4.29 (t, 2H), 4.07 (t, 2H), 3.97 (s, 3H), 3.95 (s, 3H); MS for $C_{29}H_4N_4O_7$: m/z 541.0 (MH+).

N-[4-[(6,7-Dimethoxy-1,5-naphthyridin-4-yl)oxy]phenyl]-8-oxo-7-thiophen-2-yl-3,4-dihydro-1H-pyrido[2,1-c][1,4]oxazine-9-carboxamide (299): Intermediate I-1 was replaced with Intermediate I-2 and Compound 286 was replaced with Compound 287. $^1$H NMR (400 MHz, DMSO-$d_6$) δ 12.7 (s, 1H), 8.59 (s, 1H), 8.54 (d, 1H), 7.79-7.75 (m, 3H), 7.64-7.59 (m, 2H), 7.2-7.16 (m, 3H), 6.79 (d, 1H), 5.22 (s, 2H), 4.27 (t, 2H), 4.09 (t, 2H), 3.96 (s, 3H), 3.95 (s, 3H); MS for $C_{29}H_4N_4O_6S$: m/z 556.9 (MH+).

N-[4-[(6,7-Dimethoxy-1,5-naphthyridin-4-yl)oxy]-3-fluorophenyl]-8-oxo-7-thiophen-3-yl-3,4-dihydro-1H-pyrido[2,1-c][1,4]oxazine-9-carboxamide (300): Compound 286 was replaced with Compound 288. $^1$H NMR (400 MHz, DMSO-$d_6$) δ 13.17 (s, 1H), 8.54 (d, 1H), 8.37 (t, 2H), 7.97 (s, 1H), 7.67-7.64 (m, 3H), 7.41 (d, 1H), 7.34 (t, 1H), 6.81 (d, 1H), 5.22 (s, 2H), 4.24 (t, 2H), 4.08 (t, 2H), 3.97 (s, 3H), 3.96 (s, 3H); MS for $C_{29}H_{23}FN_4O_6S$: m/z 575.2 (MH+).

N-[4-[(6,7-Dimethoxy-1,5-naphthyridin-4-yl)oxy]phenyl]-8-oxo-7-thiophen-3-yl-3,4-dihydro-1H-pyrido[2,1-c][1,4]oxazine-9-carboxamide (301): Intermediate I-1 was replaced with Intermediate I-2 and Compound 286 was replaced with Compound 288. $^1$H NMR (400 MHz, DMSO-$d_6$) δ 12.99 (s, 1H), 8.54 (d, 1H), 8.38 (d, 1H), 8.35 (s, 1H), 7.77 (d, 2H), 7.65-7.62 (m, 3H), 7.19 (dd, 2H), 6.78 (d, 1H), 5.23 (s, 2H), 4.24 (t, 2H), 4.08 (t, 2H), 3.97 (s, 3H), 3.95 (s, 3H); MS for $C_{29}H_{24}N_4O_6S$: m/z 557.2 (MH+).

N-[4-[(6,7-Dimethoxy-1,5-naphthyridin-4-yl)oxy]-3-fluorophenyl]-7-(4-methylthiophen-2-yl)-8-oxo-3,4-dihydro-1H-pyrido[2,1-c][1,4]oxazine-9-carboxamide (302): Compound 286 was replaced with Compound 289. $^1$H NMR (400 MHz, DMSO-$d_6$) δ 12.87 (s, 1H), 8.55 (d, 2H), 7.98 (dd, 1H), 7.65 (s, 1H), 7.58 (s, 1H), 7.41 (m, 1H), 7.34 (t, 1H), 7.18 (s, 1H), 6.82 (d, 1H), 5.21 (s, 2H), 4.26 (t, 2H), 4.08 (t, 2H), 3.97 (s, 3H), 3.96 (s, 3H), 2.26 (s, 3H); MS for $C_{30}H_{25}FN_4O_6S$: m/z 589.0 (MH+).

N-[4-[(6,7-Dimethoxy-1,5-naphthyridin-4-yl)oxy]phenyl]-7-(4-methylthiophen-2-yl)-8-oxo-3,4-dihydro-1H-pyrido[2,1-c][1,4]oxazine-9-carboxamide (303): Intermediate I-1 was replaced with Intermediate I-2 and Compound 286 was replaced with Compound 289. $^1$H NMR (400 MHz, DMSO-$d_6$) δ 12.72 (s, 1H), 8.54 (m, 2H), 7.77 (d, 2H), 7.64 (s, 1H), 7.58 (s, 1H), 7.20-7.18 (m, 3H), 6.79 (d, 1H), 5.22 (s, 2H), 4.25 (t, 2H), 4.09 (t, 2H), 3.97 (s, 3H), 3.95 (s, 3H), 2.27 (s, 3H); MS for $C_{30}H_{26}N_4O_6S$: m/z 571.2 (MH+).

N-[4-[(6,7-Dimethoxy-1,5-naphthyridin-4-yl)oxy]-3-fluorophenyl]-7-(5-methylthiophen-2-yl)-8-oxo-3,4-dihydro-1H-pyrido[2,1-c][1,4]oxazine-9-carboxamide (304): 5 Compound 286 was replaced with Compound 290. $^1$H NMR (400 MHz, DMSO-$d_6$) δ 12.98 (s, 1H), 8.56 (d, 1H), 8.51 (s, 1H), 7.99 (d, 1H), 7.66 (s, 1H), 7.55 (d, 1H), 7.43 (d, 1H), 7.36 (t, 1H), 6.84-6.83 (m, 2H), 5.22 (s, 2H), 4.26 (t, 2H), 4.08 (t, 2H), 3.98 (s, 3H), 3.96 (s, 3H), 2.48 (s, 3H); MS for $C_{30}H_{25}FN_4O_6S$: m/z 589.1 (MH+).

N-[4-[(6,7-Dimethoxy-1,5-naphthyridin-4-yl)oxy]phenyl]-7-(5-methylthiophen-2-yl)-8-oxo-3,4-dihydro-1H-pyrido[2,1-c][1,4]oxazine-9-carboxamide (305): Intermediate I-1 was replaced with Intermediate I-2 and Compound 286 was replaced with Compound 290. $^1$H NMR (400 MHz, DMSO-$d_6$) δ 12.82 (s, 1H), 8.54 (d, 1H), 8.50 (s, 1H), 7.77 (d, 2H), 7.64 (s, 1H), 7.55 (d, 1H), 7.19 (d, 2H), 6.85 (s, 1H), 6.80 (d, 1H), 5.23 (s, 2H), 4.26 (t, 2H), 4.08 (t, 2H), 3.97 (s, 3H), 3.95 (s, 3H), 2.48 (s, 3H); MS for $C_{30}H_{26}N_4O_6S$: m/z 571.0 (MH+).

N-[4-[(6,7-Dimethoxy-1,5-naphthyridin-4-yl)oxy]-3-fluorophenyl]-7-(furan-3-yl)-8-oxo-3,4-dihydro-1H-pyrido[2,1-c][1,4]oxazine-9-carboxamide (306): Compound 286 was replaced with Compound 291. $^1$H NMR (400 MHz, DMSO-$d_6$) δ 13.2 (s, 1H), 8.66-8.63 (m, 2H), 8.37 (s, 1H), 8.01 (d, 1H), 7.76 (d, 1H), 7.67 (s, 1H), 7.45-7.38 (m, 2H), 7.07 (d, 1H), 6.95 (d, 1H), 5.32 (s, 2H), 4.23 (t, 2H), 4.08 (t, 2H), 4.00 (s, 6H); MS for $C_{29}H_{23}FN_4O_7$: m/z 559.2 (MH+).

N-[4-[(6,7-Dimethoxy-1,5-naphthyridin-4-yl)oxy]-3-fluorophenyl]-6-methyl-8-oxo-7-thiophen-3-yl-3,4-dihydro-1H-pyrido[2,1-c][1,4]oxazine-9-carboxamide (307): Compound 286 was replaced with Compound 292. $^1$H NMR (400 MHz, DMSO-$d_6$) δ 13.48 (s, 1H), 8.51 (d, 1H), 7.91 (d, 1H), 7.56 (s, 1H), 7.5 (m, 1H), 7.48 (d, 1H), 7.24 (bs, 1H), 7.15 (t, 1H), 7.07 (d, 1H), 6.73 (d, 1H), 5.58 (s, 2H), 4.15-4.04 (m, 7H), 3.5 (d, 3H), 2.37 (s, 3H); MS for $C_{30}H_{25}FN_4O_6S$: m/z 589.1 (MH+).

N-[4-[(6,7-Dimethoxy-1,5-naphthyridin-4-yl)oxy]-3-fluorophenyl]-7-(furan-3-yl)-6-methyl-8-oxo-3,4-dihydro-1H-pyrido[2,1-c][1,4]oxazine-9-carboxamide (308): Compound 286 was replaced with Compound 293. $^1$H NMR (400 MHz, DMSO-$d_6$) δ 13.27 (s, 1H), 8.53 (d, 1H), 7.95 (br d, 1H), 7.75 (br s, 2H), 7.64 (s, 1H), 7.41-7.35 (m, 1H), 7.33-7.26 (m, 1H), 6.79 (br d, 1H), 6.53 (s, 1H), 5.27 (s, 2H), 4.14 (br d, 2H), 4.06 (br d, 2H), 3.95 (br d, 6H), 2.43 (s, 3H); MS for 30 $C_{30}H_{25}FN_4O_7$: m/z 573.3 (MH+).

N-[4-[(6,7-Dimethoxy-1,5-naphthyridin-4-yl)oxy]-3-fluorophenyl]-8-oxo-7-thiophen-2-yl-3,4-dihydro-1H-pyrido[2,1-c][1,4]oxazine-9-carboxamide (309): Compound 286 was replaced with Compound 287. $^1$H NMR (400 MHz, DMSO-$d_6$) δ 12.85 (s, 1H), 8.59 (s, 1H), 8.55 (d, 1H), 8.00 (s, 1H), 7.76 (d, 1H), 7.65 (s, 1H), 7.60 (d, 1H), 7.42 (s, 1H), 7.34 (s, 1H), 7.17 (t, 1H), 6.82 (d, 1H), 5.22 (s, 2H), 4.28 (t, 2H), 4.09 (t, 2H), 3.97 (s, 3H), 3.96 (s, 3H); MS for $C_{29}H_{23}FN_4O_6S$: m/z 575.0 (MH+).

N-[4-[(6,7-Dimethoxy-1,5-naphthyridin-4-yl)oxy]phenyl]-7-(furan-3-yl)-8-oxo-3,4-dihydro-1H-pyrido[2,1-c][1,4]oxazine-9-carboxamide (310): Intermediate I-1 was replaced with Intermediate I-2 and Compound 286 was replaced with Compound 291. $^1$H NMR (400 MHz, DMSO-$d_6$) δ 13.00 (s, 1H), 8.63 (s, 1H), 8.54 (d, 1H), 8.35 (s, 1H), 7.78-7.76 (m, 3H), 7.64 (s, 1H), 7.19 (d, 2H), 7.06 (d, 1H), 6.79 (d, 1H), 5.24 (s, 2H), 4.25 (t, 2H), 4.08 (t, 2H), 3.97 (s, 3H), 3.95 (s, 3H); MS for $C_{29}H_{24}N_4O_7$: m/z 541.2 (MH+).

N-[4-[(6,7-Dimethoxy-1,5-naphthyridin-4-yl)oxy]phenyl]-7-(furan-3-yl)-6-methyl-8-oxo-3,4-dihydro-1H-pyrido[2,1-c][1,4]oxazine-9-carboxamide (311): Intermediate I-1 was replaced with Intermediate I-2 and Compound 286 was replaced with Compound 293. MS for $C_{30}H_{26}N_4O_7$: m/z 555.2 (MH+).

N-[4-[(6,7-Dimethoxy-1,5-naphthyridin-4-yl)oxy]phenyl]-6-methyl-8-oxo-7-thiophen-3-yl-3,4-dihydro-1H-pyrido[2,1-c][1,4]oxazine-9-carboxamide (312): Intermediate I-1 was replaced with Intermediate I-2 and Compound 286 was replaced with Compound 292. MS for $C_{30}H_{26}N_4O_6S$: m/z 571.2 (MH+).

N-[4-[(6,7-Dimethoxy-1,5-naphthyridin-4-yl)oxy]phenyl]-6-methyl-7-(4-methylthiophen-2-yl)-8-oxo-3,4-dihydro-1H-pyrido[2,1-c][1,4]oxazine-9-carboxamide (313): Intermediate I-1 was replaced with Intermediate I-2 and Compound 286 was replaced with Compound 294. MS for $C_{31}H_{28}N_4O_6S$: m/z 585.2 (MH+).

N-[4-[(6,7-Dimethoxy-1,5-naphthyridin-4-yl)oxy]-3-fluorophenyl]-7-(furan-2-yl)-6-methyl-8-oxo-3,4-dihydro-1H-pyrido[2,1-c][1,4]oxazine-9-carboxamide (314): Compound 286 was replaced with Compound 295. MS for $C_{30}H_{25}FN_4O_7$: m/z 573.2 (MH+).

N-[4-[(6,7-Dimethoxy-1,5-naphthyridin-4-yl)oxy]phenyl]-7-(furan-2-yl)-6-methyl-8-oxo-3,4-dihydro-1H-pyrido[2,1-c][1,4]oxazine-9-carboxamide (315): Intermediate I-1 was replaced with Intermediate I-2 and Compound 286 was replaced with Compound 295. MS for $C_{30}H_{26}N_4O_7$: m/z 555.2 (MH+).

N-[4-[(6,7-Dimethoxy-1,5-naphthyridin-4-yl)oxy]phenyl]-6-methyl-8-oxo-7-thiophen-2-yl-3,4-dihydro-1H-pyrido[2,1-c][1,4]oxazine-9-carboxamide (316): Intermediate I-1 was replaced with Intermediate I-2 and Compound 286 was replaced with Compound 296. MS for $C_{30}H_{26}N_4O_6S$: m/z 571.2 (MH+).

N-[4-[(6,7-Dimethoxy-1,5-naphthyridin-4-yl)oxy]-3-fluorophenyl]-6-methyl-8-oxo-7-thiophen-2-yl-3,4-dihydro-1H-pyrido[2,1-c][1,4]oxazine-9-carboxamide (317): Compound 286 was replaced with Compound 296. MS for $C_{30}H_{25}FN_4O_6S$: m/z 589.4 (MH+).

N-[4-[(6,7-Dimethoxy-1,5-naphthyridin-4-yl)oxy]-3-fluorophenyl]-6-methyl-7-(4-methylthiophen-2-yl)-8-oxo-3,4-dihydro-1H-pyrido[2,1-c][1,4]oxazine-9-carboxamide (318): Compound 286 was replaced with Compound 294. MS for $C_{31}H_{27}FN_4O_6S$: m/z 603.3 (MH+).

Example 58: N-[4-[(6,7-Dimethoxy-1,5-naphthyridin-4-yl)oxy]-3-fluorophenyl]-2-ethyl-5-(furan-2-yl)-1,6-dimethyl-4-oxopyridine-3-carboxamide (324)

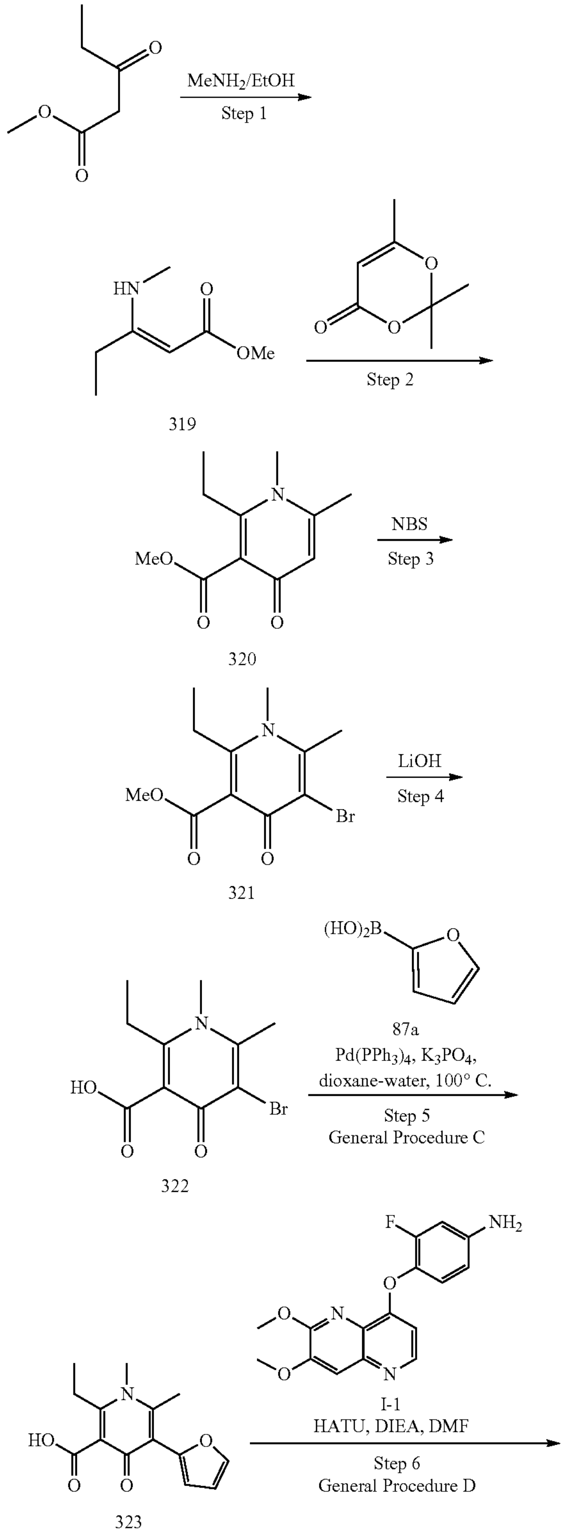

-continued

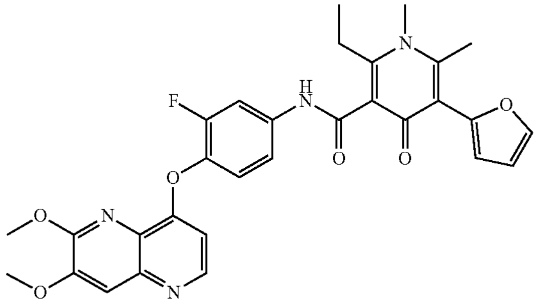

324

Step 1: Methyl 3-(methylamino)pent-2-enoate (319): A mixture of methyl 3-oxopentanoate (20 g, 154 mmol, 1 eq) and 33% methylamine in EtOH (50 mL, 154 mmol) was stirred at 25° C. for 30 min. The reaction mixture was concentrated under reduced pressure to give crude Compound 319 as a yellow oil (20 g, 91% yield) which was used without further purification.

Steps 2-6: N-[4-[(6,7-Dimethoxy-1,5-naphthyridin-4-yl)oxy]-3-fluorophenyl]-2-ethyl-5-(furan-2-yl)-1,6-dimethyl-4-oxopyridine-3-carboxamide (324): Compound 324 was synthesized in 5 steps from Compound 319 using the same 5 step sequence exemplified by the synthesis of Compound 160 in Example 32. $^1$H NMR (400 MHz, DMSO-$d_6$) δ 10.83 (s, 1H), 8.45 (d, 1H), 7.87 (dd, 11H), 7.65 (dd, 111), 7.58 (s, 1H), 7.41 (ddd, 1H), 7.28 (t, 1H), 6.70 (dd, 1H), 6.49 (dd, 111), 6.45 (dd, 1H), 3.91 (s, 3H), 3.90 (s, 3H), 3.60 (s, 3H), 2.75 (q, 2H), 2.28 (s, 3H), 1.18 (t, 3H); MS for $C_{30}H_{27}FN_4O_6$: m/z 559.2 (MH+).

The following compounds were made using the same procedure as exemplified by the synthesis of Compound 160 in Example 32:

N-[4-[(6,7-Dimethoxy-1,5-naphthyridin-4-yl)oxy]phenyl]-2-ethyl-5-(furan-2-yl)-1,6-dimethyl-4-oxopyridine-3-carboxamide (325): Intermediate I-1 was replaced with Intermediate I-2 in Step 6. $^1$H NMR (400 MHz, DMSO-$d_6$) δ 10.61 (s, 1H), 8.44 (d, 1H), 7.77-7.68 (m, 2H), 7.67-7.62 (m, 1H), 7.57 (s, 1H), 7.16-7.07 (m, 2H), 6.67 (d, 1H), 6.49 (dd, 1H), 6.45 (dd, 1H), 3.90 (s, 3H), 3.90 (s, 3H), 3.59 (s, 3H), 2.75 (q, 2H), 2.27 (s, 3H), 1.18 (t, 3H); MS for $C_{30}H_2N_4O_6$: m/z 541.1 10 (MH+).

2-Ethyl-N-[3-fluoro-4-[[6-methoxy-7-(2-methoxyethoxy)-1,5-naphthyridin-4-yl]oxy]phenyl]-5-(furan-2-yl)-1,6-dimethyl-4-oxopyridine-3-carboxamide (326): Intermediate I-1 was replaced with Compound 17 in Step 6. $^1$H NMR (400 MHz, DMSO-$d_6$) δ 10.83 (s, 1H), 8.45 (d, 1H), 7.87 (dd, 1H), 7.65 (dd, 1H), 7.61 (s, 1H), 7.41 (ddd, 1H), 7.28 (t, 1H), 6.70 (dd, 1H), 6.49 (dd, 1H), 6.45 (dd, 1H), 4.28-4.21 (m, 2H), 3.92 (s, 3H), 3.72-3.65 (m, 2H), 3.59 (s, 3H), 3.27 (s, 3H), 2.74 (q, 2H), 2.28 (s, 3H), 1.18 (t, 3H); MS for $C_{32}H_{31}FN_4O_7$: m/z 603.2 (MH+).

Example 59: N-[4-[(6,7-Dimethoxy-1,5-naphthyridin-4-yl)oxy]-3-fluorophenyl]-1-(2-fluoroethyl)-6-methyl-4-oxo-5-thiophen-2-ylpyridine-3-carboxamide (327)

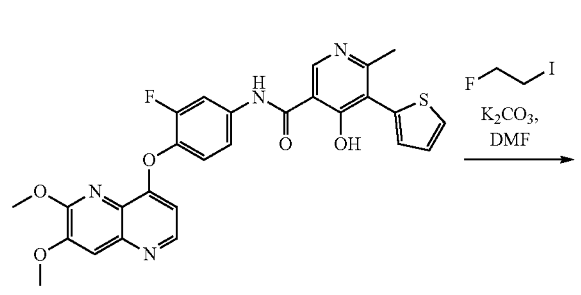

90

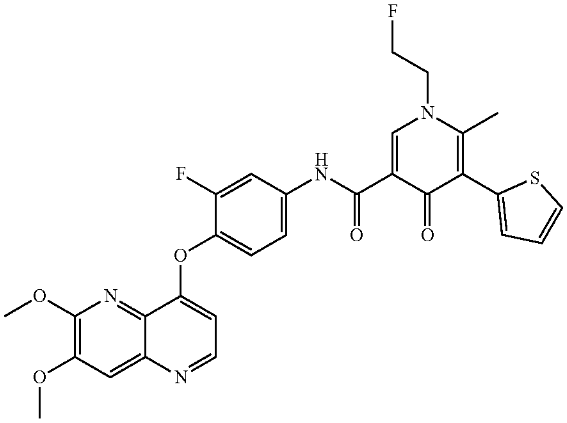

327

N-[4-[(6,7-Dimethoxy-1,5-naphthyridin-4-yl)oxy]-3-fluorophenyl]-1-(2-fluoroethyl)-6-methyl-4-oxo-5-thiophen-2-ylpyridine-3-carboxamide (327): Compound 327 was synthesized from Compound 90 using the same method as that used to make Compound 66 from Compound 61 in Example 18. $^1$H NMR (400 MHz, DMSO-$d_6$) δ 12.88 (s, 1H), 8.67 (s, 1H), 8.50 (s, 1H), 7.94 (dd, 1H), 7.62 (dd, 1H), 7.59 (s, 1H), 7.37 (dd, 1H), 7.27 (dd, 1H), 7.09 (dd, 1H), 6.95 (dd, 1H), 6.76 (d, 1H), 4.83 (t, 1H), 4.72 (t, 1H), 4.62 (t, 1H), 4.55 (t, 1H), 3.90 (s, 3H), 3.87 (s, 3H), 2.31 (s, 3H); MS for $C_{29}H_{24}F_2N_4O_5S$: m/z 579.1 (MH+).

The following compounds were made using the same procedure as exemplified by the synthesis of Compound 327 in Example 59:

1-(2-Fluoroethyl)-N-[3-fluoro-4-[(7-methoxy-1,5-naphthyridin-4-yl)oxy]phenyl]-6-methyl-5-(4-methylthiophen-2-yl)-4-oxopyridine-3-carboxamide (328): Compound 90 was replaced with Compound 102. $^1$H NMR (400 MHz, DMSO-$d_6$) δ 13.01 (s, 1H), 8.75 (d, 1H), 8.74 (s, 1H), 8.71 (d, 1H), 8.05 (dd, 1H), 7.80 (d, 1H), 7.49 (dd, 1H), 7.43 (t, 1H), 7.25 (t, 1H), 6.83 (d, 1H), 6.76 (dd, 1H), 4.90 (t, 1H), 4.78 (t, 1H), 4.68 (t, 1H), 4.62 (t, 1H), 4.01 (s, 3H), 2.39 (s, 3H), 2.26 (d, 3H); MS for $C_{29}H_{24}F_2N_4O_4S$: m/z 563.1 (MH+).

1-(2-Fluoroethyl)-N-[3-fluoro-4-[(7-methoxy-1,5-naphthyridin-4-yl)oxy]phenyl]-6-methyl-5-(5-methylthiophen-2-yl)-4-oxopyridine-3-carboxamide (329): Compound 90 was replaced with Compound 101. MS for $C_{29}H_{24}F_2N_4O_4S$: m/z 563.1 (MH+).

1-(2-Fluoroethyl)-N-[3-fluoro-4-[(7-methoxy-1,5-naphthyridin-4-yl)oxy]phenyl]-6-methyl-4-oxo-5-thiophen-3-ylpyridine-3-carboxamide (330): Compound 90 was replaced with Compound 98. $^1$H NMR (400 MHz, DMSO-$d_6$) δ 13.08 (s, 1H), 8.68 (d, 1H), 8.66 (s, 1H), 8.64 (d, 1H), 7.98 (dd, 1H), 7.73 (d, 1H), 7.55 (dd, 1H), 7.46-7.37 (m, 2H), 7.35 (t, 1H), 7.02 (dd, 1H), 6.68 (d, 1H), 4.86-4.79 (m, 1H), 4.74-4.67 (m, 1H), 4.65-4.59 (m, 1H), 4.58-4.52 (m, 1H), 3.94 (s, 3H), 2.25 (s, 3H); MS for $C_{28}H_{22}F_2N_4O_4S$: m/z 549.1 (MH+).

1-(2-Fluoroethyl)-N-[3-fluoro-4-[(7-methoxy-1,5-naphthyridin-4-yl)oxy]phenyl]-6-methyl-4-oxo-5-thiophen-2-ylpyridine-3-carboxamide (331): Compound 90 was replaced with Compound 100. $^1$H NMR (400 MHz, DMSO-$d_6$) δ 12.92 (s, 1H), 8.71-8.66 (m, 2H), 8.64 (d, 1H), 7.98 (dd, 1H), 7.73 (d, 1H), 7.63 (dd, 1H), 7.43 (dd, 1H), 7.35 (dd, 1H), 7.10 (dd, 1H), 6.96 (dd, 1H), 6.69 (dd, 1H), 4.84 (t, 1H), 4.72 (t, 1H), 4.63 (t, 1H), 4.56 (t, 1H), 3.94 (s, 3H), 2.32 (s, 3H); MS for $C_{28}H_{22}F_2N_4O_4S$: m/z 549.1 (MH+).

N-[4-[(6,7-Dimethoxy-1,5-naphthyridin-4-yl)oxy]-3-fluorophenyl]-1-(2-fluoroethyl)-6-methyl-4-oxo-5-thiophen-3-ylpyridine-3-carboxamide (332): Compound 90 was replaced with Compound 93. $^1$H NMR (400 MHz, DMSO-$d_6$) δ 13.04 (s, 1H), 8.65 (s, 1H), 8.48 (d, 1H), 7.94 (dd, 1H), 7.58 (s, 1H), 7.55 (dd, 1H), 7.39 (dd, 1H), 7.36 (ddd, 1H), 7.26 (t, 1H), 7.01 (dd, 1H), 6.75 (d, 1H), 4.82 (t, 1H), 4.70 (t, 1H), 4.64-4.59 (m, 1H), 4.58-4.52 (m, 1H), 3.90 (s, 3H), 3.87 (s, 3H), 2.25 (s, 3H); MS for $C_{29}H_{24}F_2N_4O_5S$: m/z 579.1 (MH+).

N-[4-[(6,7-Dimethoxy-1,5-naphthyridin-4-yl)oxy]-3-fluorophenyl]-1-(2-fluoroethyl)-5-(furan-2-yl)-6-methyl-4-oxopyridine-3-carboxamide (333): Compound 90 was replaced with Compound 89. $^1$H NMR (400 MHz, DMSO-$d_6$) δ 12.87 (s, 1H), 8.66 (s, 1H), 8.48 (d, 1H), 7.94 (dd, 1H), 7.72 (dd, 1H), 7.58 (s, 1H), 7.38 (dd, 1H), 7.28 (dd, 1H), 6.76 (d, 1H), 6.58-6.52 (m, 2H), 4.82 (t, 1H), 4.70 (t, 1H), 4.61 (t, 1H), 4.55 (t, 1H), 3.90 (s, 3H), 3.87 (s, 3H), 2.30 (s, 3H); MS for $C_{29}H_{24}F_2N_4O_6$: m/z 563.1 (MH+).

1-(2-Fluoroethyl)-N-[3-fluoro-4-[(7-methoxy-1,5-naphthyridin-4-yl)oxy]phenyl]-5-(furan-3-yl)-6-methyl-4-oxopyridine-3-carboxamide (334): Compound 90 was replaced with Compound 99. $^1$H NMR (400 MHz, DMSO-$d_6$) δ 13.14 (s, 1H), 8.75 (d, 1H), 8.73-8.68 (m, 2H), 8.05 (dd, 1H), 7.80 (d 1H), 7.79-7.74 (m, 2H), 7.48 (dd, 1H), 7.42 (dd, 1H), 6.75 (d, 1H), 6.60-6.56 (m, 1H), 4.88 (t, 1H), 4.76 (t, 1H), 4.69 (d, 1H), 4.62 (d, 1H), 4.00 (s, 3H), 2.42 (s, 3H); MS for $C_{28}H_{22}F_2N_4O_5$: m/z 533.1 (MH+).

Example 60: N-[4-[[7-(2-Cyclobutylethoxy)-6-methoxy-1,5-naphthyridin-4-yl]oxy]-3-fluorophenyl]-5-(furan-2-yl)-1 2,6-trimethyl-4-oxopyridine-3-carboxamide (337)

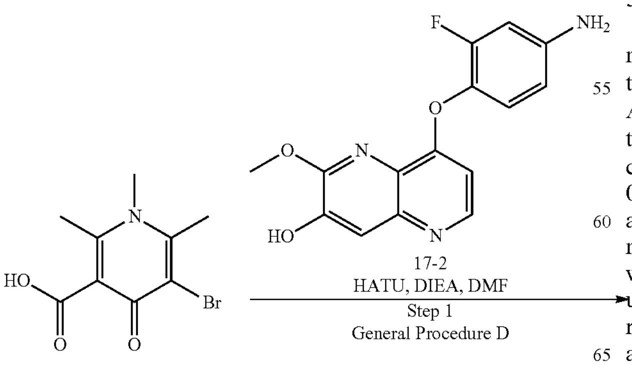

158 17-2

-continued

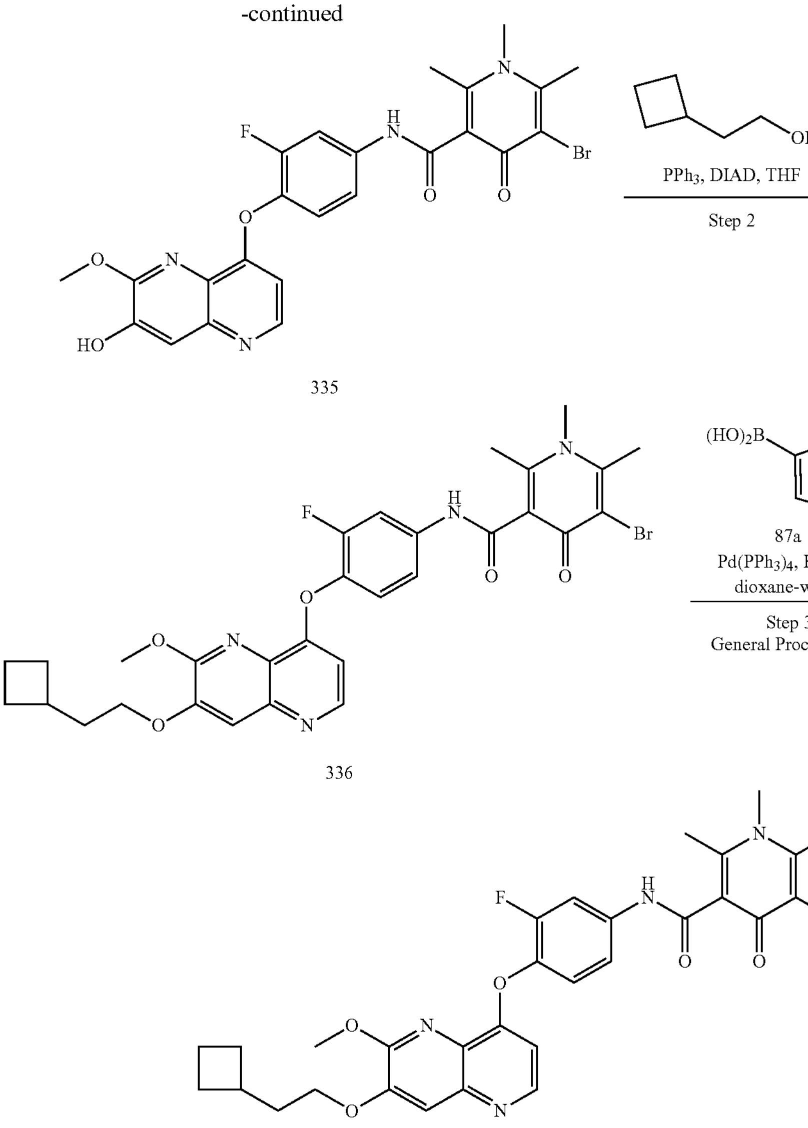

335

87a

336

337

Step 1: 5-Bromo-N-(3-fluoro-4-((7-hydroxy-6-methoxy-1,5-naphthyridin-4-yl)oxy)phenyl)-1,2,6-trimethyl-4-oxo-1,4-dihydropyridine-3-carboxamide (335): Compound 335 was synthesized from Compound 158 and Compound 17-2 using General Procedure D. MS for $C_{24}H_{20}BrFN_4O_5$: m/z 543 (MH+).

Step 2: 5-Bromo-N-(4-((7-(2-cyclobutylethoxy)-6-methoxy-1,5-naphthyridin-4-yl)oxy)-3-fluorophenyl)-1,2,6-trimethyl-4-oxo-1,4-dihydropyridine-3-carboxamide (336): A mixture of Compound 335 (54 mg, 0.1 mmol, 1 eq), triphenylphosphine (78 mg, 0.30 mmol, 3.0 eq) and 2-cyclobutylethanol (II mg, 0.11 mmol, 1.1 eq) in THF (0.5 mL, 0.2M) was cooled to 0° C. in an ice bath followed by the addition of DIAD (61 mg, 0.3 mmol, 3.0 eq). The resulting mixture was allowed to warm to room temperature overnight with stirring. The reaction mixture was then concentrated under reduced pressure. EtOAc was added to the resulting residue and the solution with washed with water, dried over anhyd. $Na_2SO_4$ and concentrated under reduced pressure. The resulting residue was purified by flash column chromatography over silica gel (DCM/MeOH) to give Compound 336 as an oil (40 mg, 64% yield). $^1$H NMR (400 MHz, DMSO-$d_6$) δ 10.81 (s, 1H), 8.58 (d, 1H), 7.96 (dd, 1H), 7.55-7.43 (m, 2H), 7.40 (t, 1H), 6.86 (d, 1H), 4.14 (t, 2H), 4.01 (s, 3H), 3.67 (s, 3H), 2.70 (s, 3H), 2.46 (m, 1H), 2.42 (s, 3H), 2.08 (dt, 2H), 1.93 (q, 2H), 1.89-1.78 (m, 2H), 1.78-1.61 (m, 2H); MS for $C_{30}H_{30}BrFN_4O_5$: m/z 627 (MH+).

Step 3: N-[4-[[7-(2-Cyclobutylethoxy)-6-methoxy-1,5-naphthyridin-4-yl]oxy]-3-fluorophenyl]-5-(furan-2-yl)-1,2,6-trimethyl-4-oxopyridine-3-carboxamide (337): Compound 337 was synthesized from Compound 336 using General Procedure C. $^1$H NMR (400 MHz, DMSO-$d_6$) δ 10.96 (s, 1H), 8.44 (d, 1H), 7.88 (dd, 1H), 7.65 (d, 1H), 7.55 (s, 1H), 7.44-7.34 (m, 1H), 7.27 (t, 1H), 6.69 (dd, 1H), 6.55-6.34 (m, 2H), 4.04 (t, 2H), 3.91 (s, 3H), 3.56 (s, 3H), 2.42 (s, 3H), 2.38 (d, 1H), 2.27 (s, 3H), 2.01 (m, 2H), 1.85 (t, 2H), 1.83-1.73 (m, 2H), 1.66 (ddd, 2H); MS for $C_{34}H_{33}FN_4O_6$: m/z 613 (MH+).

KINASE ASSAYS

Example A: Kinase Assays

Kinase activity and compound inhibition were investigated using the HTRF® KinEase assay (Cisbio Cat #62TK0PEB) per manufacturer's instructions. In short, compounds were delivered in 300 nL volumes at 10 different concentrations in DMSO (3% final) to empty 384-well assay plates (Corning cat #3824). A mixture of enzyme, 1 μM biotynlated peptide substrate, and buffer in 10 μL volume was added. The assay was started upon the addition of ATP (at Km). The 10 μL reaction was incubated at room temperature. The reaction was stopped upon the addition of detection buffer containing streptavidin-XL665 (5 μL) and TK antibody-Eu3+(5 μL). After a 60 min incubation at room temperature, the fluorescence at 665 nm and 620 nm was read on an Envision microplate reader (Perkin Elmer). Kinase activity normalized to DMSO (100% activity) and reference compound at 1 μM and (0% activity) was calculated using the fluorescence ratio 620/665×10,000. $IC_{50}$ values were calculated by nonlinear regression analysis using a 4-parameter logistic curve fit in ActivityBase XE (IDBS).

Example B: Human AXL Kinase Assay

Human AXL (residues 464-885; CarnaBio, 1 ng/well) was incubated with enzymatic buffer (Cisbio) supplemented with 5 mM $MgCl_2$, 1 mM DTT, and Supplemental Enzymatic Buffer (SEB; Cisbio). The mixture was added to the pre-plated compounds. The reaction was initiated upon addition of ATP at Km (1.0 μM). The reaction was incubated at room temperature for 50 min and stopped upon the addition of SA-XL665 and TK-antibody both diluted in EDTA-containing kinase detection buffer (Cisbio). The kinase activity was calculated as stated above and the $IC_{50}$ values were reported.

Example C: Human MET Kinase Assay

Human MET (residues 956-1390; CarnaBio, 0.1 ng/well) was incubated with enzymatic buffer (Cisbio) supplemented with 5 mM $MgCl_2$, 1 mM DTT and 1 mM $MnCl_2$. The mixture was added to the pre-plated compounds. The reaction was initiated upon addition of ATP at Km (3.0 μM). The reaction was incubated at room temperature for 40 min and stopped upon the addition of SA-XL665 and TK-antibody both diluted in EDTA-containing kinase detection buffer (Cisbio). The kinase activity was calculated as stated above and the $IC_{50}$ values were reported.

Example D: Human MER Kinase Assay

Human MER (residues 528-999; CarnaBio, 1 ng/well) was incubated with enzymatic buffer (Cisbio) supplemented with 5 mM $MgCl_2$ and 1 mM DTT. The mixture was added to the pre-plated compounds. The reaction was initiated upon addition of ATP at Km (40 μM). The reaction was incubated at room temperature for 60 min and stopped upon the addition of SA-XL665 and TK-antibody both diluted in EDTA-containing kinase detection buffer (Cisbio). The kinase activity was calculated as stated above and the $IC_{50}$ values were reported.

Example E: Human KDR Kinase Assay

Human KDR (residues 790-1356; CarnaBio, 0.1 ng/well) was incubated with enzymatic buffer (Cisbio) supplemented with 5 mM $MgCl_2$, 1 mM $MnCl_2$, and 1 mM DTT. The mixture was added to the pre-plated compounds. The reaction was initiated upon addition of ATP at Km (4.0 μM). The reaction was incubated at room temperature for 40 min and stopped upon the addition of SA-XL665 and TK-antibody both diluted in EDTA-containing kinase detection buffer (Cisbio). The kinase activity was calculated as stated above and the $IC_{50}$ values were reported.

Example F: AXL Autophosphorylation ELISA in A-172 Cells

A-172 glioblastoma cells (ATCC #CRL-1620) were seeded at 2.5×$10^5$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). A-172 cells were incubated at 37° C., 5% $CO_2$ for 24 h and then starved for 24 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 1 μg/mL recombinant human Gas6 (R&D Systems #885-GSB-500) for 15 min, washed with cold PBS, and immediately lysed with 150 μL of cold 1X lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 μL/well added into the human phospho-AXL DuoSet IC ELISA (R&D Systems #DYC2228-2). Assay was performed according to manufacturer's instructions and sample phospho-AXL concentrations were extrapolated using human phospho-AXL control (R&D Systems #841645) as a standard. Positive control wells (100% activity) contained Gas6-stimulated, DMSO-treated cell lysates. Negative control wells (0% activity) contained Gas6-stimulated, reference inhibitor-treated cell lysates. $IC_{50}$ values were calculated by nonlinear regression analysis using a 4-parameter logistic curve fit in ActivityBase XE (IDBS).

Example G: Met Autophosphorylation ELISA in PC-3 Cells

PC-3 prostate cancer cells (ATCC #CRL-1435) were seeded at 4×$10^4$ cells/well onto 24-well plates (Greiner

#662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). PC-3 cells were incubated at 37° C., 5% $CO_2$ for 24 h and then starved for 3 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human HGF (R&D Systems #294-HG-250) for 10 min, washed with cold PBS, and immediately lysed with 130 μL of cold 1X lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 100 μL/well added into the PathScan phospho-Met (panTyr) Sandwich ELISA (Cell Signaling Technology #7333). Assay was performed according to manufacturer's instructions. Positive control wells (100% activity) contained HGF-stimulated, DMSO-treated cell lysates. Negative control wells (0% activity) contained HGF-stimulated, reference inhibitor-treated cell lysates. $IC_{50}$ values were calculated by nonlinear regression analysis using a 4-parameter logistic curve fit in ActivityBase XE (IDBS).

Example H: KDR Autophosphorylation ELISA in HUVEC Cells

Human umbilical vein endothelial cells or HUVEC (Lonza #C2519A) were seeded at $2\times10^4$ cells/well onto 96-well plates (Corning #3904), in EGM-2 growth medium (Lonza #CC-3162) containing 1% Penicillin Streptomycin (Thermo Fisher #15140-122). HUVEC cells were incubated at 37° C., 5% $CO_2$ for 24 h and then starved for 24 h in serum-free EBM-2 basal medium (Lonza #CC-3156) containing 1% Penicillin Streptomycin. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human VEGF165 (R&D Systems #293-VE-500) for 5 min, washed with cold PBS, and immediately lysed with 130 μL of cold 1X lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 μL/well added into the human phospho-KDR DuoSet IC ELISA (R&D Systems #DYC1766-2). Assay was performed according to manufacturer's instructions and sample phospho-KDR concentrations were extrapolated using human phospho-KDR control (R&D Systems #841421) as a standard. Positive control wells (100% activity) contained VEGF165-stimulated, DMSO-treated cell lysates. Negative control wells (0% activity) contained non-stimulated cell lysates. $IC_{50}$ values were calculated by nonlinear regression analysis using a 4-parameter logistic curve fit in ActivityBase XE (IDBS).

Example I: Mer Autophosphorylation ELISA in Transient Transfected 293A Cells 293A cells (Thermo Fisher #R70507) were seeded at $1.5\times10^6$ cells/well onto 100 mm dish (Greiner #664169), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). 293A cells were incubated at 37° C., 5% $CO_2$ for 24 h and then transfected with 6 μg MERTK DNA (Genecopoeia #EX-Z8208-M02) using TransIT LT1 transfection reagent (Mirus-Bio #MIR2305). After 24 h incubation, the transfected 293A cells were seeded at $1\times10^5$ cells/well onto 96-well plates (Corning #3904) in DMEM growth medium overnight. Test compounds were serially diluted to produce an 8-point dose curve in fresh serum-free medium to a final concentration of 0.3% DMSO (vehicle) and added to the cells and incubated for 1 h. Cells were then immediately lysed with 150 μL of cold 1X lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 50 μL/well added into the human phospho-Mer DuoSet IC ELISA (R&D Systems #DYC2579-2). Assay was performed according to manufacturer's instructions and sample phospho-Mer concentrations were extrapolated using human phospho-Mer control (R&D Systems #841793) as a standard. Positive control wells (100% activity) contained DMSO-treated cell lysates. Negative control wells (0% activity) contained reference inhibitor-treated cell lysates. $IC_{50}$ values were calculated by nonlinear regression analysis using a 4-parameter logistic curve fit in ActivityBase XE (IDBS).

Compounds of the present disclosure, as exemplified in Examples 1-23, were assessed in each of the assays (Examples A-I). Results for the test compounds are summarized in Table 2 and Table 3. A, B, and C of Tables 2 and 3 have the following meanings: A=$IC_{50}\leq100$ nM; B=100 nM $<IC_{50}\leq300$ nM; C=300 nM$<IC_{50}\leq1$ μM

TABLE 2

Biological Activities of Selected Compounds

| Compound No. | Axl $IC_{50}$ (nM) | Mer $IC_{50}$ (nM) | c-Met $IC_{50}$ (nM) | KDR $IC_{50}$ (nM) |
|---|---|---|---|---|
| 41 | A | A | A | A |
| 42 | A | A | A | A |
| 43 | A | A | A | A |
| 44 | A | A | A | A |
| 45 | A | A | A | B |
| 46 | A | A | A | C |
| 47 | A | A | B | C |
| 48 | A | A | A | C |
| 49 | NT | A | A | B |
| 50 | A | A | A | A |
| 51 | A | A | A | B |
| 52 | A | A | A | C |
| 53 | A | A | A | C |
| 54 | NT | NT | NT | NT |
| 54A | NT | A | B | C |
| 56 | NT | A | A | C |
| 59 | A | A | A | C |
| 68 | A | A | A | A |
| 69 | A | A | A | A |
| 70 | A | A | A | A |
| 71 | NT | A | NT | C |
| 72 | NT | B | C | C |
| 73 | NT | B | C | C |
| 85 | A | A | A | A |
| 86 | A | A | A | C |
| 214 | A | NT | A | NT |
| 216 | A | NT | A | NT |

TABLE 2-continued

| Biological Activities of Selected Compounds | | | | |
|---|---|---|---|---|
| Compound No. | Axl $IC_{50}$ (nM) | Mer $IC_{50}$ (nM) | c-Met $IC_{50}$ (nM) | KDR $IC_{50}$ (nM) |
| 217 | A | NT | A | NT |
| 218 | A | NT | A | NT |
| 220 | A | NT | A | NT |
| 221 | A | NT | A | NT |

NT means not tested

TABLE 3

| Cellular Activities of Selected Compounds | | | | |
|---|---|---|---|---|
| Compound No. | Axl $IC_{50}$ (nM) | Mer $IC_{50}$ (nM) | c-Met $IC_{50}$ (nM) | KDR $IC_{50}$ (nM) |
| 41 | A | A | A | A |
| 42 | A | A | A | A |
| 43 | A | A | A | A |
| 44 | A | A | A | A |
| 45 | A | A | A | A |
| 46 | A | A | A | A |
| 47 | A | A | A | A |
| 48 | A | A | A | C |
| 49 | A | A | A | A |
| 50 | A | A | A | A |
| 51 | A | A | A | A |
| 52 | A | A | A | A |
| 53 | A | A | A | A |
| 54 | A | A | A | A |
| 54A | B | A | A | B |
| 55 | A | A | A | C |
| 56 | A | A | A | C |
| 59 | A | A | A | B |
| 68 | A | A | A | A |
| 69 | A | A | A | A |
| 70 | A | A | A | A |
| 71 | A | A | A | C |
| 72 | A | A | A | C |
| 73 | A | A | A | C |
| 85 | A | A | A | A |
| 86 | A | A | A | C |
| 89 | A | A | A | A |
| 90 | A | A | A | A |
| 91 | A | A | A | A |
| 92 | A | A | A | A |
| 93 | A | A | A | A |
| 94 | A | A | A | A |
| 95 | A | A | A | A |
| 96 | A | A | A | A |
| 97 | A | A | B | A |
| 98 | A | A | A | A |
| 99 | A | A | A | A |
| 100 | A | A | A | A |
| 101 | A | A | A | A |
| 102 | A | A | A | A |
| 103 | A | A | A | A |
| 104 | A | A | A | A |
| 105 | A | A | B | A |
| 106 | A | A | A | A |
| 107 | A | A | A | A |
| 108 | A | A | A | A |
| 109 | A | A | A | A |
| 110 | A | A | A | A |
| 111 | A | A | A | A |
| 112 | A | A | A | A |
| 115 | A | A | A | A |
| 116 | A | A | A | A |
| 117 | A | A | A | A |
| 118 | A | A | A | A |
| 119 | A | A | A | A |
| 120 | A | A | A | A |
| 121 | NT | A | B | A |
| 122 | NT | A | A | A |
| 123 | A | A | A | A |

TABLE 3-continued

| Cellular Activities of Selected Compounds | | | | |
|---|---|---|---|---|
| Compound No. | Axl $IC_{50}$ (nM) | Mer $IC_{50}$ (nM) | c-Met $IC_{50}$ (nM) | KDR $IC_{50}$ (nM) |
| 124 | NT | A | A | A |
| 125 | A | A | A | A |
| 126 | A | A | A | A |
| 127 | A | A | A | A |
| 128 | A | A | A | A |
| 129 | A | A | A | A |
| 135 | A | A | A | A |
| 136 | B | A | A | A |
| 137 | A | A | A | A |
| 138 | A | A | A | A |
| 139 | A | A | A | A |
| 140 | A | A | A | A |
| 141 | A | A | A | A |
| 142 | A | A | A | A |
| 143 | A | A | A | A |
| 147 | A | A | A | A |
| 148 | A | A | A | A |
| 151 | A | A | A | A |
| 152 | B | A | B | A |
| 153 | A | A | B | A |
| 154 | A | A | A | A |
| 155 | A | A | A | A |
| 155A | A | A | A | A |
| 155B | A | A | A | A |
| 160 | A | A | A | B |
| 161 | NT | A | A | C |
| 162 | NT | A | A | C |
| 163 | A | A | A | C |
| 164 | A | A | A | C |
| 165 | A | A | A | C |
| 166 | A | A | A | C |
| 167 | A | A | A | C |
| 168 | A | A | A | A |
| 195 | A | A | A | A |
| 196 | NT | A | A | A |
| 197 | NT | A | A | A |
| 198 | NT | A | A | A |
| 200 | A | A | A | A |
| 212 | NT | NT | B | NT |
| 213 | NT | NT | C | NT |
| 214 | A | A | A | A |
| 215 | A | A | A | C |
| 216 | A | A | A | A |
| 217 | A | A | A | A |
| 218 | A | A | A | A |
| 219 | A | A | A | A |
| 220 | A | A | A | A |
| 221 | A | A | A | A |
| 222 | A | A | A | A |
| 223 | A | A | A | A |
| 224 | NT | A | A | A |
| 225 | NT | A | A | C |
| 226 | A | A | A | A |
| 227 | A | A | A | A |
| 228 | A | A | A | A |
| 229 | A | A | A | A |
| 230 | A | A | A | A |
| 231 | A | A | A | B |
| 232 | A | A | A | C |
| 233 | A | A | A | A |
| 234 | A | A | A | B |
| 235 | A | A | A | C |
| 236 | A | A | C | C |
| 237 | A | A | C | C |
| 238 | B | C | C | C |
| 239 | NT | C | C | C |
| 240 | A | A | C | C |
| 243 | A | A | A | B |
| 244 | A | A | A | C |
| 245 | A | A | A | A |
| 246 | A | A | A | B |
| 247 | C | A | A | B |
| 248 | C | C | A | C |
| 254 | A | A | A | A |
| 255 | A | A | A | A |

TABLE 3-continued

| Cellular Activities of Selected Compounds | | | | |
|---|---|---|---|---|
| Compound No. | Axl $IC_{50}$ (nM) | Mer $IC_{50}$ (nM) | c-Met $IC_{50}$ (nM) | KDR $IC_{50}$ (nM) |
| 256 | A | A | A | A |
| 257 | A | A | A | A |
| 258 | A | A | A | A |
| 259 | A | A | A | A |
| 260 | A | A | A | A |
| 261 | A | B | C | C |
| 262 | A | A | C | C |
| 263 | A | B | C | C |
| 264 | A | A | A | C |
| 265 | NT | C | C | C |
| 266 | NT | A | A | C |
| 269 | C | A | A | C |
| 275 | NT | A | A | C |
| 297 | A | A | A | C |
| 298 | A | A | C | C |
| 299 | A | A | A | C |
| 300 | NT | A | A | B |
| 301 | NT | A | A | C |
| 302 | A | A | A | A |
| 303 | A | A | B | C |
| 304 | A | A | A | C |
| 305 | A | A | A | C |
| 306 | A | A | A | C |
| 307 | A | A | A | B |
| 308 | NT | A | A | C |
| 309 | A | A | A | C |
| 310 | A | A | C | C |
| 311 | NT | A | A | NT |
| 312 | NT | A | A | NT |
| 313 | NT | A | B | NT |
| 314 | NT | A | A | NT |
| 315 | NT | A | A | NT |
| 316 | NT | A | A | NT |
| 324 | A | A | A | A |
| 325 | NT | A | C | C |
| 326 | NT | A | A | A |
| 327 | A | A | A | B |
| 328 | A | A | A | C |
| 329 | A | A | A | C |
| 330 | A | A | A | C |
| 331 | A | A | A | C |
| 332 | A | A | A | A |
| 333 | A | A | A | B |
| 334 | A | A | A | C |
| 337 | A | A | A | A |

NT means not tested

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound of Formula (I):

(I)

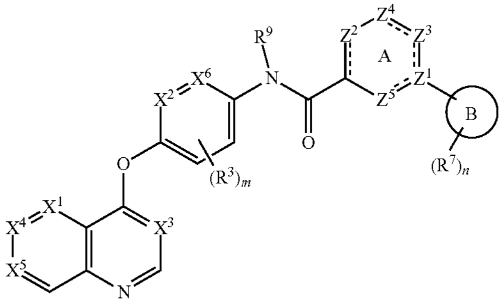

or a pharmaceutically acceptable salt or stereoisomer thereof, wherein:

ring B is a 5-membered heteroaryl having 1, 2 or 3 heteroatoms as ring members selected from N, O and S, a 9-10-membered heteroaryl having 1, 2 or 3 heteroatoms as ring members selected from N, O and S, or a 6-membered heteroaryl having 1 or 2 nitrogen atoms as ring members;

$X^1$ is N;

$X^2$ is N, CH, or $CR^3$;

$X^3$ is N or CH;

$X^4$ is N or $CR^1$;

$X^5$ is N or $CR^2$;

$X^6$ is N, CH, or $CR^3$;

no more than one of $X^1$, $X^4$, and $X^5$ is N;

$Z^1$ is N, C, or CH;

$Z^2$ is N, $NR^{13}$, —C(═O)—, or $CR^5$;

$Z^3$ is N, $NR^{12}$, $CR^6$, —C(═O)—, or —C(═S)—;

$Z^4$ is N, $NR^4$, $CR^{10}$, —C(═O)—, or a bond;

$Z^5$ is N, $COR^8$, —C(═O)—, or $CR^{14}$;

only one or two of $Z^1$, $Z^2$, $Z^3$, and $Z^4$ contain a N;

no more than two of $Z^2$, $Z^3$, $Z^4$, and $Z^5$ are —C(═O)—;

$\overset{\cdot\cdot\cdot}{—}$ is a single bond or a double bond;

$R^1$ and $R^2$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, and (4-14 membered heterocycloalkyl)-$C_{1-4}$ alkylene- of $R^1$ and $R^2$ are each optionally substituted with 1, 2, 3, 4, or 5 independently selected $R^b$ substituents;

each $R^3$ is independently selected from halo, OH, CN, —C(O)OH, —C(O)NH($C_{1-6}$ alkyl), —$SO_2$($C_{1-6}$ alkyl), —$SO_2$NH($C_{1-6}$ alkyl), $C_1$-$C_6$ alkyl, $C_1$-$C_6$ alkoxy, $C_1$-$C_6$ haloalkoxy, $NH_2$, —NH($C_1$-$C_6$ alkyl), —N($C_1$-$C_6$ alkyl)$_2$, and $C_3$-$C_6$ cycloalkyl, wherein the $C_1$-$C_6$ alkyl, $C_1$-$C_6$ alkoxy, —NH($C_1$-$C_6$alkyl), —N($C_1$-$C_6$ alkyl)$_2$, and $C_3$-$C_6$ cycloalkyl of $R^3$ are each optionally substituted with 1, 2, or 3 independently selected $R^g$ substituents;

$R^4$, $R^{12}$, and $R^{13}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, N═C($NR^aR^a$)$_2$, $NR^aC$(═$NR^a$)$R^a$, $NR^aC(O)OR^a$, $NR^aC(O)NR^aR^a$, C(═$NR^a$)$R^a$, C(═NOH)$R^a$, C(═NOH)$NR^a$, C(═NCN)$NR^aR^a$, $NR^aC$(═NCN)$NR^aR^a$, C(═$NR^a$)$NR^aR^a$, $NR^aC$(═$NR^a$)$NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, and (4-14 membered heterocycloalkyl)-$C_{1-4}$ alkylene- of $R^4$, $R^{12}$, and $R^{13}$ are each optionally substituted with 1, 2, 3, 4, or 5 independently selected $R^b$ substituents;

$R^5$, $R^6$, and $R^{10}$ are each independently H, halo, $C_{1-6}$ alkyl, $C_{2-6}$ alkenyl, $C_{1-6}$ alkoxy, $C_{1-6}$ alkylthio, CN, $C_{1-4}$ haloalkyl, $C_{1-4}$ haloalkoxy, OH, $C_{1-4}$alkyl-C(O)—, $C_{1-4}$alkyl-OC(O)—, —C(O)NH($C_{1-4}$ alkyl), $NH_2$, —NH$Cl_{1-4}$alkyl, or —N($C_{1-4}$ alkyl)$_2$, wherein the $C_{1-6}$ alkyl, $C_{2-6}$ alkenyl, $C_{1-6}$ alkoxy, $C_{1-6}$ alkylthio, $C_{1-6}$ alkyl-C(O)—, and $C_{1-4}$ alkyl of —NH($C_{1-4}$alkyl) or —N($C_{1-4}$ alkyl)$_2$ of $R^5$, $R^6$, and $R^{10}$ are each optionally substituted with 1 or 2 independently selected $R^9$ substituents;

each $R^7$ is independently selected from halo, OH, $C(O)OR^a$, $C(O)R^a$, $C(O)NR^aR^a$, CN, $NH_2$, —NH($C_1$-$C_6$ alkyl), —N($C_1$-$C_6$ alkyl)$_2$, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, $C(O)NR^aR^a$, $NR^aC(O)R^a$, $NR^aC(O)NR^aR^a$, $SO_2R^a$, $NR^aS(O)_2R^a$, $NR^aS(O)_2NR^aR^a$, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene-; wherein the $C_1$-$C_6$ alkyl, $C_1$-$C_6$ alkoxy, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene- of $R^7$ are each optionally substituted with 1, 2, or 3 independently selected $R^f$ substituents;

$R^8$ is H, $C_{1-6}$ alkyl optionally substituted with 1 or 2 $R^g$ substituents, or a hydroxy protecting group;

$R^9$ is H or $C_{1-6}$ alkyl optionally substituted with 1, 2, or 3 independently selected $R^g$ substituents;

$R^{14}$ is H, halo, CN, or $C_{1-6}$ alkyl optionally substituted with 1 or 2 $R^g$ substituents;

or $R^{13}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^4$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{10}$ and $R^5$ taken together with the atoms to which they are attached form fused $C_{3-7}$ cycloalkyl, 4- to 6-membered fused heterocycloalkyl, fused 5- or 6-membered heteroaryl or fused phenyl, wherein the fused $C_{3-7}$ cycloalkyl, 4- to 6-membered fused heterocycloalkyl, 5- or 6-membered heteroaryl, or fused phenyl is each optionally substituted with 1 or 2 independently selected $R^g$ substituents and wherein one or two ring carbon atoms of the fused $C_{3-7}$ cycloalkyl or fused heterocycloalkyl are optionally replaced by a carbonyl group;

or when $Z^4$ is a bond, $R^{13}$ and $R^6$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{12}$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^6$ and $R^5$ taken together with the atoms to which they are attached form fused $C_{3-7}$ cycloalkyl, 4- to 6-membered fused heterocycloalkyl, 5- to 6-membered fused heteroaryl, or fused phenyl, wherein the fused $C_{3-7}$ cycloalkyl, 4- to 6-membered fused heterocycloalkyl, 5- to 6-membered fused heteroaryl, and fused phenyl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

or $R^{12}$ and $R^{10}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^4$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^6$ and $R^{10}$ taken together with the atoms to which they are attached form fused $C_{3-7}$ cycloalkyl, 4- to 6-membered fused heterocycloalkyl, 5- to 6-membered fused heteroaryl, or fused heteroaryl, wherein the fused $C_{3-7}$ cycloalkyl, 4- to 6-membered fused heterocycloalkyl, 5- to 6-membered fused heteroaryl, and fused heteroaryl are each optionally substituted with 1 or 2 independently selected $R^g$ substituents and wherein one or two ring carbon atoms of the fused $C_{3-7}$ cycloalkyl or 4- to 6-membered fused heterocycloalkyl are optionally replaced by a carbonyl;

each $R^a$ is independently selected from the group consisting of H, CN, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_1$ cycloalkyl, 5-14 membered heteroaryl, 4-14 membered heterocycloalkyl, $C_6$-$C_{10}$ aryl-$C_1$-$C_4$ alkylene-, $C_3$-$C_1$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene-, wherein the $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_1$ cycloalkyl, 5-14 membered heteroaryl, 4-14 membered heterocycloalkyl, $C_6$-$C_{10}$ aryl-$C_1$-$C_4$ alkylene-, $C_3$-$C_1$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene- of $R^a$ are each optionally substituted with 1, 2, 3, 4, or 5 independently selected $R^d$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^b$ is independently selected from the group consisting of halo, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_6$-$C_{10}$ aryl, $C_3$-$C_1$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C({=}NOH)R^c$, $C({=}NOH)NR^c$, $C({=}NCN)NR^cR^c$, $NR^cC({=}NCN)NR^cR^c$, $C({=}NR^c)NR^cR^c$, $NR^cC({=}NR^c)NR^cR^c$, $NHR^c$, $NR^cR^c$, $NR^cC(O)R^c$, $NR^cC({=}NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $Si(R^c)_3$, $P(O)R^cR^c$, $P(O)(OR^c)(OR^c)$, $B(OH)_2$, $B(OR^c)_2$, and $S(O)_2NR^cR^c$; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^b$ are each further optionally substituted with 1, 2, or 3 independently selected $R^d$ substituents;

each $R^c$ is independently selected from the group consisting of H, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_1$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene-; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^c$ are each optionally substituted with 1, 2, 3, 4, or 5 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^d$ is independently selected from the group consisting of $C_1$-$C_6$ alkyl, $C_1$-$C_6$ haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C({=}NR^e)NR^eR^e$, $NR^eC({=}NR^e)NR^eR^e$, $NR^eC({=}NOH)NR^eR^e$, $NR^eC({=}NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_1$-$C_6$ alkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^d$ are each optionally substituted with 1, 2, or 3 independently selected $R^f$ substituents;

each $R^e$ is independently selected from the group consisting of H, $C_1$-$C_6$ alkyl, $C_1$-$C_6$ alkoxy, $C_3$-$C_6$ cycloalkyl, $C_3$-$C_6$ cycloalkyl-$C_1$-$C_4$ alkylene-, $C_6$-$C_{10}$ aryl, $C_6$-$C_{10}$ aryl-$C_1$-$C_4$ alkylene-, 5- or 6-membered heteroaryl, (5- or 6-membered heteroaryl)-$C_1$-$C_4$ alkylene-, 4-7-membered heterocycloalkyl, (4-7-membered heterocycloalkyl)-$C_1$-$C_4$ alkylene-, $C_1$-$C_6$ haloalkyl, $C_1$-$C_6$ haloalkoxy, $C_2$-$C_4$ alkenyl, and $C_2$-$C_4$ alkynyl, wherein the $C_1$-$C_6$ alkyl, $C_1$-$C_6$ alkoxy, $C_3$-$C_6$ cycloalkyl, $C_6$-$C_{10}$ aryl, 5 or 6-membered heteroaryl, 4-7-membered heterocycloalkyl, $C_6$-$C_{10}$ aryl-$C_1$-$C_4$ alkylene-, (5- or 6-membered heteroaryl)-$C_1$-$C_4$ alkylene-, (4-7-membered heterocycloalkyl)-$C_1$-$C_4$ alkylene-, $C_2$-$C_4$ alkenyl, and $C_2$-$C_4$ alkynyl of $R^e$ are each optionally substituted with 1, 2, or 3 $R^f$ substituents;

or any two $R^e$ substituents together with the nitrogen atom to which they are attached form a 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo, OH, CN, C(O)OH, $NH_2$, —NH($C_1$-$C_6$ alkyl), —N($C_1$-$C_6$ alkyl)$_2$, $C_1$-$C_6$ alkyl, vinyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl, wherein the $C_1$-$C_6$ alkyl, $C_1$-$C_6$ alkoxy, $C_1$-$C_6$ alkylthio, phenyl, $C_3$-$C_6$ cycloalkyl, 4-6 membered heterocycloalkyl, and 5-6 membered heteroaryl of $R^f$ are each optionally substituted with 1, 2, or 3 substituents selected from halo, OH, CN, —C(O)OH, —$NH_2$, $C_1$-$C_4$ alkyl, $C_1$-$C_4$ alkoxy, $C_1$-$C_4$ haloalkyl, $C_1$-$C_4$ haloalkoxy, phenyl, $C_3$-$C_{10}$ cycloalkyl, 5-6 membered heteroaryl, and 4-6 membered heterocycloalkyl;

each $R^g$ is independently selected from the group consisting of halo, OH, CN, C(O)OH, —C(O)O—$C_1$-$C_4$ alkyl, $NH_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl;

a ring nitrogen atom in Formula (I) is optionally oxidized;

the subscript m is 0, 1 or 2; and the subscript n is 0, 1, 2, 3 or 4.

2. The compound of claim 1, wherein:

ring B is 6-membered heteroaryl having 1 or 2 nitrogen atoms as ring members.

3. The compound of claim 1, having formula (Ia):

(Ia)

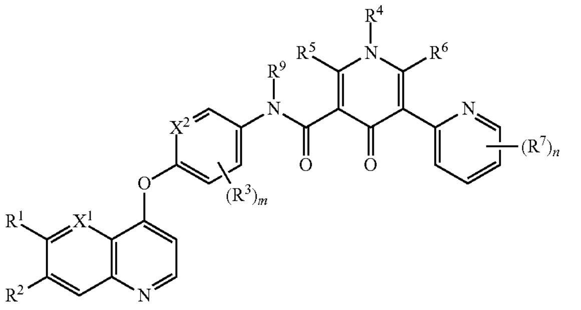

or a pharmaceutically acceptable salt or stereoisomer thereof.

4. The compound of claim 1, having formula (Ia-1):

(Ia-1)

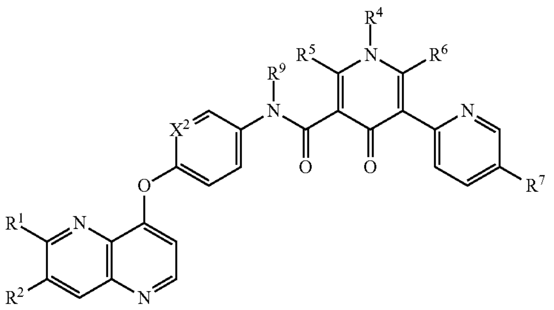

or a pharmaceutically acceptable salt or stereoisomer thereof.

5. The compound of claim 1, having formula (Ib):

(Ib)

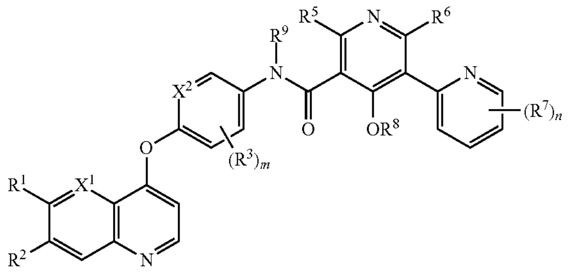

or a pharmaceutically acceptable salt or stereoisomer thereof.

6. The compound of claim 1, having formula (Ib-1):

(Ib-1)

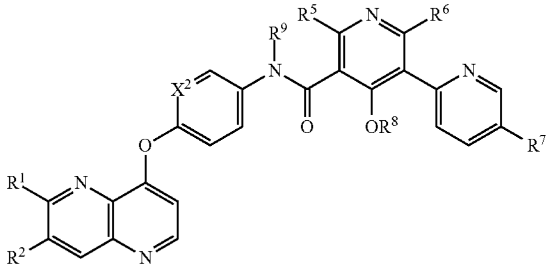

or a pharmaceutically acceptable salt or stereoisomer thereof.

7. The compound of claim 1, having formula (Ic):

(Ic)

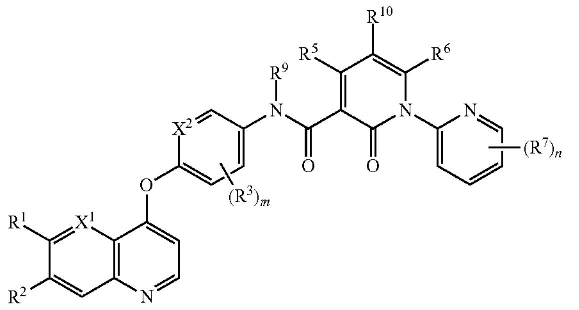

or a pharmaceutically acceptable salt or stereoisomer thereof.

8. The compound of claim 1, having formula (Ic-1):

(Ic-1)

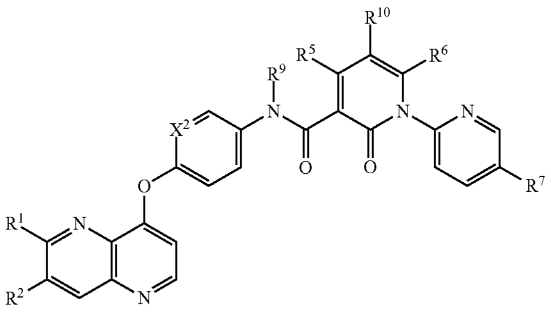

or a pharmaceutically acceptable salt or stereoisomer thereof.

9. The compound of claim 1, having formula (Id):

(Id)

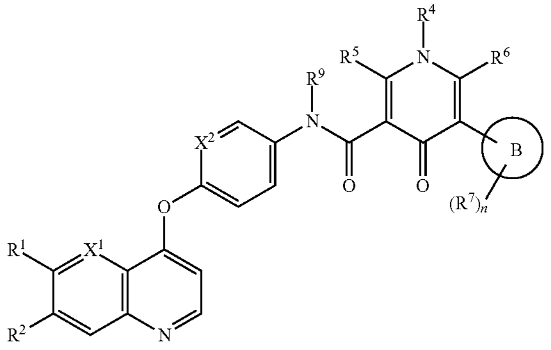

or a pharmaceutically acceptable salt or stereoisomer thereof.

10. The compound of claim 1, having formula (Ie):

(Ie)

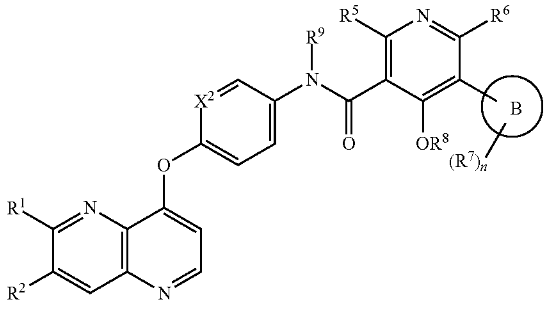

or a pharmaceutically acceptable salt or stereoisomer thereof.

11. The compound of claim 1, having formula (If):

(If)

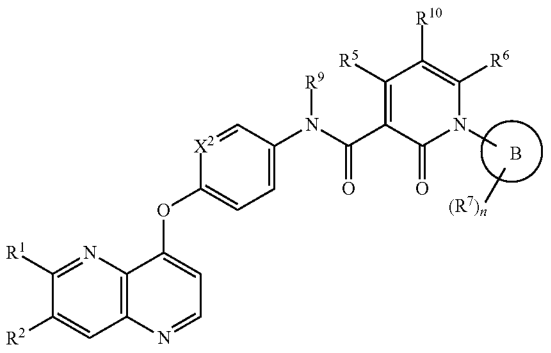

or a pharmaceutically acceptable salt or stereoisomer thereof.

12. The compound of claim 1, having formula (Ij):

(Ij)

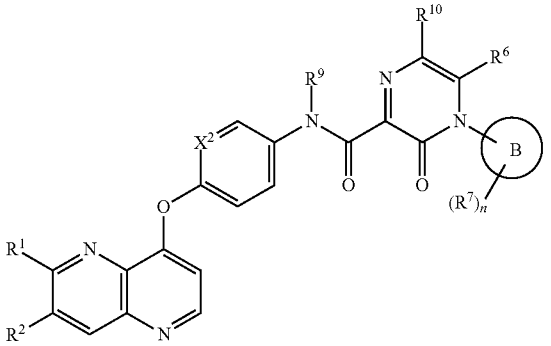

or a pharmaceutically acceptable salt or stereoisomer thereof.

13. The compound of claim 1, having formula (Ik):

(Ik)

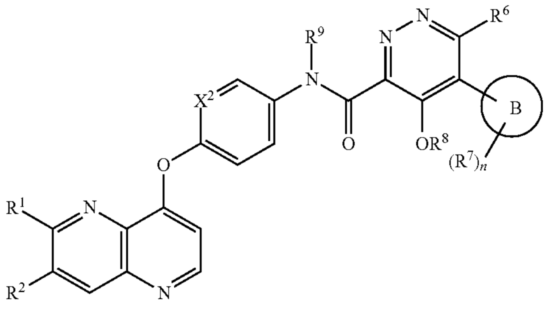

or a pharmaceutically acceptable salt or stereoisomer thereof.

14. The compound of claim 1, having formula (Im):

(Im)

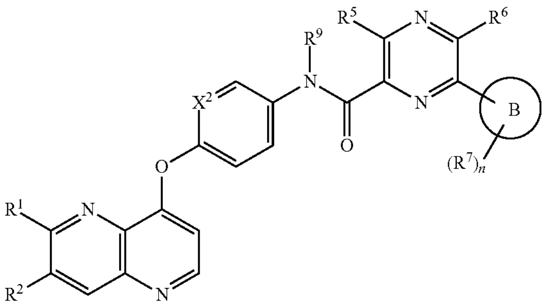

or a pharmaceutically acceptable salt or stereoisomer thereof.

15. The compound of claim 1, selected from

N-[4-[(6,7-dimethoxy-1,5-naphthyridin-4-yl)oxy]-3-fluorophenyl]-1-(5-fluoropyridin-2-yl)-4-methyl-2-oxopyridine-3-carboxamide;

N-[4-[(6,7-dimethoxy-1,5-naphthyridin-4-yl)oxy]-3-fluorophenyl]-1-(5-fluoropyridin-2-yl)-2-oxopyridine-3-carboxamide;

N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide;

N-[4-[(6,7-dimethoxy-1,5-naphthyridin-4-yl)oxy]phenyl]-1-(5-fluoropyridin-2-yl)-6-methyl-2-oxopyridine-3-carboxamide;

N-[3-fluoro-4-[(7-methoxy-1,5-naphthyridin-4-yl)oxy]phenyl]-1-(5-fluoropyridin-2-yl)-6-methyl-2-oxopyridine-3-carboxamide;

1-(5-fluoropyridin-2-yl)-N-[4-[(7-methoxy-1,5-naphthyridin-4-yl)oxy]phenyl]-6-methyl-2-oxopyridine-3-carboxamide;

N-[3-fluoro-4-[(6-methoxy-1,5-naphthyridin-4-yl)oxy]phenyl]-1-(5-fluoropyridin-2-yl)-6-methyl-2-oxopyridine-3-carboxamide;

N-[3-fluoro-4-(1,5-naphthyridin-4-yloxy)phenyl]-1-(5-fluoropyridin-2-yl)-6-methyl-2-oxopyridine-3-carboxamide;

N-[3-fluoro-4-[[6-methoxy-7-(2-methoxyethoxy)-1,5-naphthyridin-4-yl]oxy]phenyl]-1-(5-fluoropyridin-2-yl)-6-methyl-2-oxopyridine-3-carboxamide;

N-[4-[(6,7-dimethoxy-1,5-naphthyridin-4-yl)oxy]-3-fluorophenyl]-1-(5-fluoro-3-methylpyridin-2-yl)-6-methyl-2-oxopyridine-3-carboxamide;

N-[3-fluoro-4-[(7-methoxy-1,5-naphthyridin-4-yl)oxy]phenyl]-1-(5-fluoro-3-methylpyridin-2-yl)-6-methyl-2-oxopyridine-3-carboxamide;

N-[3-fluoro-4-[(6-methoxy-1,5-naphthyridin-4-yl)oxy]phenyl]-1-(5-fluoro-3-methylpyridin-2-yl)-6-methyl-2-oxopyridine-3-carboxamide;

5-bromo-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide;

5-cyano-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide;

5-acetyl-N-[4-[(6,7-dimethoxy-1,5-naphthyridin-4-yl)oxy]-3-fluorophenyl]-1-(5-fluoropyridin-2-yl)-6-methyl-2-oxopyridine-3-carboxamide;

N-[4-[(6,7-dimethoxy-1,5-naphthyridin-4-yl)oxy]-3-fluorophenyl]-5-(5-fluoropyridin-2-yl)-4-hydroxy-2-methylpyridine-3-carboxamide;

N-[4-[(6,7-dimethoxy-1,5-naphthyridin-4-yl)oxy]-3-fluorophenyl]-4-hydroxy-2-methyl-5-pyridin-2-ylpyridine-3-carboxamide;

N-[3-fluoro-4-[(7-methoxy-1,5-naphthyridin-4-yl)oxy]phenyl]-4-hydroxy-2-methyl-5-pyridin-2-ylpyridine-3-carboxamide;

N-[4-[(6,7-dimethoxy-1,5-naphthyridin-4-yl)oxy]-3-fluorophenyl]-5-(5-fluoropyridin-2-yl)-1,2-dimethyl-4-oxopyridine-3-carboxamide;

N-[4-[(6,7-dimethoxy-1,5-naphthyridin-4-yl)oxy]phenyl]-5-(5-fluoropyridin-2-yl)-1,2-dimethyl-4-oxopyridine-3-carboxamide;

N-[3-fluoro-4-[(7-methoxy-1,5-naphthyridin-4-yl)oxy]phenyl]-5-(5-fluoropyridin-2-yl)-1,2-dimethyl-4-oxopyridine-3-carboxamide;

N-[4-[(6,7-dimethoxy-1,5-naphthyridin-4-yl)oxy]-3-fluorophenyl]-5-(5-fluoropyridin-2-yl)-4-hydroxy-6-methylpyridine-3-carboxamide;

N-[4-[(6,7-dimethoxy-1,5-naphthyridin-4-yl)oxy]phenyl]-5-(5-fluoropyridin-2-yl)-1,6-dimethyl-4-oxopyridine-3-carboxamide;

N-[4-[(6,7-dimethoxy-1,5-naphthyridin-4-yl)oxy]-3-fluorophenyl]-5-(furan-2-yl)-4-hydroxy-6-methylpyridine-3-carboxamide;

N-[4-[(6,7-dimethoxy-1,5-naphthyridin-4-yl)oxy]-3-fluorophenyl]-4-hydroxy-6-methyl-5-thiophen-2-ylpyridine-3-carboxamide;

N-[4-[(6,7-dimethoxy-1,5-naphthyridin-4-yl)oxy]-3-fluorophenyl]-4-hydroxy-6-methyl-5-(4-methylthiophen-2-yl)pyridine-3-carboxamide;

N-[4-[(6,7-dimethoxy-1,5-naphthyridin-4-yl)oxy]-3-fluorophenyl]-4-hydroxy-6-methyl-5-(5-methylfuran-2-yl)pyridine-3-carboxamide;

N-[4-[(6,7-dimethoxy-1,5-naphthyridin-4-yl)oxy]-3-fluorophenyl]-4-hydroxy-6-methyl-5-thiophen-3-ylpyridine-3-carboxamide;

N-[4-[(6,7-dimethoxy-1,5-naphthyridin-4-yl)oxy]-3-fluorophenyl]-4-hydroxy-6-methyl-5-(5-methylthiophen-2-yl)pyridine-3-carboxamide;

N-[4-[(6,7-dimethoxy-1,5-naphthyridin-4-yl)oxy]-3-fluorophenyl]-5-(furan-3-yl)-4-hydroxy-6-methylpyridine-3-carboxamide;

N-[3-fluoro-4-[(7-methoxy-1,5-naphthyridin-4-yl)oxy]phenyl]-5-(furan-2-yl)-4-hydroxy-6-methylpyridine-3-carboxamide;

N-[3-fluoro-4-[(7-methoxy-1,5-naphthyridin-4-yl)oxy]phenyl]-4-hydroxy-6-methyl-5-(5-methylfuran-2-yl)pyridine-3-carboxamide;

N-[3-fluoro-4-[(7-methoxy-1,5-naphthyridin-4-yl)oxy]phenyl]-4-hydroxy-6-methyl-5-thiophen-3-ylpyridine-3-carboxamide;

N-[3-fluoro-4-[(7-methoxy-1,5-naphthyridin-4-yl)oxy]phenyl]-5-(furan-3-yl)-4-hydroxy-6-methylpyridine-3-carboxamide;

N-[3-fluoro-4-[(7-methoxy-1,5-naphthyridin-4-yl)oxy]phenyl]-4-hydroxy-6-methyl-5-thiophen-2-ylpyridine-3-carboxamide;

N-[3-fluoro-4-[(7-methoxy-1,5-naphthyridin-4-yl)oxy]phenyl]-4-hydroxy-6-methyl-5-(5-methylthiophen-2-yl)pyridine-3-carboxamide;

N-[3-fluoro-4-[(7-methoxy-1,5-naphthyridin-4-yl)oxy]phenyl]-4-hydroxy-6-methyl-5-(4-methylthiophen-2-yl)pyridine-3-carboxamide;

N-[4-[(6,7-dimethoxy-1,5-naphthyridin-4-yl)oxy]-3-fluorophenyl]-4-hydroxy-6-methyl-5-(3-methylthiophen-2-yl)pyridine-3-carboxamide;

N-[4-[(6,7-dimethoxy-1,5-naphthyridin-4-yl)oxy]-3-fluorophenyl]-4-hydroxy-6-methyl-5-(2-methylpyrazol-3-yl)pyridine-3-carboxamide;

N-[4-[(6,7-dimethoxy-1,5-naphthyridin-4-yl)oxy]-3-fluorophenyl]-4-hydroxy-6-methyl-5-[2-methyl-5-(trifluoromethyl)pyrazol-3-yl]pyridine-3-carboxamide;

N-[4-[(6,7-dimethoxy-1,5-naphthyridin-4-yl)oxy]-3-fluorophenyl]-4-hydroxy-2,6-dimethyl-5-thiophen-3-ylpyridine-3-carboxamide;

N-[4-[(6,7-dimethoxy-1,5-naphthyridin-4-yl)oxy]-3-fluorophenyl]-4-hydroxy-2,6-dimethyl-5-thiophen-2-ylpyridine-3-carboxamide;

N-[4-[(6,7-dimethoxy-1,5-naphthyridin-4-yl)oxy]-3-fluorophenyl]-4-hydroxy-2,6-dimethyl-5-(2-methylpyrazol-3-yl)pyridine-3-carboxamide;

N-[4-[(6,7-dimethoxy-1,5-naphthyridin-4-yl)oxy]-3-fluorophenyl]-5-(2,5-dimethylpyrazol-3-yl)-4-hydroxy-2,6-dimethylpyridine-3-carboxamide;

N-[4-[(6,7-dimethoxy-1,5-naphthyridin-4-yl)oxy]-3-fluorophenyl]-4-hydroxy-2,6-dimethyl-5-(5-methylfuran-2-yl)pyridine-3-carboxamide;

N-[4-[(6,7-dimethoxy-1,5-naphthyridin-4-yl)oxy]-3-fluorophenyl]-4-hydroxy-2,6-dimethyl-5-(5-methylthiophen-2-yl)pyridine-3-carboxamide;

N-[4-[(6,7-dimethoxy-1,5-naphthyridin-4-yl)oxy]-3-fluorophenyl]-5-(furan-3-yl)-4-hydroxy-2,6-dimethylpyridine-3-carboxamide;

N-[4-[(6,7-dimethoxy-1,5-naphthyridin-4-yl)oxy]-3-fluorophenyl]-4-hydroxy-2-(methoxymethyl)-6-methyl-5-thiophen-2-ylpyridine-3-carboxamide;

N-[4-[(6,7-dimethoxy-1,5-naphthyridin-4-yl)oxy]-3-fluorophenyl]-5-(furan-2-yl)-4-hydroxy-2-(methoxymethyl)-6-methylpyridine-3-carboxamide;

N-[4-[(6,7-dimethoxy-1,5-naphthyridin-4-yl)oxy]-3-fluorophenyl]-4-hydroxy-2-(methoxymethyl)-6-methyl-5-(5-methylfuran-2-yl)pyridine-3-carboxamide;

N-[3-fluoro-4-[(6-methoxy-1,5-naphthyridin-4-yl)oxy]phenyl]-5-(furan-2-yl)-4-hydroxy-6-methylpyridine-3-carboxamide;

N-[4-[(6,7-dimethoxy-1,5-naphthyridin-4-yl)oxy]-3-fluorophenyl]-5-(furan-2-yl)-4-hydroxy-2-methylpyridine-3-carboxamide;

N-[4-[(6,7-dimethoxy-1,5-naphthyridin-4-yl)oxy]-3-fluorophenyl]-4-hydroxy-2-methyl-5-(5-methylfuran-2-yl)pyridine-3-carboxamide;

N-[4-[(6,7-dimethoxy-1,5-naphthyridin-4-yl)oxy]-3-fluorophenyl]-5-(5-formylfuran-2-yl)-4-hydroxy-2-methylpyridine-3-carboxamide;

N-[4-[(6,7-dimethoxy-1,5-naphthyridin-4-yl)oxy]-3-fluorophenyl]-5-(furan-3-yl)-4-hydroxy-2-methylpyridine-3-carboxamide;

N-[4-[(6,7-dimethoxy-1,5-naphthyridin-4-yl)oxy]-3-fluorophenyl]-4-hydroxy-2-methyl-5-thiophen-2-ylpyridine-3-carboxamide;

N-[4-[(6,7-dimethoxy-1,5-naphthyridin-4-yl)oxy]-3-fluorophenyl]-4-hydroxy-2-methyl-5-(5-methylthiophen-2-yl)pyridine-3-carboxamide;

N-[4-[(6,7-dimethoxy-1,5-naphthyridin-4-yl)oxy]-3-fluorophenyl]-4-hydroxy-2-methyl-5-(4-methylthiophen-2-yl)pyridine-3-carboxamide;

N-[4-[(6,7-dimethoxy-1,5-naphthyridin-4-yl)oxy]-3-fluorophenyl]-4-hydroxy-2-methyl-5-(3-methylthiophen-2-yl)pyridine-3-carboxamide;

N-[4-[(6,7-dimethoxy-1,5-naphthyridin-4-yl)oxy]-3-fluorophenyl]-4-hydroxy-2-methyl-5-thiophen-3-ylpyridine-3-carboxamide;

N-[3-fluoro-4-[(6-methoxy-1,5-naphthyridin-4-yl)oxy]phenyl]-4-hydroxy-6-methyl-5-thiophen-2-ylpyridine-3-carboxamide;

5-(furan-2-yl)-4-hydroxy-N-[4-[(7-methoxy-1,5-naphthyridin-4-yl)oxy]phenyl]-6-methylpyridine-3-carboxamide;

N-[4-[(6,7-dimethoxy-1,5-naphthyridin-4-yl)oxy]-3-fluorophenyl]-5-(furan-2-yl)-4-hydroxy-2,6-dimethylpyridine-3-carboxamide;

N-[4-[(6,7-dimethoxy-1,5-naphthyridin-4-yl)oxy]-3-fluorophenyl]-5-(2,5-dimethylpyrazol-3-yl)-4-hydroxy-6-methylpyridine-3-carboxamide;

N-[4-[(6,7-dimethoxy-1,5-naphthyridin-4-yl)oxy]-3-fluorophenyl]-4-hydroxy-2,6-dimethyl-5-(4-methylthiophen-2-yl)pyridine-3-carboxamide;

N-[4-[(6,7-dimethoxy-1,5-naphthyridin-4-yl)oxy]-3-fluorophenyl]-4-hydroxy-2,6-dimethyl-5-[2-methyl-5-(trifluoromethyl)pyrazol-3-yl]pyridine-3-carboxamide;

N-[4-[(6,7-dimethoxy-1,5-naphthyridin-4-yl)oxy]-3-fluorophenyl]-4-hydroxy-2,6-dimethyl-5-(3-methylthiophen-2-yl)pyridine-3-carboxamide;

N-[4-[(6,7-dimethoxy-1,5-naphthyridin-4-yl)oxy]-3-fluorophenyl]-4-hydroxy-6-methyl-5-(1,2-oxazol-4-yl)pyridine-3-carboxamide;

N-[4-[(6,7-dimethoxy-1,5-naphthyridin-4-yl)oxy]-3-fluorophenyl]-4-hydroxy-6-methyl-5-(1,3-thiazol-5-yl)pyridine-3-carboxamide;

N-[4-[(6,7-dimethoxy-1,5-naphthyridin-4-yl)oxy]-3-fluorophenyl]-4-hydroxy-6-methyl-5-(1,3-thiazol-4-yl)pyridine-3-carboxamide;

N-[4-[(6,7-dimethoxy-1,5-naphthyridin-4-yl)oxy]-3-fluorophenyl]-4-hydroxy-6-methyl-5-(1,3-thiazol-2-yl)pyridine-3-carboxamide;

N-[4-[(6,7-dimethoxy-1,5-naphthyridin-4-yl)oxy]-3-fluorophenyl]-5-(5-ethylfuran-2-yl)-4-hydroxy-2,6-dimethylpyridine-3-carboxamide;

N-[4-[(6,7-dimethoxy-1,5-naphthyridin-4-yl)oxy]-3-fluorophenyl]-4-hydroxy-2,6-dimethyl-5-(5-propan-2-ylfuran-2-yl)pyridine-3-carboxamide;

N-[4-[(6,7-dimethoxy-1,5-naphthyridin-4-yl)oxy]-3-fluorophenyl]-5-(5-ethenylfuran-2-yl)-4-hydroxy-6-methylpyridine-3-carboxamide;

N-[4-[(6,7-dimethoxy-1,5-naphthyridin-4-yl)oxy]-3-fluorophenyl]-4-hydroxy-6-methyl-5-(5-prop-1-en-2-ylfuran-2-yl)pyridine-3-carboxamide;

N-[4-[(6,7-dimethoxy-1,5-naphthyridin-4-yl)oxy]-3-fluorophenyl]-5-(5-ethylfuran-2-yl)-4-hydroxy-6-methylpyridine-3-carboxamide;

N-[4-[(6,7-dimethoxy-1,5-naphthyridin-4-yl)oxy]-3-fluorophenyl]-4-hydroxy-6-methyl-5-(5-propan-2-ylfuran-2-yl)pyridine-3-carboxamide;

N-[4-[(6,7-dimethoxy-1,5-naphthyridin-4-yl)oxy]-3-fluorophenyl]-4-hydroxy-6-methyl-5-(5-prop-2-enylfuran-2-yl)pyridine-3-carboxamide;

N-[4-[(6,7-dimethoxy-1,5-naphthyridin-4-yl)oxy]-3-fluorophenyl]-5-(furan-2-yl)-1,2,6-trimethyl-4-oxopyridine-3-carboxamide;

5-(5-cyclopropylfuran-2-yl)-N-[4-[(6,7-dimethoxy-1,5-naphthyridin-4-yl)oxy]-3-fluorophenyl]-4-hydroxy-6-methylpyridine-3-carboxamide;

5-(5-cyclopropylfuran-2-yl)-N-[4-[(6,7-dimethoxy-1,5-naphthyridin-4-yl)oxy]-3-fluorophenyl]-4-hydroxy-2,6-dimethylpyridine-3-carboxamide;

5-(furan-2-yl)-N-[4-[(7-methoxy-1,5-naphthyridin-4-yl)oxy]phenyl]-1,2,6-trimethyl-4-oxopyridine-3-carboxamide;

N-[3-fluoro-4-[(7-methoxy-1,5-naphthyridin-4-yl)oxy]phenyl]-5-(furan-2-yl)-1,2,6-trimethyl-4-oxopyridine-3-carboxamide;

N-[4-[(6,7-dimethoxy-1,5-naphthyridin-4-yl)oxy]-2,5-difluorophenyl]-5-(furan-2-yl)-1,2,6-trimethyl-4-oxopyridine-3-carboxamide;

N-[4-[(6,7-dimethoxy-1,5-naphthyridin-4-yl)oxy]phenyl]-5-(furan-2-yl)-1,2,6-trimethyl-4-oxopyridine-3-carboxamide;

N-[4-[(7-methoxy-1,5-naphthyridin-4-yl)oxy]phenyl]-1,2,6-trimethyl-4-oxo-5-thiophen-2-ylpyridine-3-carboxamide;

N-[3-fluoro-4-[(7-methoxy-1,5-naphthyridin-4-yl)oxy]phenyl]-1,2,6-trimethyl-4-oxo-5-thiophen-2-ylpyridine-3-carboxamide;

N-[4-[(6,7-dimethoxy-1,5-naphthyridin-4-yl)oxy]phenyl]-1,2,6-trimethyl-4-oxo-5-thiophen-2-ylpyridine-3-carboxamide;

N-[4-[(6,7-dimethoxy-1,5-naphthyridin-4-yl)oxy]-3-fluorophenyl]-1,2,6-trimethyl-4-oxo-5-thiophen-2-ylpyridine-3-carboxamide;

N-[4-[(6,7-dimethoxy-1,5-naphthyridin-4-yl)oxy]-3-fluorophenyl]-4-hydroxy-2-(methoxymethyl)-6-methyl-5-pyridin-2-ylpyridine-3-carboxamide;

N-[4-[(6,7-dimethoxy-1,5-naphthyridin-4-yl)oxy]-3-fluorophenyl]-4-hydroxy-2-(methoxymethyl)-6-methyl-5-(3-methylpyridin-2-yl)pyridine-3-carboxamide;

N-[4-[(6,7-dimethoxy-1,5-naphthyridin-4-yl)oxy]-3-fluorophenyl]-4-hydroxy-2-(methoxymethyl)-6-methyl-5-(6-methylpyridin-2-yl)pyridine-3-carboxamide;

N-[4-[(6,7-dimethoxy-1,5-naphthyridin-4-yl)oxy]-3-fluorophenyl]-4-hydroxy-2-(methoxymethyl)-6-methyl-5-(2-methylpyridin-4-yl)pyridine-3-carboxamide;

N-[4-[(6,7-dimethoxy-1,5-naphthyridin-4-yl)oxy]-3-fluorophenyl]-5-(5-fluoro-3-methylpyridin-2-yl)-4-hydroxy-2-methylpyridine-3-carboxamide;

N-[4-[(6,7-dimethoxy-1,5-naphthyridin-4-yl)oxy]-3-fluorophenyl]-1-(5-ethoxypyridin-2-yl)-6-methyl-2-oxopyridine-3-carboxamide;

1-(5-ethoxypyridin-2-yl)-N-[3-fluoro-4-[(7-methoxy-1,5-naphthyridin-4-yl)oxy]phenyl]-6-methyl-2-oxopyridine-3-carboxamide;

N-[4-[(6,7-dimethoxy-1,5-naphthyridin-4-yl)oxy]-3-fluorophenyl]-5-(5-fluoropyridin-2-yl)-4-hydroxy-2-(methoxymethyl)-6-methylpyridine-3-carboxamide;

N-[4-[(6,7-dimethoxy-1,5-naphthyridin-4-yl)oxy]-3-fluorophenyl]-5-(5-fluoropyridin-2-yl)-4-methoxy-6-methylpyridazine-3-carboxamide;

N-[4-[(6,7-dimethoxy-1,5-naphthyridin-4-yl)oxy]phenyl]-5-(5-fluoropyridin-2-yl)-4-hydroxy-2,6-dimethylpyridine-3-carboxamide;

N-[3-fluoro-4-[(7-methoxy-1,5-naphthyridin-4-yl)oxy]phenyl]-5-(5-fluoropyridin-2-yl)-4-hydroxy-2,6-dimethylpyridine-3-carboxamide;

N-[4-[(6,7-dimethoxy-1,5-naphthyridin-4-yl)oxy]-3-fluorophenyl]-5-(5-fluoropyridin-2-yl)-4-hydroxy-2,6-dimethylpyridine-3-carboxamide;

N-[4-[(6,7-dimethoxy-1,5-naphthyridin-4-yl)oxy]-3-fluorophenyl]-4-(5-fluoropyridin-2-yl)-5-methyl-3-oxopyrazine-2-carboxamide;

N-[4-[(6,7-dimethoxy-1,5-naphthyridin-4-yl)oxy]-3-fluorophenyl]-1-(3-fluoropyridin-4-yl)-6-methyl-2-oxopyridine-3-carboxamide;

N-[4-[(6,7-dimethoxy-1,5-naphthyridin-4-yl)oxy]-3-fluorophenyl]-6-methyl-2-oxo-1-pyridin-4-ylpyridine-3-carboxamide;

N-[4-[(6,7-dimethoxy-1,5-naphthyridin-4-yl)oxy]-3-fluorophenyl]-6-methyl-2-oxo-1-pyridin-3-ylpyridine-3-carboxamide;

N-[4-[(6,7-dimethoxy-1,5-naphthyridin-4-yl)oxy]-3-fluorophenyl]-1-[2-[2-(2-ethoxyethoxy)ethoxy]pyridin-4-yl]-6-methyl-2-oxopyridine-3-carboxamide;

N-[4-[(6,7-dimethoxy-1,5-naphthyridin-4-yl)oxy]-3-fluorophenyl]-6-methyl-2-oxo-1-(2-propan-2-yloxypyridin-4-yl)pyridine-3-carboxamide;

N-[4-[(6,7-dimethoxy-1,5-naphthyridin-4-yl)oxy]-3-fluorophenyl]-1-(2-methoxypyridin-4-yl)-6-methyl-2-oxopyridine-3-carboxamide;

N-[4-[(6,7-dimethoxy-1,5-naphthyridin-4-yl)oxy]-3-fluorophenyl]-1-(5-fluoro-6-methylpyridin-2-yl)-6-methyl-2-oxopyridine-3-carboxamide;

N-[4-[(6,7-dimethoxy-1,5-naphthyridin-4-yl)oxy]-3-fluorophenyl]-4-hydroxy-2-methyl-5-pyridin-3-ylpyridine-3-carboxamide;

N-[4-[(6,7-dimethoxy-1,5-naphthyridin-4-yl)oxy]-3-fluorophenyl]-2-oxo-1-pyridin-4-ylpyridine-3-carboxamide;

N-[4-[(6,7-dimethoxy-1,5-naphthyridin-4-yl)oxy]-3-fluorophenyl]-6-methyl-1-(2-methylpyridin-4-yl)-2-oxopyridine-3-carboxamide;

N-[4-[(6,7-dimethoxy-1,5-naphthyridin-4-yl)oxy]-3-fluorophenyl]-6-methyl-1-(1-oxidopyridin-1-ium-4-yl)-2-oxopyridine-3-carboxamide;

N-[4-[(6,7-dimethoxy-1,5-naphthyridin-4-yl)oxy]-3-fluorophenyl]-1-(2-hydroxypyridin-4-yl)-6-methyl-2-oxopyridine-3-carboxamide;

N-[4-[(6,7-dimethoxy-1,5-naphthyridin-4-yl)oxy]-3-fluorophenyl]-1-(2-fluoropyridin-4-yl)-6-methyl-2-oxopyridine-3-carboxamide;

N-[4-[(6,7-dimethoxy-1,5-naphthyridin-4-yl)oxy]-3-fluorophenyl]-6-methyl-2-oxo-1-pyridazin-3-ylpyridine-3-carboxamide;

5-acetyl-N-[4-[(6,7-dimethoxy-1,5-naphthyridin-4-yl)oxy]-3-fluorophenyl]-1-(furan-3-yl)-6-methyl-2-oxopyridine-3-carboxamide;

5-acetyl-N-[4-[(6,7-dimethoxy-1,5-naphthyridin-4-yl)oxy]-3-fluorophenyl]-1-(furan-2-yl)-6-methyl-2-oxopyridine-3-carboxamide;

5-acetyl-N-[4-[(6,7-dimethoxy-1,5-naphthyridin-4-yl)oxy]phenyl]-1-(furan-2-yl)-6-methyl-2-oxopyridine-3-carboxamide;

5-acetyl-N-[3-fluoro-4-[(7-methoxy-1,5-naphthyridin-4-yl)oxy]phenyl]-1-(furan-2-yl)-6-methyl-2-oxopyridine-3-carboxamide;

5-acetyl-N-[4-[(6,7-dimethoxy-1,5-naphthyridin-4-yl)oxy]phenyl]-1-(furan-3-yl)-6-methyl-2-oxopyridine-3-carboxamide;

5-acetyl-N-[3-fluoro-4-[(7-methoxy-1,5-naphthyridin-4-yl)oxy]phenyl]-1-(furan-3-yl)-6-methyl-2-oxopyridine-3-carboxamide;

5-acetyl-N-[4-[(6,7-dimethoxy-1,5-naphthyridin-4-yl)oxy]-3-fluorophenyl]-6-methyl-2-oxo-1-thiophen-3-ylpyridine-3-carboxamide;

5-acetyl-N-[4-[(6,7-dimethoxy-1,5-naphthyridin-4-yl)oxy]phenyl]-6-methyl-2-oxo-1-thiophen-3-ylpyridine-3-carboxamide;

N-[4-[(6,7-dimethoxy-1,5-naphthyridin-4-yl)oxy]-3-fluorophenyl]-4-ethoxy-1-(5-fluoropyridin-2-yl)-2-oxopyridine-3-carboxamide;

N-[4-[(6,7-dimethoxy-1,5-naphthyridin-4-yl)oxy]phenyl]-4-ethoxy-1-(5-fluoropyridin-2-yl)-2-oxopyridine-3-carboxamide;

N-[4-[(6,7-dimethoxy-1,5-naphthyridin-4-yl)oxy]phenyl]-1-(5-fluoropyridin-2-yl)-4,6-dimethyl-2-oxopyridine-3-carboxamide;

N-[4-[(6,7-dimethoxy-1,5-naphthyridin-4-yl)oxy]-3-fluorophenyl]-4-(5-fluoropyridin-2-yl)-3-oxopyrazine-2-carboxamide;

N-[4-[(6,7-dimethoxy-1,5-naphthyridin-4-yl)oxy]-3-fluorophenyl]-1-(1-oxidopyridin-1-ium-4-yl)-2-oxopyridine-3-carboxamide;

N-[4-[(6,7-dimethoxy-1,5-naphthyridin-4-yl)oxy]-3-fluorophenyl]-1-(2-hydroxypyridin-4-yl)-2-oxopyridine-3-carboxamide;

N-[3-fluoro-4-[[6-methoxy-7-(2-methoxyethoxy)-1,5-naphthyridin-4-yl]oxy]phenyl]-5-(furan-2-yl)-1,2,6-trimethyl-4-oxopyridine-3-carboxamide;

N-[4-[(6,7-dimethoxy-1,5-naphthyridin-4-yl)oxy]phenyl]-5-(furan-2-yl)-4-hydroxy-6-methylpyridine-3-carboxamide;

N-[4-[(6,7-dimethoxy-1,5-naphthyridin-4-yl)oxy]phenyl]-4-hydroxy-6-methyl-5-thiophen-2-ylpyridine-3-carboxamide;

4-hydroxy-N-[4-[(7-methoxy-1,5-naphthyridin-4-yl)oxy]phenyl]-6-methyl-5-thiophen-2-ylpyridine-3-carboxamide;

N-[3-fluoro-4-[[6-methoxy-7-(2-methoxyethoxy)-1,5-naphthyridin-4-yl]oxy]phenyl]-5-(furan-2-yl)-4-hydroxy-6-methylpyridine-3-carboxamide;

5-(1-benzofuran-2-yl)-N-[4-[(6,7-dimethoxy-1,5-naphthyridin-4-yl)oxy]-3-fluorophenyl]-1,2,6-trimethyl-4-oxopyridine-3-carboxamide;

5-(1-benzofuran-3-yl)-N-[4-[(6,7-dimethoxy-1,5-naphthyridin-4-yl)oxy]-3-fluorophenyl]-1,2,6-trimethyl-4-oxopyridine-3-carboxamide;

5-(1-benzofuran-2-yl)-N-[3-fluoro-4-[[6-methoxy-7-(2-methoxyethoxy)-1,5-naphthyridin-4-yl]oxy]phenyl]-1,2,6-trimethyl-4-oxopyridine-3-carboxamide;

5-(1-benzofuran-3-yl)-N-[3-fluoro-4-[[6-methoxy-7-(2-methoxyethoxy)-1,5-naphthyridin-4-yl]oxy]phenyl]-1,2,6-trimethyl-4-oxopyridine-3-carboxamide;

5-(1-benzofuran-3-yl)-N-[3-fluoro-4-[[7-(2-methoxyethoxy)-1,5-naphthyridin-4-yl]oxy]phenyl]-1,2,6-trimethyl-4-oxopyridine-3-carboxamide;

N-[3-fluoro-4-[[7-(2-methoxyethoxy)-1,5-naphthyridin-4-yl]oxy]phenyl]-5-(furan-2-yl)-1,2,6-trimethyl-4-oxopyridine-3-carboxamide;

N-[4-[(6,7-dimethoxy-1,5-naphthyridin-4-yl)oxy]-3-fluorophenyl]-6-(furan-2-yl)-5-methylpyrazine-2-carboxamide;

1-(2,2-difluoroethyl)-N-[4-[(6,7-dimethoxy-1,5-naphthyridin-4-yl)oxy]-3-fluorophenyl]-5-(furan-2-yl)-2-methyl-4-oxopyridine-3-carboxamide;

N-[4-[(6,7-dimethoxy-1,5-naphthyridin-4-yl)oxy]-3-fluorophenyl]-7-(furan-2-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]phenyl]-7-(furan-2-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]phenyl]-8-oxo-7-thiophen-2-yl-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-8-oxo-7-thiophen-3-yl-3,4-dihydro-1H-pyrido[2,1-c][1,4]oxazine-9-carboxamide;

N-[4-[(6,7-dimethoxy-1,5-naphthyridin-4-yl)oxy]phenyl]-8-oxo-7-thiophen-3-yl-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-7-(4-methylthiophen-2-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]phenyl]-7-(4-methylthiophen-2-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-7-(5-methylthiophen-2-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]phenyl]-7-(5-methylthiophen-2-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-7-(furan-3-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-6-methyl-8-oxo-7-thiophen-3-yl-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-7-(furan-3-yl)-6-methyl-8-oxo-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-8-oxo-7-thiophen-2-yl-3,4-dihydro-1H-pyrido[2,1-c][1,4]oxazine-9-carboxamide;

N-[4-[(6,7-dimethoxy-1,5-naphthyridin-4-yl)oxy]phenyl]-7-(furan-3-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]phenyl]-7-(furan-3-yl)-6-methyl-8-oxo-3,4-dihydro-1H-pyrido[2,1-c][1,4]oxazine-9-carboxamide;

N-[4-[(6,7-dimethoxy-1,5-naphthyridin-4-yl)oxy]phenyl]-6-methyl-8-oxo-7-thiophen-3-yl-3,4-dihydro-1H-pyrido[2,1-c][1,4]oxazine-9-carboxamide;

N-[4-[(6,7-dimethoxy-1,5-naphthyridin-4-yl)oxy]phenyl]-6-methyl-7-(4-methylthiophen-2-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-7-(furan-2-yl)-6-methyl-8-oxo-3,4-dihydro-1H-pyrido[2,1-c][1,4]oxazine-9-carboxamide;

N-[4-[(6,7-dimethoxy-1,5-naphthyridin-4-yl)oxy]phenyl]-7-(furan-2-yl)-6-methyl-8-oxo-3,4-dihydro-1H-pyrido[2,1-c][1,4]oxazine-9-carboxamide;

N-[4-[(6,7-dimethoxy-1,5-naphthyridin-4-yl)oxy]phenyl]-6-methyl-8-oxo-7-thiophen-2-yl-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-6-methyl-8-oxo-7-thiophen-2-yl-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-6-methyl-7-(4-methylthiophen-2-yl)-8-oxo-3,4-dihydro-1H-pyrido[2,1-c][1,4]oxazine-9-carboxamide;

N-[4-[(6,7-dimethoxy-1,5-naphthyridin-4-yl)oxy]-3-fluorophenyl]-2-ethyl-5-(furan-2-yl)-1,6-dimethyl-4-oxopyridine-3-carboxamide;

N-[4-[(6,7-dimethoxy-1,5-naphthyridin-4-yl)oxy]phenyl]-2-ethyl-5-(furan-2-yl)-1,6-dimethyl-4-oxopyridine-3-carboxamide;

2-ethyl-N-[3-fluoro-4-[[6-methoxy-7-(2-methoxyethoxy)-1,5-naphthyridin-4-yl]oxy]phenyl]-5-(furan-2-yl)-1,6-dimethyl-4-oxopyridine-3-carboxamide;

N-[4-[(6,7-dimethoxy-1,5-naphthyridin-4-yl)oxy]-3-fluorophenyl]-1-(2-fluoroethyl)-6-methyl-4-oxo-5-thiophen-2-ylpyridine-3-carboxamide;

1-(2-fluoroethyl)-N-[3-fluoro-4-[(7-methoxy-1,5-naphthyridin-4-yl)oxy]phenyl]-6-methyl-5-(4-methylthiophen-2-yl)-4-oxopyridine-3-carboxamide;

1-(2-fluoroethyl)-N-[3-fluoro-4-[(7-methoxy-1,5-naphthyridin-4-yl)oxy]phenyl]-6-methyl-5-(5-methylthiophen-2-yl)-4-oxopyridine-3-carboxamide;

1-(2-fluoroethyl)-N-[3-fluoro-4-[(7-methoxy-1,5-naphthyridin-4-yl)oxy]phenyl]-6-methyl-4-oxo-5-thiophen-3-ylpyridine-3-carboxamide;

1-(2-fluoroethyl)-N-[3-fluoro-4-[(7-methoxy-1,5-naphthyridin-4-yl)oxy]phenyl]-6-methyl-4-oxo-5-thiophen-2-ylpyridine-3-carboxamide;

N-[4-[(6,7-dimethoxy-1,5-naphthyridin-4-yl)oxy]-3-fluorophenyl]-1-(2-fluoroethyl)-6-methyl-4-oxo-5-thiophen-3-ylpyridine-3-carboxamide;

N-[4-[(6,7-dimethoxy-1,5-naphthyridin-4-yl)oxy]-3-fluorophenyl]-1-(2-fluoroethyl)-5-(furan-2-yl)-6-methyl-4-oxopyridine-3-carboxamide;

1-(2-fluoroethyl)-N-[3-fluoro-4-[(7-methoxy-1,5-naphthyridin-4-yl)oxy]phenyl]-5-(furan-3-yl)-6-methyl-4-oxopyridine-3-carboxamide; and N-[4-[[7-(2-cyclobutylethoxy)-6-methoxy-1,5-naphthyridin-4-yl]oxy]-3-fluorophenyl]-5-(furan-2-yl)-1,2,6-trimethyl-4-oxopyridine-3-carboxamide;

or a pharmaceutically acceptable salt or stereoisomer thereof.

* * * * *